United States Patent
Forsell

(10) Patent No.: US 12,318,572 B2
(45) Date of Patent: *Jun. 3, 2025

(54) OPERABLE IMPLANT

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 85 days.

This patent is subject to a terminal disclaimer.

(21) Appl. No.: 17/377,455

(22) Filed: Jul. 16, 2021

(65) Prior Publication Data

US 2022/0184299 A1 Jun. 16, 2022

Related U.S. Application Data

(63) Continuation of application No. 16/214,178, filed on Dec. 10, 2018, now Pat. No. 11,110,220, which is a
(Continued)

(51) Int. Cl.
*A61M 5/142* (2006.01)
*A61B 5/00* (2006.01)
(Continued)

(52) U.S. Cl.
CPC ......... *A61M 5/14276* (2013.01); *A61B 5/076* (2013.01); *A61B 5/686* (2013.01); *A61F 2/004* (2013.01); *A61F 2/12* (2013.01); *A61F 2/28* (2013.01); *A61F 5/0013* (2013.01); *A61M 5/14526* (2013.01); *A61M 27/002* (2013.01); *A61M 31/002* (2013.01); *A61M 39/22* (2013.01); *A61M 60/178* (2021.01); *A61M 60/191* (2021.01); *A61M 60/279* (2021.01); *A61M 60/289* (2021.01); *A61M 60/495* (2021.01); *A61M 60/508* (2021.01); *A61M 60/837* (2021.01); *A61M 60/875* (2021.01); *A61M 60/876* (2021.01); *A61N 1/05* (2013.01); *A61N 1/3787* (2013.01); *F04B 43/12* (2013.01); *F04B 43/1253* (2013.01); *F04C 2/10* (2013.01); *F04C 11/008* (2013.01); *F04C 13/001* (2013.01); *F04C 15/0061* (2013.01);
(Continued)

(58) Field of Classification Search
CPC .......... A61M 5/14276; A61M 5/14526; A61M 27/002; A61B 5/076; A61B 5/0031; A61B 5/686; F04C 11/008; F04C 2/10; F04C 13/001; A61F 5/0013; A61F 2/0004; A61N 1/05
See application file for complete search history.

(56) References Cited

U.S. PATENT DOCUMENTS

| | | |
|---|---|---|
| 5,945,762 A | 8/1999 | Chen |
| 6,451,055 B1 | 9/2002 | Weiss |

(Continued)

*Primary Examiner* — Thaddeus B Cox

(57) ABSTRACT

An operable implant adapted to be implanted in the body of a patient, the operable implant comprising an operation device and a body engaging portion, wherein the operation device comprises a first unit comprising a receiving unit for receiving wireless energy and a first gear system adapted to receive mechanical work having a first force and first velocity, and output mechanical work having a different second force and a different second velocity. The operation device further comprises a second unit comprising an electrical motor adapted to transform electrical energy to the mechanical work, and a distance element adapted to separate the first and second units such that the receiving unit, when receiving wireless energy, is not substantially affected by the second unit.

19 Claims, 41 Drawing Sheets

Related U.S. Application Data continuation of application No. 14/852,660, filed on Sep. 14, 2015, now Pat. No. 10,149,936, which is a continuation of application No. PCT/EP2014/055111, filed on Mar. 14, 2014.

(51) Int. Cl.

| | | |
|---|---|---|
| *A61B 5/07* | (2006.01) | |
| *A61F 2/00* | (2006.01) | |
| *A61F 2/12* | (2006.01) | |
| *A61F 2/28* | (2006.01) | |
| *A61F 5/00* | (2006.01) | |
| *A61M 5/145* | (2006.01) | |
| *A61M 27/00* | (2006.01) | |
| *A61M 31/00* | (2006.01) | |
| *A61M 39/22* | (2006.01) | |
| *A61M 60/178* | (2021.01) | |
| *A61M 60/191* | (2021.01) | |
| *A61M 60/279* | (2021.01) | |
| *A61M 60/289* | (2021.01) | |
| *A61M 60/495* | (2021.01) | |
| *A61M 60/508* | (2021.01) | |
| *A61M 60/837* | (2021.01) | |
| *A61M 60/875* | (2021.01) | |
| *A61M 60/876* | (2021.01) | |
| *A61N 1/05* | (2006.01) | |
| *A61N 1/378* | (2006.01) | |
| *F04B 43/12* | (2006.01) | |
| *F04C 2/10* | (2006.01) | |
| *F04C 11/00* | (2006.01) | |
| *F04C 13/00* | (2006.01) | |
| *F04C 15/00* | (2006.01) | |
| *A61B 17/00* | (2006.01) | |
| *A61B 90/00* | (2016.01) | |
| *A61F 2/48* | (2006.01) | |
| *A61M 60/148* | (2021.01) | |
| *A61M 60/405* | (2021.01) | |
| *A61M 60/419* | (2021.01) | |
| *A61M 60/422* | (2021.01) | |

(52) U.S. Cl.
CPC ....... *F04C 15/0069* (2013.01); *A61B 2017/00039* (2013.01); *A61B 2017/00402* (2013.01); *A61B 2017/00539* (2013.01); *A61B 2090/061* (2016.02); *A61F 2/0036* (2013.01); *A61F 2/484* (2021.08); *A61F 2250/0001* (2013.01); *A61F 2250/0002* (2013.01); *A61F 2250/0004* (2013.01); *A61F 2310/00023* (2013.01); *A61F 2310/00047* (2013.01); *A61F 2310/00161* (2013.01); *A61F 2310/00179* (2013.01); *A61M 60/148* (2021.01); *A61M 60/405* (2021.01); *A61M 60/419* (2021.01); *A61M 60/422* (2021.01); *A61M 2205/0272* (2013.01); *A61M 2205/103* (2013.01); *A61M 2205/32* (2013.01); *A61M 2205/33* (2013.01); *A61M 2205/3303* (2013.01); *A61M 2205/3365* (2013.01); *A61M 2205/3515* (2013.01); *A61M 2205/3538* (2013.01); *A61M 2210/1021* (2013.01); *F04C 2240/40* (2013.01)

(56) References Cited

U.S. PATENT DOCUMENTS

| | | |
|---|---|---|
| 8,617,049 B2 | 12/2013 | Dlugos, Jr. et al. |
| 8,992,409 B2 | 3/2015 | Forsell |
| 2004/0039423 A1 | 2/2004 | Dolgin |

Fig.6
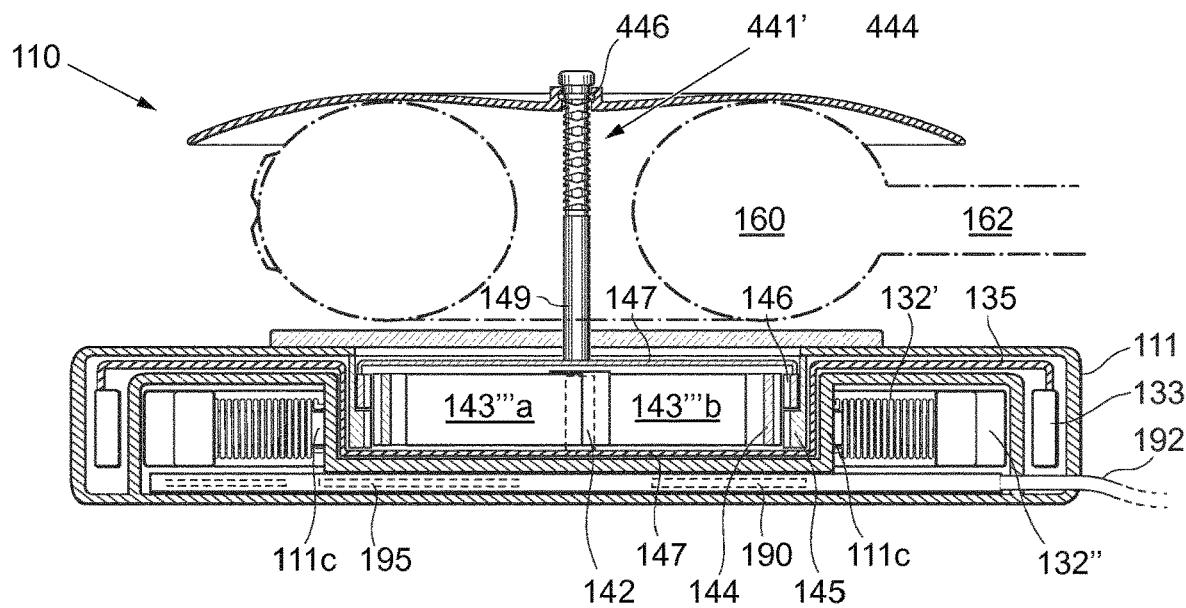
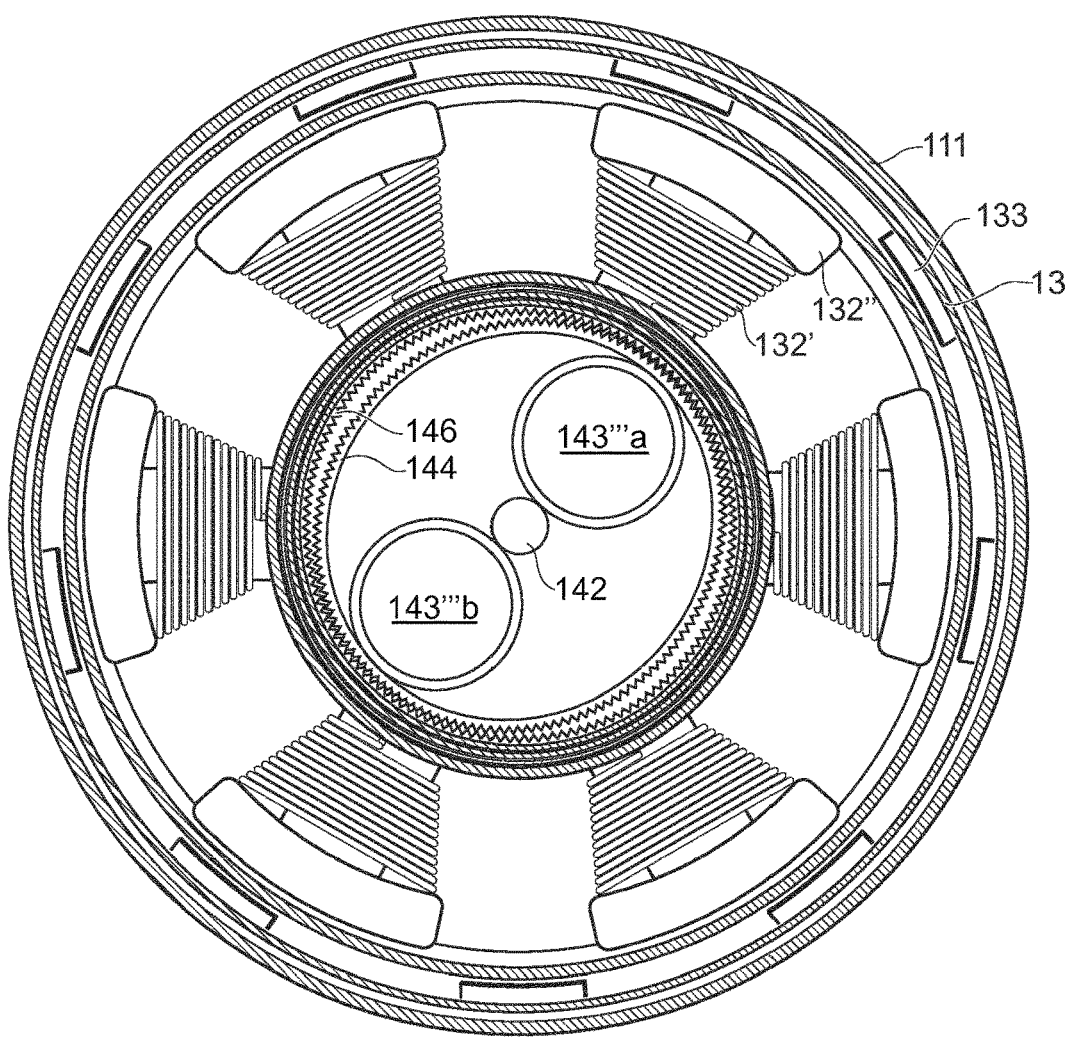

Fig.7
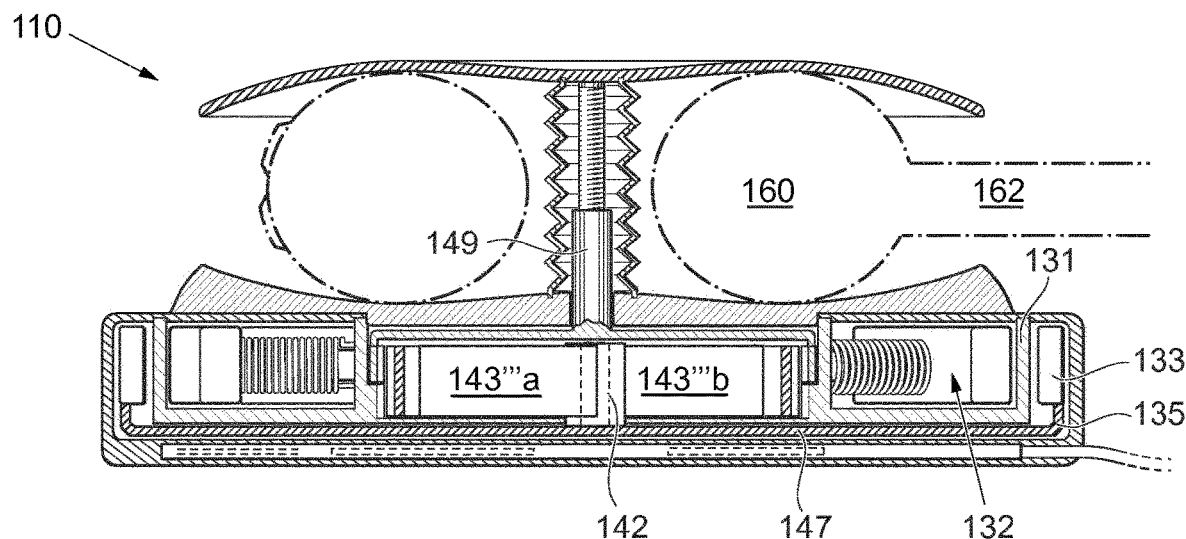
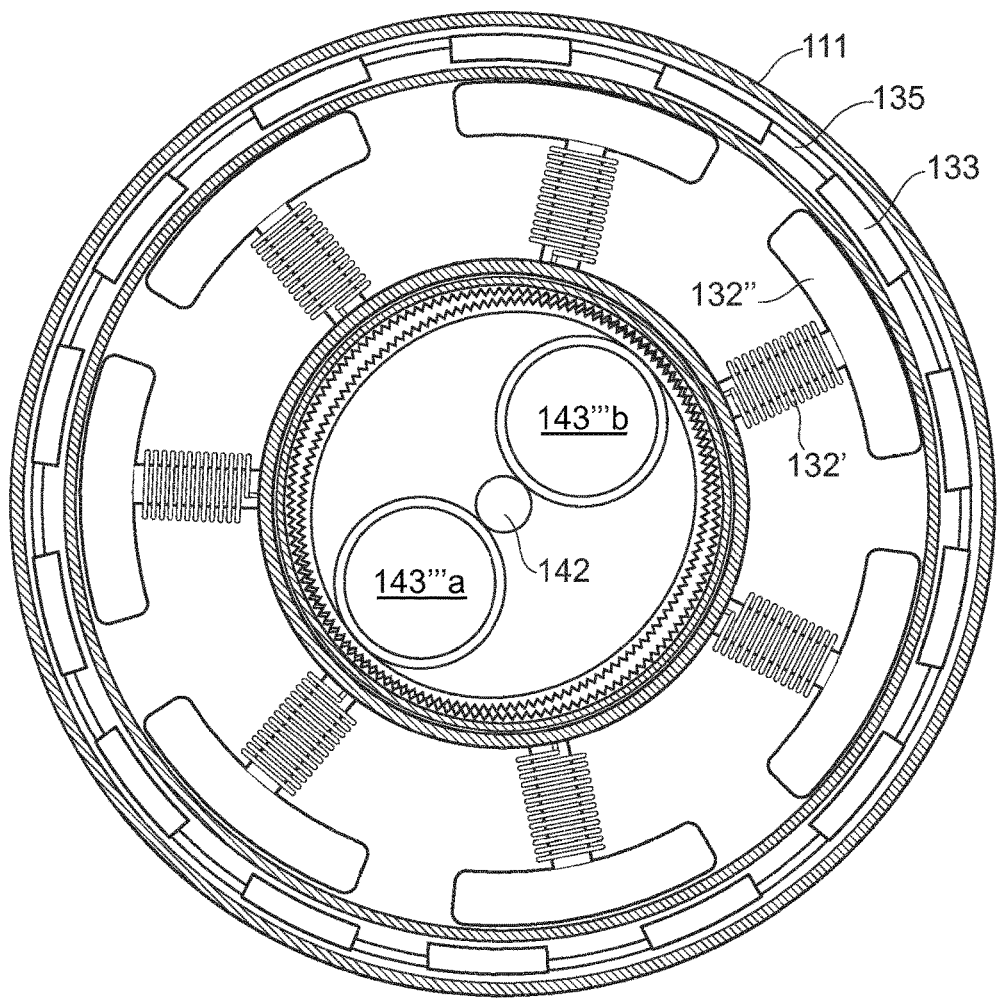

Fig.8
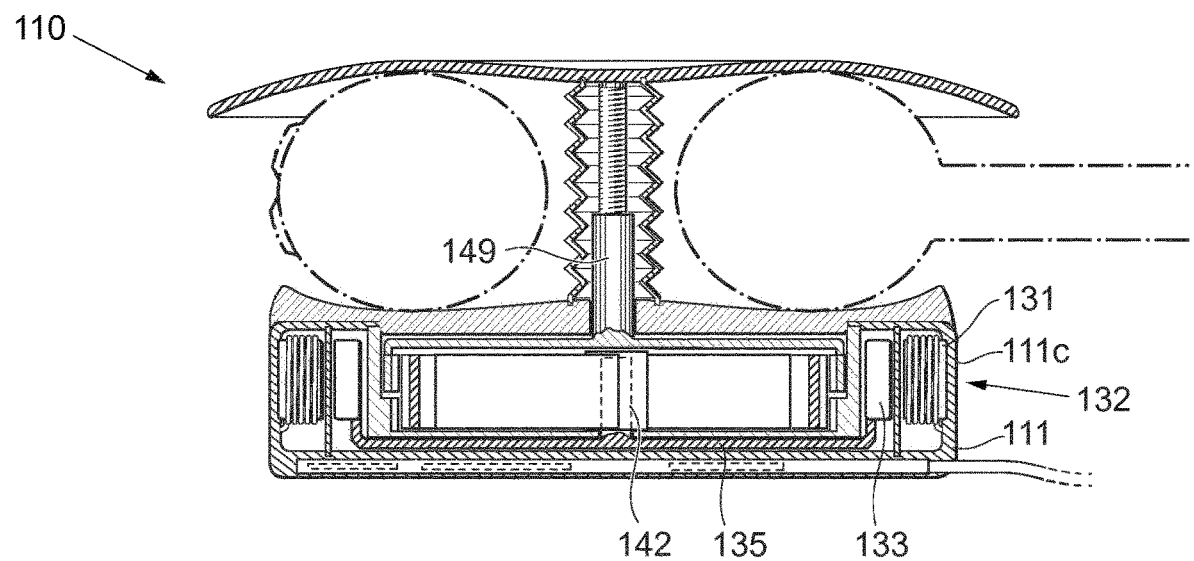
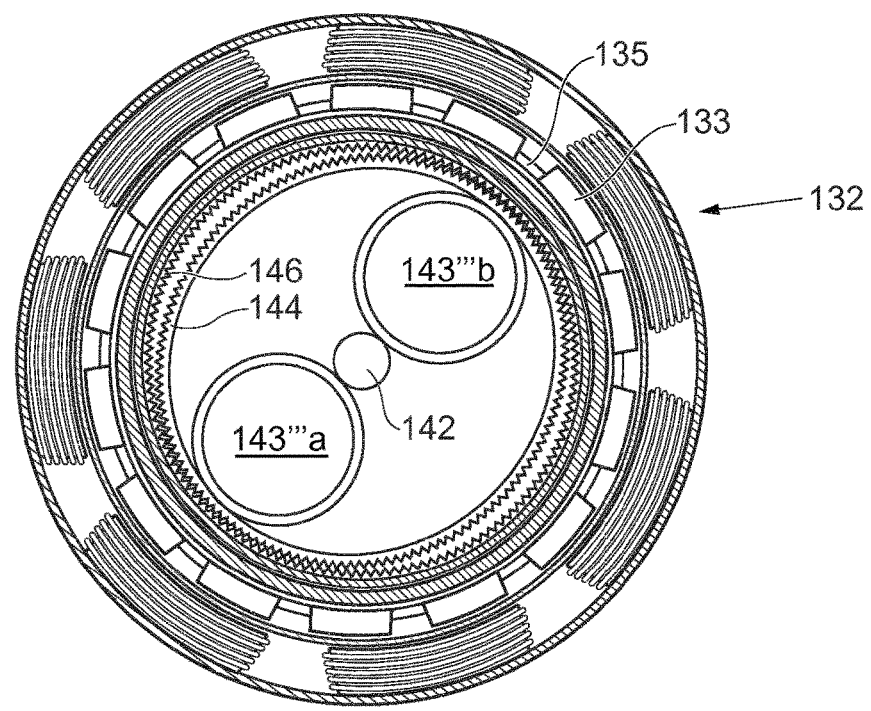

Fig.9
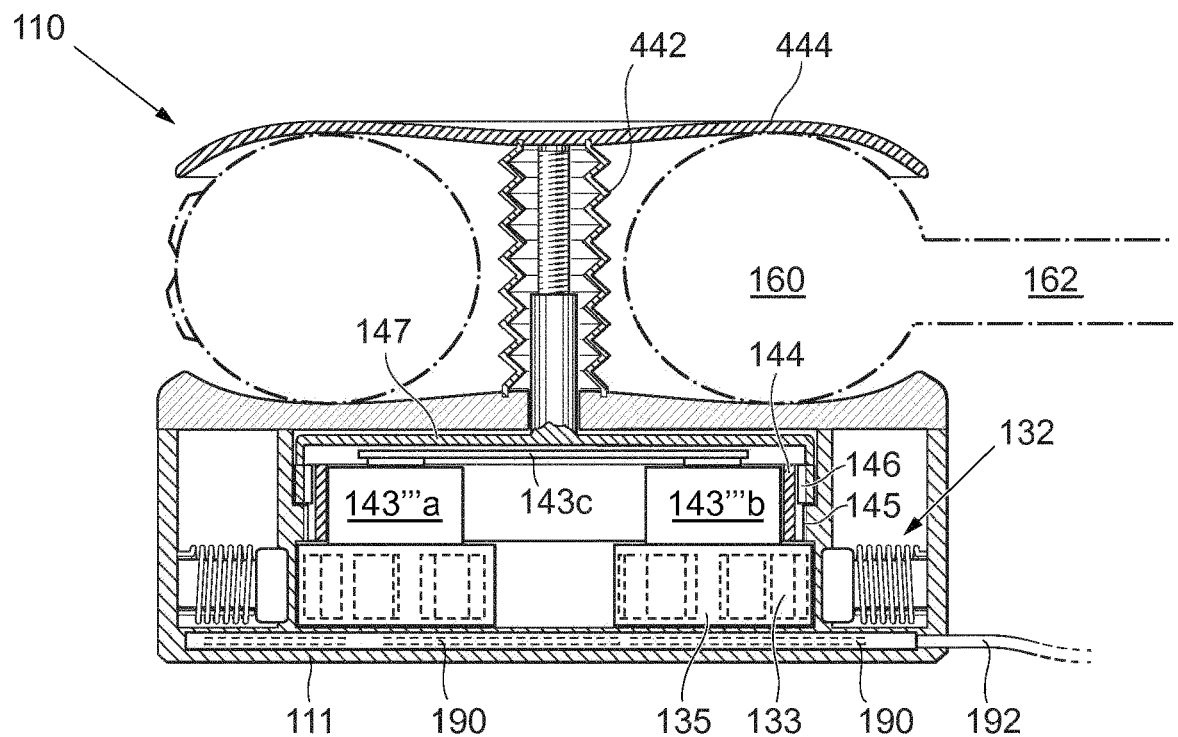
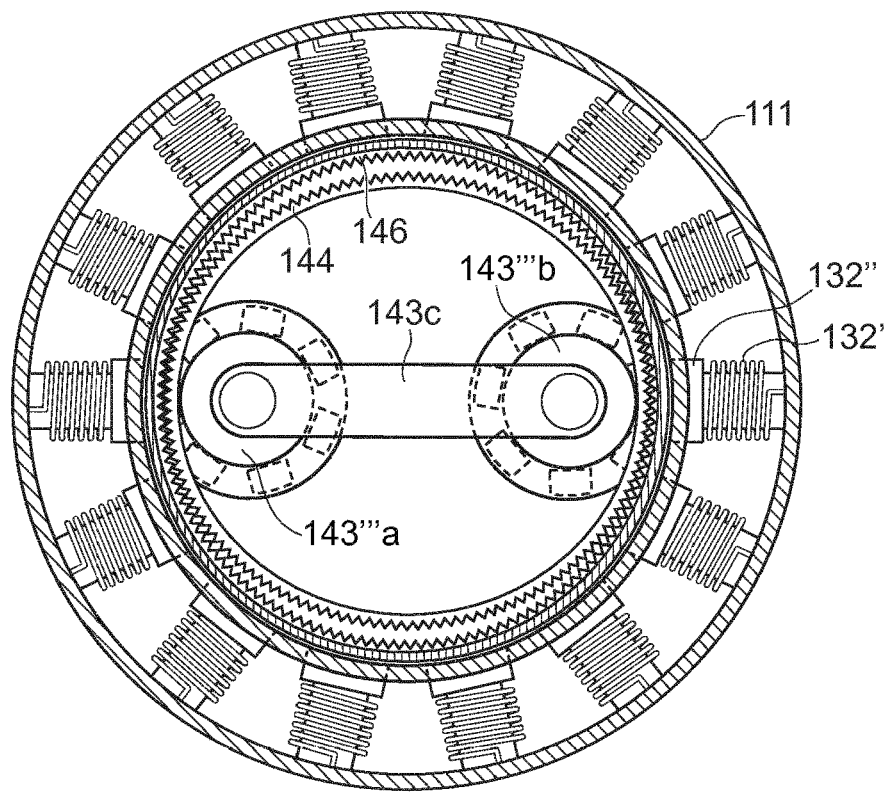

Fig.10a
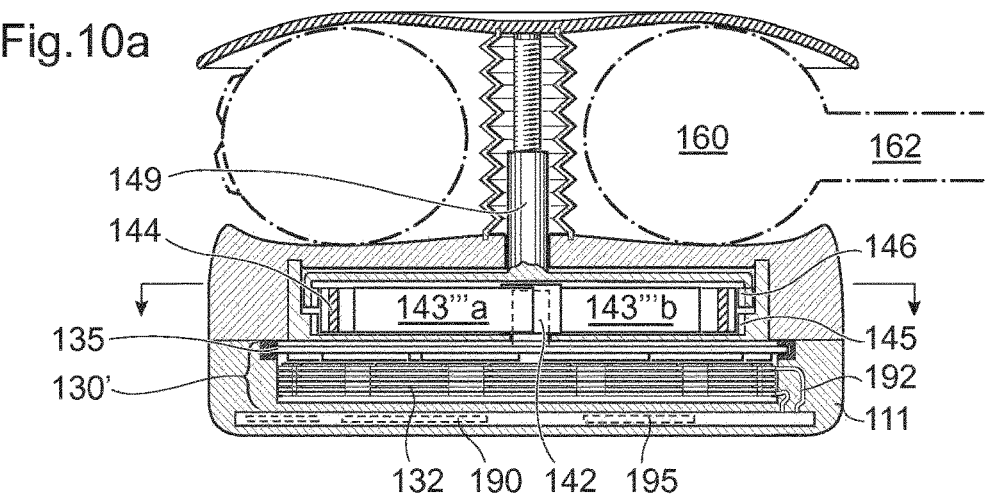
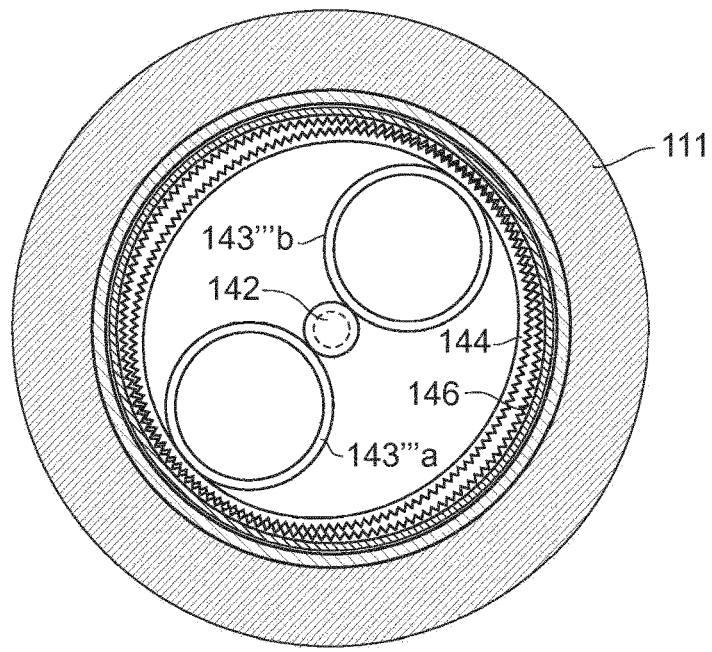
Fig.10b
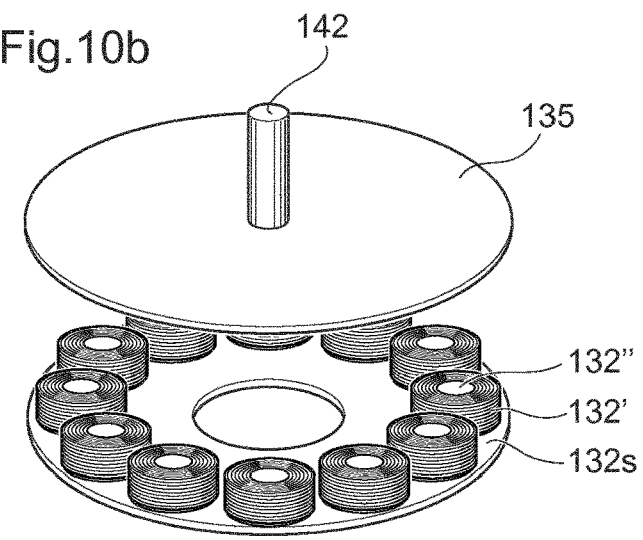

Fig.11a
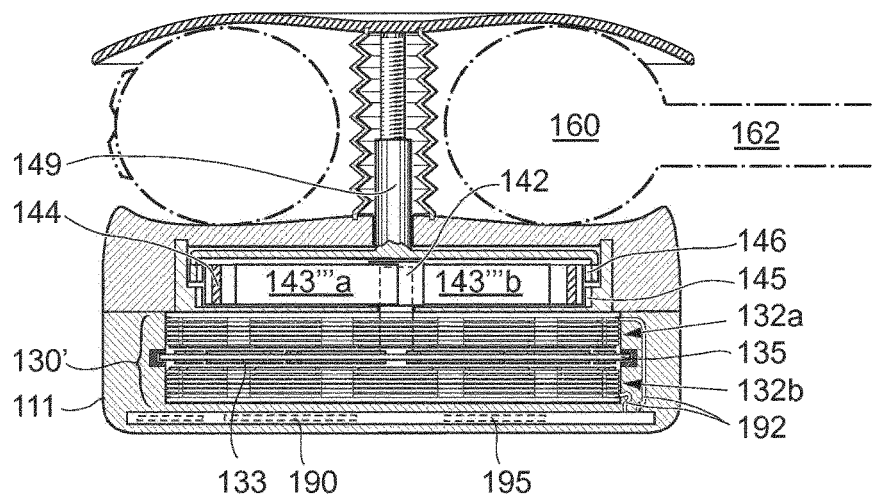
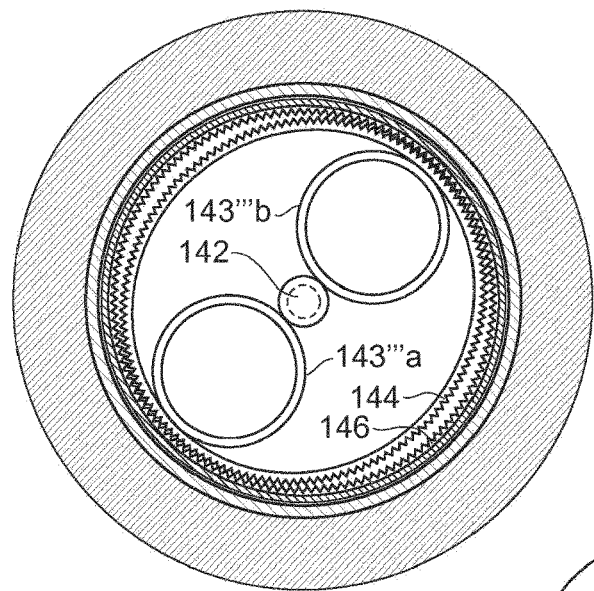
Fig.11b
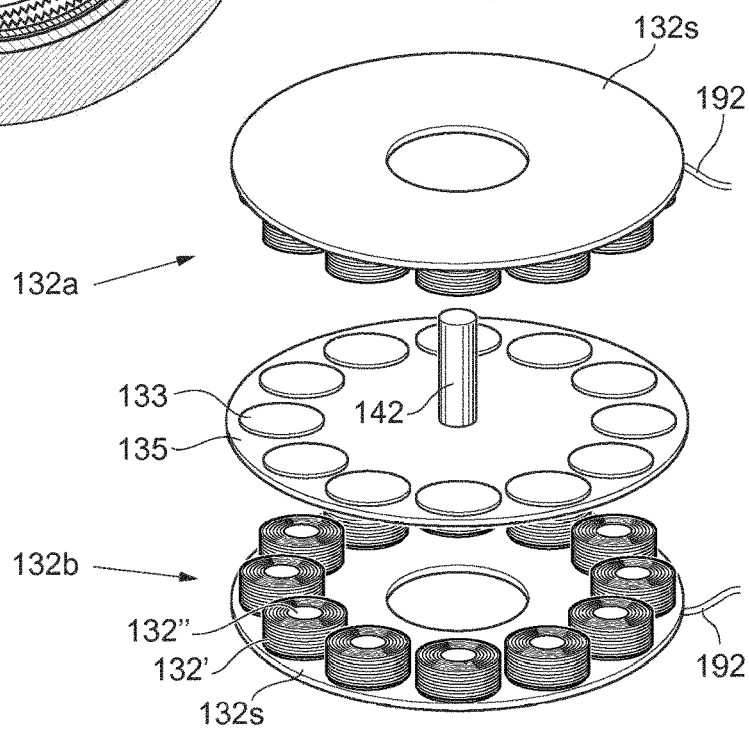

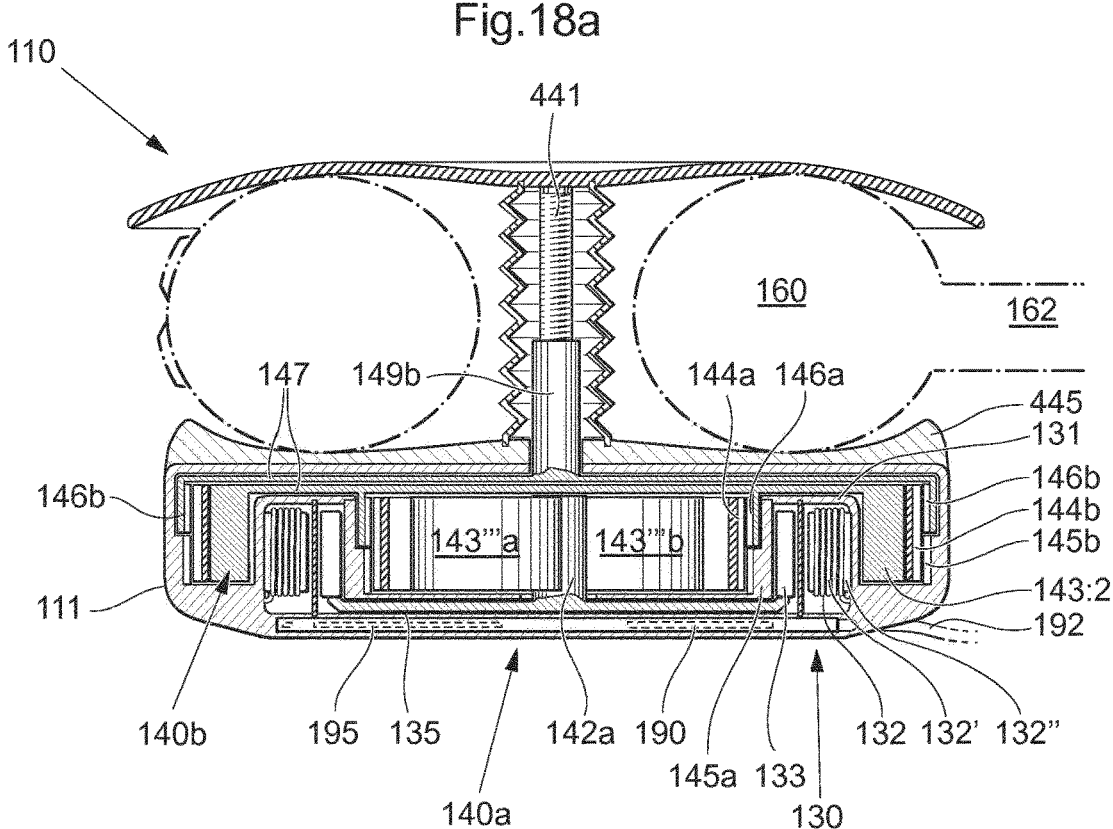
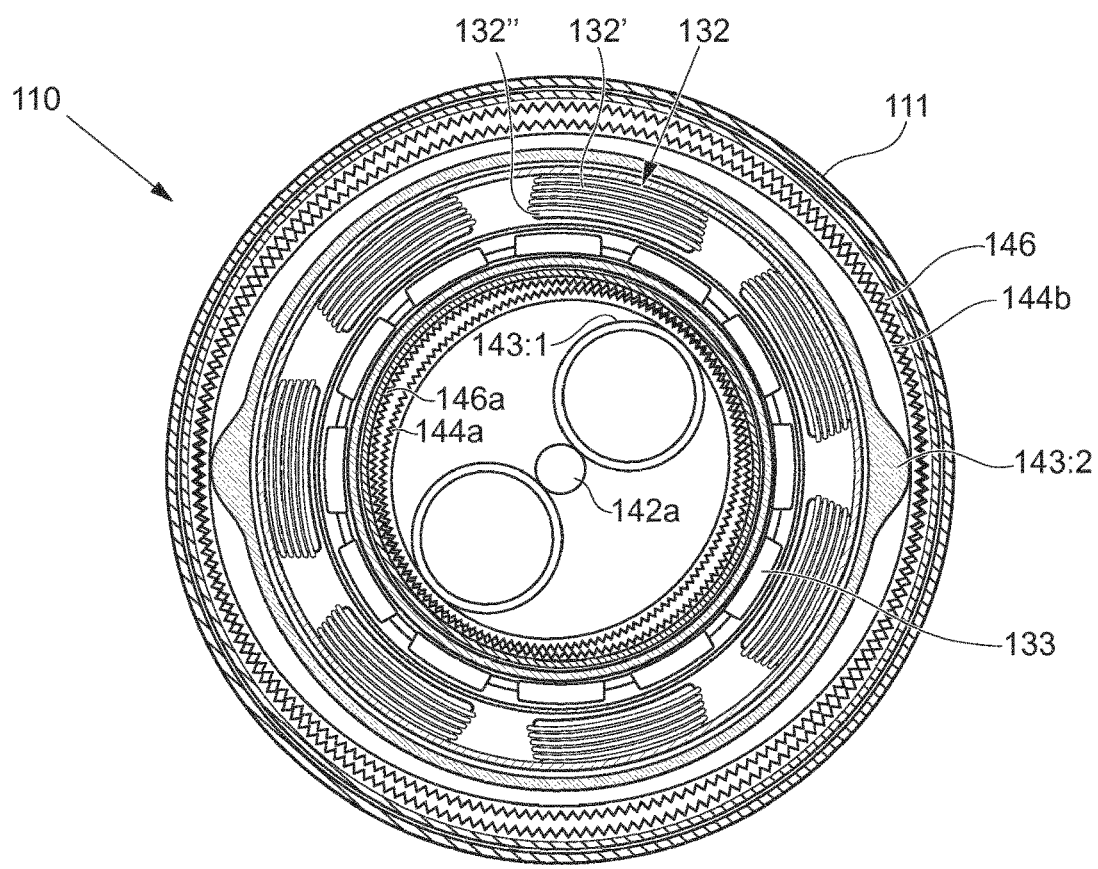
Fig.18a

Fig.19
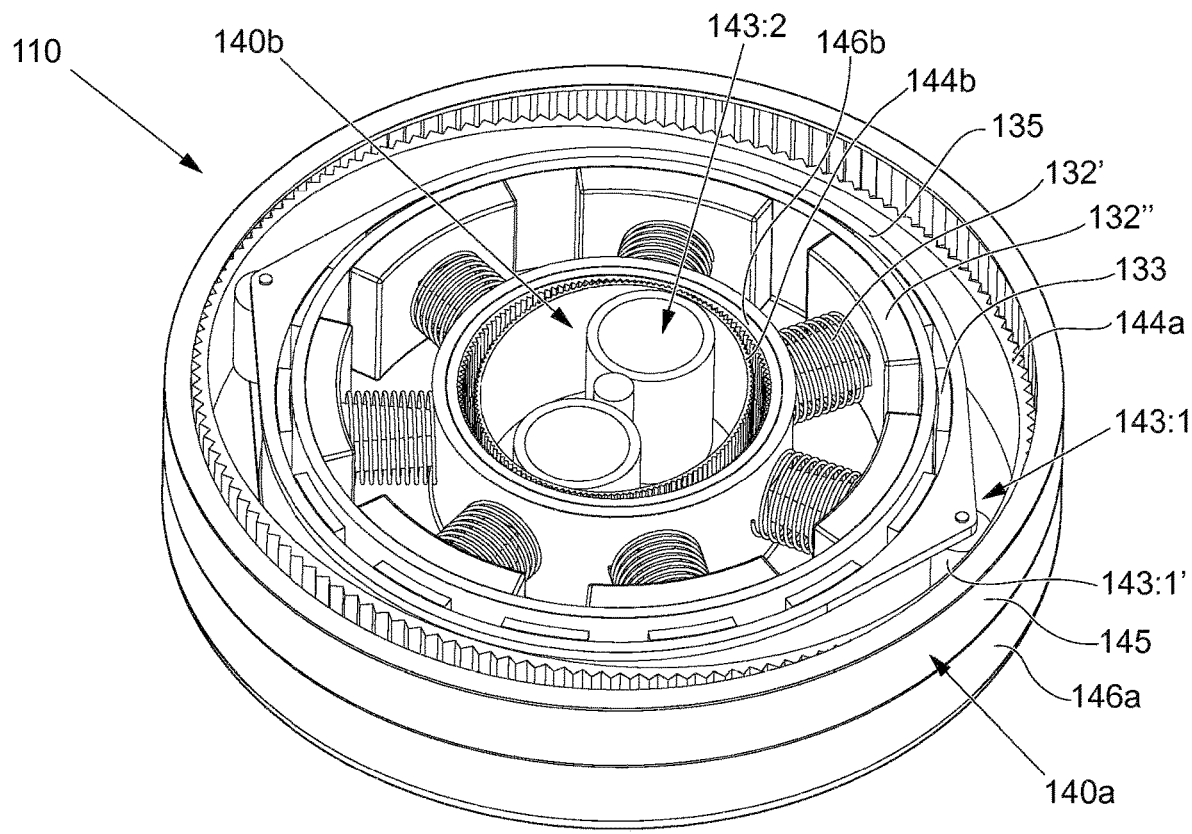
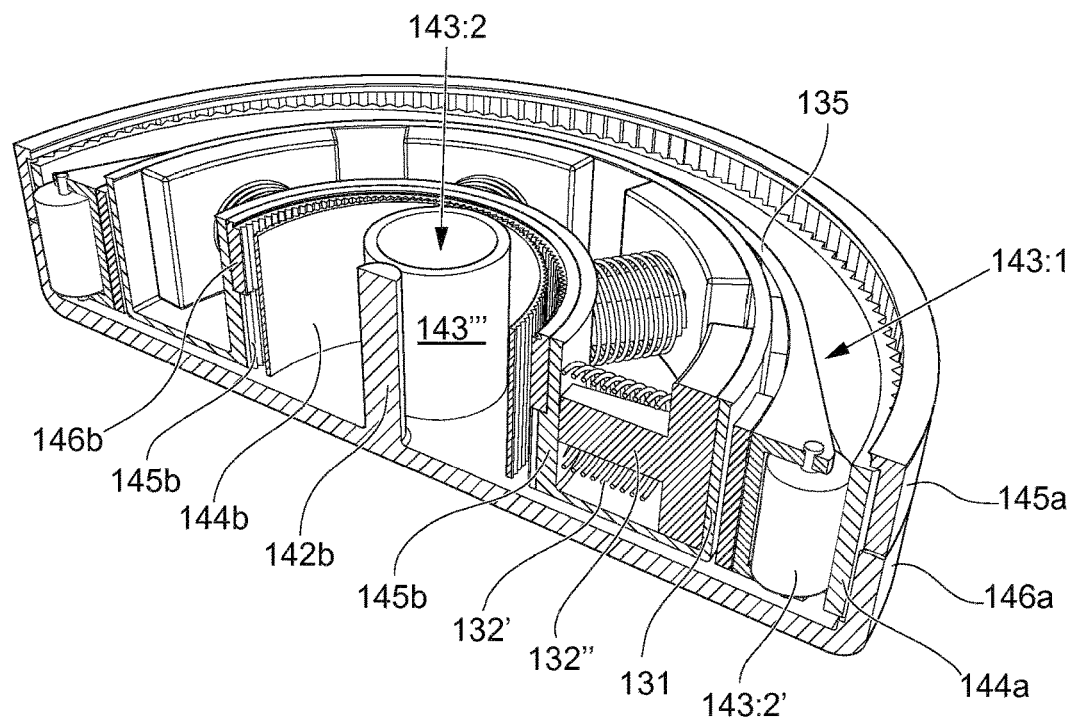

Fig.20
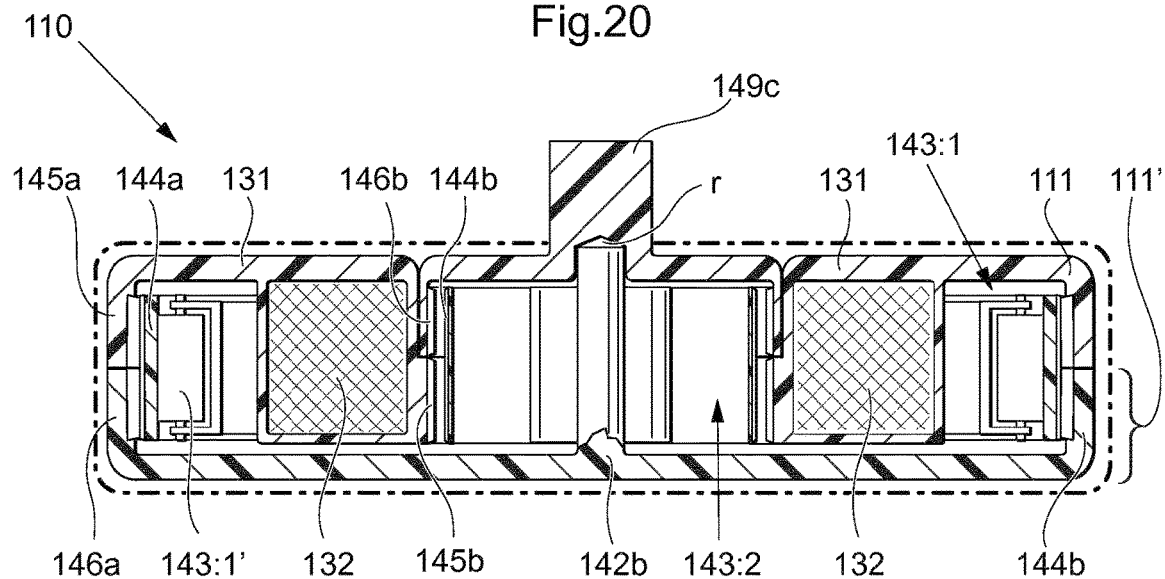
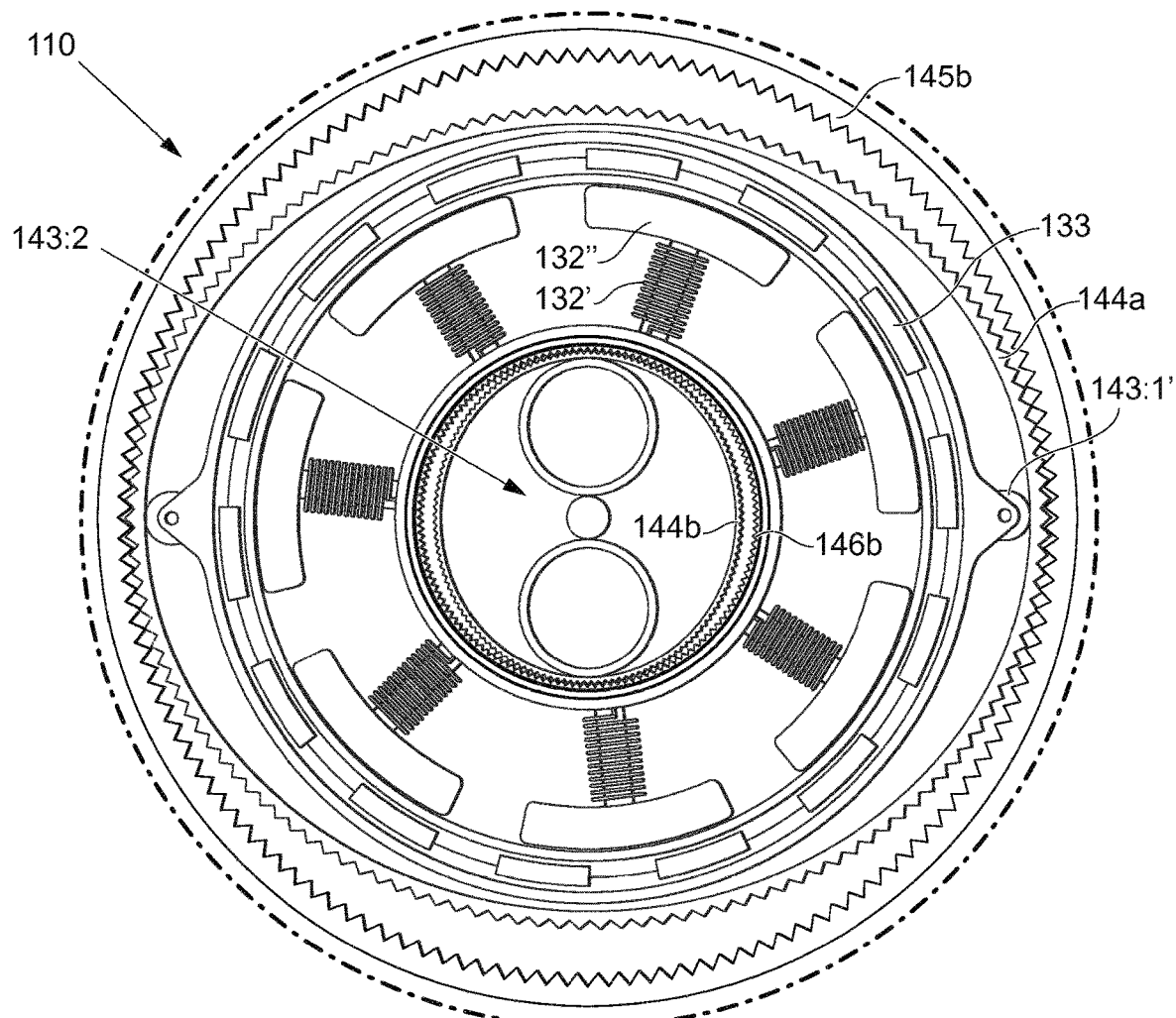

Fig.33
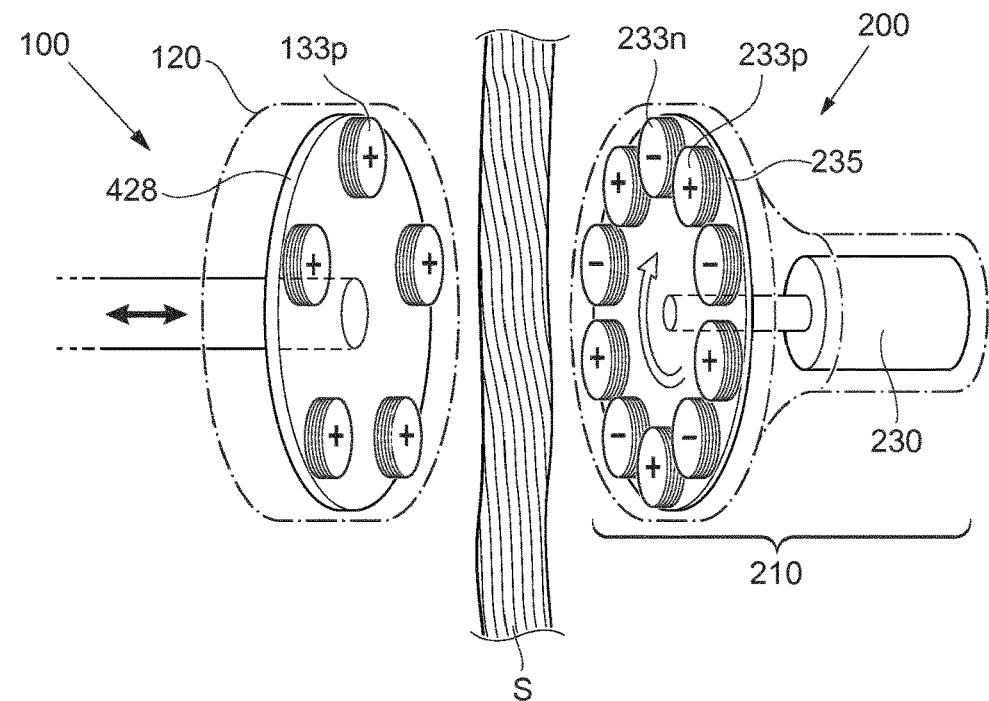
Fig.34
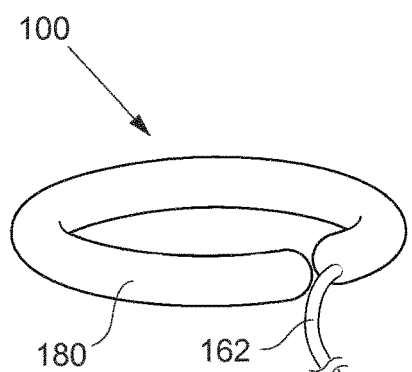
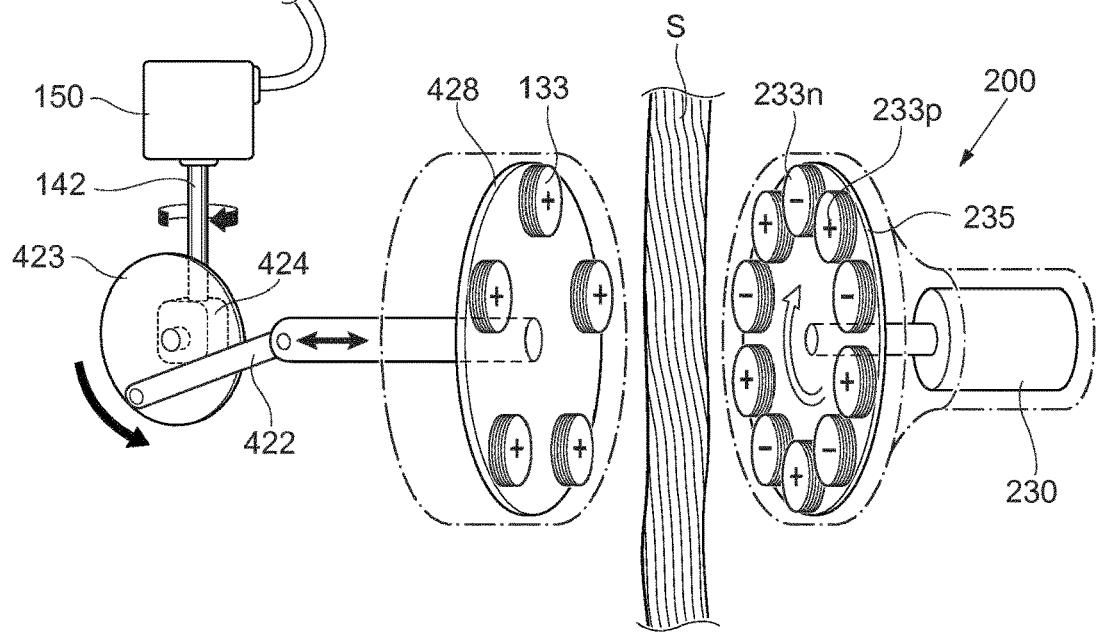

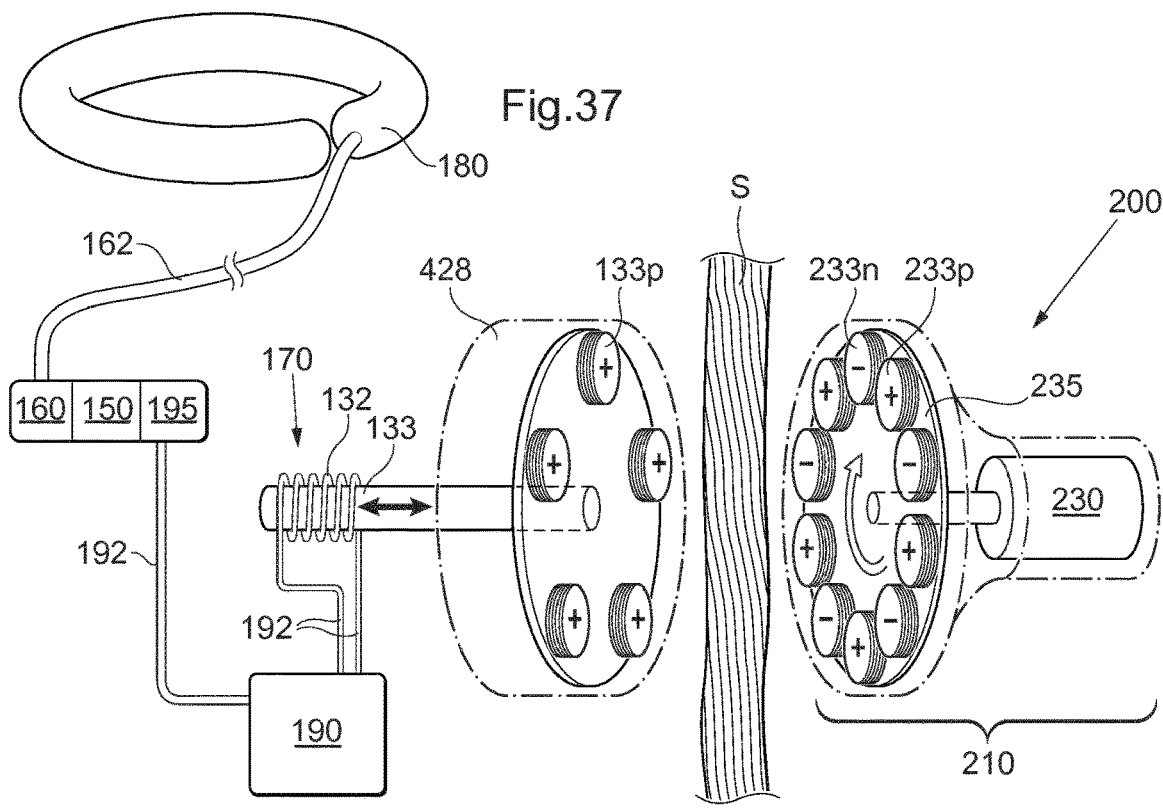
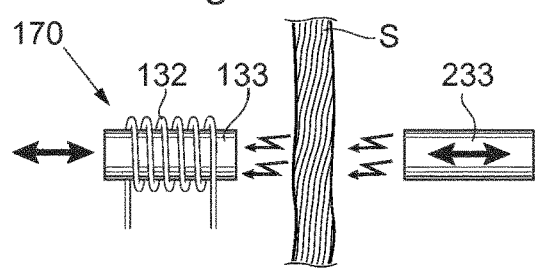
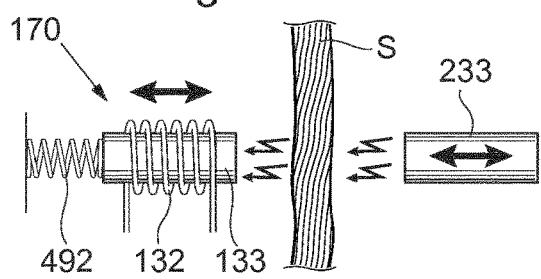
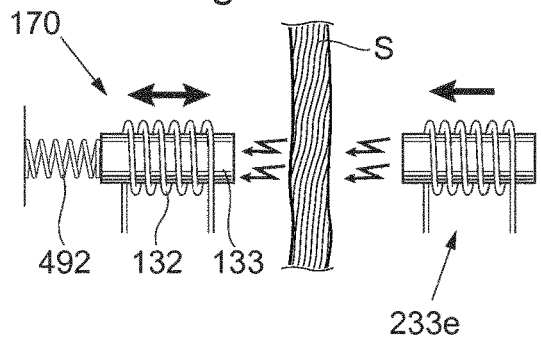

OPERABLE IMPLANT

This application is a continuation of U.S. application Ser. No. 16/214,178, filed Dec. 10, 2018, which is a continuation of U.S. patent application Ser. No. 14/852,660, filed Sep. 14, 2015 and issued as U.S. Pat. No. 10,149,936, which is a U.S. National phase entry of International Application No. PCT/EP2014/055111, filed Mar. 14, 2014, which claims priority from Swedish Patent Application 1350317-2, filed Mar. 15, 2013, the entire contents of each of which are hereby incorporated by reference.

TECHNICAL FIELD

The present invention relates to the field of operable implants, and devices, systems and methods for energizing and communicating with operable implants.

BACKGROUND

Providing a reliable operation device for energized and operable implants has proven to be difficult. The hostile environment of the body affects all parts of an implant and moving parts are particularly sensitive to bodily fluids and fibrotic tissue growth. Fibrotic tissue will eventually surround and enclose all foreign matter placed in the body which risks affecting the function of an implant. A more reliable, general purpose operation device for operable implants would thus be advantageous.

SUMMARY

An operable implant adapted to be implanted in the body of a patient is provided. The operable implant comprises an operation device and a body engaging portion. The operation device comprises a first unit comprising: a receiving unit for receiving wireless energy, and a first gear system adapted to receive mechanical work having a first force and first velocity, and output mechanical work having a different second force and a different second velocity. The operation device further comprises a second unit comprising an electrical motor adapted to transform electrical energy to the mechanical work, and a distance element comprising: a lead for transferring the electrical energy from the first unit to the second unit, and a mechanical transferring member adapted to transfer the mechanical work from the electrical motor in the second unit to the gear system in the first unit. The distance element is adapted to separate the first and second units such that the receiving unit, when receiving wireless energy, is not substantially affected by the second unit.

According to one embodiment, the receiving unit comprises at least one coil adapted to transform wireless energy received in form of a magnetic field into electrical energy. The receiving unit may comprise at least a first coil having a first number of windings, and at least a second coil having a second, different number of windings.

According to one embodiment, the gear system comprises an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

According to one embodiment, operable element comprises at least one of; a planetary gear and a structure or wheel at least partly using friction to interconnect with the first gear.

According to one embodiment, the second unit comprises a second gear system adapted to receive the mechanical work output from the first gear system with the different second force and the different second velocity as input, and output mechanical work having a third different force and third different velocity. The gear system of the second unit may be connected in series with the gear system of the first unit, via the mechanical transferring member of the distance element.

In one embodiment, the first unit may comprise a second gear system adapted receive mechanical work of a first force and velocity as input, and output mechanical work having a different force and velocity. The second gear system may be connected in series with the first gear system.

In any of the embodiments herein, the first unit may be adapted to be placed at least in one of the following places: subcutaneously, subcutaneously in the abdominal wall and in the abdomen.

The electrical motor in any of the embodiments, may comprise magnetic material, and the first unit may remain substantially unaffected by the magnetic material in the second unit, during wirelessly energy transfer.

The first gear system in any of the embodiments may comprise a third gear, and the inside of the third gear may comprise the same amount of teeth as the outside of the first gear, and the teeth of the third gear are adapted to interengage with the teeth of the first gear such that the third gear rotates in relation to the second gear, along with the at least one interengaged position.

The second unit in any of the embodiments may comprise at least one fixation portion for fixating the second unit to at least one of: fibrosis, a fascia and a muscular layer towards the inside of the subcutaneous space of the patient.

The distance element in any of the embodiments may be adapted to be at least one of; placed through the muscular layers of the abdominal wall, and fixated to the muscular fascia facing the subcutaneous space.

According to one embodiment, the distance element is flexible such that the first and second unit can move in relation to each other.

The mechanical transferring member in any of the embodiments may comprise a mechanical transferring member selected from: a hydraulic tube for transferring hydraulic force, a rotating shaft for transferring rotational force, a flexible member for transferring rotational force, a wire, a belt, a rod, a worm gear, and a gear for changing rotational force in substantially 90 degrees direction.

The operable implant may further comprise an enclosure adapted to hermetically enclose the operable implant.

According to one embodiment, the medical device may further comprise a metallic enclosure adapted to enclose at least one of the second unit and the distance element. The metallic enclosure could be a titanium enclosure and/or an aluminum enclosure and/or a stainless steel enclosure.

One of the first and second units may comprise a battery adapted to store electrical energy received at the receiving unit.

The electrical motor may comprise an electrical motor selected from: an alternating current (AC) electrical motor, a direct current (DC) electrical motor, a linear electrical motor, an axial electrical motor, a piezo-electric motor, a three-phase motor, a more than one-phase motor, a bimetal motor, and a memory metal motor.

According to one embodiment, the implantable system further comprises a control unit for controlling at least one parameter of at least one of: the operation device, and the body engaging portion.

The electrical motor may in one embodiment be an alternating current (AC) motor, and the control unit may comprise a frequency converter for altering the frequency of an alternating current for controlling the alternating current motor.

The first unit of the operable implant may comprise a hydraulic pump adapted to transfer mechanical work into hydraulic power for powering a hydraulically operable body engaging portion. The hydraulic pump may be connected to the force output of the first or second gear system. The hydraulic pump may be a hydraulic pump selected from: at least one reservoir acting as a pump by a wall moving by the mechanical work, at least one reservoir acting as a pump to move fluid by changing volume, at least one non-valve pump, at least one valve pump, at least one peristaltic pump, at least one membrane pump, at least one gear pump, and at least one bellows pump.

According to one embodiment, the first unit comprises a reservoir for supplying fluid to a hydraulically operable body engaging portion.

The operable implant may comprise a third unit comprising a second reservoir for supplying fluid to a hydraulically operable body engaging portion. The reservoir may be operable and may comprise at least one movable wall portion.

The reservoir may comprise at least one of; at least one bellows shaped portion, a shape adapted to allow movement although covered with fibrosis and a plate shaped surface, in all cases enabling movement of the at least one movable wall portion.

The reservoir in any of the embodiments may be in fluid connection with a hydraulically operable body engaging portion, and the reservoir may be adapted to operate the hydraulically operable body engaging portion by movement of the at least one movable wall portion. The reservoir may be circular or torus shaped.

The operable implant may further comprise a threaded member arranged to move the wall portion of the reservoir.

In one embodiment, the operable implant further comprises at least one of: a pressure sensor, a flow sensor and position sensor arranged in connection with at least one of the pump and the reservoir for determining the pressure and/or volume in the reservoir, and the pressure or flow from the hydraulic pump.

The first unit of the operable implant of any of the embodiments may comprise an injection port for supplying fluid to at least one of: a/the reservoir, and a/the hydraulically operable body engaging portion.

According to one embodiment, at least one of the first unit and the distance element may be free from at least one of: metallic and magnetizable components.

At least one of the first and second unit and the distance element may be free from magnetic components.

The first unit of the operable implant may comprise a communication unit adapted to wirelessly communicate with an external unit on the outside of the body of the patient.

The operable element may be adapted to deflect the first gear, and to maintain the first gear deflected such that the teeth of the first gear are interengaged with the teeth of the second gear in at least one of; one position, two positions, three positions, and four or more positions. The two, three or four positions are angularly spaced positions interspaced by positions at which the teeth are not interengaged.

An operable implant for implantation in the body of a patient is further provided. The operable implant may comprise an operation device and a body engaging portion. The operation device comprises an electrical motor comprising: a set of coils circularly distributed around a rotational axis of the electrical motor, a set of magnets connected to a rotatable structure at least partially axially overlapping said coils, such that sequential energizing of said coils magnetically propels the magnets and causes the rotatable structure to rotate around the rotational axis, a gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The second gear has a smaller diameter than the rotatable structure and is at least partially placed in the same axial plane, such that the rotatable structure at least partially axially overlaps the second gear, such that the gear system is at least partially placed inside of the electrical motor. Placing the gear system at least partially inside of the electrical motor creates a very compact and efficient design.

The operable element may be adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.

According to one embodiment of the operable implant, the operable element is adapted to deflect the first gear, and to maintain the first gear deflected such that the teeth of the first gear are interengaged with the teeth of the second gear in at least two angularly spaced positions interspaced by positions at which the teeth are not interengaged.

The operable implant may comprise at least one of; a planet gear and a structure or wheel at least partly using friction to interconnect with the first gear.

According to one embodiment, the operation device further comprises a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein the first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

The first and second gear systems in any of the embodiments herein may be positioned coaxially, along the rotational axis of the first and second gear systems.

The second gear of at least one of; the first and second gear system may have a smaller diameter than the rotatable structure and be at least partially placed in the same axial plane, such that the rotatable structure at least partially axially overlaps the second gear of at least one of; the first and second gear system, such that at least one of; the first and second gear system is at least partially placed inside of the electrical motor.

The first and second gears of the second gear system may have a larger diameter than the rotatable structure, and be at least partially placed in the same axial plane, such that the first and second gears of the second gear system at least partially axially overlaps the rotatable structure, such that the electrical motor is at least partially placed inside the second gear system.

According to one embodiment, operable implant further comprises a radially extending connecting structure directly or indirectly connecting the first gear of the first gear system to the operable element of the second gear system, to transfer force from the first gear system to the second gear system.

The first gear system of the operable implant may comprise a third gear, and the inside of the third gear may comprise the same amount of teeth as the outside of the first gear. The teeth of the third gear is adapted to interengage with the teeth of the third gear such that the third gear rotates in relation to the second gear, along with the angularly spaced positions.

In any of the embodiments, the first gear of the first gear system may indirectly connect with the operable element of the second gear system via the third gear.

The rotatable structure of the operable element may be placed radially on the inside of the circularly distributed coils or placed radially on the outside of the circularly distributed coils.

According to one embodiment, the operable implant further comprises a coil enclosure adapted to enclose the coils, such that the coils remain enclosed during operation of the operation device.

According to one embodiment, the first gear of at least one of; the first and second gear system may directly or indirectly connect to a threaded member adapted to transform the radially rotating force to an axially reciprocating force.

The threaded member of the operable implant may directly or indirectly connect to a movable wall portion of a first reservoir for changing the volume of the first reservoir.

The threaded member may be directly or indirectly connected to a movable wall portion of a second reservoir for changing the volume of the second reservoir. The movement of the movable wall portion of the first reservoir by the threaded member in a first direction causes the first reservoir to expand and the volume in the reservoir to increase, and wherein the movement of the movable wall of the second reservoir by the threaded member in a first direction causes the second reservoir to contract and the volume in the second reservoir to decrease.

The first reservoir in any of the embodiments may be in fluid connection with a first hydraulically operable body engaging portion, and the second reservoir in any of the embodiments may be in fluid connection with a second hydraulically operable body engaging portion. Operation of the electrical motor in a first direction, via the gear system and its direct or indirect connection with the threaded member, causes: transportation of fluid from the first reservoir to the first hydraulically operable body engaging portion, and transportation of fluid from the second hydraulically operable body engaging portion to the second reservoir.

The reservoir in any of the embodiments may be at least one of: circular and torus shaped.

According to one embodiment of the medical device, the operation device may comprise a circular reservoir encircling the operation device, and the circular reservoir may comprise a movable wall portion adapted to compress and expand the circular reservoir, thereby altering the volume of the reservoir, and the movable wall portion may be connected to the operation device, such that the operation of the operation device changes the volume of the circular reservoir.

According to one embodiment of the operable implant, a portion of the wall of the reservoir comprises at least one of: a bellows structure, a shape adapted to allow movement although covered with fibrosis, and a plate shaped surface, in all cases enabling movement of the at least one movable wall portion, enabling the compression and/or expansion of the reservoir.

According to one embodiment, the operable implant further comprises a peristaltic pump comprising a hollow member for fluid transportation, and an operable compression member adapted to engage and compress the hollow member. The first gear of the operable implant may be in direct or indirect connection with the compression member, such that the operation of the electrical motor operates the compression member such that fluid is transported in the hollow member. The operable compression member may be connected to the third gear of any of the embodiments herein.

The hollow member of the peristaltic pump may form a loop or part of a loop adapted to at least partially encircle the operation device in at least partially the same axial plane. The operation device may be adapted to propel the compressing member such that the compression member compresses the hollow member towards the outer periphery of the loop or part of loop.

According to one embodiment, the operation device comprises an alternating current (AC) motor, and the operation device further comprises a frequency converter for altering the frequency of an alternating current for controlling the alternating current motor.

According to one embodiment of the operable implant, the operable implant further comprises a separate unit comprising a receiving unit adapted to receive wireless energy transmitted from outside the body. The receiving unit may comprise at least one coil adapted to transform wireless energy received in form of a magnetic, electric or electromagnetic field into electrical energy.

The receiving unit in the embodiments may comprise at least a first coil having a first number of windings, and at least a second coil having a second, different number of windings.

According to one embodiment, the separate unit may be adapted to be placed at least one of; subcutaneously and subcutaneously in the abdominal wall.

The operable implant according to any one of the preceding embodiments may further comprise at least one fixation portion for fixating at least a part of the operable implant to at least one of fibrosis, a fascia and a muscular layer towards the inside of the subcutaneous space of the patient.

The operable implant according to any one of the preceding embodiments may further comprise a distance element connecting the operation device and the separate unit, the distance element may comprise an electric lead adapted to transfer electrical energy between the separate unit and the operation device. The distance element may be adapted to be placed through the muscular layers of the abdominal wall and/or be fixated to the muscular fascia facing the subcutaneous space.

According to one embodiment, the distance element may be flexible such that the first and second unit can move in relation to each other.

The separate unit in any of the embodiments may comprise a reservoir for supplying fluid to a hydraulic implant.

The distance element in any of the embodiments herein may comprise a fluid conduit for transportation of fluid from the operation device to separate unit to control the size of the reservoir, or in the opposite direction. The distance element may further comprise a mechanical transferring member adapted to transfer mechanical work from the operation device to the separate unit. The mechanical transferring member may comprise a mechanical transferring member selected from: a hydraulic tube for transferring hydraulic force, a rotating shaft for transferring rotational force, a flexible member for transferring rotational force, a wire, a belt, a rod, a worm gear, and a gear for changing rotational force in substantially 90 degrees direction.

The operable implant may further comprise an enclosure adapted to hermetically enclose the operation device and the separate unit, such that the operation device and the separate unit are sealed from bodily fluids when implanted.

At least one of the operation device and the separate unit may comprise a battery adapted to store electrical energy received at the receiving unit. The separate unit may further comprise an injection port for supplying fluid to the reservoir and/or the body engaging portion being hydraulically operable.

The separate unit, apart from the energy receiving unit, may be free from metallic and/or magnetizable and/or magnetic components, such that the elements of the separate unit does not interfere with the wireless energy transfer.

The separate unit may further comprise a control unit for controlling at least one parameter of at least one of: the operation device, and the body engaging portion.

The separate unit may comprise a communication unit adapted to wirelessly communicate with an external unit on the outside of the body of the patient.

In one embodiment, the operable implant may comprise a hydraulic pump selected from: at least one reservoir with a wall moving by the mechanical work acting as a pump, at least one reservoir changing volume to move fluid acting as a pump, at least one non-valve pump, at least one valve pump, at least one peristaltic pump, at least one membrane pump, at least one gear pump, and at least one bellows pump.

The operable implant may comprise an electrical motor selected from: an alternating current (AC) electrical motor, a direct current electrical motor, a linear electrical motor, an axial electrical motor, a piezo-electric motor, a three-phase motor, a more than one-phase motor, a bimetal motor, and a memory metal motor.

An operable implant adapted to be implanted in the body of a patient, the operable implant comprises an operation device and a body engaging portion, wherein the operation device comprises: an axial electrical motor comprising: a set of coils circularly distributed around a rotational axis of the electrical motor, a set of magnets connected to a radially extending rotatable structure at least partially radially overlapping said magnets, such that sequential energizing of said coils magnetically axially propels the magnets and causes rotation of the rotatable structure around the rotational axis. The operable implant further comprises a gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The gear system and the axial electrical motor are positioned coaxially, along the rotational axis of electrical motor, which creates a compact design with few moving parts.

The operable element may comprise at least one of: a planet gear, and a structure or wheel at least partly using friction to interconnect with the first gear.

According to one embodiment, the first set of coils are circularly distributed around a rotational axis of the electrical motor and positioned on a magnetizable core structure. The radially extending rotatable structure comprises a rotatable disc, and the magnetizable core structure and the rotatable disc are positioned coaxially and the rotatable disc is connected to a driving shaft connected to the operable element.

According to one embodiment, the operation device further comprises a second magnetizable core structure comprising a second sets of coils, wherein the second magnetizable core structure is coaxially positioned to at least partly overlap the magnets of the rotatable disc, such that the first set of coils propels the magnets on the first side thereof, and the second sets of coils propels the magnets on the second side thereof.

According to one embodiment, the peripheral diameter of the circular configuration of at least one of the first and second set of coils is smaller than the inner diameter of the first gear, and the first and second set of coils are positioned in the same axial plane as the first gear, such that the axial electrical motor is at least partially placed inside of the gear system.

According to one embodiment, the rotatable disc is directly connected to the operable element.

The operable implant may further comprise a coil enclosure adapted to enclose the coils, such that the coils remain enclosed separated from the magnets during operation of the operation device.

According to one embodiment, the operable element is adapted to deflect the first gear, and to maintain the first gear deflected such that the teeth of the first gear are interengaged with the teeth of the second gear in one of; one position, two positions, three positions, and four or more positions. The two, three and four positions are angularly spaced positions interspaced by positions at which the teeth are not interengaged.

The operation device of the operable implant may further comprise a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

The first and second gear systems may be positioned coaxially, along the rotational axis of the first and second gear systems.

The operable implant may further comprise a radially extending connecting structure directly or indirectly connecting the first gear of the first gear system to the operable element of the second gear system, to transfer force from the first gear system to the second gear system.

The first gear system in any of the embodiments may comprise a third gear, and the inside of the third gear may comprise the same amount of teeth as the outside of the first gear. The teeth of the third gear may be adapted to interengage the teeth of the third gear such that the third gear rotates in relation to the second gear, along with the angularly spaced positions.

According to one embodiment, the first gear of the first gear system indirectly connects with the operable element of the second gear system via the third gear in any of the embodiments.

The first gear of the first gear system could be directly or indirectly connected to a threaded member adapted to transform the radially rotating force to an axially reciprocating force.

According to one embodiment, the threaded member could be directly or indirectly connected to a movable wall of a first or second reservoir for changing the volume of the reservoir.

According to one embodiment, the movement of the movable wall of the first reservoir by the threaded member in a first direction causes the first fluid reservoir to expand and the volume in the first fluid reservoir to increase, and the movement of the movable wall of the second reservoir by the threaded member in a first direction causes the second reservoir to contract and the volume in the second reservoir to decrease.

The first reservoir of the operable implant may be in fluid connection with a first hydraulically operable body engaging portion, and the second reservoir is in fluid connection with a second hydraulically operable body engaging portion, and wherein operation of the electrical motor in a first direction, by the via the gear system and its direct or indirect connection with the threaded member, causes: transportation of fluid from the first reservoir to the first hydraulically operable body engaging portion, and transportation of fluid from the second hydraulically operable body engaging portion to the second reservoir.

The reservoir in any of the embodiments herein could be a circular or torus shaped reservoir. In one embodiment the operation device comprises a circular reservoir encircling the operation device, and the circular reservoir comprises a movable wall portion adapted to compress and expand the circular reservoir, thereby altering the volume of the reservoir, and wherein the movable wall portion is connected to the operation device, such that the operation of the operation device changes the volume of the circular reservoir.

A portion of the wall of the reservoir could comprise at least one of; a bellows structure, a shape adapted to allowing movement although covered with fibrosis and a plate shaped surface, in all cases enabling movement of the at least one movable wall portion, enabling the compression and/or expansion of the reservoir.

According to one embodiment, the operable implant further comprises a peristaltic pump, and the peristaltic pump comprises a hollow member for fluid transportation, and an operable compression member adapted to engage and compress the hollow member. The first gear is in direct or indirect connection with the compression member, such that the operation of the electrical machine operates the compression member such that fluid is transported in the hollow member.

According to one embodiment, the operable compression member is connected to the third gear of any of the embodiments herein.

According to one embodiment, the hollow member of the peristaltic pump forms a loop or part of a loop adapted to at least partially encircle the operation device in at least partially the same axial plane. The operation device is adapted to propel the compressing member such that the compression member compresses the hollow member towards the outer periphery of the loop or part of loop.

According to one embodiment, the operation device comprises an alternating current (AC) motor, and the operation device further comprises a frequency converter for altering the frequency of an alternating current for controlling the alternating current motor.

The operable implant in any of the embodiments herein may further comprise a separate unit comprising a receiving unit adapted to receive wireless energy transmitted from outside the body. The separate unit could be adapted to be placed at least one of; subcutaneously and subcutaneously in the abdominal wall. The separate unit could comprise a reservoir for supplying fluid to a hydraulic implant.

According to one embodiment, the receiving unit comprises at least one coil adapted to transform wireless energy received in form of a magnetic, electromagnetic field into electrical energy. The receiving unit could comprise at least a first coil having a first number of windings, and at least a second coil having a second, different number of windings.

The operable implant could further comprise at least one fixation portion for fixating at least part of the operable implant to at least one of fibrosis, a fascia and a muscular layer towards the inside of the subcutaneous space of the patient.

The operable implant may further comprise a distance element connecting the operation device and the separate unit, the distance element could comprise an electric lead adapted to transfer electrical energy between the separate unit and the operation device.

The distance element could be adapted to be placed through the muscular layers of the abdominal wall and/or fixated to the muscular fascia facing the subcutaneous space.

The distance element could be flexible such that the first and second unit can move in relation to each other.

The distance element in any of the embodiments could comprise a fluid conduit for transportation of fluid from the operation device to control the size of the reservoir, or in the opposite direction.

The distance element could further comprise a mechanical transferring member adapted to transfer mechanical work from the operation device to the separate unit. The mechanical transferring member could be a mechanical transferring member selected from: a hydraulic tube for transferring hydraulic force, a rotating shaft for transferring rotational force, a flexible member for transferring rotational force, a wire, a belt, a rod, a worm gear, and a gear for changing rotational force in substantially 90 degrees direction.

The operable implant may further comprise an enclosure adapted to hermetically enclose the operation device and the separate unit, such that the operation device and the separate unit are sealed from bodily fluids when implanted.

At least one of the operation device and the separate unit could comprise a battery adapted to store electrical energy received at the receiving unit.

The separate unit in any of the embodiments could comprise an injection port for supplying fluid to at least one of: a or the reservoir and the body engaging portion being hydraulically operable.

The separate unit could in one embodiment, apart from the energy receiving unit, be free from at least one of; metallic, magnetizable and magnetic components.

The separate unit could further comprise a control unit for controlling at least one parameter of at least one of: the operation device, and the body engaging portion.

The separate unit could comprise a communication unit adapted to wirelessly communicate with an external unit on the outside of the body of the patient.

According to one embodiment, the coil enclosure in any of the embodiments herein could comprise a material selected from: a carbon material, a boron material, a mixture of material, a Peek® material, an alloy of material, a metallic material, titanium, aluminum, a ceramic material, a polymer material, polyurethane, polyether ether ketone, silicone, and Parylene® coated silicone.

The operation device of the operable implant in any of the preceding embodiments could comprise an electrical motor selected from: an alternating current (AC) electrical motor, a direct current electrical motor, a linear electrical motor, an axial electrical motor, a piezo-electric motor, a three-phase motor, a more than one-phase motor, a bimetal motor, and a memory metal motor.

An operable implant adapted to be implanted in the body of a patient is further provided. The operable implant comprises an operation device and a body engaging portion. The operation device could comprise an electrical motor comprising a static part comprising a plurality of coils and a movable part comprising a plurality of magnets, such that sequential energizing of said coils magnetically propels the magnets and thus propels the movable part. The operation device could further comprise an enclosure adapted to hermetically enclose the coils of the static part, such that a seal is created between the static part and the propelled moving part with the included magnets, such that the coils of the static part are sealed from the bodily fluids, when implanted.

According to one embodiment, the operation device further comprises a control unit for controlling at least one of the operation device and the body engaging portion, wherein the enclosure is adapted to enclose the coils and the control unit.

The operation device of the operable implant could further comprise at least one electrical circuit adapted to indirectly receive energy drawn from wireless energy supplied from outside the body of the patient, wherein the enclosure is adapted to enclose the coils and the electrical circuit.

According to one embodiment, the operable implant comprises a separate wireless energy receiving unit comprising at least one coil adapted to transform wireless energy received in form of a magnetic, electric or electromagnetic field into electrical energy.

The operable implant could according to one embodiment comprise a distance element adapted to create a distance between the receiving unit and the electrical motor, such that the receiving unit remains substantially unaffected by metallic and/or magnetic parts of the static or movable part of the electrical motor.

The electrical motor in any of the embodiments could be an axial electrical motor in which the coils are circularly distributed around a rotational axis of the implantable electrical motor such that the center axis of the helix of the coils are extending in the axial direction of the implantable electrical motor, parallel to the rotational axis, and the movable part comprises a radially extending rotor on which the magnets are circularly distributed around the rotational axis, the magnets in axial direction facing the coils, such that the magnets at least partially radially overlaps said coils, such that sequential energizing of said coils magnetically axially propels the magnets and causes rotation of the rotor around the rotational axis of the electrical motor.

In alternative embodiments, the electrical motor could be a radial electrical motor, and the coils could be circularly distributed around a rotational axis of the implantable electrical motor such that the center axis of the helix of the coils are extending in the radial direction of the rotational axis of the implantable electrical motors, substantially perpendicular to the rotational axis, and the movable part could comprise an axially extending rotor on which the magnets are circularly distributed around the rotational axis, the magnets in radial direction facing the coils, such that the magnets at least partially axially overlaps said coils, such that sequential energizing of said coils magnetically propels the magnets and causes rotation of the rotor around the rotational axis of the electrical motor.

In alternative embodiments, the electrical motor is a linear electrical motor in which the coils are linearly distributed along a direction of movement of the movable part, and the movable part comprises linearly distributed magnets along a direction of movement of the movable part, such that sequential energizing of the coils magnetically propels the magnets and causes linear movement of the movable part.

The implantable electrical motor could be an alternating current (AC) electrical motor, and the control unit could comprise a frequency converter for altering the frequency of an alternating current for controlling the alternating current electrical motor.

According to one embodiment, the implantable electrical motor further comprises a second enclosure adapted to enclose the movable part, such that the movable part is sealed from bodily fluids when implanted.

The second enclosure could be sealingly connected to the first enclosure, such that the enclosure wall between the movable part and the static part is engaged in sealing both the first enclosure and the second enclosure. The first and/or second enclosure could comprise a material selected from: a carbon material, a boron material, a mixture of material, a Peek® material, an alloy of material, a metallic material, titanium, aluminum, a ceramic material, a polymer material, polyurethane, polyether ether ketone, silicone, and Parylene® coated silicone.

According to one embodiment, the second enclosure is sealingly connected to the first enclosure, such that both the movable part and a distance element between the movable part and the static part is sealed by the second enclosure.

The operable implant according to any one of the preceding embodiments could further comprise a gear system adapted receive mechanical work having a first force and velocity as input, from the rotating part of the electrical motor, and output mechanical work having a different force and velocity.

The gear system could further comprise an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element could be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

According to one embodiment, the second gear has a smaller diameter and is at least partially placed in the same axial plane as at least one of the movable part and the static part, such that at least one of the movable part and the static part at least partially axially overlaps the second gear, such that the gear system is at least partially placed inside of the electrical motor.

The operable implant may be adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.

According to one embodiment, the operable element is adapted to deflect the first gear, and to maintain the first gear deflected such that the teeth of the first gear are interengaged with the teeth of the second gear in at least two angularly spaced positions interspaced by positions at which the teeth are not interengaged.

The operation device in any of the embodiments herein may further comprise a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

The first and second gear systems in any of the embodiments herein may be positioned coaxially, along the rotational axis of the first and second gear systems.

The second gear of at least one of the first and second gear systems could have a smaller diameter than the rotatable structure of any of the embodiments herein and be at least partially placed in the same axial plane, such that the rotatable structure at least partially axially overlaps the second gear of at least one of; the first and second gear system, such that at least one of; the first and second gear system is at least partially placed inside of the electrical motor.

The first and second gears of the second gear system may in one embodiment have a larger diameter than the rotatable structure, and are at least partially placed in the same axial plane, such that the first and second gears of the second gear system at least partially axially overlaps the rotatable structure, such that the electrical motor is at least partially placed inside the second gear system.

The operable implant could further comprise a radially extending connecting structure directly or indirectly connecting the first gear of the first gear system to the operable element of the second gear system, to transfer force from the first gear system to the second gear system.

The first gear system could comprise a third gear, and the inside of the third gear could comprise the same amount of teeth as the outside of the first gear, and the teeth of the third gear could be adapted to interengage with the teeth of the third gear such that the third gear rotates in relation to the second gear, along with the angularly spaced positions.

According to one embodiment, the first gear of the first gear system indirectly connects with the operable element of the second gear system via the third gear of embodiment.

The rotatable structure may in any of the embodiments be placed radially on the inside of the circularly distributed coils.

The rotatable structure could be placed radially on the outside of the circularly distributed coils.

The coils could in any one of the embodiment remain enclosed during operation of the operation device.

The first gear of at least one of; the first and second gear system could directly or indirectly connect to a threaded member adapted to transform the radially rotating force to an axially reciprocating force. The threaded member could be directly or indirectly connected to a movable wall portion of a reservoir.

In any one of the embodiments herein, the operable implant could comprise at least one fixation portion for fixating at least a part of the operable implant to at least one of fibrosis, a fascia and a muscular layer towards the inside of the subcutaneous space of the patient.

The operable implant may further comprise a separate unit comprising a receiving unit adapted to receive wireless energy transmitted from outside the body.

The operable implant may further comprise a first reservoir in fluid connection with the body engaging portion being hydraulically operable. The operation device may be adapted to cause transportation of fluid from the first reservoir to the hydraulically operable body engaging portion.

A portion of the wall of the reservoir could comprise at least one of: a bellows structure, a shape adapted to allow movement although covered with fibrosis and a plate shaped surface, in all cases enabling movement of the at least one movable wall portion, enabling the compression and/or expansion of the reservoir.

According to one embodiment, the operation device comprises a hydraulic pump for transporting the fluid from the first reservoir to the hydraulically operable body engaging portion. The hydraulic pump could be a hydraulic pump selected from: at least one reservoir with a wall moving by the mechanical work acting as a pump, at least one reservoir changing volume to move fluid acting as a pump, at least one non-valve pump, at least one valve pump, at least one peristaltic pump, at least one membrane pump, at least one gear pump, and at least one bellows pump.

The electrical motor could be an electrical motor selected from: an alternating current (AC) electrical motor, a direct current electrical motor, a linear electrical motor, an axial electrical motor, a piezo-electric motor, a three-phase motor, a more than one-phase motor, a bimetal motor, and a memory metal motor.

The operation device may further comprise a first unit comprising: a receiving unit for receiving wireless energy, and a first gear system adapted to receive mechanical work having a first force and first velocity, and output mechanical work having a different second force and a different second velocity, a second unit comprising an electrical motor adapted to transform electrical energy into the mechanical work, and a distance element comprising: a lead for transferring the electrical energy from the first unit to the second unit, and a mechanical transferring member adapted to transfer the mechanical work from the electrical motor in the second unit to the gear system in the first unit, wherein the distance element is adapted to separate the first and second units such that the receiving unit, when receiving wireless energy, is not substantially affected by the second unit.

According to one embodiment, the second unit comprises a second gear system adapted to receive the mechanical work output from the first gear system with the different second force and the different second velocity as input, and output mechanical work having a third different force and third different velocity, and wherein the gear system of the second unit is connected in series with the gear system of the first unit, via the mechanical transferring member of the distance element.

The first unit could comprise a second gear system adapted receive mechanical work of a first force and velocity as input, and output mechanical work having a different force and velocity. The second gear system may be connected in series with the first gear system.

The first unit of the operable implant may be adapted to be placed at least in one of the following places: subcutaneously, subcutaneously in the abdominal wall and in the abdomen.

The motor could comprise magnetic material and the first unit could be adapted to be substantially unaffected or not importantly affected by the magnetic material in the second unit, during wirelessly energy transfer.

The first unit may comprise a reservoir for supplying fluid to the body engaging portion being hydraulically operable.

The first unit could comprise hydraulic pump adapted to transfer mechanical work into hydraulic power for powering a hydraulically operable body engaging portion, wherein the hydraulic pump is connected to the force output of the first or second gear system.

The operable implant may further comprise a gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein the gear system and the axial electrical motor are positioned coaxially, along the rotational axis of electrical motor.

According to one embodiment, the operable element comprises at least one of a planet gear, and a structure or wheel at least partly using friction to interconnect with the first gear.

The first set of coils circularly distributed around a rotational axis of the electrical motor may be positioned on a magnetizable core structure, and the radially extending rotatable structure may comprise a rotatable disc, wherein a surface part of the magnetizable core structure and the rotatable disc are positioned coaxially and the rotatable disc is connected to a driving shaft connected to the operable element.

The operation device may in one embodiment comprise an electrical motor having a force outlet, a gear system connected to the force outlet of the electrical motor, the gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the positions and thereby causes relative rotation between the first gear and the second gear, and a gear system force outlet connected to the first gear of the gear system and adapted for supplying force directly or indirectly to the body engaging portion, the gear system force outlet comprises a magnetic force coupling for magnetically, directly or indirectly, connecting to the body engaging portion for supplying force, and an enclosure for hermetically enclosing the operation device.

According to one embodiment, the magnetic force coupling comprises an inside rotating structure placed inside the enclosure comprising at least one magnet or a portion comprising magnetic or magnetizable material. The magnet or portion comprising magnetic or magnetizable material may be adapted to rotate to transfer force to a corresponding rotating structure on the outside of the hermetic enclosure, for directly or indirectly supplying force to the body engaging portion through the sealed enclosure.

The operable implant may according to one embodiment further comprise the corresponding rotating structure on the outside of the hermetic enclosure, for directly or indirectly supplying force directly or indirectly to the body engaging portion.

According to one embodiment, the operable implant further comprises a reservoir for holding a hydraulic fluid. The reservoir comprises a movable wall portion adapted to change the volume of the reservoir, the movable wall portion could be directly or indirectly connected to the gear system force outlet, such that operation of the electrical motor, via the gear system changes the volume of the reservoir.

According to one embodiment, the operable implant further comprises a corresponding rotating structure on the outside of the hermetic enclosure. The corresponding rotating structure directly or indirectly connects to a threaded member adapted to transform the radially rotating force to an axially reciprocating force.

The threaded member may in any of the embodiments herein be directly or indirectly connected to the movable wall of the reservoir for changing the volume of the reservoir.

The operable implant may further comprise a peristaltic pump, and the peristaltic pump may comprise a hollow member for fluid transportation, and an operable compression member adapted to engage and compress the hollow member. The gear system force outlet via the magnetic coupling connects to the compression member, such that the operation of the electrical motor, via the gear system, operates the compression member, such that fluid is transported in the hollow member.

According to one embodiment, the operation device further comprises a control unit for controlling at least one of the operation device and the body engaging portion, and the enclosure is adapted to enclose the operation device including the control unit.

The operation device of the operable implant further comprises at least one receiving unit adapted to receive wireless energy supplied from outside the body of the patient, wherein the receiving unit is placed separate from the operation device, wherein the enclosure is adapted to include both the operation device, a distance element connecting the operation device and the receiving unit and the receiving unit.

The distance element of the operable implant is adapted to create a distance between the wireless energy receiver and at least one of the electrical motor and the magnetic coupling, such that the wireless energy receiver remains substantially unaffected or not importantly affected by metallic and/or magnetic components of the electrical motor and the magnetic coupling.

The receiving unit further comprises at least one coil adapted to transform wireless energy received in form of a magnetic, electric or electromagnetic field into electrical energy.

The electrical motor of the operable implant could be an axial electrical motor comprising: a plurality of coils, circularly distributed around a rotational axis of the electrical motor such that the center axis of the helix of the coils are extending in the axial direction of the electrical motor, parallel to the rotational axis of the electrical motor, and magnets, circularly distributed on a radially extending rotatable structure, on which the magnets are circularly distributed around the rotational axis, the magnets in axial direction facing the coils, such that the magnets at least partially radially overlaps the coils, such that sequential energizing of the coils magnetically axially propels the magnets and causes rotation of the rotatable structure around the rotational axis of the electrical motor.

In one embodiment, the electrical motor is a radial electrical motor, comprising: a plurality of coils circularly distributed around a rotational axis of the implantable electrical motor, such that the center axis of the helix of the coils are extending in the radial direction of the implantable electrical motor, substantially perpendicular to the rotational axis of the motor, and a plurality of magnets, circularly distributed on an axially extending rotatable structure on which the magnets are circularly distributed around the rotational axis, the magnets in radial direction facing the coils, such that the magnets at least partially axially overlaps the coils, such that sequential energizing of the coils magnetically propels the magnets and causes rotation of the rotatable structure around the rotational axis of the electrical motor.

The electrical motor in any of the embodiment may be a linear electrical motor in which the coils are linearly distributed along a direction of movement of a movable part of the linear electrical motor, and the movable part comprises linearly distributed magnets along a direction of movement of the movable part, such that sequential energizing of the coils magnetically propels the magnets and causes linear movement of the movable part.

The electrical motor of the operation device could be an alternating current (AC) electrical motor, and the control unit could comprise a frequency converter for altering the frequency of an alternating current for controlling the alternating current electrical motor.

According to one embodiment, the enclosure may comprise a material selected from: a carbon material, a boron material, a mixture of material, a Peek® material, an alloy of material, a metallic material, titanium, aluminum, a ceramic material, a polymer material, polyurethane, polyether ether ketone, silicone, and Parylene® coated silicone.

The operation device could comprise a hydraulic pump for transporting hydraulic fluid from a reservoir to the body engaging portion being hydraulically operable.

According to one embodiment, the electrical motor comprises an electrical motor selected from: an alternating current (AC) electrical motor, a direct current electrical motor, a linear electrical motor, an axial electrical motor, a piezo-electric motor, a three-phase motor, a more than one-phase motor, a bimetal motor, and a memory metal motor.

The electrical motor may be adapted to drive a comprised hydraulic pump selected from: at least one reservoir with a wall moving by the mechanical work acting as a pump, at least one reservoir changing volume to move fluid acting as a pump, at least one non-valve pump, at least one valve pump, at least one peristaltic pump, at least one membrane pump, at least one gear pump, and at least one bellows pump.

According to one embodiment, the electrical motor comprises: a set of coils circularly distributed around a rotational axis of the electrical motor, a set of magnets connected to a rotatable structure at least partially axially overlapping said coils, such that sequential energizing of said coils magnetically propels the magnets and causes the rotatable structure to rotate around the rotational axis. The second gear has a smaller diameter than the rotatable structure and is at least partially placed in the same axial plane, such that the rotatable structure at least partially axially overlaps the second gear, such that the gear system is at least partially placed inside of the electrical motor.

According to one embodiment, the operable element is adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.

The operable element may be adapted to deflect the first gear, and to maintain the first gear deflected such that the teeth of the first gear are interengaged with the teeth of the second gear in at least two angularly spaced positions interspaced by positions at which the teeth are not interengaged.

The operation device may further comprise a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear. The first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

The first and second gear systems may be positioned coaxially, along the rotational axis of the first and second gear systems.

According to one embodiment, the second gear of at least one of; the first and second gear system has a smaller diameter than the rotatable structure and is at least partially placed in the same axial plane, such that the rotatable structure at least partially axially overlaps the second gear of at least one of; the first and second gear system, such that at least one of; the first and second gear system is at least partially placed inside of the electrical motor.

The first and second gears of the second gear system may have a larger diameter than the rotatable structure and be at least partially placed in the same axial plane, such that the first and second gears of the second gear system at least partially axially overlaps the rotatable structure, such that the electrical motor is at least partially placed inside the second gear system.

The operable implant may further comprise a radially extending connecting structure directly or indirectly connecting the first gear of the first gear system to the operable element of the second gear system, for transferring force from the first gear system to the second gear system.

The first gear system may comprise a third gear, and wherein the inside of the third gear may comprise the same amount of teeth as the outside of the first gear. The teeth of the third gear may be adapted to interengage with the teeth of the first gear such that the third gear rotates in relation to the second gear, along with the angularly spaced positions.

The first gear of the first gear system could be adapted to indirectly connect with the operable element of the second gear system via the third gear.

The rotatable structure of any of the embodiments may be placed radially on the inside or outside of the circularly distributed coils.

The coils of the operable implant may be adapted to remain enclosed during operation of the operation device.

According to one embodiment, the first gear of at least one of; the first and second gear system directly or indirectly connects to a threaded member adapted to transform the radially rotating force to an axially reciprocating force. The threaded member may be directly or indirectly connected to a movable wall portion of the reservoir.

The operable implant may further comprise at least one fixation portion for fixating at least a part of the operable implant to at least one of fibrosis, a fascia and a muscular layer towards the inside of the subcutaneous space of the patient.

According to one embodiment, the first reservoir is in fluid connection with the body engaging portion being hydraulically operable, and wherein the operation device, is adapted to cause: transportation of fluid from the first reservoir to the hydraulically operable body engaging portion.

A portion of the wall of the reservoir may comprise at least one of: a bellows structure, a shape adapted to allowing movement although covered with fibrosis and a plate shaped surface, in all cases enabling movement of the at least one movable wall portion, enabling the compression and/or expansion of the reservoir.

An operable implant may comprising an operation device and a body engaging portion is further provided. The operation device comprises: an electrical motor having a force output, and a start resistance delay member positioned between the force output of the electrical motor and the body engaging portion, wherein the start resistance delay member is adapted to enable the electrical motor to operate with at least one of; less force or less friction induced by the direct or indirect connection with the body engaging portion for a time period, such that the electrical motor can start with less resistance.

The force output of the electrical motor could according to one embodiment be directly or indirectly connected to a force input of a gear system. The gear system may comprise: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the gear system comprises a force output connected to the first gear.

In any of the embodiments, operable implant may further comprise a second gear system positioned between the first gear system and the start resistance delay. The second gear system could comprise a force input connected to an operable element, directly or indirectly connected to the force output of the first gear system, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the second gear system comprises a force output connected to the first gear of the second gear system.

The start resistance delay member could be positioned between the force output of the electrical motor and the force input of the gear system or between the force output of the gear system and the body engaging portion.

In alternative embodiments, the start resistance delay member is positioned one of: between the force output of the first gear system and the force input of the second gear systems, and between the force output of the second gear system and the body engaging portion.

According to one embodiment, the start resistance delay member comprises a spring, which could be a helical spring or a leaf spring.

In alternative embodiments, the start resistance delay member comprise a mechanical play, which could be one of a radial mechanical play and a linear mechanical play.

The start resistance delay member could comprise a radial mechanical play enabling the force output of the electrical motor to perform at least one of: ⅒ of a revolution, ⅛ of a revolution, ⅙ of a revolution, ¼ of a revolution, ½ of a revolution and 1 revolution, before the force output directly or indirectly engages the driving member.

According to one embodiment, the start resistance delay member is positioned between one of: the force output of the first gear system, and the force input of the second gear system, and the force output of the second gear system, and the body engaging portion. The start resistance delay could comprise a radial mechanical play enabling the force output of the gear system to perform at least one of: ⅒ of a revolution, ⅛ of a revolution, ⅙ of a revolution, ¼ of a revolution, ½ of a revolution and 1 revolution, before the force output engages the driving member, such that the force output of the electrical motor can perform at least one of ⅒ of a revolution*the transmission of the gear system, ⅛ of a revolution*the transmission of the gear system, ⅙ of a revolution*the transmission of the gear system, ¼ of a revolution*the transmission of the gear system, ½ of a revolution*the transmission of the gear system and 1 revolution*the transmission of the gear system.

In alternative embodiments, the start resistance delay device may comprise a friction clutch.

In yet alternative embodiments, the start resistance delay device may comprise at least one element adapted to be operated by centrifugal force. The at least one element could be connected to the electrical motor and adapted to engage, directly or indirectly, the body engaging portion when the centrifugal force exerted on the element exceeds a centrifugal delay force.

According to one embodiment, the operable element of the first and/or second gear system could comprise an element adapted to be operated by centrifugal force, such that the operable element of the gear system engages the first gear when the centrifugal force exerted on the element exceeds the centrifugal delay force.

The electrical motor could be an electrical motor selected from: an alternating current (AC) electrical motor, a direct current electrical motor, a linear electrical motor, an axial electrical motor, a piezo-electric motor, a three-phase motor, a more than one-phase motor, a bimetal motor, and a memory metal motor.

According to one embodiment, the body engaging portion is a hydraulically operable body engaging portion connected to a hydraulic pump for transporting hydraulic fluid for operating the hydraulically operable body engaging portion. The hydraulic pump could comprise a reservoir comprising at least one movable wall portion, and the at least one movable wall portion could be in direct or indirect connection with the electrical motor, such that the electrical motor is arranged to operate the movable wall portion for changing the volume of the reservoir.

According to one embodiment, the force output of the electrical motor directly or indirectly connects to a threaded member adapted to transform a radially rotating force of the electrical motor to an axially reciprocating force. The threaded member could be directly or indirectly connected to the movable wall portion of the reservoir for changing the volume of the reservoir.

According to one embodiment of the operable implant, the threaded member is directly or indirectly connected to a movable wall portion of a second reservoir for changing the volume of the second reservoir.

The movement of the movable wall portion of the first reservoir by the threaded member in a first direction could cause the first fluid reservoir to expand and the volume in the first reservoir to increase. The movement of the movable wall portion of the second reservoir by the threaded member in a first direction causes the second reservoir to contract and the volume in the second reservoir to decrease.

According to one embodiment, the first reservoir is in fluid connection with a first hydraulically operable body engaging portion, and the second reservoir is in fluid connection with a second hydraulically operable body engaging portion. Operation of the electrical motor in a first direction, by the connection with the threaded member, causes: transportation of fluid from the first reservoir to the first hydraulically operable implant, and transportation of fluid from the second hydraulic operable body engaging portion to the second fluid reservoir.

The reservoir could for example be circular or torus shaped. According to one embodiment of the operable implant, the operable implant comprises a circular reservoir encircling the operation device. The circular reservoir comprises a movable wall portion adapted to compress and expand the circular reservoir, thereby altering the volume of the reservoir, and the movable wall portion is connected to the electrical motor, such that the operation of the electrical motor changes the volume of the circular reservoir.

A portion of the wall of the reservoir could comprises at least one of; a bellows structure, a shape adapted to allowing movement although covered with fibrosis and a plate shaped surface, in all cases enabling movement of the at least one movable wall portion, enabling the compression and/or expansion of the reservoir.

In one embodiment, the operable implant comprises a hydraulic pump, which could be a peristaltic pump comprising: a hollow member for fluid transportation, and an operable compression member adapted to engage and compress the hollow member, and wherein the electrical motor is in direct or indirect connection with the compression member, such that the operation of the electrical machine operates the compression member such that fluid is transported in the hollow member.

An operable implant adapted to be implanted in the body of a patient is further provided. The operable implant comprises an operation device and a body engaging portion. The operation device comprises a first gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the interengaged positions and thereby causes relative rotation between the first gear and the second gear. The operation device further comprises a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the at least one position and thereby causes relative rotation between the first gear and the second gear.

The first gear of the first gear system is directly or indirectly connected to the operable element of the second gear system, such that the first and second gear systems functions as a single gear system.

According to one embodiment, the first gear of the first and second gear system comprises a deflectable wall. The operable element is adapted to deflect the first gear, and to maintain the first gear deflected such that the teeth of the first gear are interengaged with the teeth of the second gear in at least one angularly spaced positions interspaced by positions in which the teeth are not interengaged. The operation of the pressing element rotatively advances the angularly spaced positions and thereby causes relative rotation between the first gear and the second gear.

According to one embodiment, the operable element is adapted to deflect the first gear, and to maintain the first gear deflected such that the teeth of the first gear are interengaged with the teeth of the second gear in at least one of; at least two angularly spaced positions and at least three angularly spaced positions, interspaced by positions at which the teeth are not interengaged.

In one embodiment of the operable implant, at least one of the first and second gear systems comprises a third gear having the shape of a hollow cylinder. The inside of the third gear comprises the same amount of teeth as the outside of the first gear, and the teeth of the third gear are adapted to interengage the teeth of the first gear such that the third gear rotates in relation to the second gear, along with the at least one interengaged position.

According to one embodiment, the first gear system comprises a third gear having the shape of a hollow cylinder, and the inside of third gear comprises the same amount of teeth as the outside of the first gear of the first gear system. The teeth of the third gear are adapted to interengage the teeth of the first gear such that the third gear rotates in relation to the second gear, along with the at least one interengaged position, wherein the operable element of the second gear system is connected directly or indirectly to the third gear of the first gear system.

The first gear could at least partially be positioned radially inside of the second gear system, such that the second gear system axially at least partially overlaps the first gear system. In alternative embodiments, the first and second gear systems could be positioned coaxially, along the rotational axis of the first and second gear systems.

According to one embodiment, the operable implant further comprises a radially extending connecting structure directly or indirectly connecting the first gear of the first gear system with the operable element of the second gear system, to transfer force from the first gear system to the second gear system.

The operable implant according to any one of the preceding embodiments could further comprise an enclosure adapted to hermetically enclose the first and second gear systems, such that the first and second gear systems are sealed from bodily fluids when implanted.

The operable element of the first and second gear systems of any of the embodiments herein could further comprise at least one of; a planet gear and a structure or wheel comprising a frictional surface connection.

In one embodiment, the operable implant further comprises an electrical motor. The electrical motor could comprise an electrical motor selected from: an alternating current (AC) electrical motor, a direct current electrical motor, a linear electrical motor, an axial electrical motor, a piezoelectric motor, a three-phase motor, a more than one-phase motor, a bimetal motor, and a memory metal motor.

The operable implant in any of the embodiments could further comprise an enclosure adapted to hermetically enclose the first gear system and the electrical motor. The enclosure could comprise a sealed outlet for rotational force, such that the force can be transferred from the hermetically enclosed first gear system to the second gear system.

The operable implant in any of the embodiments could further comprise a system enclosure adapted to hermetically enclose the first gear system, the second gear system and the electrical motor.

The operable implant may further comprise a sealed outlet for rotational force, such that the force can be transferred from the hermetically enclosed second gear system to an operable implant.

The operable implant may further comprise an enclosure adapted to hermetically enclose the electrical motor, which may comprise a sealed outlet for rotational force, such that the force can be transferred from the hermetically enclosed motor to the first gear system.

The operable implant may further comprise an enclosure adapted to hermetically enclose the static part of the electrical motor, comprising at least one of; at least two coils and at least one core.

According to one embodiment, the enclosure of the static part of the motor could comprise a wall, the operable implant could be adapted to create rotational force from the hermetically enclosed static part wirelessly through the sealed wall, to create rotational force for rotating a rotor part of the motor, comprising at least one of; at least one magnet, magnetizable material and at least one coil, the rotor adapted to directly or indirectly be further connected to the first gear system.

According to one embodiment, the operable implant further comprises an enclosure adapted to hermetically enclose the rotor part of the electrical motor and at least one of; the first gear system and the first and second gear system.

An operable implant adapted to be implanted in the body of a patient is further provided. The operable implant comprises an operation device and a body engaging portion. The operation device comprises: at least one of; at least one magnet, at least one magnetic material and at least one magnetizable material adapted to be affected by a moving magnetic field created by an external unit, when implanted, such that the magnet or magnetic or magnetizable material moves along with the moving magnetic field of the external unit. The operation device further comprises a gear system comprising: an operable element directly or indirectly connected to the at least one magnet, magnetic material, or magnetizable material, such that the operable element is propelled by the magnet or magnetic material moving along with the moving magnetic field of the external unit, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element is adapted to engage the inside of the first gear, such that the outside of the first gear is pressed against the inside of the second gear such that the teeth of the first gear are interengaged with the teeth of the second gear in at least one position interspaced by positions in which the teeth are not interengaged. The operation of the operable element advances the positions and thereby causes relative rotation between the first gear and the second gear.

The operation device of any of the embodiments herein may be adapted to be implanted subcutaneously, which could be subcutaneously in the abdominal region.

In any of the embodiments, the operation device could comprise a first unit and a second unit, and the at least one magnet, magnetic material, or magnetizable material is placed in the first unit, and the gear system is placed in the second unit.

The operable implant may further comprise a distance element adapted to create a distance between the first and second units. The distance element is adapted to be at least one of; placed through the muscular layers of the abdominal wall, and fixated to the muscular fascia at the inner side of the subcutaneous space. The distance element could be flexible such that the first and second units can move in relation to each other. The distance element could be adapted to be fixated to at least one of; the fascia and muscular layer of the abdominal wall, such that the distance between the first portion of the operation device and the skin of the patient can be controlled. The distance element could comprise a mechanical transferring member adapted to transfer force from the first unit to the second unit, such that force can be transferred from the at least one magnet, magnetic material, or magnetizable material to the operable element of the gear system.

In one embodiment, the operable implant further comprises an enclosure adapted to hermetically enclose at least one of; the operable implant, the operation device, the body engaging portion, the first unit, the second unit or the distance element, for sealing from the bodily fluids of the patient.

In one embodiment, the enclosure constitutes a reservoir for supplying fluid to a hydraulically operable body engaging portion, such that the at least one magnet, magnetic material, or magnetizable material and gear system is placed inside of the reservoir.

The operable implant could further comprise a reservoir comprising a movable wall portion adapted to change the volume of the reservoir, wherein the movable wall portion is directly or indirectly connected to the first gear of the gear system, such that operation of the gear system changes the volume of the reservoir.

The first gear of the gear system could be directly or indirectly connected to a threaded member adapted to transform a rotating force to a reciprocating force.

The threaded member could be directly or indirectly connected to the movable wall portion of the reservoir for changing the volume of the reservoir.

The operable implant according to any one of the preceding embodiments could further comprise a peristaltic pump. The peristaltic pump comprises a hollow member for fluid transportation, and an operable compression member adapted to engage and compress the hollow member, and wherein first gear of the gear system is in direct or indirect connection with the compression member, such that the operation of the gear system operates the compression member such that fluid is transported in the hollow member.

The operable implant in any of the preceding embodiments could further comprise a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element could be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear, wherein the first gear of the first gear system is connected, directly or indirectly to the operable element of the second gear system, such that the first and second gear systems functions as a single gear system.

The operable element of one of the first and second gear systems could comprise at least one of; a planet gear and a structure or wheel at least partly using friction to enable rotating force to be transported.

The operable implant in any of the preceding embodiments could further comprise a wireless communication unit adapted to at least one of: receive wireless communication signals from an external unit, and transmit wireless communication signals to an external unit.

An external unit for supplying force to an implanted operation device is further provided. The external unit comprises: an external drive unit adapted to create a moving magnetic field on the outside of the patient's skin adapted to affect at least one magnet or magnetic material or magnetizable material of an implanted operation device, such that the magnet or magnetic material moves along with the moving magnetic field of the external drive unit.

The external drive unit could further comprise a set of coils circularly distributed around a rotational axis of the external unit, such that sequential energizing of the coils creates a rotating magnetic field adapted to affect the magnet or magnetic material or magnetizable material of the implanted operation device, such that the magnet or magnetic material moves along with the moving magnetic field of the external drive unit.

The external drive unit could further comprise a rotatable structure comprising at least one magnet or magnetic material, and the rotatable structure could affect the magnet or magnetic material or magnetizable material of the implanted operation device to cause rotation thereof, such that the magnet or magnetic material or magnetizable material rotates along with the rotatable structure of the external unit.

According to one embodiment, the external unit further comprises a wireless communication unit adapted to at least one of: receive wireless communication signals from an implantable unit, and transmit wireless communication signals to an implantable unit.

A medical system is further provided. The medical system comprises an operable implant according to any one of the embodiments herein, and an external unit according to any one of the embodiments herein.

In one of the embodiments, the operation device comprises a rotatable structure adapted to hold at least one of; at least one magnet, at least one magnetic material and at least one magnetizable material, and further adapted to be affected by the moving externally created magnetic field, such that the rotatable structure rotates.

The operable implant could further comprise an enclosure adapted to hermetically enclose at least one of; the rotational structure according to any of the embodiments, the reservoir according to any of the embodiments, and the treaded member according to any of the embodiments, for sealing from the bodily fluids of the patient.

In any of the preceding embodiments, the operation device could comprise a reservoir adapted to contain a hydraulic fluid and at least one movable wall portion for changing the volume of the reservoir. The operation device is adapted to operate the movable wall of the reservoir, wherein the operation device comprises a gear system placed within the reservoir, the gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

An operable implant adapted to be implanted in the body of a patient is further provided. The operable implant comprises a hydraulic operation device for supplying hydraulic force and a body engaging portion adapted to receive the hydraulic force. The hydraulic operation device comprises a reservoir adapted to contain a hydraulic fluid, the reservoir comprises at least one movable wall portion for changing the volume of the reservoir, and an operation device adapted to operate the movable wall. The operation device comprises a gear system placed within the reservoir, the gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

The first gear of the operable implant directly or indirectly connects to a threaded member adapted to transform a rotating force to a reciprocating force.

The threaded member could directly or indirectly be connected to the movable wall portion of the reservoir such that operation of the operation device changes the volume of the reservoir.

The operable implant according to any one of the embodiments, could further comprise a rotatable structure positioned on the inside of the reservoir and connected to the operable element of the gear system, the rotatable structure comprising at least one magnet, at least one magnetic material or at least one magnetizable material adapted to be in magnetic connection with a rotating magnetic field outside of the reservoir, such that the rotating magnetic field on the outside of the reservoir propels the rotatable structure inside of the reservoir.

The rotatable structure of the operable implant could comprise a radially extending disc comprising a plurality of magnets, and the plurality of magnets could be adapted to axially be in magnetic connection with the rotating magnetic field.

According to one embodiment, the operable implant further comprises a drive unit comprising a plurality of axially positioned coils circularly distributed around a rotational axis of the rotatable structure positioned on the inside of the reservoir, such that the center axis of the helix of the coils extends in the axial direction, substantially parallel or substantially aligned in the center of the rotational axis of the rotatable structure, and wherein sequential energizing of the coils creates the rotating magnetic field axially propelling the rotatable structure.

The operable implant could further comprise a magnetic coupling comprising a driving rotatable structure comprising a plurality of magnets circularly distributed around a rotational axis of the rotatable structure. The driving rotatable structure could be adapted to be in magnetic connection with the rotatable structure positioned on the inside of the reservoir, and the driving rotatable structure is connected to an electrical motor adapted to propel the driving rotatable structure such that the rotatable structure positioned on the inside of the reservoir rotates along with the driving rotatable structure.

The rotatable structure could comprise an axially extending cylinder comprising a plurality of magnets positioned on the peripheral surface of the cylinder, and wherein the plurality of magnets are adapted to radially be in magnetic connection with the rotating magnetic field.

The operable implant could further comprise a drive unit comprising a plurality of radially positioned coils circularly distributed around a rotational axis of the rotatable structure positioned on the inside of the reservoir, such that the center axis of the helix of the coils are extending in the radial direction, substantially perpendicular to the rotational axis of the rotatable structure, and wherein sequential energizing of the coils creates the rotating magnetic field propelling the rotatable structure.

The operable implant may further comprise a drive unit comprising a driving rotatable structure comprising a plurality of magnets circularly distributed around a rotational axis of the rotatable structure. The driving rotatable structure could be adapted to radially be in magnetic connection with the rotatable structure positioned on the inside of the reservoir, and the driving rotatable structure could be connected to an electrical motor adapted to propel the driving rotatable structure such that the rotatable structure positioned on the inside of the reservoir rotates along with the driving rotatable structure, adapted to rotate radially on the outside thereof.

According to one embodiment, the drive unit is an external drive unit adapted to be positioned on the outside of the skin of the patient and propel the rotatable structure in the hydraulic operation device.

According to one embodiment, the hydraulic operation device comprises an electrical motor adapted to propel the operable element of the gear system. The electrical motor could be an electrical motor selected from: an alternating current (AC) electrical motor, a direct current electrical motor, a linear electrical motor, an axial electrical motor, a radial motor, a three phase motor, a more than one phase motor, a piezo-electric motor, a bimetal motor, and a memory metal motor.

The electrical motor could be adapted to be positioned on the inside of the reservoir.

The operable implant according to any one of the preceding embodiments could further comprise a force transferring member, adapted to at least one of; penetrating a wall of the fluid reservoir, not penetrating a wall of the reservoir, transferring force from outside of the reservoir to inside of the reservoir, and transferring force between the motor and gear system inside the reservoir.

The force transferring member could be connected to an implantable electrical motor and to the operable element of the gear system and adapted to transfer rotational force from the electrical motor to the operable element.

The operable implant could further comprise a second gear system comprising: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear. The first gear of the first gear system could be connected to the operable element of the second gear system, such that the first and second gear systems functions as a single gear system.

According to one embodiment, the operable element of at least one of the first and second gear systems comprises at least one of; a planet gear and a wheel or structure adapted to use frictional connection direct or indirect between the operable element and the first gear.

The hydraulic operation device further comprises at least one receiving unit adapted to receive wireless energy supplied from outside the body of the patient.

The receiving unit of the operable implant comprises at least one coil adapted to transform wireless energy received in form of a magnetic or electromagnetic field into electrical energy.

The operable implant could further comprise a distance element adapted to create a distance between the receiving unit and at least one of; the reservoir and the electrical motor, such that the receiving unit remains substantially unaffected by metallic and/or magnetic parts of the reservoir and/or electrical motor. The distance element is adapted to at least one of; be placed through the muscular layers of the abdominal wall and be fixated to the fascia of a muscle facing the inside of the subcutaneous space.

According to one embodiment, the distance element is flexible such that the wireless energy receiver can move in relation to the reservoir and/or electrical motor. The distance element could be adapted to be fixated to at least one muscular layer of the abdominal wall, such that at least one of; the distance between the first portion of the implantable unit and the skin of the patient can be controlled and the movement of the distance element including rotation is minimized.

The operable implant could further comprise an injection port for directly or indirectly supplying fluid to the reservoir or the operable implant, being hydraulically operated.

An implantable electrical generator for transforming mechanical work to electrical energy is further provided. The implantable electrical generator comprises a movable structure comprising at least one magnet or at least one magnetic material or at least one magnetizable material, the movable structure being adapted to be in magnetic connection with an external drive unit creating a moving magnetic field, such that the movable structure moves along with the moving magnetic field. The implantable electrical generator further comprises an electrical generator unit connected to the movable structure and being adapted to transform the movements of the movable structure to electrical energy.

The electrical generator unit comprises: a movable generator portion comprising at least one magnet. The movable generator portion is connected to the movable structure, and at least one coil in magnetic connection with the at least one magnet, the electrical current is induced in the coil by the movement of the movable generator portion in relation to the coil.

According to one embodiment, the movable structure comprises a rotatable disc, and the at least one magnet or magnetic material is positioned on the rotatable disc and adapted to be in magnetic connection with an external unit creating a rotating magnetic field. The electrical generator unit is a rotating electrical generator unit connected to the rotatable disc, such that the rotating electrical generator unit rotates along with, or is part of, the rotatable disc for inducing electrical current.

The movable structure is adapted to perform reciprocating movement, and the movable structure is adapted to be in magnetic connection with an external unit creating a reciprocating magnetic field, such that the movable structure performs reciprocating movement along with the reciprocating magnetic field.

According to one embodiment, the movable structure is connected to an elastic element or spring, such that the movable structure can operate in a first direction by the magnetic force supplied by the external unit, and in a second direction by the elastic element or spring.

The elastic element could comprise at least one of; an elastic material, a flexible material, a construction adapted to create elastic movement, and a spring.

The electrical generator unit could in one embodiment be a linear electrical generator unit comprising: a movable generator portion comprising at least one magnet, wherein the movable generator portion is in connection with the movable structure adapted to perform reciprocating movement, and at least one coil in magnetic connection with the at least one magnet, such that reciprocating movement of the movable structure propagates to the movable generator portion and induces current in the at least one coil.

According to one embodiment, the implantable electrical generator further comprises a battery connected to the electrical generator unit, wherein the battery is adapted to store electrical energy generated in the generator unit.

The implantable electrical generator could further comprise an enclosure adapted to hermetically enclose the implantable electrical generator, such that the implantable electrical generator is sealed from the bodily fluids of the patient.

The implantable electrical generator could further comprise a wireless communication unit adapted to at least one of: receive wireless communication signals from an external unit, and transmit wireless communication signals to an external unit.

The implantable electrical generator could be adapted to be implanted subcutaneously, which could be subcutaneously in the abdomen.

An external unit for supplying force to an implantable electrical generator is further provided. The external unit comprises an external drive unit adapted to create a moving magnetic field on the outside of the patient's skin adapted to affect at least one magnet or at least one magnetic material or at least one magnetizable material of an implantable electrical generator, such that the magnet or magnetic material moves along with the moving magnetic field of the external drive unit.

According to one embodiment, the external drive unit comprises at least one an electro magnet adapted to be alternatingly energized and not energized, such that an alternating magnetic field is created for affecting at least one magnet or magnetic material of the implantable electrical generator.

The external drive unit could comprise at least one permanent magnet, and a positive pole of the permanent magnet is adapted to affect a permanent magnet of the implantable generator, and a negative pole of the permanent magnet could be adapted to affect the permanent magnet of the implantable generator. At least one permanent magnet could be adapted to move such that the positive and negative pole alternatingly affects the permanent magnet of the implantable generator.

According to one embodiment, the external drive unit comprises a set of circularly distributed coils, such that sequential energizing of the coils creates a rotating magnetic field adapted to affect the magnet, magnetic material, or magnetizable material of the implantable electrical generator, such that the magnet, magnetic material, or magnetizable material rotates along with the rotating magnetic field of the external drive unit.

In one embodiment, the external unit comprises a set of linearly distributed coils, such that sequential energizing of the coils creates a linearly moving magnetic field adapted to affect the magnet or magnetic material or magnetizable material of the implantable electrical generator, such that the magnet, magnetic material, or magnetizable material moves along with the linear magnetic field of the external unit.

The external unit could comprise a rotatable structure comprising at least one magnet or magnetic material, and rotation of the rotatable structure could affect a magnet or magnetic material of the implantable electrical generator causing rotation thereof, such that the magnet or magnetic material rotates along with the rotatable structure of the external unit.

The external unit could comprise a reciprocating structure comprising at least one of: magnetic material, a permanent magnet, and an electromagnet. The reciprocating structure could be adapted to move the magnetic material, permanent magnet or electromagnet between a first position close to the skin of the patient, and a second position further from the skin of the patient, such that a reciprocating magnetic field adapted to affect the magnet or magnetic material of the implantable electrical generator is created, or be adapted to intermittently receive electric pulses to the at least one electromagnet to cause movement of the magnetic field, while the reciprocating structure substantially stands still.

According to one embodiment, the external unit further comprises a wireless communication unit adapted to at least one of: receive wireless communication signals from the implantable electrical generator, and transmit wireless communication signals to the implantable electrical generator.

A system for generating electrical current inside of the body of a patient is further provided. The system comprises: an implantable electrical generator according to any one of the embodiments herein, and an external unit according to any one of the embodiments herein.

An operable hydraulic implant comprising a hydraulic operation device is further provided. The hydraulic operation device comprises an enclosure adapted to hermetically enclose: a reservoir adapted to contain a hydraulic fluid for operating the operable hydraulic implant, and a gear system adapted receive mechanical work of a first force and velocity as input, and output mechanical work having a different force and velocity. The reservoir and the gear system are sealed from the bodily fluids when implanted.

The reservoir could comprise at least one movable wall portion, for changing the volume of the reservoir.

In one embodiment, the gear system is connected to the movable wall for changing the volume of the reservoir. In one embodiment, the operable hydraulic implant further comprises an electrical motor connected to the gear system and enclosed by the enclosure.

In one of the embodiments herein, the gear system comprises: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

In one embodiment of the operable hydraulic implant, the operable element of the gear system is adapted to receive mechanical work of a first force and velocity from the electrical motor. The first gear of the gear system is directly or indirectly connected to the at least one movable wall portion for supplying mechanical work having a different second force and velocity to the at least one wall portion, such that operation of the electrical motor moves the movable wall portion and changes the volume of the reservoir.

In one embodiment, the first gear of the gear system directly or indirectly connects to a threaded member adapted to transform the radially rotating force to an axially reciprocating force, and wherein the threaded member is directly or indirectly connected to the movable wall portion for changing the volume of the reservoir. The threaded member could be directly or indirectly connected to a movable wall portion of a second fluid reservoir for changing the volume of the second reservoir.

The movement of the movable wall portion of the first reservoir, by the threaded member in a first direction causes the first reservoir to expand and the volume in the first reservoir to increase, and the movement of the movable wall portion of the second reservoir by the threaded member in a first direction causes the second reservoir to contract and the volume in the second reservoir to decrease.

The first reservoir could be in fluid connection with a first hydraulically operable body engaging portion, and wherein the second reservoir could be in fluid connection with a second hydraulically operable body engaging portion, and operation of the electrical motor unit in a first direction, by the connection with the threaded member, could cause transportation of fluid from the first reservoir to the first hydraulically operable body engaging portion, and transportation of fluid from the second hydraulically operable body engaging portion to the second reservoir.

According to one embodiment of the operable hydraulic implant, a wall of the enclosure constitutes at least a portion of the wall of the reservoir, and at least one movable wall portion could be positioned between the reservoir and the gear system, such that the portion of the at least one movable wall portion separates the reservoir from a portion of the enclosure enclosing the gear system, such that the gear system is sealed from the reservoir.

The operable hydraulic implant further comprises a second gear system enclosed by the enclosure, and the second gear system is adapted to receive mechanical work of the different second force and velocity from the output of the first gear system, and output mechanical work having a different third force and velocity.

The second gear system comprises: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the first gear of the first gear system is directly or indirectly connected to the operable element of the second gear system, such that the first and second gear systems functions as a single gear system.

According to one embodiment, the operable element of at least one of the first and second gear systems could comprise at least one of; a planet gear and a wheel or structure using a frictional connection.

The operable hydraulic implant could, further comprise at least one battery enclosed by the enclosure, and adapted to energize the electrical motor.

According to one embodiment, the operable hydraulic implant further comprises a receiving unit adapted to receive wireless energy transmitted from outside the patient's body.

The receiving unit is adapted to be enclosed by the enclosure, such that the receiving unit is sealed from the bodily fluids.

The operable hydraulic implant may further comprise a distance element adapted to create a distance between the receiving unit and at least one of; the gear system and the electrical motor, such that the receiving unit is removed from metallic and/or magnetic components of the gear system and/or electrical motor.

The receiving unit could be adapted to charge the battery according to any one of the embodiments herein.

In one embodiment, the operable hydraulic implant further comprises a magnetic coupling comprising a first part connected to the operable element of the gear system and enclosed by the enclosure, and a second part being: positioned on the outside of the enclosure, connected to an electrical motor positioned such that operation of the electrical motor operates the second part of the magnetic coupling, and magnetically connected to the first part of the magnetic coupling, such that the first part of the magnetic coupling rotates along with the second part of the magnetic coupling, such that the electrical motor propels the gear system through the wall of the enclosure.

The operable hydraulic implant could according to one embodiment further comprise an implanted electrical motor, and the second part could be connected to the implantable electrical motor. The second part of the magnetic coupling could be connected to an external drive unit adapted to propel the first unit from the outside of the patient's body.

The electrical motor could be an electrical motor selected from: an alternating current (AC) electrical motor, a direct current electrical motor, a linear electrical motor, an axial electrical motor, a radial motor, a three-phase motor, a more than one-phase motor, a piezo-electric motor, a bimetal motor, and a memory metal motor.

The enclosure of the implantable hydraulic unit could comprise a material selected from: a carbon material, a boron material, a mixture of material, a Peck® material, an alloy of material, a metallic material, titanium, aluminum, a ceramic material, a polymer material, polyurethane, polyether ether ketone, silicone, and Parylene® coated silicone.

An operable implant for implantation in the body of a patient is provided. The operable implant comprises at least one fixation member adapted to directly or indirectly fixate the operable implant towards at least one of; at least one muscular fascia, at least one bone fascia, at least one cortical bone layer, at least one muscular layer, fibrotic tissue, any part of the abdominal wall, and any part of the subcutaneous space and its surroundings in the body, and at least one adjustable distance element adapted to; in one end thereof, be directly or indirectly connected to at least a part of the operable implant, in the other end thereof, be directly or indirectly connected to the fixation member, and adjust the distance between the part of the operable implant connected to the adjustable distance element, and the fixation member.

The operable implant could comprise at least one part selected from a list consisting of: an operation device, a control unit a receiving unit, for receiving wireless energy, a coil, for receiving wireless energy, a receiving unit, for receiving a magnetic field or an electromagnetic field, a magnetic force transferring coupling, an electrical circuit, a push button for controlling any function of the operable implant, an energy storage device, a pushable construction for adjusting the adjustable distance element, an integrated operation device and receiving unit, for receiving wireless energy or a magnetic field or an electromagnetic field adapted to generate kinetic energy, a casing for enclosing at least one of the different parts of the operable implant two or more casings for enclosing at least one of the different parts of the operable implant in each casing. The at least one adjustable distance element could be adapted to adjust the distance between: the fixation member, and at least one of the parts above.

According to one embodiment of the operable implant, the at least one fixation member is integrated with at least one of: an operation device, a control unit, a receiving unit, for receiving wireless energy, a coil, for receiving wireless energy, a receiving unit, for receiving a magnetic field or an electromagnetic field, a magnetic force transferring coupling, an electrical circuit, a push button for controlling any function of the operable implant, an energy storage device, a pushable construction for adjusting the adjustable distance element, an integrated operation device and receiving unit, for receiving wireless energy or a magnetic field or an electromagnetic field adapted to generate kinetic energy, a casing for enclosing at least one of the different parts of the operable implant, two or more casings for enclosing at least one of the different parts of the operable implant in each casing, and an integrated unit comprising two or more of the parts. The at least one adjustable distance element is adapted to adjust the distance between; the fixation member integrated with one or more of the parts of the operable implant.

According to one embodiment, the at least one adjustable distance element is adjustable from outside the body of the patient.

According to one embodiment, the at least one adjustable distance element is adjustable electrically or manually from outside the body of the patient. The at least one adjustable distance element could comprise two, three, four or more adjustable distance elements.

According to one embodiment, the at least one adjustable distance element comprises a threaded member for transferring a rotating movement to a linear movement for adjusting the distance.

The at least one adjustable distance element or operable implant could comprise an x-ray detectable element, such that the distance adjusted by the at least one adjustable distance element can be measured on an x-ray image, and/or an element detectable by means of ultrasound, such that the distance adjusted by the at least one adjustable distance element can be measured by means of ultrasound.

At least one part of the operable implant may be adapted to be placed subcutaneously and/or the operation device may be adapted to be placed subcutaneously.

The operation device of the operable implant may be adapted to be fixated to at least one of, at least one fascia layer and at least one muscular layer of the abdominal wall.

The at least one adjustable distance element may be adapted to be placed through at least one of, at least one fascia layer and at least one muscular layer of the abdominal wall.

The adjustable distance element in any of the embodiments herein may be flexible such that the different parts of the operable implant can flex in relation to each other.

In one embodiment, the receiving unit comprises at least one coil adapted to transform wireless energy, received in form of an electric, magnetic or electromagnetic field, into electrical energy. Alternatively, the receiving unit comprises at least a first coil having a first number of windings, and at least a second coil having a second, different number of windings.

The operable implant may further comprise at least one enclosure adapted to hermetically enclose at least one part of the operable implant and/or the adjustable distance element.

The at least one adjustable distance element in any of the embodiments may comprise a lead for transferring electrical current from the receiving unit to the operation device.

The operable implant may further comprise a control unit for controlling at least one parameter of the operable implant. The control unit may be adapted to wirelessly communicate with an external unit, such that the control unit can be wirelessly controlled from outside the body.

According to one embodiment, at least one of; the receiving unit and the at least one adjustable distance element may be free from magnetic components.

The at least one enclosure in any of the embodiments may comprise two or more enclosures, and the at least one adjustable distance element may be adapted to adjust the distance between the enclosures.

A surgical kit for an operable implant enabling adjustment of a distance between at least one fixation member of the operable implant and at least one part of the operable implant is further provided. The surgical kit comprises at least one first distance element having: a first connecting portion adapted to directly or indirectly connect to the at least one part of the operable implant, and a second connecting portion adapted to directly or indirectly connect to the at least one fixation member of the operable implant, for creating a first distance between the at least one part of the operable implant and the at least one fixation member of the operable implant, and at least one second distance element having: a first connecting portion adapted to directly or indirectly connect to at least one part of the operable implant, and a second connecting portion adapted to directly or indirectly connect to the at least one fixation member of the operable implant for creating a second longer distance between the at least one part of the operable implant and the at least one fixation member of the operable implant.

According to one embodiment of the surgical kit, at least one of the at least one first and second distance elements comprises an x-ray detectable element, such that the distance between the at least one part of the operable implant and the at least one fixation member of the operable implant can be measured on an x-ray image.

In one embodiment of the surgical kit, at least one of; the at least one first and second distance elements comprises an element detectable by means of ultrasound, such that the distance between the at least one part of the operable implant and the at least one fixation member of the operable implant can be measured by means of ultrasound.

According to one embodiment, at least one of the at least one first and second distance elements may be adapted to be placed subcutaneously.

At least one of; the at least one the first and second distance elements may be adapted to be fixated to at least one of; at least one muscular fascia, at least one bone fascia, at least one cortical bone layer, at least one muscular layer, fibrotic tissue, any part of the abdominal wall, and any part of the subcutaneous space and its surroundings in the body.

At least one of the first and second distance elements in any of the embodiments of the surgical kit may be adapted to create a distance between the muscular layer of the abdominal wall and an operation device of the operable implant.

At least one of the first and second distance elements of the surgical kit may be adapted to be placed through at least one of, at least one fascia layer and at least one muscular layer of the abdominal wall.

At least one of the first and second distance elements may be flexible such that the different parts of the operable implant can move in relation to each other.

In any of the embodiments herein, at least one of the first and second distance elements may be free from magnetic components.

At least one of the first and second distance elements may be adapted to guide a lead for transferring electrical current from a wireless energy receiving unit to an operation device of the operable implant.

At least one of the first and second distance element may be adapted to fixate a wireless energy receiving unit in the body of the patient in an optimal position and hinder the body from rejecting the wireless energy receiving unit.

A system for adjusting a distance in an operable implant is further provided. The system comprises the surgical kit according to any one of the embodiments herein and an operable implant comprising at least one fixation member and at least one part selected from a list consisting of: an operation device, a control unit, a receiving unit, for receiving wireless energy, a coil, for receiving wireless energy, a receiving unit, for receiving a magnetic field or an electromagnetic field, a magnetic force transferring coupling, an electrical circuit, a push button for controlling any function of the operable implant, an energy storage device, a pushable construction for adjusting the adjustable distance element, an integrated operation device and receiving unit, for receiving wireless energy or a magnetic field or an electromagnetic field adapted to generate kinetic energy, a casing for enclosing at least one of the different parts of the operable implant, and two or more casings for enclosing at least one of the different parts of the operable implant in each casing. At least one of the first and second distance elements may be adapted to create a distance between the fixation member and at least one of the parts above.

The at least one fixation member may be integrated with at least one of: an operation device, a control unit a receiving unit, for receiving wireless energy, a coil, for receiving wireless energy, a receiving unit, for receiving a magnetic field or an electromagnetic field, a magnetic force transferring coupling, an electric circuit, a push button for controlling any function of the operable implant, an energy storage device, a pushable construction for adjusting the adjustable distance element, an integrated operation device and receiving unit, for receiving wireless energy or a magnetic field or an electromagnetic field adapted to generate kinetic energy, a casing for enclosing at least one of the different parts of the operable implant, and two or more casings for enclosing at least one of the different parts of the operable implant in each casing. At least one of; the first and second distance element may be adapted to create a distance between; the fixation member integrated with one or more of parts above, and one or more other parts of any of the embodiments.

According to one embodiment, at least one of the first and second distance elements comprises a lead for transferring electrical current from the wireless energy receiving unit to the operation device.

At least one part of the operable implant may be adapted to be placed subcutaneously, or the operation device may be adapted to be placed subcutaneously.

According to one embodiment, the operation device is adapted to be fixated to at least one of, at least one fascia layer and at least one muscular layer of the abdominal wall.

The receiving unit could further comprise at least one coil adapted to transform wireless energy, received in form of an electric, magnetic or electromagnetic field, into electrical energy. The receiving unit may comprise at least a first coil having a first number of windings, and at least a second coil having a second, different number of windings.

The system may further comprise at least one enclosure adapted to hermetically enclose at least any one part according to any one of the embodiments, and the adjustable distance element.

According to one embodiment, the system further comprises at least one enclosure adapted to hermetically enclose at least one of the parts of any of the embodiments herein.

The control unit of the system may be adapted to control at least one parameter of the operable implant, and the control unit may be adapted to wirelessly communicate with an external unit, such that the control unit can be wirelessly controlled from outside the body.

According to one embodiment, the at least one enclosure comprises two or more enclosures, and one of the first and second distance element may be adapted to adjust the distance between the two enclosures.

An operable implant for implantation in a patient is provided. The operable implant comprises a body engaging portion and an operation device for supplying force to the body engaging portion. The operation device comprises an implantable gear system adapted to, at a force input; receive mechanical work of a first force and velocity, and, at a force output; supply mechanical work having a different second force and second velocity to operate the body engaging portion. The gear system comprises an operable element connected to the force input, a first gear connected to the force output, first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

According to one embodiment, the operable element is adapted to deflect the first gear, and to maintain the first gear deflected such that the teeth of the first gear are interengaged with the teeth of the second gear in one or more angularly spaced positions interspaced by positions at which the teeth are not interengaged.

The operable element may be adapted to deflect the first gear, and to maintain the first gear deflected such that the teeth of the first gear are interengaged with the teeth of the second gear in at least two or more angularly spaced positions interspaced by positions at which the teeth are not interengaged.

According to one embodiment, the operation device comprises an implantable electrical motor for transforming electrical energy to mechanical work. The electrical motor may be connected to the force input.

The electrical motor may be an electrical motor selected from: an alternating current (AC) electrical motor, a direct current electrical motor, a linear electrical motor, an axial electrical motor, a piezo-electric motor, a three-phase motor, a more than one-phase motor, bimetal motor, and a memory metal motor.

The operable implant according to any one of the embodiments herein may further comprise a magnetic coupling connected to the force input, such that mechanical work of the first force and velocity is supplied to the gear system by means of the magnetic coupling. The magnetic coupling could be connected to the force output, such that mechanical work of the second force and velocity is supplied to the body engaging portion by means of the magnetic coupling.

According to one embodiment, the magnetic coupling is adapted to transfer at least one of; rotating force and reciprocating force.

The magnetic coupling may comprise a rotating element placed inside a sealed enclosure enclosing at least the gear system of the operable implant, the rotating element comprising at least one magnet or a portion comprising magnetic or magnetizable material. The magnet or portion comprising magnetic or magnetizable material may be adapted to rotate to transfer force to a corresponding rotating element on the outside of the sealed enclosure, for directly or indirectly supplying force to the body engaging portion through the sealed enclosure.

The magnetic force coupling may comprise a rotating element placed inside a sealed enclosure comprising at least one magnet or a portion comprising magnetic or magnetizable material, adapted to be rotated when receiving transfer force from a corresponding external rotating element placed on the outside of the hermetic enclosure and on the outside of the body, for directly supplying force to the rotating element placed inside the sealed enclosure.

The operable implant may further comprise an enclosure adapted to hermetically enclose the operable implant.

The gear system in any of the embodiments may further comprise a third gear having the shape of a hollow cylinder. The inside of the third gear may comprise the same amount of teeth as the outside of the first gear, the teeth of the third gear may be adapted to interengage the teeth of the first gear such that the third gear rotates in relation to the second gear, along with the at least one interengaged position.

According to one embodiment, the third gear is connected to a second gear system, such that the first and second gear systems functions as a single gear system. The second gear system comprises a force input adapted to receive mechanical work of the second force and second velocity from the force output of the first gear system, and a force output adapted to supply mechanical work to the body engaging portion having a different third force and third velocity. The second gear system may comprise an operable element connected to the force input of the second gear system, a first gear connected to the force output of the second gear system, having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear.

According to one embodiment, the operable element of at least one of the first and second gear systems comprises at least one of; a planetary gear and a structure or wheel at least partly using friction to enable rotating force to be transported.

In any of the embodiments herein, the force output of the first or second gear system may be directly or indirectly connected to a threaded member adapted to transform rotating force to linear force.

According to another embodiment, the operable implant further comprises a reservoir comprising a movable wall portion adapted to change the volume of the reservoir. The threaded member may be directly or indirectly connected to the movable wall portion, such that operation of the threaded member changes the volume of the reservoir.

The operable implant may in some embodiments additionally comprise a second reservoir comprising a movable wall portion, and the threaded member may be directly or indirectly connected to the movable wall portion of the second reservoir for changing the volume of the second reservoir. The movement of the movable wall portion of the first reservoir, by the threaded member in a first direction, may cause the first reservoir to expand and the volume of the first fluid reservoir to increase, and the movement of the movable wall portion of the second reservoir by the threaded member in a first direction may cause the second reservoir to contract and the volume of the second reservoir to decrease.

The first reservoir may be in fluid connection with a first body engaging portion, and the second reservoir may be in fluid connection with a second body engaging portion, and operation of the operation device in a first direction, by the connection with the threaded member, may cause: transportation of fluid from the first reservoir to the first body engaging portion, and transportation of fluid from the second body engaging portion to the second reservoir.

The reservoir in any of the embodiments may be at least one of circular and torus shaped.

The operable implant in any of the embodiments may further comprise a peristaltic pump comprising a hollow member for fluid transportation, and an operable compression member adapted to engage and compress the hollow member. The force output may be in direct or indirect connection with the compression member, such that the operation of the operation device operates the compression member such that fluid is transported in the hollow member.

The operable implant may further comprise a friction coupling adapted to limit the torque that can be supplied by the operation device. The friction coupling may be positioned between the operation device and the body engaging portion, such that the torque required to start the operation device is reduced.

The operable implant may further comprise a reservoir for holding a hydraulic fluid. The reservoir comprising a movable wall portion adapted to change the volume of the reservoir. The movable wall portion may be directly or indirectly connected to the gear system force outlet, such that operation of the gear system changes the volume of the reservoir.

The electrical motor in any one of the preceding embodiments may be a one, two, three or more phase motor, comprising at least one of; an axial electrical motor, a radial electrical motor, and a linear electrical motor.

The operable implant may further comprise a separate receiving unit adapted to receive wireless energy; the receiving unit may comprise at least one coil adapted to transform wireless energy received in form of a magnetic, electric or electromagnetic field into electrical energy.

The operable implant may further comprise at least one distance element adapted to create a distance between the receiving unit and at least one of the skin of the patient and any metallic, magnetic or magnetizable part of the operable implant, such that the receiving unit remains substantially unaffected by metallic and/or magnetic parts of the operable implant.

The at least one distance element may be adjustable.

The operable implant may further comprise at least one fixation member for fixating at least a part of the operable implant to at least one of muscular fascia, bone fascia, cortical bone, muscular layer, fibrotic tissue, and a at least one layer towards the inside of the subcutaneous space of the patient.

A medical system for transferring energy from the outside of the body of a patient to an operable implant placed inside the body of the patient is further provided. The medical system comprises: an external drive unit, and an operable implant. The external drive unit comprises an external rotating structure comprising at least one magnet for creating a rotating magnetic field adapted to magnetically connect to at least one of: a magnet, magnetizable material or magnetic material of the operable implant for transferring force from the external drive unit to the magnet or magnetic material of the implant in the body of the patient, and at least one coil of the operable implant for inducing electrical current in the body of the patient. The provided medical system can transfer rotating kinetic force for directly or indirectly powering a medical implant.

The magnet or magnetic material of the operable implant is may be fixated to an internal rotating structure adapted to rotate along with the rotating magnetic field of the external drive unit for operating the operable implant.

According to one embodiment, the magnet or magnetic material of the operable implant may be fixated to an internal reciprocating structure adapted to reciprocate with the rotating magnetic field of the external drive unit for operating the operable implant.

The internal reciprocating structure may be adapted to reciprocate due to the magnetic connection with a magnetic field which shifting polarity, such that the magnets of the internal reciprocating structure is alternatingly attracted and repelled by the rotating magnetic field created by the external drive unit.

The external rotating structure may have a larger diameter than the internal rotating structure, and the magnets may be arranged such that the radial force, enabling the magnets of the internal rotating structure to rotate along with the magnets of the external rotating structure, is greater than the axial force, exerted by the magnets, pressing the internal structure against the external structure, thus reducing the risk that the magnetic force will injure the patient's skin.

According to one embodiment, at least one of the internal rotating structure and the external rotating structure may comprise a repelling magnet adapted to decrease the axial forces created by the magnetic connection between the internal and external magnets and/or magnetic material, such that the squeezing effect on the patient's skin is reduced.

The force of the repelling or attracting magnet may be adjustable, such that the squeezing effect on the patient's skin can be adjusted.

The repelling magnet of any of the embodiments may be an repelling electromagnet, and the force of the repelling electromagnet may be adjusted by altering the current to the electromagnet.

According to one embodiment, the repelling magnet is a permanent magnet and the force of the repelling permanent magnet may be adjustable by altering the distance between or position of the permanent magnet in relation to the patient's skin.

The internal rotating structure may comprise an internal spherical cap, and the magnets or magnetic material of the internal rotating structure may be positioned on the outside of said internal spherical cap. The external rotating structure may comprise an external spherical cap, and the magnets or magnetic material of the external rotating structure may be positioned on inside of said external spherical cap, such that rotating force can be transferred radially by means of the magnetic connection between the internal and external spherical caps.

According to one embodiment, the internal spherical cap comprises a centrally placed magnet, and the external spherical cap comprises a centrally placed magnet, and wherein the magnets of the internal and external spherical caps are adapted to exert repelling forces on each other such that the axial forces created by the magnetic connection between the internal and external magnets and/or magnetic material is reduced, such that the squeezing effect on the patient's skin is reduced.

The medical system may further comprise a gear system connected to the internal rotating structure. The gear system may be adapted to receive mechanical work of a first force and velocity and supply mechanical work having a different force and velocity.

The gear system may comprise: an operable element, a first gear comprising a first number of teeth, on the outside thereof, and a second gear comprising a greater number of teeth than the first gear, on the inside thereof. The operable element may be adapted to press the outside of the first gear towards the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

According to one embodiment, the operable implant comprises an operation device and a body engaging portion. The operation device may comprise a hydraulic operation device. The body engaging portion may be a hydraulically operable body engaging portion, and the operable implant may further comprise a hydraulic pump and a reservoir adapted to hold hydraulic fluid, the reservoir being connected to the hydraulic pump. The hydraulic pump may be adapted to transport hydraulic fluid from the reservoir to the body engaging portion.

The hydraulic pump may comprise a movable wall portion of the reservoir, and the hydraulic pump may be adapted to transport hydraulic fluid from the reservoir to the hydraulically operable body engaging portion by moving the movable wall portion and thereby changing the volume of the reservoir.

According to one embodiment, the operation device comprises an electrical motor comprising a static part comprising a plurality of coils and a movable part comprising a plurality of magnets, such that sequential energizing of said coils magnetically propels the magnets and thus propels the movable part. The operation device may further comprise an enclosure adapted to hermetically enclose the coils of the static part, such that a seal is created between the static part and the propelled moving part with the included magnets, such that the coils of the static part are sealed from the bodily fluids, when implanted.

The medical system may further comprise an implantable electrical generator comprising: a movable generator portion comprising at least one generator magnet connected to the magnet or magnetic material of the operable implant, such that the movement of the magnet or magnetic material moves the movable generator portion, and at least one coil in magnetic connection with the at least one generator magnet, such that electrical current is induced in the coil by the movement of the movable generator portion in relation to the coil.

According to one embodiment, the movable generator portion is adapted to perform rotating movements.

The implantable electrical generator may be an implantable rotational electrical generator, and the movable generator portion may be adapted to perform rotating movement, and at least one coil may be in magnetic connection with the at least one magnet, such that rotating movement of the movable generator portion induces current in the at least one coil.

The movable generator portion may be adapted to perform reciprocating movements.

The implantable electrical generator may be an implantable linear electrical generator, and the movable generator portion may be adapted to perform reciprocating movement, and the at least one coil may be in magnetic connection with the at least one magnet, such that reciprocating movement of the movable generator portion induces current in the at least one coil.

According to one embodiment, the operable implant comprises a plurality of coils arranged in a circular configuration, such that the rotating magnetic field by the external drive unit sequentially induces electrical current in the plurality of coils.

The medical system may further comprise at least one battery or energy storage device connected to the at least one coil, such that the current induced in the at least one coil can be stored as electrical energy in the battery.

The medical system may further comprise an enclosure adapted to hermetically enclose the operable implant, such that the operable implant is sealed from the bodily fluids of the patient.

The operable implant in any of embodiments may be adapted to be implanted subcutaneously.

According to one embodiment, the operable implant comprises an operation device and a body engaging portion. The operation device comprises a movable part directly or indirectly connected to the body engaging portion, the movable part being connected to at least one magnet, magnetizable material or magnetic material. The movable part may be adapted to magnetically connect to a moving magnetic field on the outside of the patient's body, such that the movable part moves along with the movable magnetic field. The operation device further comprises an implantable generator connected to the movable part and adapted to transform movement to electrical current, such that the movement of the movable part operates the body engaging portion and generates electrical current.

At least one magnet, magnetizable material or magnetic material may be connected to a rotating structure and adapted to magnetically connect to a rotating magnetic field on the outside of the skin of the patient, such that the rotating structure rotates along with the rotating magnetic field.

At least one magnet, magnetizable material or magnetic material may be connected to a structure adapted for reciprocating movement and adapted to magnetically connect to a reciprocating magnetic field on the outside of the skin of the patient, such that the structure for reciprocating movement moves along with the reciprocating magnetic field.

The implantable generator may further comprise at least one magnet and at least one coil, and the movement of the at least one magnet in relation to the at least one coil may induce an electrical current in the at least one coil. At least one magnet of the movable part may be adapted to magnetically connect to a moving magnetic field on the outside of the patient's body, also functions as the at least one magnet in the implantable generator.

According to one embodiment, the operable implant further comprises a battery or energy storage adapted to be charged by the implantable generator. The battery or energy storage may be adapted to power the body engaging portion.

The operable implant may further comprise a control unit for controlling at least one parameter of the operable implant.

The control unit may be connected to the battery or energy storage such that the battery powers the control unit.

The operation device may comprise a hydraulic operation device.

According to one embodiment, the body engaging portion may be a hydraulically operable body engaging portion, and the operable implant may further comprise a hydraulic pump and a reservoir adapted to hold hydraulic fluid, the reservoir being connected to the hydraulic pump. The hydraulic pump may be adapted to transport hydraulic fluid from the reservoir to the body engaging portion.

The hydraulic pump may comprise a movable wall portion of the reservoir, and the hydraulic pump may be adapted to transport hydraulic fluid from the reservoir to the hydraulically operable body engaging portion by moving the movable wall portion and thereby changing the volume of the reservoir.

According to one embodiment, the hydraulic pump may be a hydraulic pump selected from: peristaltic pumps, membrane pumps, gear pumps, and bellows pumps.

The operation device in any of the embodiments herein, may comprise a gear system adapted to receive mechanical work of a first force and velocity as input, and output mechanical work having a different force and velocity.

The gear system of the operation device may comprise: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof. The operable element may be adapted to engage the inside of the first gear, such that the outside of the first gear is pressed against the inside of the second gear such that the teeth of the first gear are interengaged with the teeth of the second gear in at least one position interspaced by positions at which the teeth are not interengaged. The operation of the operable element advances the positions and thereby causes relative rotation between the first gear and the second gear.

According to one embodiment, the operable element is connected to the movable part, such that the movement of the movable part operates the gear system.

According to one embodiment, the operable implant further comprises an enclosure adapted to enclose the operable implant.

In any of the embodiments herein, the movable part of the gear system may be placed subcutaneously.

The operation device may be adapted to be fixated to at least one fascia, fibrotic tissue, skin, muscular layer or any tissue subcutaneously in the abdominal wall or in the abdomen.

The operation device may further comprise a distance element adapted to create a distance between the operation device and the movable part.

The distance element may be adapted to control the position of the movable part hindering the body from rejecting the movable part.

According to one embodiment, of the operable implant, the operable implant further comprises a wireless communication unit adapted to wirelessly communicate with an external unit.

According to one embodiment, the system further comprises an external unit comprising an external drive unit for supplying a driving force to the operable implant.

The external drive unit may comprise moving magnets adapted to create the moving magnetic field, or may comprise coils, and wherein sequential energizing of the coils creates the moving magnetic field.

According to one embodiment, the external drive unit further comprises a wireless communication unit adapted to wirelessly communicate with the operable implant.

An operable hydraulic implant is further provided. The operable hydraulic implant comprises a body engaging portion, a powered operation device, in fluid connection with the body engaging portion. The operation device comprises: a reservoir for holding a hydraulic fluid, wherein the reservoir comprises a movable wall portion adapted to move to alter the volume of the reservoir and thereby transport hydraulic fluid from the reservoir to the body engaging portion, and an operation member connected to the movable wall portion, such that operation of the operation member alters the volume of the reservoir, and a flexible enclosure adapted to; have its volume altered by changing the outer size and shape of the enclosure and enclose the movable wall portion and the operation member. The movable wall portion may be adapted to move inside of the enclosure, such that the volume of the reservoir can be changed by affecting the outer dimensions of the operable hydraulic implant by the movement of the movable wall portion inside of the enclosure.

The reservoir further comprises a manual portion adapted to be compressed by manual force from outside of the body of the patient, such that fluid can be transported from the reservoir to the body engaging portion of the operable hydraulic implant, by means of manual force, for temporarily increasing the hydraulic pressure at the body engaging portion. The manual portion may enable manual override and/or the addition of pressure to the reservoir and/or emergency operation.

The reservoir in any of the embodiments herein may be substantially circular or elliptic.

According to one embodiment, the average thickness of the movable wall portion is less than the average thickness of the manual portion of the reservoir.

According to one embodiment of the operable hydraulic implant, the reservoir comprises Parylene® coated silicone.

In one embodiment, the operation device is connected to a threaded member adapted to transform a radially rotating force to an axially reciprocating force, and the threaded member may be connected to the operation member.

The operable hydraulic implant may further comprise an electrical circuit and a control unit for controlling the operable hydraulic implant.

The operable hydraulic implant may further comprise an injection port for injecting hydraulic fluid into the reservoir from outside the body of the patient.

At least a portion of the operable hydraulic implant may be adapted to be implanted subcutaneously.

The operable hydraulic implant may further comprise at least one fixation member adapted to directly or indirectly fixate at least a portion of the operable hydraulic implant towards at least one of; at least one muscular fascia, at least one bone fascia, at least one cortical bone layer, at least one muscular layer, fibrotic tissue, any part of the abdominal wall, and any part of the subcutaneous space and its surroundings in the body.

The operable hydraulic may further comprise a second body engaging portion and a second reservoir in fluid connection with the second body engaging portion. The second reservoir may comprise a movable wall portion adapted to move to alter the volume of the second reservoir and thereby transport hydraulic fluid from the second reservoir to the second body engaging portion.

The movable walls of the first and second reservoirs may be connected to the same operation member, adapted to increase or decrease the size of the reservoirs, and the volume of the first reservoir may be adapted to be changed in the opposite direction from the second reservoir.

According to one embodiment, the operation device comprises an electrical motor connected to the operation member. The electrical motor may be an electrical motor selected from: an alternating current (AC) electrical motor, a direct current electrical motor, a linear electrical motor, an axial electrical motor, a piezo-electric motor, a two or more phase motor, a three phase motor, a bimetal motor, and a memory metal motor.

According to one embodiment, operation of the electrical motor affects both the movable walls of both the first and second reservoirs.

The operation device may comprise a gear system adapted to receive mechanical work of a first force and velocity and supply mechanical work having a different second force and second velocity. The gear system may comprise a force input connected to an electrical motor, and a force output connected directly or indirectly to the operation member.

The gear system may comprise: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

The gear system may be connected to a threaded member adapted to transform a radially rotating force to an axially reciprocating force, and wherein the threaded member is connected to the operation member.

According to one embodiment, the operation device comprises a magnetic coupling adapted to be in magnetic connection with an external portion of a magnetic coupling, adapted to be positioned on the outside of the patient's body, such that the internal portion of the magnetic coupling moves along with the external portion of the magnetic coupling, for operating the movable wall portion.

The operable hydraulic implant may further comprise a wireless communication unit for wirelessly communicating with an external unit positioned on the outside of the patient's body.

The operable hydraulic implant may further comprise at least one battery adapted to store electrical energy in the body of the patient.

A medical system comprising an operable implant adapted to be placed inside the body of the patient is further provided. The operable implant comprises a movable structure adapted for reciprocating movement, the movable structure comprising at least one magnet or magnetic material, and the movable structure may be adapted to be in magnetic connection with an external unit creating a reciprocating magnetic or electromagnetic field, such that the movable structure reciprocates along with the reciprocating magnetic or electromagnetic field.

According to one embodiment, the operable implant further comprises an electrical generator connected to the movable structure and being adapted to transform the reciprocating movements of the movable structure to electrical energy.

The electrical generator may comprise: a movable generator portion comprising at least one magnet, wherein the movable generator portion is connected to the movable structure and at least one coil in magnetic connection with the at least one magnet. The electrical current is induced in the coil by the movement of the movable generator portion in relation to the coil.

According to one embodiment, the at least one magnet of the movable generator portion is the magnet of the movable structure.

The operable implant may further comprise a force transforming member adapted to transform reciprocating force to rotating force. The electrical generator may be a rotating electrical generator connected to the force transforming member.

The electrical generator may be a linear electrical generator comprising: a reciprocating generator portion comprising at least one magnet, wherein the reciprocating generator portion is in connection with the movable structure adapted to perform reciprocating movement, and at least one coil in magnetic connection with the at least one magnet, such that reciprocating movement of the reciprocating generator portion induces current in the at least one coil.

According to one embodiment, the movable structure is spring loaded in one direction, such that the reciprocating movement is created by magnetic force from the magnetic connection with the external unit in one direction, and by the movable portion being spring loaded in the opposite direction.

The operable implant may further comprise a battery or energy storing device connected to the electrical generator unit, the battery may be adapted to store electrical energy generated in the generator unit.

According to one embodiment, the operable implant may further comprise body engaging portion in connection with the movable structure, such that movement of the movable structure operates the body engaging portion.

The medical system in any of the embodiments may further comprise an enclosure adapted to hermetically enclose the operable implant, such that the implantable electrical generator is sealed from the bodily fluids of the patient.

The medical system according to any one of the preceding embodiments may further comprise a wireless communication unit adapted to at least one of: receive wireless communication signals from the external unit, and transmit wireless communication signals to the external unit.

The operable implant in any of the embodiments herein may be adapted to be implanted subcutaneously, which may be subcutaneously in the abdomen.

According to one embodiment, the operable implant further comprises an external unit comprising an external drive unit adapted to create a reciprocating magnetic field on the outside of the patient's skin adapted to affect at least one magnet or magnetic material of an operable implant such that the magnet or magnetic material reciprocates along with the reciprocating magnetic field of the external unit.

The external drive unit may further comprise a reciprocating structure comprising at least one magnet, electromagnet or magnetic material, and the reciprocation of the reciprocating structure may affects a magnet or magnetic material of a movable structure of an implantable electrical generator causing reciprocation thereof.

According to one embodiment, the external drive unit may comprise a rotatable structure comprising at least one magnet, electromagnet or magnetic material. Rotation of the rotatable structure affects a magnet or magnetic material of a movable structure of an implantable electrical generator causing reciprocation thereof.

The rotatable structure of the external drive unit may comprise: a first magnet or electromagnet creating a positive magnetic field, and a second magnet or electromagnet creating a negative magnetic field, such that rotation of the rotatable structure causes the first and second magnet or electromagnet to alternatingly affect the magnet or magnetic material of the operable implant, causing reciprocation thereof.

According to one embodiment, the external drive unit comprises an electromagnet for alternatingly creating a magnetic field with positive and negative polarity, which causes reciprocation of a magnet or magnetic material of an implantable electrical generator.

According to one embodiment, the operable implant further comprises a gear system adapted to receive mechanical work of a first force and velocity as input, and output mechanical work having a different force and velocity, the gear system comprises: an operable element, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

According to one embodiment, the operable implant comprises an operation device and a body engaging portion, the operation device comprises an electrical motor comprising a static part comprising a plurality of coils, and a movable part comprising a plurality of magnets, such that sequential energizing of said coils magnetically propels the magnets and thus propels the movable part. The operation device further comprises an enclosure adapted to hermetically enclose the coils of the static part, such that a seal is created between the static part and the propelled moving part with the included magnets, such that the coils of the static part are sealed from the bodily fluids, when implanted.

According to one embodiment, the external unit further comprises a wireless communication unit adapted to at least one of: receive wireless communication signals from the operable implant, and transmit wireless communication signals to the operable implant.

A medical system for creating a magnetic connection between an external unit and an operable implant is provided. The medical system comprises: an operable implant comprising at least one of; a magnet, a magnetic material, and a magnetizable material, and an external unit comprising at least one of; an external permanent magnet and an external electro magnet, adapted to magnetically connect to at least one of: the magnet, the magnetic material and the magnetizable material of the operable implant. The magnetic force of the external magnet can be arranged or adjusted such that the squeezing force on the skin of the patient can be arranged or adjusted. The medical system thus reduces the risk that the skin of the patient is injured.

According to one embodiment, the external magnet comprises at least one permanent magnet, and the external unit further comprises: a skin contacting portion, and an adjustment device for adjusting the distance between or position of the permanent magnet in relation to the skin contacting portion.

According to one embodiment, the operable implant comprises: at least one of; a first magnet, a first portion of magnetic material and a first portion of magnetizable material, and at least one of: a second magnet, a second portion of magnetic material, and a second portion of magnetizable material. The external unit comprises: at least one first magnet or first electro magnet, and at least a second magnet or second electro magnet, at least one of; the first magnet, portion of magnetic material and magnetizable material of the operable implant is adapted to be attracted by the first magnet or first electro magnet of the external unit, and at least one of; the second magnet, portion of magnetic material and magnetizable material of the operable implant may be adapted to be repelled by the second magnet or second electro magnet of the external unit for balancing the squeezing force on the skin of the patient.

According to one embodiment, the external unit is adapted to create, in different positions or at different times in the same position, a first and second magnetic field having different polarity. The operable implant may be adapted to create, in different positions, a first and second magnetic field having different polarity, wherein the first magnetic field is adapted to decrease the attracting force between the operable implant and the external unit, caused the second magnetic field, such that the squeezing effect on the patient's skin is reduced.

According to one embodiment, the external unit comprises at least one electro magnet, and the external unit comprises a control unit for controlling the magnetic force of the electro magnet.

According to one embodiment, the medical system is adapted to transfer moving force from the external unit to the operable implant by means of magnetic connection, the external unit comprises an external drive unit adapted to create a moving magnetic field adapted to magnetically connect to the operable implant for transferring force from the external drive unit to at least one of; a magnet, a magnetic material and a magnetizable material of the operable implant.

According to one embodiment, the medical system is adapted to transfer a rotating force through the skin of the patient, and the external drive unit comprises an external rotating structure comprising at least one of; at least one permanent magnet and at least one electro magnet for creating a rotating magnetic field adapted to magnetically connect to an internal rotating structure, such that the internal rotating structure rotates along with the external rotating structure. The squeezing force on the skin of the patient exerted by the magnets of the internal and external rotating structures may be adjusted such that rotating force can be transferred without excessive force to the patient's skin.

According to one embodiment, the external rotating structure has a larger diameter than the internal rotating structure, and the magnets are arranged such that the radial force, enabling the magnets of the internal rotating structure to rotate along with the magnets of the external rotating structure, is greater than the axial forces pressing the internal structure against the external structure.

According one embodiment the external unit is adapted to create a rotating magnetic field comprising both the first and second magnetic field according to any of the embodiments herein, being present in at least one of the following alternatives;

1. the first magnetic field being created at least when rotating the external rotating structure and comprising at least one of; an angularly intermittent first magnetic field, a central first magnetic field and a peripheral substantially continuous first magnetic field, wherein the first magnetic field is additionally creating at least a part of a magnetic coupling force allowing rotation of the internal rotating structure to join in at least one of; the rotational movement of the external rotating structure and the rotational movement of the magnetic field created by the rotational structure, wherein the force squeezing the skin of the patient is reduced by the first magnetic field,
2. the first magnetic field being created by one or more negative permanent magnets placed both on the internal and external rotating structure and comprising at least one of; an angularly intermittent first magnetic field, a central first magnetic field, and a peripheral substantially continuous first magnetic field, wherein the first magnetic field is additionally creating at least a part of a magnetic coupling force allowing rotation of the internal rotating structure to join in at least one of; the rotational movement of the external rotating structure and the rotational movement of the magnetic field created by the rotational structure when standing still, wherein the force squeezing the skin of the patient is reduced by the first magnetic field, and
3. the first magnetic field being created by one or more negative permanent magnets placed both on the internal and external rotating structure, creating a repelling magnetic force between the internal and external rotating structure and the permanent magnets is adapted to create at least one of; an angularly intermittent first magnetic field, a central first magnetic field and a peripheral substantially continuous first magnetic field,
4. the first magnetic field being caused by one or more negative permanent magnets placed on at the internal rotating structure, the permanent magnets adapted to create at least one of; an angularly intermittent second magnetic fields, a central second magnetic field and a peripheral substantially continuous second magnetic field, the magnetic field caused by the internal rotating structure is adapted to create a magnetic coupling force towards the external unit,
5. the second magnetic field being adapted to be created by the external structure comprising at least one of; two or more coils and two or more positive permanent magnets, adapted to cause at least one of; an angularly intermittent second magnetic fields, a central second magnetic field and a peripheral substantially continuous second magnetic field, and at least one of; when having two or more permanent magnets, the external rotating structure rotating to cause rotation of the internal rotating structure because of the rotating magnetic field according to embodiment 7 causing a magnetic coupling force, and when having two or more coils, the external rotating structure will stand still while the magnetic field of the external rotating structure rotates by successively energize the coils causing rotation of the internal rotating structure because of the rotating magnetic field, and causing at least a part of a magnetic coupling force enabling the rotation of the internal rotating structure, 6. both the second and first magnetic fields being adapted to be created at least partially by the external structure comprising at least one of; one or more coils, one or more positive permanent magnets and one or more negative permanent magnets, adapted to cause at least one of; an angularly intermittent second and first magnetic fields, a central second or first magnetic field and a peripheral substantially continuous second or first magnetic field, and wherein both the second and first magnetic fields are created by one or more negative permanent magnets placed on the internal rotating structure, the permanent magnets are adapted to create at least one of; an angularly intermittent second magnetic fields, a central second magnetic field and a peripheral substantially continuous second magnetic field, the magnetic fields created by the internal rotating structure being adapted to create a magnetic coupling force towards the external unit, in at least one of the following alternatives; when having two or more positive permanent magnets in magnetic coupling with two or more negative permanent magnets of the internal structure, the external rotating structure will rotate to cause rotation of the internal rotating structure because of the rotating magnetic field creating at least a part of a magnetic coupling force, when having two or more negative permanent magnets in magnetic coupling with two or more negative permanent magnets of the internal structure, the external rotating structure will rotate to cause rotation of the internal rotating structure because of the rotating magnetic field causing at least a part of a magnetic coupling force, and when having two or more coils in magnetic coupling with two or more negative permanent magnets of the internal structure, the external rotating structure will stand still and the magnetic field of the external rotating structure will rotate by successively energize the coils to cause rotation of the internal rotating structure because of the rotating magnetic field, and creating at least a part of a magnetic coupling force enabling the rotation of the internal rotating structure, and 7. both the second and first magnetic field being adapted to be rotated at least partially by the internal structure, comprising at least one of; one or more coils, one or more positive permanent magnets and one or more negative permanent magnets, adapted to create at least one of; an angularly intermittent second and first magnetic fields, a central second or first magnetic field and a peripheral substantially continuous second or first magnetic field.

According to one embodiment, the internal rotating structure comprises an internal spherical cap, and the magnet or magnetic material of the internal rotating structure is positioned on the outside of said internal spherical cap. The external rotating structure comprises an external spherical cap, and the magnet of the external rotating structure is positioned on the inside of said external spherical cap, such that rotating force can be transferred radially by means of the magnetic connection between the internal and external spherical caps.

According to one embodiment, the medical system according to any one of the embodiments further comprising an implantable electrical generator comprising: at least one movable generator portion comprises at least one generator magnet adapted to magnetically connect to at least one of the; magnet, magnetic material and magnetizable material of the operable implant, such that the movement of the at least one of magnet, magnetic material and magnetizable material; moves the movable generator portion or is the generator portion, and at least one coil in magnetic connection with the at least one generator magnet, such that electrical current is induced in the coil by the movement of the movable generator portion in relation to the coil.

According to one embodiment, the movable generator portion is adapted to perform rotating movements.

According to one embodiment, the implantable electrical generator is an implantable rotational electrical generator, and the movable generator portion is adapted to perform rotating movement placed on the internal rotating structure, and the at least one coil is in magnetic connection with the at least one magnet, such that rotating movement of the movable generator portion induces current in the at least one coil.

According to one embodiment, the movable generator portion is adapted to perform reciprocating movements.

According to one embodiment, the implantable electrical generator is an implantable linear electrical generator, and the movable generator portion is adapted to perform reciprocating movement. The at least one coil is adapted to be in magnetic connection with the at least one magnet, such that reciprocating movement of the movable generator portion induces current in the at least one coil.

According to one embodiment, the external unit is adapted to create a rotating magnetic field, and the operable implant comprises a plurality of coils arranged in a circular configuration adapted to be in magnetic connection with the rotating magnetic field, such that the rotating magnetic field sequentially induces electrical current in the plurality of coils.

In one embodiment, the external unit comprises a wireless energy transmitter, and the operable implant further comprises a wireless energy receiver, such that wireless energy can be transmitted from the external unit to the internal unit. The wireless energy transmitter may comprise a wireless energy transmitting coil, and the wireless energy receiver may comprise a wireless energy receiving coil.

The medical system may further comprise at least one battery adapted to store electrical energy.

According to one embodiment, the external unit comprises a wireless communication unit, and the medical system comprises a wireless communication unit, such that the external unit and the operable implant can communicate wirelessly.

The medical system may further comprise an enclosure adapted to hermetically enclose the operable implant, such that the operable implant is sealed from the bodily fluids of the patient.

According to one embodiment, the operable implant may be adapted to be implanted subcutaneously.

An operable implant is further provided. The operable implant comprises an electrical motor adapted to transfer electrical energy to mechanical work, the electrical motor being adapted to output mechanical work of a first force and velocity, and a gear system adapted to receive mechanical work of a first force and velocity from the electrical motor as input, and output mechanical work having a second different force and velocity. The medical system further comprises a first force output adapted to output mechanical work from the electrical motor, having a first force and velocity, and a second force output adapted to output mechanical work from the gear system, having a second force and velocity.

According to one embodiment, the operable implant further comprises an implantable generator, and the first force output is connected to the implantable generator for generating electrical current inside the body of the patient.

According to one embodiment, the operable implant further comprises an operable body engaging portion connected to and operated by the second force output of the operation device.

The operable body engaging portion may be a hydraulically operable body engaging portion, and the operation device may further comprise a hydraulic pump for transferring hydraulic fluid to the hydraulically operable body engaging portion.

The hydraulic pump of the operable implant may comprise a reservoir adapted to contain a hydraulic fluid, and the reservoir may comprise a movable wall portion for changing the volume of the reservoir, and the movable wall portion may be connected to the operation device, such that the operation device operates the movable wall portion.

The hydraulic pump may be a hydraulic pump selected from: at least one non-valve pump, at least one valve pump, at least one peristaltic pump, at least one membrane pump, at least one gear pump, and at least one bellows pump.

According to one embodiment, at least one of the first and second force output is connected to a threaded member adapted to transform the radially rotating force to an axially reciprocating force. The threaded member may be directly or indirectly connected to the movable wall portion of a reservoir, for changing the volume of the reservoir.

The threaded member may be directly or indirectly mechanically connected to the body engaging portion, such that the body engaging portion is operated via the threaded member.

According to one embodiment, gear system of the operable implant comprises: an operable element connected to the first force output, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein first gear is connected to the second force output for outputting mechanical work having the second force and velocity.

According to one embodiment, the operation device further comprises a second gear system, and the second gear system is adapted receive mechanical work of a second force and velocity from the first gear system as input, and output mechanical work having a third different force and velocity.

According to one embodiment, the operation device further comprises a third force output adapted to output mechanical work from the second gear system, having a third force and velocity.

The second gear system may comprise: an operable element connected to the second output, a first gear having the shape of a hollow cylinder, comprising a first number of teeth, on the peripheral outside thereof, and a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein first gear is connected to the third force output for outputting mechanical work having the third force and velocity.

According to one embodiment, the operable implant further comprises an enclosure adapted to enclose the operation device.

The enclosure may comprise a first and second penetration, the first penetration may be adapted for the first force output, and the second penetration may be adapted for the second force output.

According to one embodiment, the enclosure comprises a first, second and third penetrating force output.

According to one embodiment, the enclosure comprises a first, second and third penetration. The first penetration is adapted for the first force output, the second penetration is adapted for the second force output and the third penetration is adapted for the third force output. The first force output may be connected to a first hydraulic pump for operating a first body engaging portion, and the second force output may be connected to a second hydraulic pump for operating a second body engaging portion.

According to one embodiment, the first force output comprises a first rotatable shaft, and the second force output comprises a second rotatable shaft.

The enclosure of may further comprise at least one of: a first sealing member adapted to seal between the enclosure and the first rotatable shaft, and a second sealing member adapted to seal between the enclosure and the second rotatable shaft. The first and second sealing member may allow rotation of the rotatable shafts.

The first rotatable shaft may be adapted to be positioned inside of the second rotatable shaft or the second rotatable shaft is adapted to be positioned inside of the first rotatable shaft.

According to one embodiment, the first force output comprises a first rotatable shaft, the second force output comprises a second rotatable shaft, and the third force output comprises a third rotatable shaft.

According to one embodiment, the enclosure comprises at least one of: a first sealing member adapted to seal between the enclosure and the first rotatable shaft, and a second sealing member adapted to seal between the enclosure and the second rotatable shaft, and a third sealing member adapted to seal between the enclosure and the third rotatable shaft. The first and second sealing members allow rotation of the rotatable shafts.

The first and second rotatable shaft may be adapted to be positioned inside of the third rotatable shaft or the second and third rotatable shaft may be adapted to be positioned inside of the first rotatable shaft or the first and third rotatable shaft is adapted to be positioned inside of the second rotatable shaft.

The operable implant may comprise at least one implantable battery, adapted to energize the electrical motor.

The operable implant may further comprise a receiving unit adapted to receive wireless energy transmitted from outside the patient's body. The receiving unit may be adapted to charge a battery.

According to one embodiment, the electrical motor is an electrical motor selected from: an alternating current (AC) electrical motor, a direct current electrical motor, a linear electrical motor, an axial electrical motor, a radial motor, a three-phase motor, a more than one-phase motor, a piezoelectric motor, a bimetal motor, and a memory metal motor.

The enclosure may comprise a material selected from: a carbon material, a boron material, a mixture of material, a Peek® material, an alloy of material, a metallic material, titanium, aluminum, a ceramic material, a polymer material, polyurethane, and Parylene® coated silicone.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way.

BRIEF DESCRIPTION OF DRAWINGS

The invention is now described, by way of example, with reference to the accompanying drawing, in which:

FIG. 6 shows a sectional side view and a sectional top view of an embodiment of an implantable hydraulic operation device, FIG. 7 shows a sectional side view and a sectional top view of an embodiment of an implantable hydraulic operation device, FIG. 8 shows a sectional side view and a sectional top view of an embodiment of an implantable hydraulic operation device, FIG. 9 shows a sectional side view and a sectional top view of an embodiment of an implantable hydraulic operation device, FIG. 10a shows a sectional side view and a sectional top view of an embodiment of an implantable hydraulic operation device, FIG. 10b shows an exploded, elevated perspective view of an embodiment of an implantable electrical motor, FIG. 11a shows a sectional side view and a sectional top view of an embodiment of an implantable hydraulic operation device, FIG. 11b shows an exploded, elevated perspective view of an embodiment of an implantable electrical motor, FIG. 18a shows a sectional side view and a sectional top view of an embodiment of an implantable hydraulic operation device, FIG. 19 shows an elevated perspective view of an embodiment of an implantable operation device, and an elevated perspective view of the implantable operation device in section, FIG. 20 shows a sectional side view and a top view of an embodiment of an implantable operation device.

FIG. 33 shows a side view of wireless energy transmitter and an implantable wireless energy receiver, FIG. 34 shows a side view an operable implant and a wireless energy transmitter, FIG. 37 shows a side view an operable implant and a wireless energy transmitter, FIGS. 38a-38c shows schematic side views illustrating principles for wireless energy transfer through the skin of a patient.

DETAILED DESCRIPTION

Figure 1A:
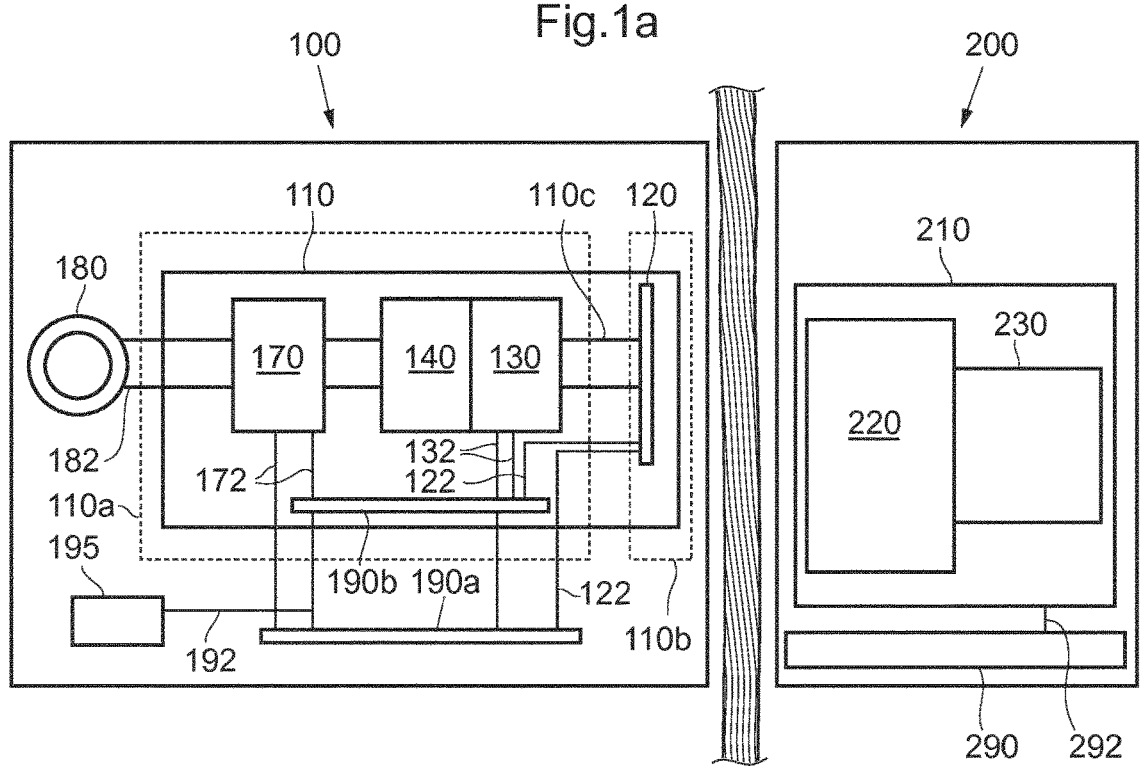
FIG. 1a shows a schematic overview of an embodiment of the operable implant and an external unit.

In the following a detailed description of embodiments of the invention will be given with reference to the accompanying drawings. It will be appreciated that the drawings are for illustration only and are not in any way restricting the scope of the invention. Thus, any references to directions, such as "up" or "down", are only referring to the directions shown in the figures. It should be noted that the features having the same reference numerals have the same function, a feature in one embodiment could thus be exchanged for a feature from another embodiment having the same reference numeral unless clearly contradictory. The descriptions of the features having the same reference numerals should thus be seen as complementing each other in describing the fundamental idea of the feature and thereby showing the features versatility.

An operable implant is to be understood as any implant that could be operated for performing a function in relation to the body of the patient. To be operated includes the altering of the size and/or shape of a portion of the implant, delivering an active or inactive substance to the body of the patient, electrically stimulating a portion of the body of the patient, sensing a physical or functional parameter of the operable implant and/or a physiological or physical parameter of the patient, communicating with an external unit on the outside of the skin of the patient and receiving or transmitting energy at the operable implant, from an external unit. An operable implant could for example be a pacemaker unit, an external heart compression device, an apparatus assisting the pump function of the heart, such as an LVAD device, an operable artificial heart valve, an implantable drug delivery device, such as an implantable device for delivering insulin or chemotherapeutic agents, a hydraulic, mechanic and/or electric constriction implant for constricting for example: an intestine for treating anal incontinence, an intestine for handling a stoma, the urethra for treating urinary incontinence, the bile duct for treating gall bladder malfunction, an oviduct for purpose of fertility control, the vas deference for the purpose of potency control, a blood vessel for purpose of increasing the blood volume in an erectile tissue, or for the purpose of constricting or restraining an aneurysm. An operable implant may further be an operable implant for treating obesity, such as an operable volume filling device for reducing the volume of the stomach, an operable gastric band for limiting the food passage way, or an operable implant for stretching the stomach wall for creating a feeling of satiety. The operable implant may be an operable device for treating GERD an operable cosmetic implant, such as an operable breast augmentation implant, or an implant for adjusting or replacing any bone part of the body. Furthermore, the implant could be replacing an organ or part of an organ, or the function thereof could be adjusted or replaced. Other examples of implants are implants treating impotence by implanted drug delivery, implants affecting blood flow, vascular treatment devices which may include blood clot removal, implants affecting fertility and/or infertility, or implants adapted to move fluid inside the body. The above listed examples of an operable implant are to be seen as examples not in any way limiting the possible application areas of the operable implant.

Body engaging portion is to be understood as any part or portion of the operable implant that is directly or indirectly connected to the body of the patient for performing a function in relation to the body of the patient. The function could for example be pressing and/or pulling against a portion of the body of the patient, delivering a substance to the body of the patient, collecting a sample from the body of the patient, electrically stimulating a portion of the body of the patient and/or filling or emptying an implantable volume filling device with a hydraulic fluid.

A physical or functional parameter of the operable implant could for example be an electrical parameter, such as voltage, current or impedance, a parameter related to a fluid, such as pressure, flow rate, temperature, volume, weight or viscosity. The parameter could be related to energy received at the operable implant, energy delivered to the body of the patient, fluid received at the operable implant, fluid delivered to the body of the patient, force exerted on the body of the patient or time elapsed since an action was performed in relation to the body of the patient.

A physiological or physical parameter of the patient could for example be the blood pressure of the patient, a blood flow, a parameter related to blood saturation, a parameter related to an ischemia marker, a temperature of the body of the patient, a parameter related to muscle activity or a parameter related to the activity of the gastro-intestinal system.

The enclosures referred to herein are in most instances adapted to separate components of the operable implant from the bodily fluids when implanted. However, the enclosures may also be used for containing a fluid or for separating a fluid used by the operable implant from other components of the operable implant. The enclosures may be enclosures made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide and tungsten carbide) or glass. In any instance the enclosure should be made from a material with low permeability, such that migration of fluid through the walls of the enclosure is prevented.

The operation device in the operable implant may comprise an electrical motor for transforming electrical energy into mechanical work. The electrical motor could for example be an alternating current (AC) electrical motor, such as a three-phase electrical motor (which may be controlled using variable-frequency drive), a direct current (DC) electrical motor, a linear electrical motor, an AC or DC axial electrical motor, a piezo-electric motor, a bimetal motor, or a memory metal motor.

Generally, a medical system including an operable implant comprising an implantable body engaging portion and an implantable operation device, and components thereof, is described herein. The implantable operation device could be adapted to electrically, mechanically or hydraulically operate the body engaging portion and could be powered by means of wireless energy transfer from the outside of the body of the patient, or by means of an implantable battery adapted to store electrical energy in the body of the patient. The operation device may comprise an electrical motor for transferring electrical energy to mechanical work (force*distance) and the electrical motor may be connected to one or more gear systems for altering the velocity and/or force/torque and/or direction of the supplied force. The operable implant may additionally comprise a communications unit for communicating with portions of the operable implant, other operable implants and/or external units. The communication with the external unit could comprise control signals from the external unit for controlling the operable implant or could comprise feedback signals from the operable implant, which for example could be sensor parameters such as physiological or physical sensor parameters related to the status of the body of the patient, or physical or functional parameters related to status of the operable implant.

Figure 1B:
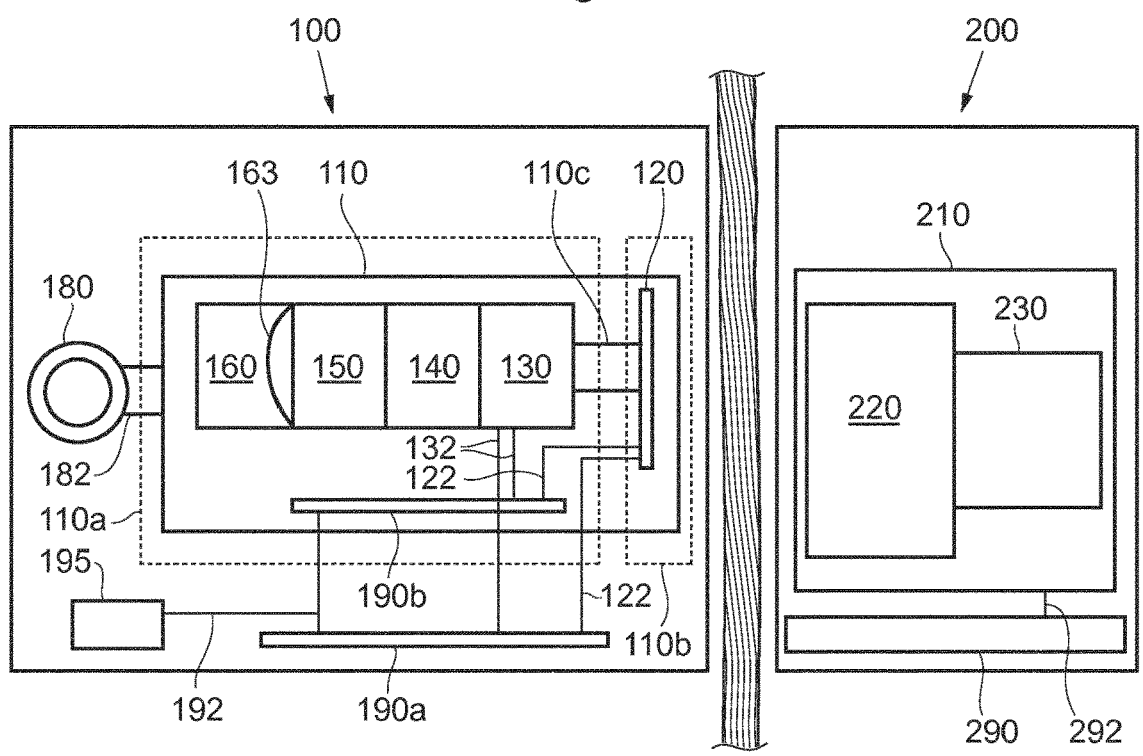
FIG. 1b shows a schematic overview of an embodiment of the operable implant and an external unit.

FIGS. 1a and 1b shows overviews of a medical system including an operable implant 100, adapted to be implanted in the body of a patient, and an external unit 200 for energizing and/or communicating with the operable implant 100. The overviews in FIGS. 1a and 1b shows examples of components that may be included in the operable implant 100 and external unit 200, respectively, and the embodiments are not to be seen as complete, just as the components shown in the figures are not the be regarded as essential for working the invention.

FIG. 1a shows an operable implant 100 implanted subcutaneously, under the skin S, of the patient. The operable implant 100 comprises an operation device 110 comprising a receiving unit 120 adapted to receive wireless energy or information from an external unit 200. The wireless energy may be in the form of an electromagnetic field transferred between a coil of the external unit 200 and a coil of the operable implant 100, by means of the coils of the operable implant 100 and external unit 200 functioning as electrical conductors inductively coupled to each other, forming a transformer like circuit for the purpose of transferring alternating electrical energy signals. The wireless energy could in alternative embodiments be in the form of a moving magnetic field magnetically connected to a movable structure of the implantable operation device 110 comprising magnets or magnetic material, such that the movable structure of the operable implant moves along with the moving magnetic field created in the external unit (such as further described with reference to FIGS. 32-39). The receiving unit 120 could further be a combination unit adapted to receive wireless energy both in the form a moving magnetic field affecting a movable structure of the operation device, and as wireless energy generating electrical current on in the implantable operation device 110 for operating a component consuming electrical energy, or charging a battery (such as 190a, 190b) for indirectly powering a component of the operable implant 100 consuming electrical energy.

Figure 35A:
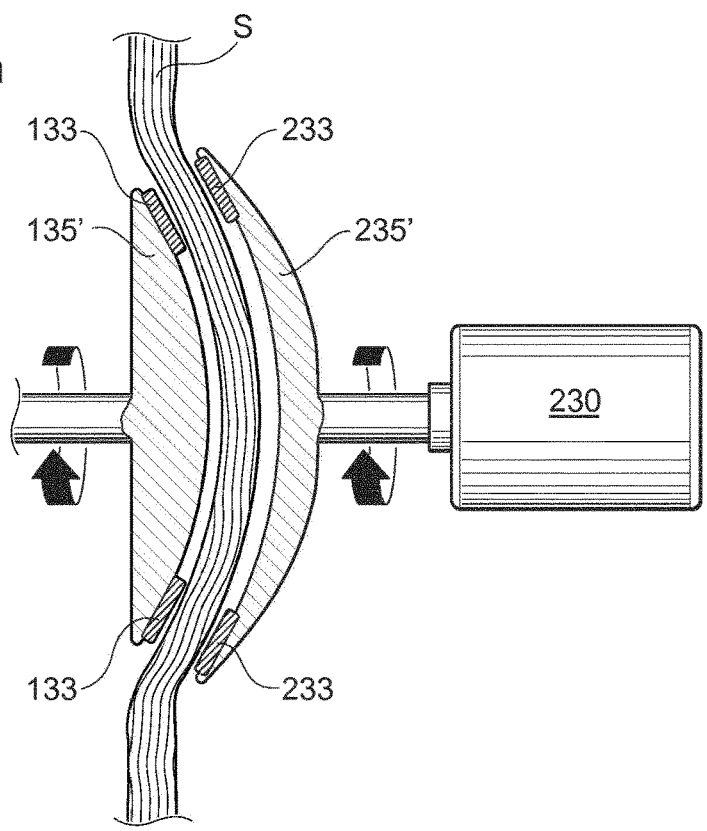
FIG. 35a shows a sectional side view of wireless energy transmitter, and a sectional side view of a wireless energy receiver placed on the inside of the skin of the patient.
Figure 35B:
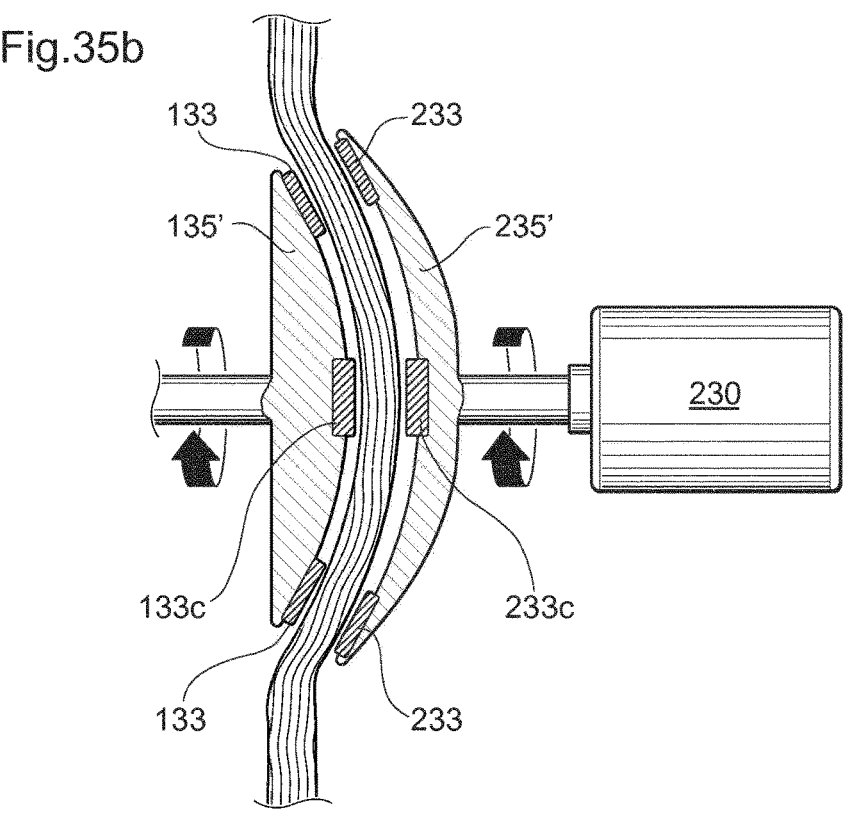
FIG. 35b shows a sectional side view of wireless energy transmitter, and a sectional side view of a wireless energy receiver placed on the inside of the skin of the patient.
Figure 35C:
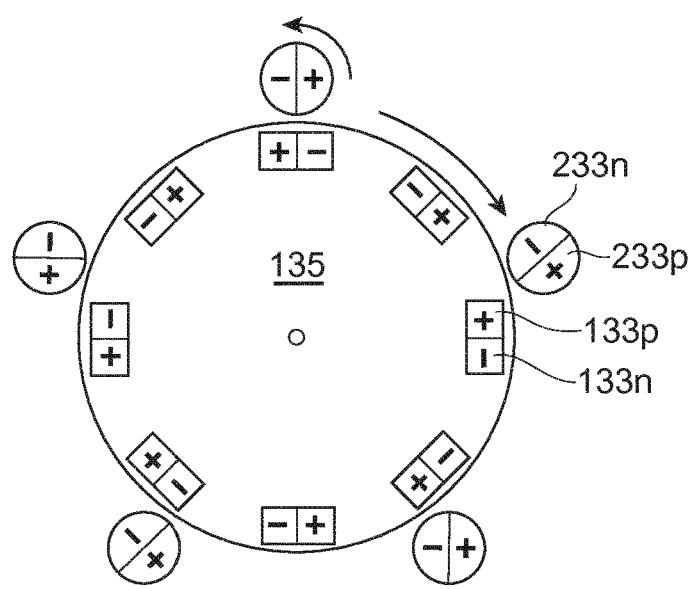
FIG. 35c shows an alternative concept for wireless energy transmission.
Figure 36:
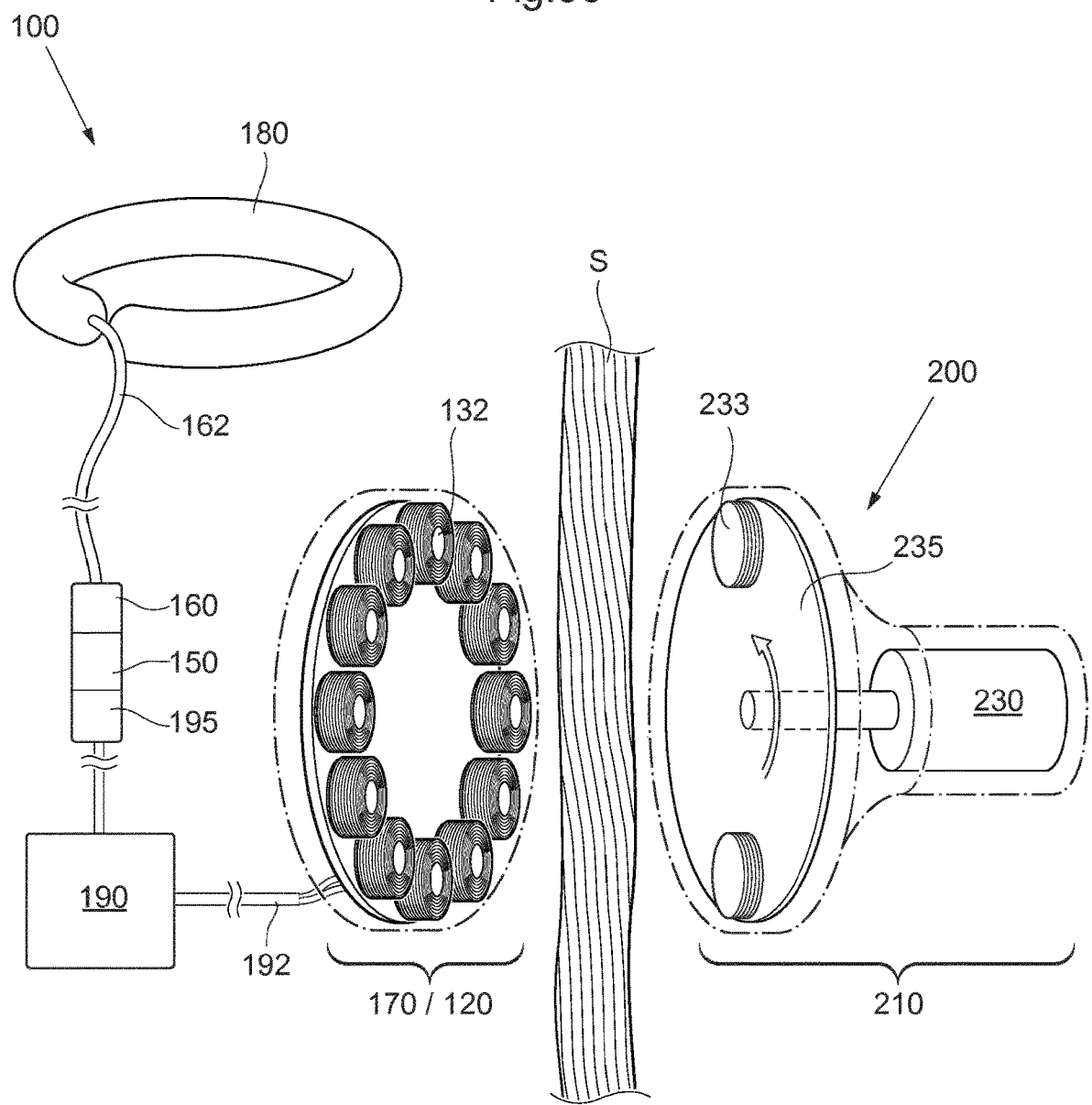
FIG. 36 shows a side view an operable implant and a wireless energy transmitter.

In the embodiment shown in FIG. 1a, the external unit 200 comprises an external drive unit 210 for creating a the mentioned rotating magnetic field by means of an external electrical motor 230 rotating an external part of a magnetic coupling 220 comprising a rotatable structure comprising magnets or electromagnets, such that the rotation of the rotatable structure by the operation of the external electrical motor 230 creates the movable magnetic field (such as further disclosed e.g. with reference to FIG. 35-36).

The operation device 110 of the operable implant 100 further comprises a distance element 110c adapted to create a distance between a first unit 110a of the operation device 110 comprising the main portion of the components of the operation device 110, and a second unit 110b of the operation device 110, comprising the receiving unit 120. The distance enables the receiving unit 120 to be substantially unaffected by the components in the first unit 110a, which could be components comprising magnetic or magnetizable material which may disturb the magnetic and/or electromagnetic field transferring wireless energy between the transmitting unit 220 and the receiving unit 120.

The distance element 110c connecting the first and second units 110a, 110b could comprises an electrical lead for transferring energy and/or information from the second unit 110b to the first unit 110a, and/or a mechanical force transferring member adapted to transfer mechanical force from the second unit 110b to the first unit 110a. The mechanical force transferring member could for example be at least one of: a rotating shaft for transferring rotational force, a flexible member for transferring rotational force, such as a Bowden cable, a wire, a belt, a rod, a worm gear, or a gear adapted to change the direction of the rotational force received at the receiving unit substantially 90 degrees, such as a Bevel gear.

The operation device of FIG. 1 further optionally comprises an electrical motor 130 adapted to transform electrical energy to the mechanical work. The electrical motor 130 may receive electrical energy from the receiving unit, directly transmitted from the external unit 200, or may receive electrical energy stored in an implantable battery 190. The electrical motor 130 may be omitted in embodiments where a moving force, such as a rotational moving force is received at the receiving unit 120, directly transmitted from the external drive unit 210. The electrical motor 130 could for example be an electrical motor 130 selected from: an alternating current (AC) electrical motor, a direct current (DC) electrical motor, a linear electrical motor, an axial electrical motor, a piezo-electric motor, a multiple phase motor, such as a three-phase motor, a bimetal motor, and a memory metal motor.

According to the overview shown in FIG. 1a, the force output of the electrical motor 130 is in connection with a force input of a gear system 140. The gear system 140 is adapted to receive mechanical work having a first force and first velocity, and output mechanical work having a different second force and a different second velocity, such that the high velocity movement supplied by the electrical motor 130 and/or the direct connection with the receiving unit 120 is transformed to low velocity movement with increased force.

The gear system 140 may for example comprise a gear system having the configuration such as any of the gear systems herein, such as the gear systems disclosed with reference to FIGS. 2-16. In alternative embodiments, it is conceivable that the gear system 140 comprises a transmission system of some other configuration, such as a conventional gear wheel system, a worm gear system or a belt transmission system. In the embodiment shown in FIG. 1a, the gear system 140 is connected to a connecting member 182, connecting the gear system 140 of the operation device 110 with the body engaging portion 180, for operating the body engaging portion. In the embodiment shown in FIG. 1a, the connection between the gear system 140 and the body engaging portion 180 comprises a mechanical connecting portion 181, such as a rotating shaft for transferring rotational force, a rod, or a flexible member for transferring rotational force, such as a Bowden cable.

The operation device may additionally comprise a generator 170 for generating electrical current (further described with reference to FIGS. 36-40). The configuration of the operable implant 100 may be such that the generator 170 is placed between the receiving unit 120 and the gear unit 140, such that the generator 170 receives force at a high velocity. In an alternative embodiment in which there is no direct mechanical connection between the receiving unit 120 and the body engaging portion 180, the gear system 140 may be entirely omitted.

The operable implant may comprise at least one implantable battery 190a, 190b which could be used to operate or control the operable implant. The battery 190a, 190b could be used in combination with direct drive from the external drive unit 210. As an example, the patient may use direct drive to operate the operable implant when at home, and battery power when away from home, or in emergency situations. The battery 190a, 190b could be adapted to power the operation of the operable implant 100, and/or could be adapted to power a control and/or communication unit. The battery 190a, 190b could be adapted to be charged, either by the receiving unit receiving wireless energy, or by an implantable generator 170. The battery could be replaced by any form of energy storing device, such as a capacitor.

Referring again to FIG. 1a, the operable implant 100 additionally comprises at least one implantable battery 190a, 190b, which may be placed in a separate unit, such as the battery 190a, or placed in the operation device 110, such as the battery 190b. The operable implant 100 may comprise a lead 122 connecting the battery 190a, 190b to the receiving unit 120, such that wireless energy received at the receiving unit 120 can be stored in the battery 190a, 190b, or a lead 172 connecting the battery 190a, 190b to the electrical generator 170, such that electrical current generated in the generator 170 can be stored in the battery 190a, 190b. The at least one battery 190a, 190b may be adapted to power at least one of: the control system 195, for controlling the operable implant 100 and the electrical motor 130. A first lead 192 connects the battery 190a, 190b to the control system 195 and a second lead 132 connects the electrical motor 130 to the battery 190a, 190b.

The control unit 195 may be contain elements for controlling the operable implant 100, which may include controlling the electrical motor 130, for example by means of adjusting the frequency of an alternating current supplied to the electrical motor 130, or by means of adjusting the voltage supplied to the electrical motor 130. The control unit 195 may be adapted to receive sensor input from one or more sensors of the operable implant 100, which may be sensors adapted to monitor a physical parameter of the operable implant 100, or a physiological parameter of the patient. The control unit 195 may in some embodiments be adapted to control a hydraulic operation device by for example controlling the actuation of a valve or a movable wall portion of a reservoir. The control unit 195 may comprise a communication unit for communicating with an external unit 200, in which case the receiving unit 120 may further comprise a unit for transmission of information, such that information related to physical parameters or the operable implant, and/or physiological parameters related to the body of the patient, may be communicated between the operable implant 100 and the external unit 200. If necessary, the control unit may comprise a rectifier circuit for converting alternating current received at the receiving unit to a direct current suitable for powering elements of the operable implant 100 or for charging at least one battery 190a, 190b of the operable implant 100. For the purpose of handling communication, information and/or data, the control unit 195 may further comprise a demodulator and a microprocessor. The demodulator demodulates signals sent from the external unit 200 and the microprocessor may decode and/or interpret the received signals. The receiving unit 120 of the operable implant and the transmitting unit 220 of the external unit 200 could be adapted to communicate by means of for example radio, IR (Infrared), ultrasonic, magnetic, inductive or capacitive signals.

The operable implant 100 or parts of the operable implant may be enclosed by an enclosure for separating components of the operable implant 100 from the bodily fluids when implanted. However, the enclosure may also be used for containing a fluid, such as in a reservoir, or for separating a fluid used by the operable implant 100, such as a lubricating fluid in the gear system, from other components of the operable implant 100. The enclosure may be made from a non-metallic and non-magnetic material not to affect the electromagnetic energy transfer between the external unit 200 and the operable implant 100. The enclosure may be made from one of or a combination of: a carbon based material (such as graphite, silicon carbide, or a carbon fiber material), a boron material, a polymer material (such as silicone, Peek®, polyurethane, UHWPE or PTFE), a metallic material (such as titanium, stainless steel, tantalum, platinum, niobium or aluminum), a ceramic material (such as zirconium dioxide, aluminum oxide and tungsten carbide) or glass. In any instance the enclosure should be made from a material with low permeability, such that migration of fluid through the walls of the enclosure is prevented.

Turning now to the external unit 200, the external unit 200 is adapted to power, control and/or communicate with the operable implant 100. The external unit 200 may comprise an external drive unit 210 which may be adapted to create a moving magnetic field adapted to be in magnetic connection with a magnet or magnetic material of the receiving unit 120 of the operable implant 100, such that the creation of a moving magnetic field on the outside of the body of the patient operates the operable implant 100 by the magnetic connection between the external drive unit 210 and a movable structure of the operable implant 100. The moving magnetic field may be created by an electrical motor 230 in connection with a moving structure comprising at least one magnet, which could be an electro magnet or permanent magnet. In alternative embodiments the moving magnetic field is created by the altering the magnetic field, for example by alternating the current to an electromagnet, such that the force supplied by the electromagnet alternates and thus is able to create a reciprocating movement of a magnetic or magnetic or magnetizable material. The creation of a moving magnetic field is further described with reference to FIGS. 32-39.

The external unit 200 could be directly energized by a connection with a power outlet of the power grid, or may comprise at least one chargeable or disposable battery 290 which may be connected by means of a conduit 292 to the drive unit 210 for powering the electrical motor 230 and/or an electromagnet. The external unit 200 may also comprise an external control/communication unit for communicating with the control/communication unit 195 of the operable implant 100. The external control/communication unit may be adapted to receive control signals from the operable implant and adjust the control of the external unit 200 in response to the control signals received.

FIG. 1b shows an embodiment of the operable implant 100, which is to be seen as an alternative to the embodiment shown in FIG. 1a. The difference being that the embodiment of FIG. 1b is a specific hydraulic embodiment adapted to operate a hydraulically operable body engaging portion 180' adapted to be connected to the operation device 110 by means of a connecting portion 182 comprising at least one conduit for transferring hydraulic fluid from the operation device 110 to the hydraulically operable body engaging portion 180'.

The operation device 110 of the embodiment shown in FIG. 1b comprises a hydraulic pump 150 in connection with a reservoir 160 for holding hydraulic fluid. The reservoir 160 may comprise at least one movable wall portion 163 which may constitute the hydraulic pump 150 (by the movable wall being operable, such as for example disclosed with reference to FIG. 4 or 5). In alternative embodiments, the hydraulic pump 150 could for example be a: non-valve pump, a pump comprising at least one valve, a peristaltic pump, a membrane pump, a gear pump or a bellows pump. The hydraulic pump 150 is operated by the connection with either an implantable electrical motor 130, or a movable structure adapted to be operated from outside the body of the patient. The connection between the hydraulic pump 150 and the electrical motor 130 or movable structure goes via a gear system 140 adapted to transform a movement of high velocity and low force to a movement of low velocity and high force.

The hydraulic body engaging portion 180' could for example comprise a hydraulic constriction or restraining device, or a volume filling device.

Figure 2A:
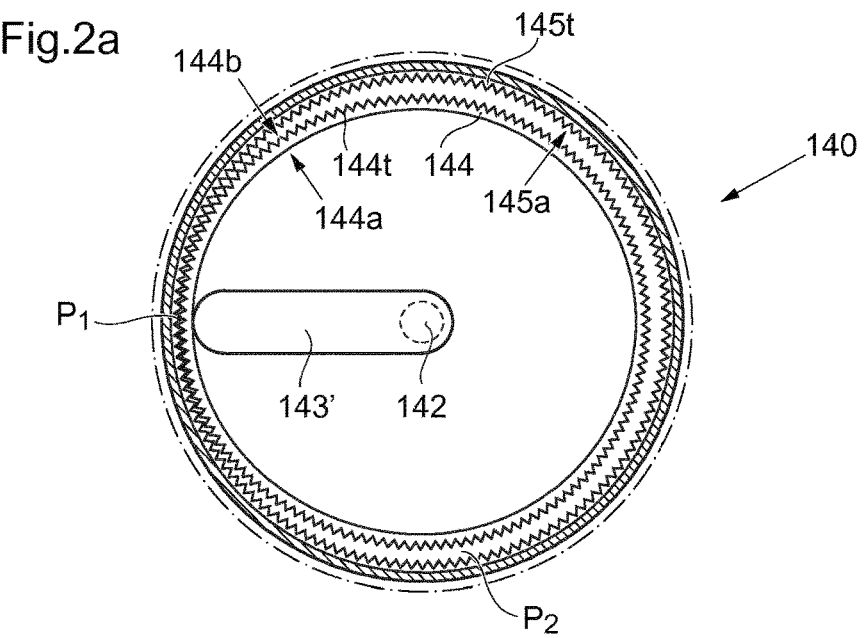
FIG. 2a shows a sectional top view of an embodiment of a gear system.

FIG. 2a shows an embodiment of an implantable gear system 140 for operation in an operation device 110. The gear system 140 is adapted to receive mechanical work having a first force and first velocity, and output mechanical work having a second, different force and a second different velocity. The gear system 140 comprises a force input 142 connected to an operable element 143' adapted to engage a first gear 144 having the shape of a hollow cylinder, comprising a first number of teeth 144t, for example 160, on the peripheral outside thereof, and a second gear 145 having the shape of a hollow cylinder, comprising a greater number of teeth 145t than the first gear, for example 162, on the inside surface thereof. The operable element 143' is adapted to engage the inside 144a of the first gear 144, such that the outside 144b of the first gear 144 is pressed against the inside 145a of the second gear 145 such that the teeth 144t of the first gear 144 are interengaged with the teeth 145t of the second gear 145 in position $P_1$ interspaced by positions (for example the position $P_2$) at which the teeth are not interengaged. The operation of the operable element 143' advances the position $P_1$ and thereby causes relative rotation between the first gear 144 and the second gear 145. In the embodiment shown in FIG. 2a, the second gear 145 comprises two more teeth 145t than the first gear 144, resulting in the first gear 144 rotating 2/160 or 1/80 of a revolution for each revolution that the operable element 143' performs, which results in a transmission of 80 times, i.e. the force output (149 of FIG. 2b) provides a force with 1/80 of the velocity and 80 times the force, thus increasing the force which can be exerted on a body engaging portion 180 of the operable implant 100, by for example an electrical motor, 80 times. In the embodiment shown in FIG. 2a the operable element slides radially against the inner surface of the first gear 144. For reducing the friction a lubricating fluid may be present in the gear system, it is further conceivable that the operable element 143' or the surface against which the operable implant 143' slides may comprise a self lubricating material, such as Graphalloy, Nyliol or PTFE.

Figure 2B:
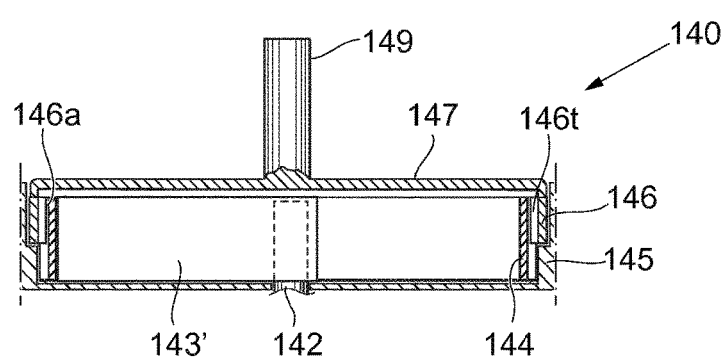
FIG. 2b shows a sectional side view of an embodiment of a gear system.

FIG. 2b shows the gear system 140 in a sectional side view, in an embodiment in which the gear system 140 comprises a third gear 146 having an inside 146a comprising the same amount of teeth 146t as the outside 144b of the first gear 144. The teeth 146t of the third gear 146 are adapted to interengage with the teeth of the first gear 144 such that the third gear 146 rotates in relation to the second gear 145, along with the interengaged position ($P_1$ of FIG. 2a). The third gear 146 is in connection with a force output 149 of the gear system 140 by means of a radially extending connecting structure 147 for transferring force from the third gear 146 to the force output 149.

Figure 2C:
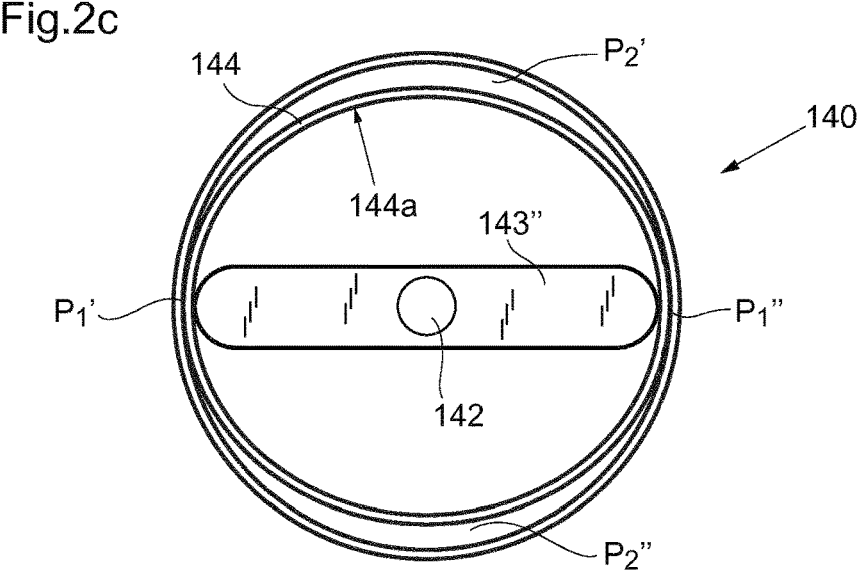
FIG. 2c shows a schematic top view of an embodiment of a gear system.

FIG. 2c shows an alternative embodiment of the medical device, wherein the operable element 143" is adapted to engage the inside 144a of the first gear 144 in two diametrically placed positions. The operable element 143" deflects the first gear 144 causing the first gear 144 to assume an oval shape, in an axial cross-section. The operable element 143" is adapted to maintain the first gear 144' deflected, such that the teeth of the first gear 144 are interengaged with the teeth of the second gear 145 in two angularly spaced, diametrically placed, positions $P_1'$ and $P_1''$. The two positions $P_1'$ and $P_1''$ are interspaced by positions at which the teeth are not interengaged, for example positions P$_2$' and P$_2$". In the embodiment of FIG. 2c, when the teeth of the first and second gears 144, 145 are interengaged in two positions, for the first gear 144 to be equally deflected, thus forming an oval shape, the difference in the number of teeth between the first gear 144 and the second gear 145 must be possible to divide by 2, such that the differing number of gears can be evenly distributed amongst the two areas between the first and second gears 144, 145 with positions in which the teeth of the first and second gears 144, 145 are not interengaged. Mathematically this can be expressed as if the first gear has x teeth, the second gear must have x+n*2 gears and the transmission provided by the gear system 140 is then calculated as: transmission=x/(x+n*2). In alternative embodiments (not shown) the operable element may be an operable element adapted to deflect the first gear 144 such that the first and second gears 144, 145 are interengaged at three, four or more positions, for the purpose of creating an even deflection of the first gear 144, the difference in the number of teeth between the first gear 144 and the second gear 145 must correspond to the number of contacting portions. In a more general mathematical expression, the relation can be expressed such that the second gear must have x+n*m number of teeth, where n is a constant selected based on the desired transmission and in is the number of positions in which the teeth of the first and second gears are interengaged.

Figure 3A:
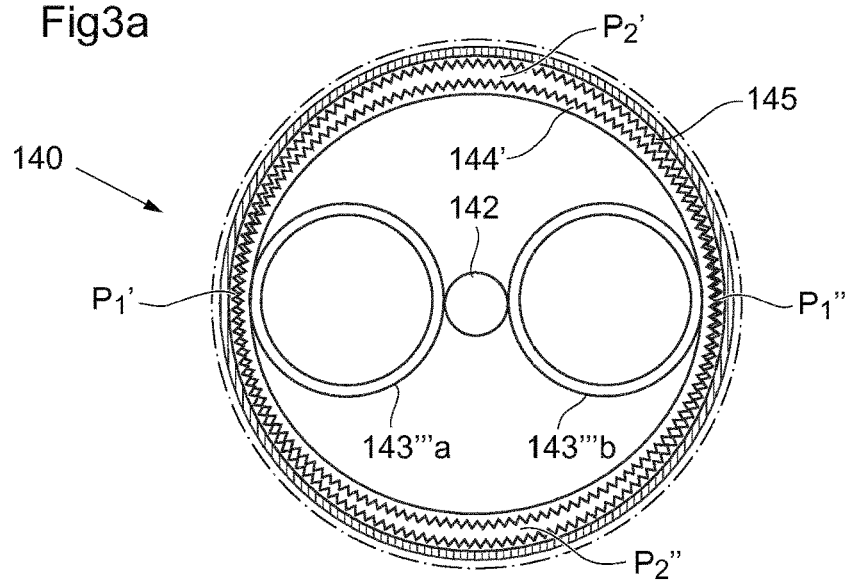
FIG. 3a shows a sectional top view of an embodiment of a gear system.

FIG. 3a shows an embodiment in which the operable element comprises a planet gear in which the force input 142 comprises a central gear in connection with a first and second planet gear 143'''a, 143'''b, which in turn deflects the first gear 144 such that the teeth of the first gear 144 interengages the teeth of the second gear 145 in a first and second position P$_1$', P$_1$'. Analogously to what was previously described with reference to FIG. 2c, for the first gear 144' to be equally deflected, thus forming an oval shape, the difference in the number of teeth between the first gear 144 and the second gear 145 must be possible to divide by 2, such that the differing number of gears can be evenly distributed amongst the two areas between the first and second gears 144, 145 with positions in which the teeth of the first and second gears 144, 145 are not interengaged.

The planetary gear of FIG. 3a further increases the transmission of the gear system with the transmission resulting from the difference in the number of teeth between the central gear 142 and the planetary gears 143'''a, 143'''b, i.e. the total transmission of the gear system 140 equals the transmission provided by the planetary gear plus the transmission provided by the difference in number of teeth between the first gear 144 and the second gear 145.

Figure 3B:
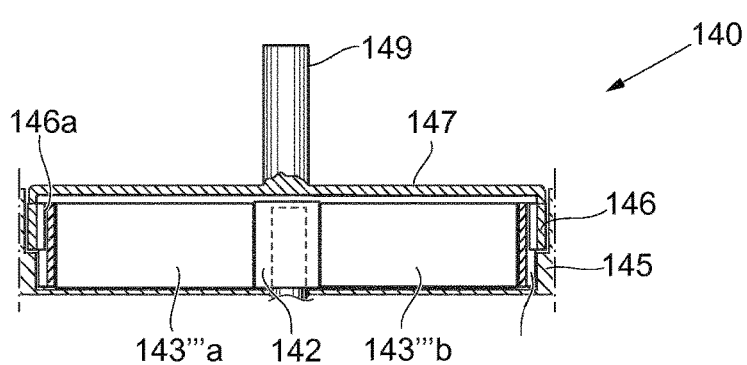
FIG. 3b shows a sectional side view of an embodiment of a gear system.

FIG. 3b shows the gear system 140 in a sectional side view. In the embodiment shown in FIG. 3b, the gear system 140 also comprises a third gear 146 analogously to the third gear described with reference to FIG. 2b, such that the third gear 146 rotates along with the first gear and the interengaged positions P1', P1". The third gear 146 is in connection with a force output 149 of the gear system 140 by means of a radially extending connecting structure 147 for transferring force from the third gear 146 to the force output 149.

Figure 3C:
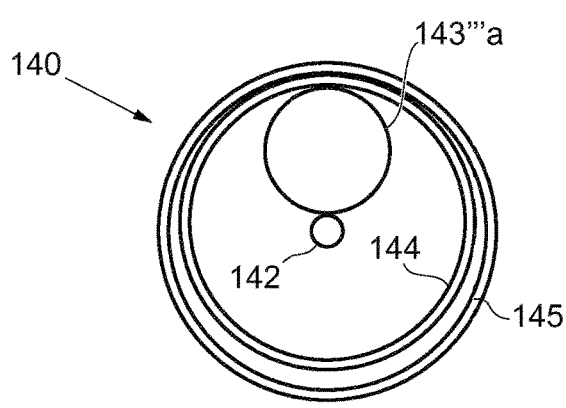
FIG. 3c shows a schematic top view of an embodiment of a gear system.

FIG. 3c shows an alternative embodiment of the planetary gear, in which the planetary gear only comprises one planet gear 143'''a in connection with the central gear 142. The embodiment functions similarly to the embodiment described with reference to FIG. 2a, the difference being that additional transmission is provided by the planetary gear.

Figure 3D:
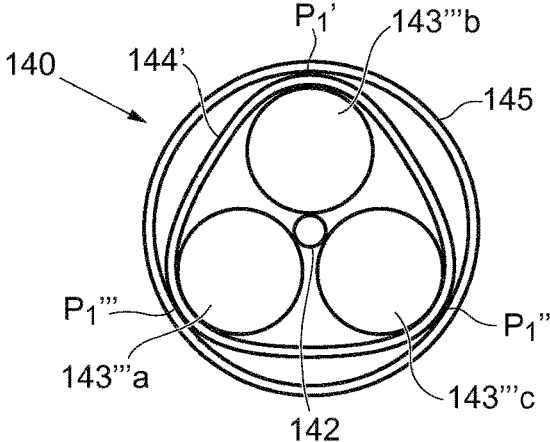
FIG. 3d shows a schematic top view of an embodiment of a gear system.

FIG. 3d shows an embodiment in which the planetary gear comprises three planet gears 143'a, 143'b, 143'c, each deflecting the first gear 144', such that the first gear 144 is pressed against the second gear 145 in three angularly spaced (substantially with 120° between each) contacting positions P$_1$', P$_1$", P$_1$'". Analogy to the other embodiments described, the difference in the number of teeth between the first gear 144 and the second gear 145 must correspond to the number of contacting portions, i.e. in the embodiment shown in FIG. 3d, the difference must be possible to divide by three for the first gear 144 to be evenly deflected.

In alternative embodiments, the gears of the planetary gears in any of the embodiments described with reference to FIGS. 3a-3d are gears without teeth and thus only uses friction to interengage each other. The central gear is thus connected to, and propels, the planet gears by means of a friction based connection.

The gear system 140 of any of the embodiment in FIGS. 2a-3d could for example be made of a metallic material, plastic material or ceramic material. In one embodiment, the gear system is made from non metallic and/or non-magnetic material, such that the gear system does not affect the energy transfer to an implantable energy receiver. The gear system may be lubricated with a biocompatible lubricant, such as hyaluronic acid, and may, for that purpose, be placed inside a reservoir adapted to hold a hydraulic fluid, which also may serve as a lubricant. The gear system may be encapsulated by an enclosure for preventing bodily fluids from affecting the gear system and/or the in-growth of human tissue in the gear system and/or the leakage of hydraulic and/or lubricating fluids. The enclosure may be a non-metallic and/or non-magnetic enclosure, such that the material of the enclosure does not affect the ability of transferring wireless energy to a wireless energy receiver of the operable implant. The gear system may be encapsulated separately, or may be encapsulated along with an electrical motor of the operation device, or additional components of the operation device.

Figure 4:
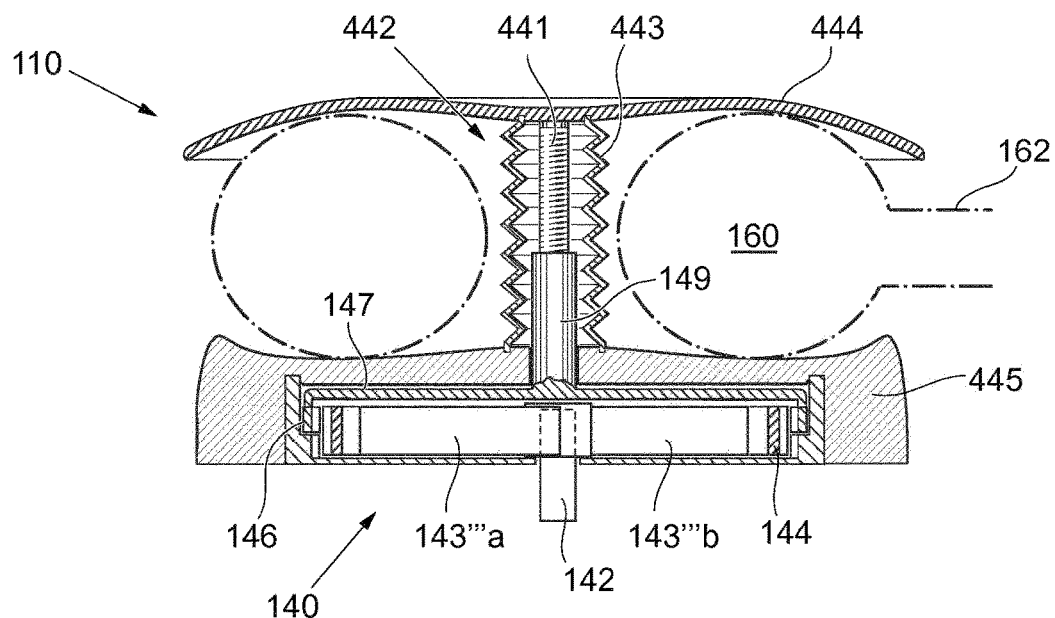
FIG. 4 shows a sectional side view of an embodiment of an implantable hydraulic operation device.

FIG. 4 shows an embodiment of an implantable operation device 110 of an operable implant 100 comprising the gear system 140 further described with reference to FIG. 3a. The gear system 140 comprises a force input 142, which for example could be connected to an electrical motor adapted to transfer electrical energy to mechanical work (such as any of the electrical motors described herein). The force input 142 is connected to the planetary gears 143'''a, 143'''b, which in turn operates the first gear 144 of the gear system 140 (further described with reference to FIG. 4). A force output 149 is connected to the gear system 140 via the third gear 146 of the gear system 140 and a radially extending connecting structure 147. The force output 149 is, in the embodiment described in FIG. 4, a hollow shaft equipped with inner threads (not shown) adapted to engage outer threads of a threaded member 441, such that the interaction between the hollow shaft 149 and the threaded member 441 transforms the radially rotating force generated by the operation of the gear system 140, to a linear, axially reciprocating force. The threaded member 441 is in the embodiment shown in FIG. 4 connected to a radially extending engaging member 444 adapted to engage a reservoir 160, adapted to contain a hydraulic fluid. In the embodiment shown in FIG. 4, the reservoir 160 is a torus shaped reservoir 160 adapted to be compressed, such that the volume in the reservoir decreases, pressing hydraulic fluid from the reservoir 160 to a fluid conduit 162 and further to a hydraulically operable body engaging portion 180 of the operable implant 100.

The operation device 110 further comprises a seat portion 445 functioning as an anvil in relation to the compression of the reservoir 160, and at the same time functioning as an enclosure, at least partially enclosing the gear system 140. The seat portion 445 connects to a portion of the enclosure 442 adapted to enclose the force output 149 and the threaded member 441, such that the threaded member 441 and force output 149 is sealed from bodily fluids. The connection of the seat portion 445 with the portion of the enclosure 442 enclosing the force output 149 and the threaded member 441 removes the need for a seal between the seat portion 445 and the force output 149 which facilitates the operation of gear system 140 and makes it possible for the gear system 140 to be hermetically enclosed. The portion of the enclosure 442 enclosing the force output 149 and the threaded member 441 comprises a pleated section 443 functioning as a bellow. The pleated section 443 is adapted to allow in-growth of fibrotic tissue without the mobility of the pleated section 443 being affected. The reservoir 160 is preferably made from a resilient and/or elastic material, such as silicone, and may be covered with a Parylene® coating to better resist the strain and wear induced by the compression of the reservoir 160. The force input 142 may be sealed against the bottom part of the enclosure, or alternatively, an operation device, such as an electrical motor, may be placed in the same sealed environment, such that sealing between the force input 142 and the enclosure is unnecessary.

Figure 5:
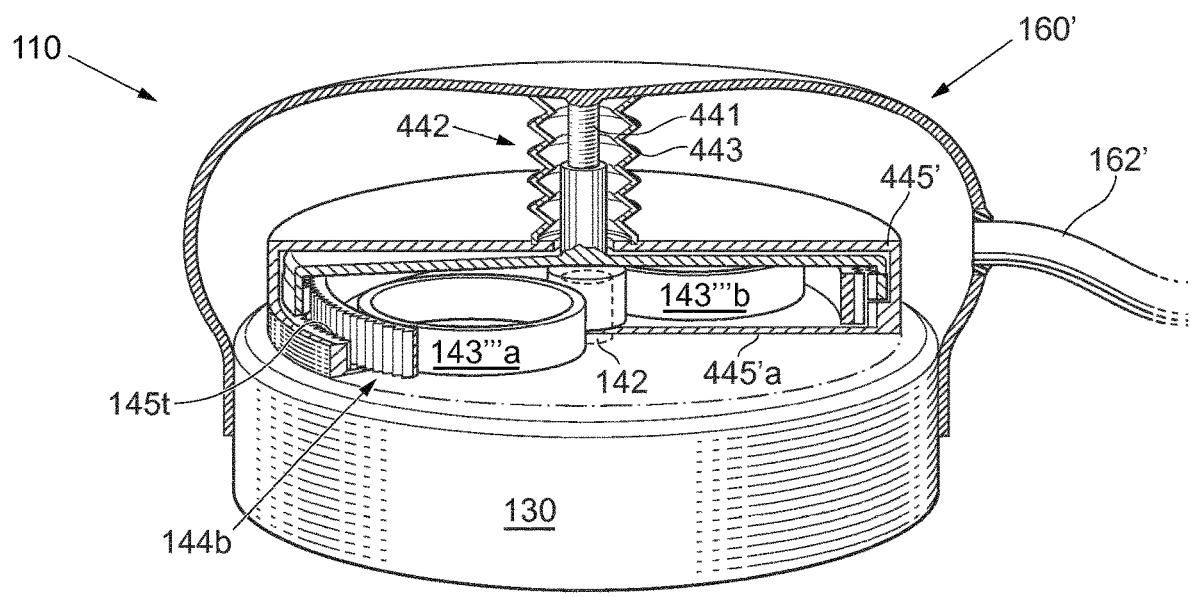
FIG. 5 shows an elevated perspective view of an embodiment of an implantable hydraulic operation device in section.

FIG. 5 shows an embodiment of the operation device 110 in which the gear system is placed inside the reservoir 160', such that the reservoir 160' at least partially surrounds the gear system 140. The embodiment shown in FIG. 5 further comprises an electrical motor 130 connected to the force input 142 of the gear system 140. The force transfer between the electrical motor 130 and the gear system 140 may comprises a shaft which exits a first enclosure enclosing the electrical motor 130 and enters a second enclosure enclosing the gear system 140 within the reservoir 160', in which case both enclosures needs to be rotatably penetrated by the shaft, which creates friction at the seals. In an alternative embodiment, the enclosure enclosing the electrical motor 130 and the enclosure enclosing the gear system 140 are connected, such that a single enclosed space is created enclosing both the gear system 140 and the electrical motor 130, in which case the force transferring shafts does not need to be sealed. The enclosure 445' thus sealingly connects to the enclosure enclosing the electrical motor 130. The force output 149 in connection with the threaded member 441 functions the same way as described with reference to FIG. 4, with the difference that the threaded member 441 is connected directly to a movable wall portion of the reservoir 160 such that the volume of the reservoir 160' is changed by the threaded member 441 moving the movable wall portion. The reservoir 160' is connected to a fluid conduit 162', such that the fluid in the reservoir 160' is transported from the reservoir 160', through the fluid conduit 162' and to a hydraulically operable body engaging portion of the operable implant, such that the compression of the reservoir 160' indirectly exerts a force on a portion of the body of the patient.

In the embodiment shown in FIG. 5, the operable elements 143'''a, 143'''b are connected to the force input and the first gear by means of friction, i.e. the operable elements 143'''a, 143'''b does not comprise any teeth.

In some embodiments, the placing of the gear system inside the reservoir enables the gear system 140 to be lubricated by a hydraulic fluid contained in the reservoir 160. The fluid may be a biocompatible lubricating fluid, such as hyaluronic acid, an isotonic solution or a glycerol-based fluid etc.

The fundamental principle of the gear system 140 described above may be implemented in combination with any of the operable implants herein. The advantages of the gear system 140 includes: low friction, high transmission in a compact format, good precision, low noise and that the gear system 140 may function without lubrication.

FIG. 6 shows an embodiment of an implantable operation device 110 for operating an operable implant. The operation device 110 comprises an implantable electrical motor comprising coils 132 and magnets 133. Energizing of the coils 132 generates a magnetic field by the electrical current in the coil winding 132' and the coil core 132", magnetically connecting with the magnets 133. The magnets 133 are fixated to a rotatable structure 135, such that sequential energizing of the coils 132 propels the magnets 133 and causes the rotatable structure 135 to rotate. The magnetic connection between the coils 132 and the magnets 133 is positioned in the periphery of the operation device 110 such that the generated torque should be as large as possible. The rotatable structure 135 comprises a radially extending portion 147 transferring the force generated by the coils 132 and magnets 133 in the periphery of the operation device 110 to the force input 142 of the gear system in connection with the operable elements 143'''a, 143'b. The operable elements engages and deflects the first gear 144 of the gear system 140 such that the outside of the first gear 144 is pressed against the inside of the second gear 145 such that the teeth of the first gear 144 are interengaged with the teeth of the second gear 145 in two positions interspaced by positions at which the teeth are not interengaged. The second gear 145 has a greater number of teeth than the first gear 144, on the inside surface thereof, and the operation of the operable element 143'''a, 143'''b thus advances the interengaged positions and thereby causes relative rotation between the first gear 144 and the second gear 145.

The gear system further comprises a third gear 146 having the shape of a hollow cylinder. The inside of the third gear 146 comprises the same amount of teeth as the outside of the first gear 144, and the teeth of the third gear 146 is adapted to interengage the teeth of the first gear 144 such that the third gear 146 rotates in relation to the second gear 145, along with the at least one interengaged position. The third gear 146 is connected to a radially extending portion 147 connecting the third gear 146 and the centrally placed force output 149 of the gear system.

Both the first 144, second 145 and third 146 gears have smaller diameters than the portion of the rotatable structure 135 at which the magnets 133 are fixated, and smaller diameters than the portion of the enclosure 111c fixating the coils 133. The gear system can thus be placed inside of the electrical motor, such that the coils 132 and magnets 133 axially overlaps the gear system. The electrical motor and gear system being placed in the same axial plane makes it possible to package the operation device 110 in a thin enclosure 111, which for example makes the operation device 110 suitable for subcutaneous implantation.

The embodiment of the operation device described with reference to FIG. 6 comprises a threaded member in the form of a worm shaft 441' having a first spiral groove in a first direction and a second spiral groove in a second direction. The worm shaft 441' is engaged by an operable portion 446 connected to a radially extending engaging member 444 in turn adapted to compress the reservoir 160. The rotation of the worm shaft 441' causes reciprocation of the operable portion 446 in the spiral grooves, by the operable portion 446 switching from engaging the first spiral groove, to the operable portion 446 engaging the second spiral groove at the end portions of the worm shaft 441'. The operation of the worm shaft 441' thus makes the reservoir 160 perform a pumping action transporting fluid in the first and second direction in the fluid conduit 162.

In the operation device 110 of FIG. 11, the coils 132 are placed in a sealed space further comprising a battery 190, adapted to power the electrical motor, and a control unit 195 adapted to control the electrical motor and/or additional operable elements of the operable implant. The battery 190 and/or control unit 195 is in connection with a lead 192 connecting the battery 190 and/or control unit 195 to a wireless energy receiver and/or a wireless communication unit and/or an additional battery 190 for supplying the operation device with additional energy. In alternative embodiments, where the electrical motor is powered directly from a wireless energy receiver, the battery 190 is only adapted to power the control unit 195.

FIG. 7 shows an operation device 110 similar to the operation device 110 shown with reference to FIG. 6, the difference being that in the operation device in FIG. 7, the magnets 133 are fixated to a rotatable structure 135 comprising a radially extending portion 147 adapted to transfer the force from the periphery of the rotatable structure 135 to the center of the rotatable structure 135 below the electrical motor and the gear system. The radially extending portion 147 transferring force to the force input 142 of the gear system, which in turn engages the operable elements 143'''*a*, 143'''*b*.

In the embodiment of FIG. 7, the coils 132 are placed and sealed in an individual coil enclosure 131, such that the coils 132 are further isolated from the bodily fluids of the patient and/or from lubricating fluids used in the gear system and/or from hydraulic fluids adapted to transfer force from the reservoir 160 to a hydraulically operable body engaging portion, through the fluid conduit 162.

FIG. 8 shows yet an alternative embodiment of an operation device 110 similar to the operation device 110 shown with reference to FIGS. 6 and 7. In the embodiment shown with reference to FIG. 8, the rotatable structure 135 comprising the magnets 133 is adapted to be propelled by coils 132 mounted to a portion 111*c* of the enclosure 111 having a peripheral diameter larger than the diameter of the rotatable structure 135 where the magnets 133 are mounted. The coils 132 are thus placed radially outside the magnets 133 and are sealed from the rest of the operation device 110 and from the bodily fluids of the patient by means of a coil enclosure 131. The rotatable structure 135 is connected to a force input 142 in the center of the rotatable structure, which in turn is adapted to engage the operable elements 143'''*a*, 143'''*b* of the gear system (as described in further detail in other embodiments herein). The embodiment shown in FIG. 8 places all rotating parts of the operation device 110 centrally in the operation device 110 which further insulates the rotating parts of the operation device 110, such that noise created by the moving parts are less likely to propagate through the enclosure 111 of the operation device 110 and the body of the patient.

FIG. 9 shows yet an alternative embodiment of the operation device, in which the magnets 133 are integrated in the operable elements 143'''*a*, 143'''*b* of the operation device 110. The operable elements 143'''*a*, 143'''*b* are rotatably connected to a connecting structure 143*c* and engages and deflects the first gear 144 of the gear system as the magnetic attraction force generated by the coils sequentially attracts the magnets 133 propelling the operable elements 143'''*a*, 143'''*b*. The portion of the operable elements 143'''*a*, 143'''*b* to which the magnets 133 are connected have a larger diameter than the portion of the operable elements 143'''*a*, 143'''*b* engaging the first gear 144 of the gear system, such that the magnets 133 can be placed in close connection with the coils 132. The distance between the coils 132 and the magnets 133 could for example be as little as one of 50 μm, 100 μm, 200 μm, 400 μm, 600 μm, 800 μm, 1 mm, 2 mm, 3 mm, or 5 mm, depending on the overall dimensions of the operation device 110 and the magnetic force created by the coils 132.

FIGS. 10*a* and 10*b* shows and embodiment of an operation device similar to the embodiments shown with reference to FIGS. 6-9. The difference between the embodiments of FIGS. 6 and 10*a* is that the embodiment of FIG. 10*a* comprises an axial electrical motor 130' adapted to propel the force input 142 of the gear system. The axial electrical motor 130' comprises a set of coils 132 circularly distributed around a rotational axis of the electrical motor 130' and a set of magnets 133 connected to a radially extending rotatable structure 135 axially overlapping the magnets 133, such that sequential energizing of the coils 132 magnetically axially propels the magnets 133 and causes rotation of the rotatable structure 135 connected to the force input 142 of the gear system in connection with the operable elements 143'''*a*, 143'''*b*, which in the embodiments shown in FIG. 10*a* is planetary gears 143'''*a*, 143'''*b*. The gear system and the axial electrical motor 130' are positioned coaxially, along the rotational axis of electrical motor 130'.

The operable elements 143'''*a*, 143'*b* engages and deflects the first gear 144 of the gear system such that the outside of the first gear 144 is pressed against the inside of the second gear 145 such that the teeth of the first gear 144 are interengaged with the teeth of the second gear 145 in two positions interspaced by positions at which the teeth are not interengaged. The second gear 145 has a greater number of teeth than the first gear 144, on the inside surface thereof, and the operation of the operable element 143'''*a*, 143'*b* thus advances the interengaged positions and thereby causes relative rotation between the first gear 144 and the second gear 145.

The force output 149 of the gear system generates a reciprocating force compressing a reservoir 160, in the same manner as described in further detail with reference to FIGS. 4 and 5. The embodiment of FIG. 10*a* further comprises a sealed space below the axial electrical motor 130' housing a battery 190, adapted to power the axial electrical motor 130', and a control unit 195 adapted to control the axial electrical motor 130' and/or additional operable elements of the operable implant. The battery 190 and/or control unit 195 is in connection with a lead 192 connecting the battery 190 and/or control unit 195 to the coils 132 for sequentially energizing the coils 132 and thereby operating the axial electrical motor 130'.

FIG. 10*b* shows the rotatable structure 133, to which the magnets 133 and force input 142 of the gear system is fixated, the rotatable structure 135 is a non-metallic disc, such that the individual magnets 133 are unaffected by their fixation to the rotatable structure 135. FIG. 10*b* also shows the coils 132 comprising the coil winding 132' and the coil core 132" connected to a core structure 132*s* adapted to position the magnets 133 and act as a magnetic interconnect between the cores 132" of each of the coils 132. The coils 132 are circularly distributed around the rotational axis of the operation device 110 and connected to the core structure 132*s*, such that the cores 132" of the individual coils 132, and the helix of the windings 132' extends axially, parallel to the rotational axis of the electrical motor and gear system.

FIG. 11a shows an embodiment similar to the embodiment shown in FIG. 10a, the difference being the axial electrical motor 130' comprises two sets of circularly arranged coils 132, each arranged to a magnetizable core structure 132s magnetically connecting the cores 132". The rotatable structure 135 comprising the magnets 133 and the two sets of coils 132a, 132b are coaxially positioned such that both the first and second sets of coils 132a, 132b overlaps the magnets of the rotatable structure 135, such that the first set of coils 132a propels the magnets 133 on the first side thereof, and the second set of coils 132b propels the magnets 133 on the second side thereof. In alternative embodiments, it is conceivable that the rotatable structure/disc 135 between the sets of coils 132a, 132b, comprises two sets of magnets, one set on each side, and it is conceivable that the first and second set of magnets are radially offset, such that the lag of the electrical motor can be made smaller. The battery 190 and/or control unit 195 is in connection with a leads 192 connecting the battery 190 and/or control unit 195 to the first and second sets of coils for sequentially energizing the coils and thereby operating the axial electrical motor 130'.

Figure 12:
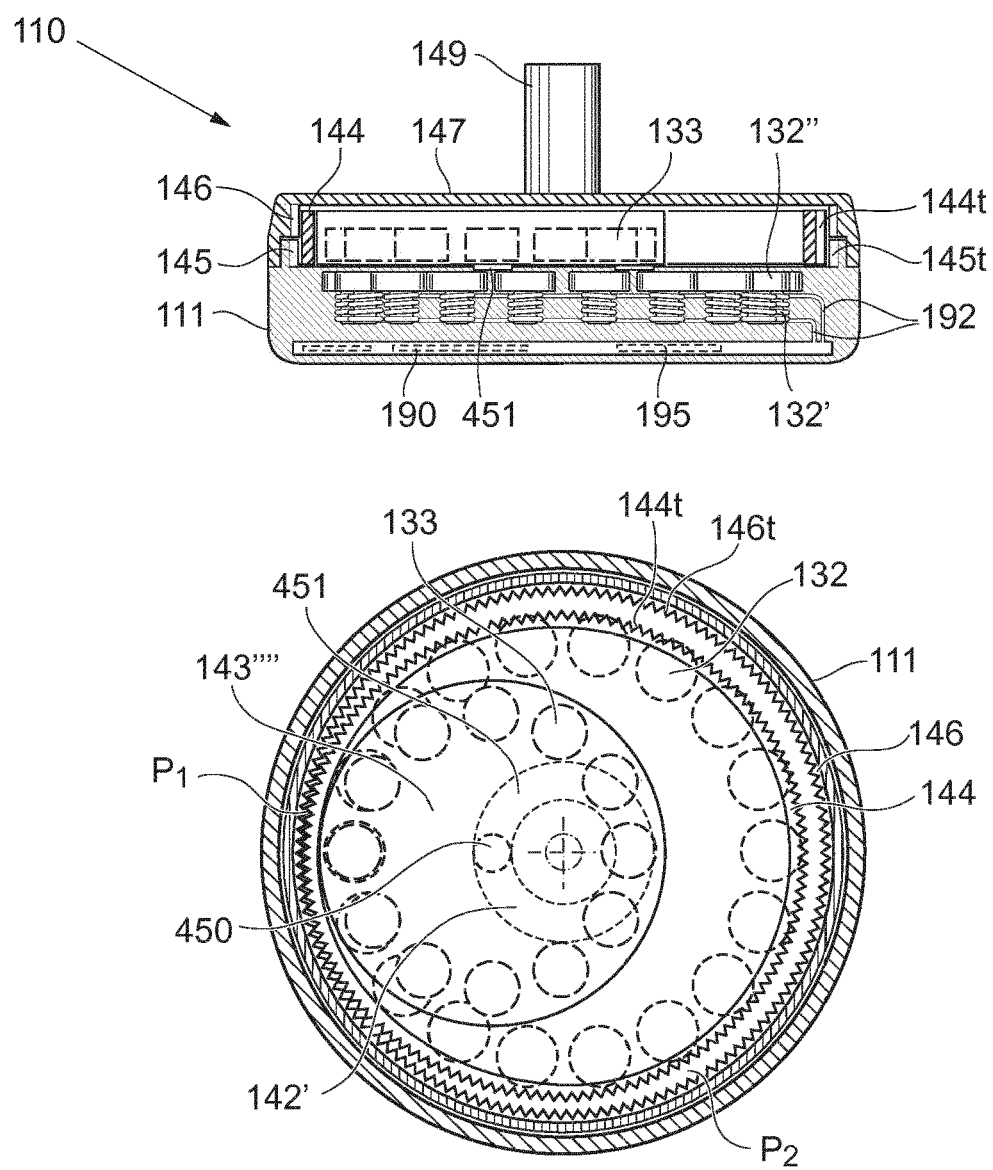
FIG. 12 shows a sectional side view and a sectional top view of an embodiment of an implantable operation device, FIGS. 13a-14b schematically shows embodiments in which a gear system is comprised of a plurality of gear systems.

FIG. 12 shows an embodiment of an operation device 110 in which the coils 132 are positioned inside of an enclosure 111 made from a cast material enclosing the coils 132 and the sealed space comprising the battery 190 and control unit 195. The coils 132 are connected to the battery 190 and control units 195 by means of leads 192, such that the coils 132 can be sequentially energized for propelling the magnets 133. The magnets 133 are integrated in an operable element 143"" fixated to a guide shaft 450 adapted to be guided by a guide recess 451. The coils 132 are circularly distributed around the rotational axis of the operation device 110 such that the cores 132" of the individual coils 132, and the helix of the windings 132' extends axially, parallel to the rotational axis of the operation device 110.

The operable element 143' is adapted to be propelled by the magnetic connection between the coils 132 in the enclosure 111 and the magnets 133. The operable element 143"" engages a first gear 144 having the shape of a hollow cylinder, comprising a first number of teeth 144t, for example 160, on the peripheral outside thereof, and a second gear 145 having the shape of a hollow cylinder, comprising a greater number of teeth 145t than the first gear 144, for example 162, on the inside surface thereof. The outside of the first gear 144 is pressed against the inside of the second gear 145 such that the teeth 144t of the first gear 144 are interengaged with the teeth 145t of the second gear 145 in position P$_1$ interspaced by positions (for example the position P$_2$) at which the teeth 144t, 144t are not interengaged. The operation of the operable element 143' advances the position P$_1$ and thereby causes relative rotation between the first gear 144 and the second gear 145. The gear system of the operation device of FIG. 12 further comprises a third gear 146 having an inside comprising the same amount of teeth 146t as the outside of the first gear 144. The teeth 146t of the third gear 146 are adapted to interengage with the teeth 144t of the first gear 144 such that the third gear 146 rotates in relation to the second gear 145, along with the interengaged position P$_1$. The third gear 146 is in connection with a force output 149 of the gear system 140 by means of a radially extending connecting structure 147 for transferring force from the third gear 146 to the force output 149.

The implantable operation device 110 described with reference to FIG. 12 allows all electrical components, in particular the coils 132, battery 190 and control unit 195 to be entirely sealed from the ambient environments, i.e. both from bodily fluids, when implanted, and from the additional components of the operation device. Furthermore, it has few moving parts, and the magnets 133 can be entirely enclosed by the operable element 143', which protects the magnets 133 from corrosion and wear. The surface of the enclosure 111 engaging the operable element 143"" is preferable made from a wear resistant material, such as a ceramic material, and preferably is also the operable element 143"" enclosing the magnets 133 made from a wear resistant material such as a ceramic material. The material of the enclosure being placed between the coils 132 and the magnets 133 is preferably non-metallic and non-magnetic, such that the magnetic connection between the coils 132 and magnets 133 are minimally affected.

Figure 13A:
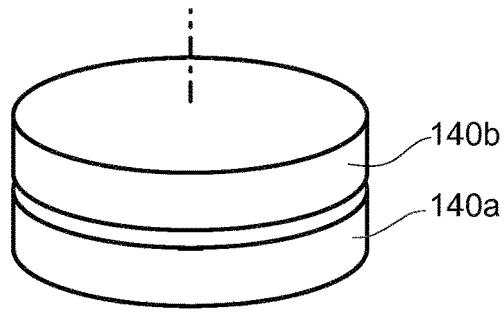

FIG. 13a schematically shows how two gear systems 140a, 140b may be positioned in series, such that they function as a single gear system having a transmission which equals the transmission of the first gear 140a system times the transmission of the second gear system 140b. The gear systems 140a, 140b may be the same type, e.g. gear systems of the type disclosed with reference to FIGS. 2a-5. Alternatively, one of the gear systems 140a, 140b may be a gear system of the type for example described with reference to FIGS. 2a-5, and the other gear system 140a, 140b, may be a gear system of a different type, such as a planetary gear system or a regular gear wheel system. The first and second gear systems 140a, 140b, may have the same transmission, or may have different transmission.

In the embodiment of FIG. 13a, the first and second gear systems are positioned coaxially (further described for example with reference to FIG. 8) such that the first gear system 140a can transfer force to the second gear system 140b axially. The force transferred between the first and second gear systems are preferably rotational force, which may be transferred centrally in both gear systems, peripherally in both gear systems, or from the center in the first gear system 140a to the periphery of the second gear system 140b.

Figure 13B:
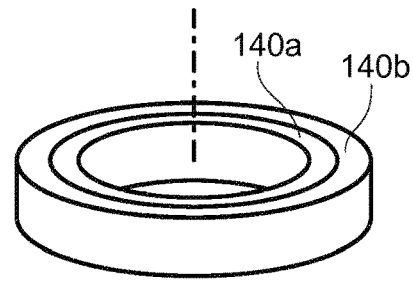

FIG. 13b, schematically shows an alternative embodiment of the gear system in which a first and second gear system 140a, 140b are connected in series. In the alternative embodiment shown in FIG. 13b, the first gear system 140a is positioned "inside" of the second gear system 140b (further described for example with reference to FIG. 16). In the alternative shown, both the first and the second gear system 140a, 140b are gear systems according of the type described with reference to FIGS. 2a-5, the first gear of the first gear system is connected to the operable element of the second gear system, such that the movement of the first gear of the first gear system relative to the second gear of the first gear system propels the operable element of the second gear system, 140b. The first gear system may have the operable element according to any one of the embodiments herein, which may, in the embodiments in which the operable element comprises a planetary gear, result in a total transmission being the transmission of the planetary gear times the transmission of the first gear system 140a times the transmission of the second gear system 140b.

Figure 14A:
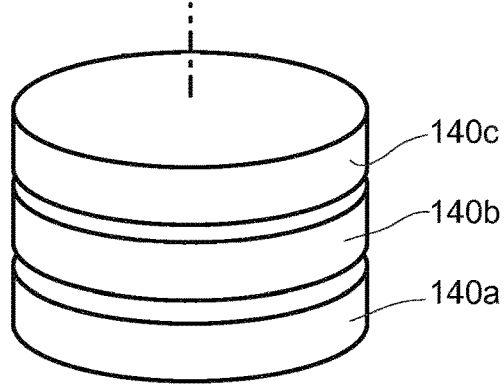
Figure 14B:
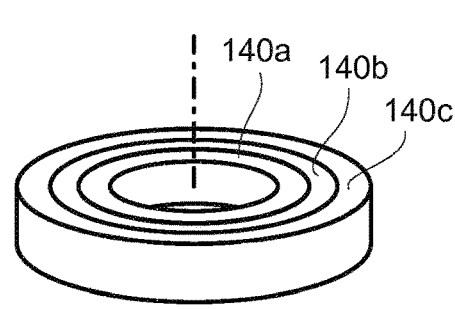

FIG. 14a shows yet another alternative, in which three gear systems are stacked coaxially and connected in series, such that the transmission is further enhanced. The total transmission thus results in the transmission of the first gear system times the transmission of the second gear system times the transmission of the third gear system. Analogously, FIG. 14b shows a system where a first 140a, second 140b and third 140c gear systems placed radially inside of each other and coupled in series in the same way as the first and second gear systems are connected in for example FIG. 13*b* and FIG. 16.

Figure 15:
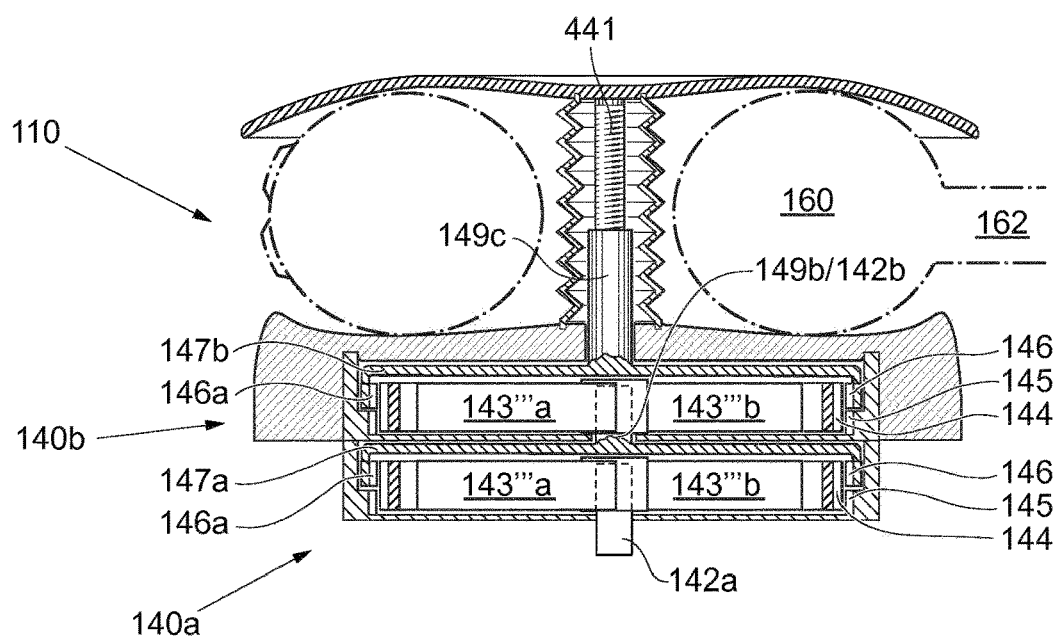
FIG. 15 shows a sectional side view of an embodiment of a hydraulic operation device comprising two gear systems.

FIG. 15 shows an embodiment of the operation device 110 of an operable implant similar to the embodiment described with reference to FIG. 4, with the difference that the embodiment shown in FIG. 15 comprises a first and second gear system 140*a*, 140*b* positioned coaxially, along the rotational axis of the first and second gear systems 140*a*, 140*b* and connected in series. Both the first and second gear systems 140*a*, 140*b* comprises force inputs 142*a*, 142*b* propelling the operable elements 143"*a*, 143"'*b* being part of a planetary gear system. The operable elements, 143"'*a*, 143"'*b* in turn engages a first gear 144 having the shape of a hollow cylinder, comprising a first number of teeth, on the peripheral outside thereof. The first gear 144 has a deflectable wall adapted to be engaged and deflected by the two operable elements 143"'*a*, 143"'*b*, such that the outside of the first gear 144 is pressed against the inside of the second gear 145 such that the teeth of the first gear 144 are interengaged with the teeth of the second gear 145 in two positions interspaced by positions at which the teeth are not interengaged. The second gear 145 has a greater number of teeth than the first gear 144, on the inside surface thereof, and the operation of the operable element 143"'*a*, 143"'*b* thus advances the interengaged positions and thereby causes relative rotation between the first gear 144 and the second gear 145.

The first and second gear systems 140*a*, 140*b* further comprises a third gear 146 having the shape of a hollow cylinder. The inside 146*a* of the third gear 146 comprises the same amount of teeth as the outside of the first gear 144, and the teeth of the third gear 146 is adapted to interengage the teeth of the first gear 144 such that the third gear 146 rotates in relation to the second gear 145, along with the at least one interengaged position. The third gear 146 of the first gear system 140*a* is connected to a radially extending connecting structure connecting the peripherally placed third gear 146 and the centrally placed force output 149*a* of the first gear system/force input 142*b* of the second gear system 140*b*. The first and second gear systems 140*a*, 140*b* are thus connected in series by the third gear 146 of the first gear system 140*a* being connected to the force input 142*b* of the second gear system 140*b*.

In the embodiment shown in FIG. 15 the force output 149*b* of the second gear system 140*b* comprises a hollow shaft connecting to a threaded member 441 which in turn operates a reservoir 160. The details of the operation of the threaded member 441 are further described with reference to FIG. 4. Even if the first and second gear systems 140*a*, 140*b* are described in relation to a hydraulic embodiment having a torus shaped reservoir 160 changing volume for pushing hydraulic fluid to a hydraulically operable body engaging portion, the details of the first and second gear systems 140*a*, 140*b* connected in series may be used in any of the other embodiments described herein. Examples of alternative embodiments include: the threaded member 441 being in direct connection with a body engaging portion, which could be in direct connection with the body of the patient, and the first and second gear systems 140*a*, 140*b* being connected to a pump for pumping hydraulic fluid; the pump could for example be a peristaltic pump or a membrane pump.

The first and second gear systems 140*a*, 140*b* is preferable enclosed in the same sealed spaced, such that the force transfer between the first and second gear systems 140*a*, 140*b* can take place without having to transfer force through a sealing. In the embodiment shown in FIG. 8 the force input 142*a* of the first gear system 140*a* penetrates the enclosure, however, in alternative embodiments, an operation device, such as an electrical motor, is tightly fitted to the gear system enclosure, or enclosed along with the first and/or second gear system 140*a*, 140*b*, such that no penetrated sealing is required between the first and second gear systems 140*a*, 140*b*.

Figure 16:
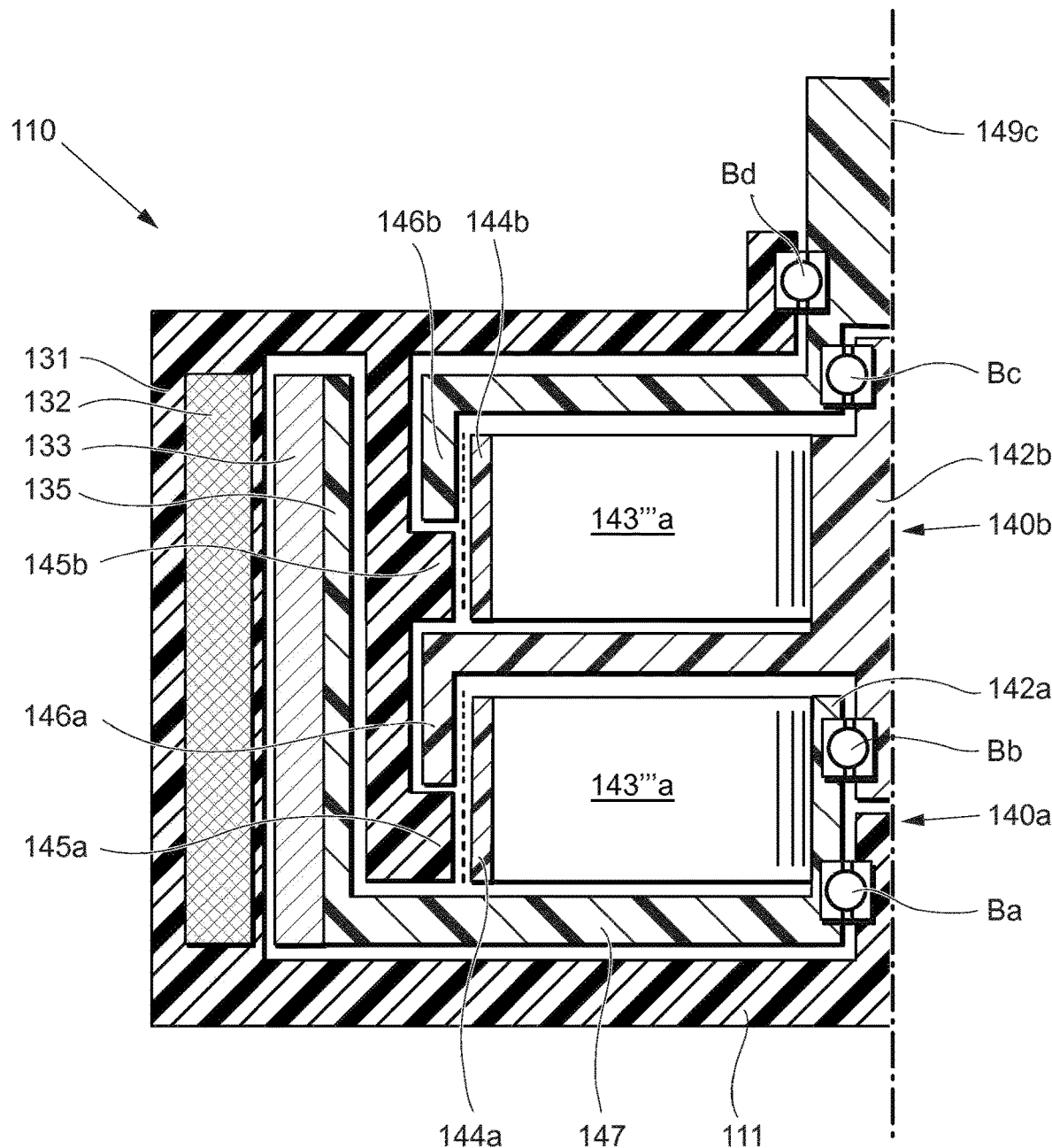
FIG. 16 shows a sectional side view of the left portion of an embodiment of a gear system comprised of two gear systems.

FIG. 16 shows an operation device 110 comprising an alternative embodiment of the gear system 140, similar to the embodiment shown in FIG. 15. FIG. 16 depicts the left half of the operation device 110 in section. The operation device comprises a housing 111, which is a rigid part for example made from a stiff polymer material, a ceramic material or a metal. A portion of the housing 111 constitutes a coil enclosure 131, enclosing a coil 132, such that the coil 132 is sealed from bodily fluids and scar tissue when implanted. The coil 132 is one element of an electrical motor further comprises magnets 133 mounted to a rotatable structure 135 having a radially extending portion 147 adapted to transfer force from the periphery of the operation device to the center thereof. The rotatable structure 135 is rotatably mounded to the housing 110 by means of a first bearing Ba such that the rotatable structure can rotate in relation to the housing 110. The central portion of the rotatable structure 135 constitutes the force input to the first gear system 140*a* adapted to propel the operable element 143"'*a* such that the operable element 143"'*a* engages the first gear 144*a* of the first gear system 140*a* causing the teeth of the first gear 144*a* to interengage with the teeth of the second and third gears 145*a*, 146*a* of the first gear system 140*a*. The second gear 145*a* of the first gear system 140*a* has more teeth than the first gear 144*a* of the first gear system 140*a*, causing the contacting portions between the first 144*a* and second gear 145*a* to rotate (as further described above). The third gear 146*a* has the same amount of teeth as the first gear 144*a* and thus rotates along with the contacting positions. The third gear 146*a* is connected to a radially extending portion 147 adapted to transfer the force from the periphery to the central portions of the operation device and to the force input 140*a* to the second gear system 140*b*. The structure comprising the third gear 146*a*, the radially extending structure 147 and the force input 142*b* of the second gear system 140*b* is rotatably connected to the force input 142*a* of the first gear system 140*a* by means of a bearing Bb, and the force output 149*c* from the second gear system 140*b* by means of a bearing Bc. The second gear system 140*b* operates analogously to the first gear system 140*a*, and a structure comprising the third gear 146*b* of the second gear system 140*b*, a radially extending portion 147 and the force output of the second gear system 149*c* is rotatably connected to the housing 110 of the operation device 110 by means of a bearing Bd.

In the operation device shown in FIG. 16, the sequential energizing of the coils 132 propels the magnets 133 connected to the rotatable structure 135, which in turn propels the first gear system 140*a*. The first gear 140*a* system is connected in series with the second gear system 140*b* which in turn provides a force output 149*c* which could be used to power a body engaging portion of the operable implant in which the operation device 110 is used. By the first and second gear systems 140*a*, 140*b* being connected in series, the total transmission of the operation device 110 equals the transmission of the first gear system 140*a* times the transmission of the second gear system 140*b*. Thus, the force output 149*c* will output force at a velocity of: the velocity of the rotatable structure comprising the magnets 133 times the transmission of the first gear system 140*a* times the transmission of the second gear system 140*b*.

Figure 17:
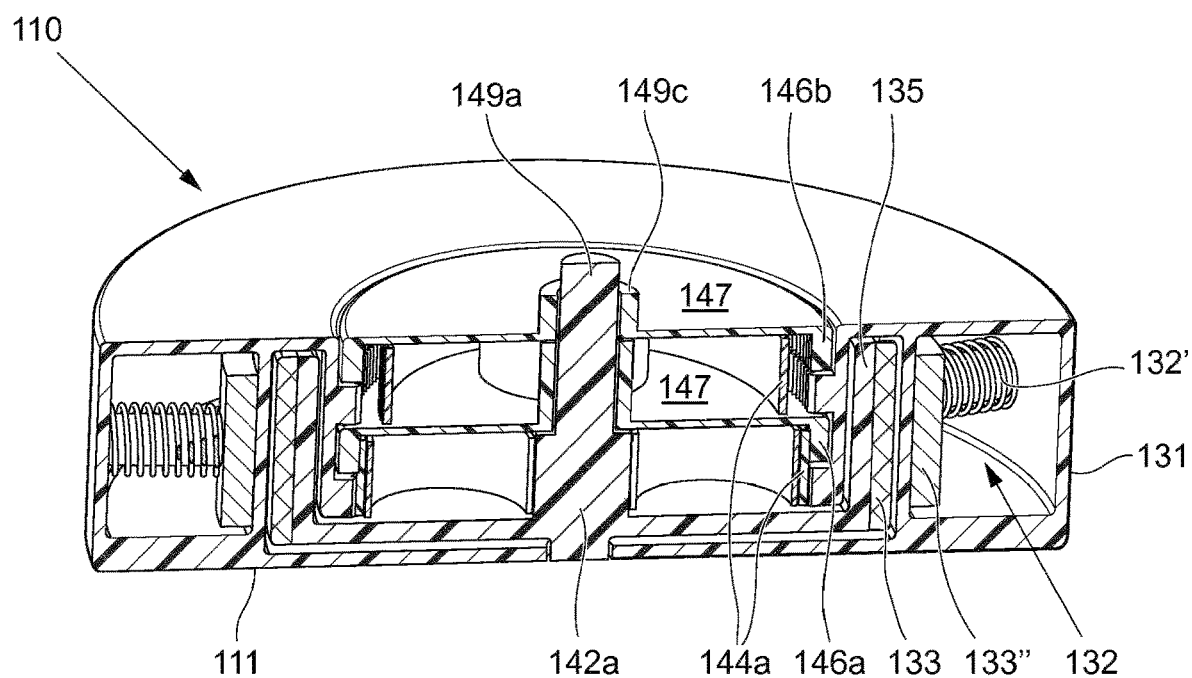
FIG. 17 shows an elevated perspective view of an embodiment of an embodiment of an implantable operation device comprising two gear systems, in section.

FIG. 17 shows an embodiment of an operation device 110 similar to the operation device described with reference to FIG. 16, with the difference that the operation device of FIG. 17 has a first and second force output 149a, 149c extending out of the enclosure 111 of the operation device 110, such that the operation device 110 can supply mechanical work of a first and second type, i.e. a first form of mechanical work having a first force and velocity, and a second form of mechanical work having a second force and velocity.

In further detail, the coils 132 enclosed in the coil enclosure 131 are sequentially energized, which propels the magnets 133 fixated to a rotatable structure 135 connected to the force input 142a of the first gear system. The rotatable structure 135 is also connected to a force output 149a of the operation device 110 such that a high velocity force output is provided from the operation device 110. The high velocity force output 149a may for example be coupled to a generator for generating electrical current inside of the body of the patient. As the first gear system is connected in series with a second gear system, the first gear system propels the second gear system which ultimately provides force output by means of the third gear 146b of the second gear system, and thus a low velocity force output 149c by mean of a connection via a radially extending rotatable structure 147. The low velocity force output 149c may for example be connected to a portion of the operable implant engaging the body of the patient and requiring mechanical work of a low velocity and high force.

FIG. 18a shows an embodiment of the operation device, in which a first gear system 140a is positioned radially inside of a second gear system 140b, such that the second gear system 140b axially overlaps the first gear system 140a (axially in relation to the rotational axis of the operation device 110. As in the operation devices described with reference to FIGS. 16 and 17, operation device comprises an electrical motor comprising a coil 132, comprising a coil winding 132' and a coil core 132", such as an iron core. The coil is adapted to be energized to produce a magnetic field adapted to affect and propel magnets 133 fixated to a rotatable structure 135. In alternative embodiments, the magnets 133 could be replaced by any magnetic material which could be attracted by the magnetic field created by the coils 132. The rotatable structure 135 in turn propels the force input 142a of the first gear system 140a, engaging the operable elements 143'''a, 143'b, which in turn engages the inside of the first gear 144a of the first gear system, such that the first gear 144a is deflected and operates the third gear 146a analogously to the gear system functionality described above. The third gear 146a of the first gear system 140a is connected to a radially extending structure 147 which constitutes the operable elements 143:2 of the second gear system 140b. The operable element 143:2 of the second gear system 140b engages the first gear 144b of the second gear system 140b having teeth interengaged with teeth of a third gear 146b of the second gear system 140b and functioning analogously. The third gear 146b of the second gear system 140b is in turn connected to a radially extending structure 147 transferring force from the periphery of the operation device to the center of the operation device 110, to propel a force output 149c of the second gear system 140b. Having the electrical motor and the first and second gear systems 140a, 140b in the same plane allows a very thin design suitable for subcutaneous implantation.

The force output 149c of the second gear system 140b is in connection with a threaded member 441 transferring rotational force to linear, reciprocating force which operates a torus shaped reservoir 160, as further described with reference to FIG. 4.

The housing of the operation device 111 encapsulates the operation device such that bodily fluids do not affect the operation device 110. The housing/enclosure 111 could for example be made from a biocompatible metal material, such as titanium or tantalum, preventing the migration of bodily fluids into the operation device 110. In alternative embodiments, the enclosure 111 could be made from a ceramic material, such as silicon carbide or zirconium carbide, or a polymer material, such as UHWPE or PTFE, or glass. In any instance the enclosure should be made from a material with low permeability, such that migration of bodily fluids through the walls of the enclosure 111 is prevented.

In the embodiment shown in FIG. 18a, the coils 132 is additionally enclosed in a coil enclosure 131, such that the coils 132 are additionally sealed from the other components of the operation device 110 and/or bodily fluids.

The operation device 110 of FIG. 18a further comprises a sealed space containing a battery 190, adapted to power an electrical motor, and a control unit 195 adapted to control the electrical motor and additional operable elements of the operable implant. The battery 190 and/or control unit 195 is in connection with a lead 192 connecting the battery 190 and/or control unit 195 to a wireless energy receiver and/or a wireless communication unit and/or an additional battery for supplying the operation device with additional energy. In alternative embodiments, where the electrical motor is powered directly from a wireless energy receiver, the battery 190 may be adapted to only power the control unit 195. The wireless energy receiver may in other embodiments be integrated and encapsulated in the same enclosure 111 encapsulating the operation device 110.

Figure 18B:
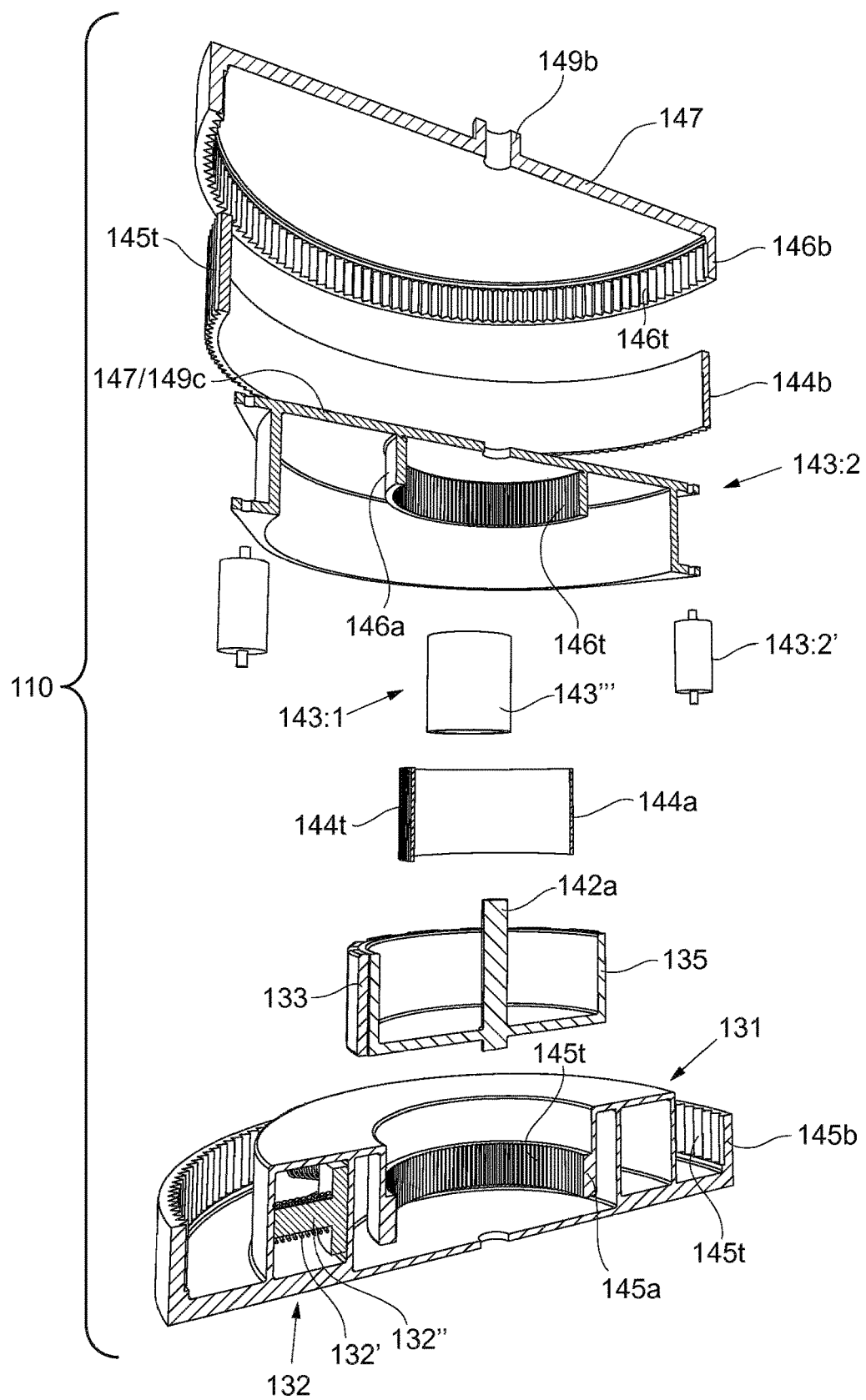
FIG. 18b shows an exploded, perspective side view of an embodiment of an implantable operation device, in section.

FIG. 18b shows the first and second gear systems and the electrical motor of the operation device 110 of FIG. 11a, in an exploded view. The lowermost piece is the static part of the operation device 110, comprising the second gear 145a of the first gear system and the second gear 145b of the second gear system 145b, the coils 132 of the electrical motor, comprising the coil cores 132" and the coil windings 132', and the coil enclosures 131, are adapted to hermetically enclose the coils 132, such that the coils 132 are sealed from bodily fluids and/or lubricants adapted to lubricate the first and/or second gear system and/or hydraulic fluids for transferring force from the operation device 110 to a hydraulically operable body engaging portion of the operable implant (further described in relation to other embodiments described herein). Above the static part 132, 145a, 145b, the rotatable structure 135 is depicted. The rotatable structure 135 comprises the magnets 133 adapted to be in magnetic connection with the coils 132, such that sequential energizing of the coils 132 propels the magnets 133 and thus the rotatable structure 135 to which the magnets 133 are fixated. The rotatable structure 145 also comprises the force input 142a to the first gear system 140a, which is adapted to propel the planetary gear 143''' being the operable element 143:1 of the first gear system 140a, by means of interengaging teeth or friction. The operable element 143' engages and deflects the first gear 144a of the first gear system 140a such that the teeth 144t on the outside of the first gear 144a interengage the teeth 145t on the inside of the second gear 145a of the first gear system, being part of the static part. As the first gear 144a of the first gear system comprises fewer teeth 144t than second gear 145b of the second gear system, the interengaging position between the first and second gears 144a, 145a are advanced, and as the third gear 146a of the first gear system comprises the same amount of teeth 146*t* as the first gear 144*a*, the third gear 146*a* moves along with the advancing positions. The third gear 146*a* of the first gear system is an integrated part of the operable element 143:2 of the second gear system, thus also comprising the force output 149*b* of the second gear system, and a radially extending structure 147 connecting the third gear 146*a* of the first gear system and the rolling operable elements 143:2' of the operable element 143:2.

The rolling operable elements 143:2' of the operable element 143:2 of the second gear system engages and deflects the first gear 144*b* of the second gear system, such that the second gear system propels the third gear 146*b* of the second gear system analogously to the first gear system. The third gear 146*b* of the second gear system is integrated in a structure (the uppermost structure depicted) further comprising a radially extending element 147 connecting the third gear 146*b* the force output 149*b* of the second gear system (and of the operation device), such that the mechanical work generated by the electrical motor 132, 133 can be outputted as rotational force through the force output 149*b*.

In the embodiment shown in FIG. 18*b* the first and second gear systems have the same transmission. However, it is conceivable that the second gear system have a higher transmission than the first gear system, i.e. that the gears of the second gear system has more teeth than the gears of the first gear system, while the difference between the number of teeth of the first and second gears 144*a*, 144*b*, 145*a*, 145*b* of the first and second gear systems are the same. For example, the first gear 144*a* of the first gear system having 98 teeth, the second gear 145*a* of the first gear system having 100 teeth, the first gear 144*b* of the second gear system having 198 teeth and the second gear 144*b* of the second gear system having 200 teeth, resulting in the first gear system having a transmission of 1:50 (plus the transmission of the planetary gear system provided by the operable element) and the second gear system having a transmission of 1:100. In some applications it may be advantageous that the gears of the second gear system has the same number of teeth as the gears of the first gear system (thus being larger), as the gears of the second gear system is required to transfer higher force with lower velocity.

FIG. 19 shows an alternative embodiment of the operation device 110 similar to the operation device described with reference to FIG. 18. The difference being the first gear system 140*a* is the gear system placed in the periphery, while the second gear system 140*b* is the gear system placed centrally. The coils 132 in the embodiment shown in FIG. 19 are placed inside the rotatable structure 135 comprising the magnets 133. The rotatable structure 135 is in the embodiment shown in FIG. 19 integrated with the operable element 143:1 of the first gear system 140*a*. The operable element 143:1, in the embodiment shown in FIG. 19 comprises a rolling operable element 143:1' adapted to engage the inside of the first gear 144*a* for deflecting the first gear 144*a*. The interengagement of the first gear 144*a* and the third gear 146*a* of the first gear system 140*a* propels the third gear 146*a* of the first gear system 140*a* which is in connection with the force input 142*b* adapted to propel the operable elements 143''', in turn deflecting the first gear 144*b* of the second gear system 140*b*, for propelling the third gear 146*b* of the second gear system 140*b*, serving as force output for the operation device 110. The structure 131, 145*b* enclosing the coils 132 constitutes the static part of the operation device 110 and is directly or indirectly connected to the second gear 145*a* of the first gear system 140*a* such that the second gear 145*a* of the first gear system 140*a* is static along with the second gear 145*b* of the second gear system 140*b* and the coil enclosure 131.

FIG. 20 shows the operation device of FIG. 19, in section. The structure 131, 145*b* enclosing the coils 132 constitutes the static part of the operation device 110 and is connected to the second gear 145*a* of the first gear system 140*a* such that the second gear 145*a* of the first gear system 140*a* is static along with the second gear 145*b* of the second gear system 140*b* and the coil enclosure 131. In the embodiment of FIGS. 12 and 13, the entire lower portion 111' of the enclosure 111 rotates for transferring force from the periphery of the operation device 110 to the center of the operation device 110, and thus forms the first gear system 140*a* to the second gear system 140*b*. The operation device 110 may additionally be enclosed by an additional enclosure, preferably connected to the static portion of the operation device 131, 145*b*, 145*a*, such that the rotatable lower portion of the enclosure 111' does not have to be in direct connection with the body of the patient.

In the embodiment shown in FIG. 20, the force input 142*b* of the second gear system 140*b* (being comprised in the same structure as the force output 149*b* of the first gear system) is rotatably fixated by a recess r in the structure comprising the force output 149*b* of the second gear system 140*b*, the third gear 146*b* of the second gear system 140*b*, and a radially extending rotatable structure 147 connecting the third gear 146*b* of the second gear system 140*b* to the force output 149*c* of the of the second gear system 140*b*.

Figure 21:
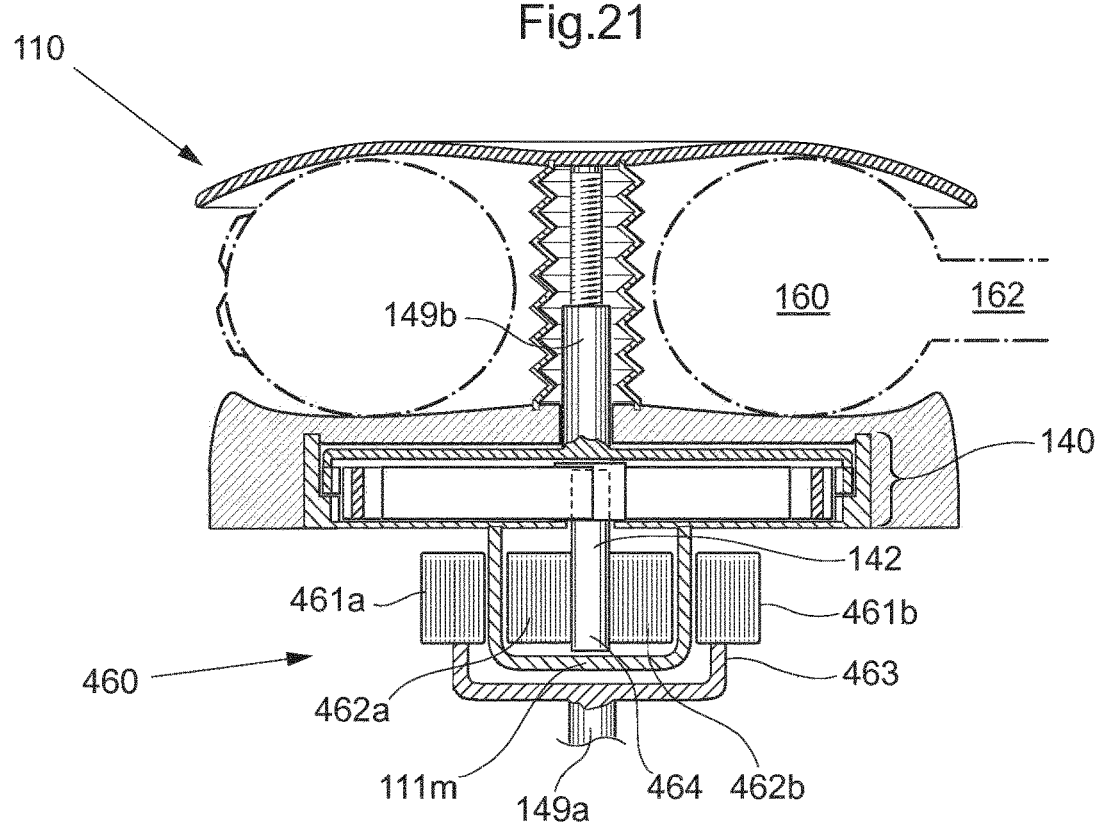
FIG. 21 shows a sectional side view of an embodiment of an implantable hydraulic operation device, comprising a magnetic coupling.

FIG. 21 shows an embodiment of an implantable operation device 110 comprising a magnetic force coupling 460 connected to the force input 142 to the operation device 110. The magnetic force coupling 460 comprises a first set of magnets 461*a*, 461*b* connected to an external rotatable structure 463 comprising a radially extending portion 147 connecting the rotating structure to the force output 149*a* of an electrical motor (not shown). The operation of the electrical motor rotates the force output 149*a* which in turn propels the rotatable structure 463 comprising the magnets 461*a*, 461*b*. The external magnets 461*a*, 461*b* are in magnetic connection with the internal magnets 462*a*, 462*b* connected to an internal rotatable structure 464 connected to the force input 142 of a gear system 140. The external rotatable structure 463 is placed radially on the outside of the internal rotatable structure 464. The gear system 140 is the gear system further described with reference to e.g. FIG. 3*b* or 4. The force output 149*b* of the gear system 140, in the embodiment shown in FIG. 21 operates an operable reservoir 160, for moving a hydraulic fluid from the reservoir 160 to a hydraulically operable body engaging portion connected to the reservoir 160 by means of a fluid conduit 162. The operation of the operable reservoir 160 is further described with reference to FIG. 4. In alternative embodiments, the force output 149*b* may be connected to a hydraulic pump for transporting hydraulic fluid to the hydraulically operable body engaging portion, such as for example a non-valve pump, a valve pump, a peristaltic pump, a membrane pump, a gear pump, or a bellows pump. In addition, it is equally conceivable that the force output 149*b* of the gear system 140 is connected to some other means for operating a body engaging portion, such as mechanical means.

The internal rotatable structure 464 is enclosed by an enclosure 111*m*, such that the gear system 140 and the internal rotatable structure 464 is hermetically enclosed and thus sealed from bodily fluids when implanted. The enclosure 111*m* is preferably made from a non-metallic and non-magnetic material, such as a polymer material, such as UHMWPE, PEEK or PUR. However, it is also conceivable that the enclosure is made from any of: a carbon material, a boron material, a mixture of material, an alloy of material, a metallic material, titanium, aluminum, a ceramic material, a polymer material, silicone, and Parylene® coated silicone.

The internal and/or external magnets 461a, 461b, 462a, 462b could for example be neodymium magnets, it is also conceivable that one of the internal set of magnets 431a, 461b and the external set of magnets 462a, 462b are magnets, and one of the internal set of magnets 461a, 461b and the external set of magnets 462a, 462b only are made from a material adapted to be attracted by magnetic force, such as iron.

The electrical motor (not shown) connected to the external rotatable structure 463 could for example be an alternating current (AC) electrical motor, a direct current electrical motor, a linear electrical motor, an axial electrical motor, a piezo-electric motor, a three-phase motor, a more than one-phase motor, a bimetal motor, and a memory metal motor.

Figure 22:
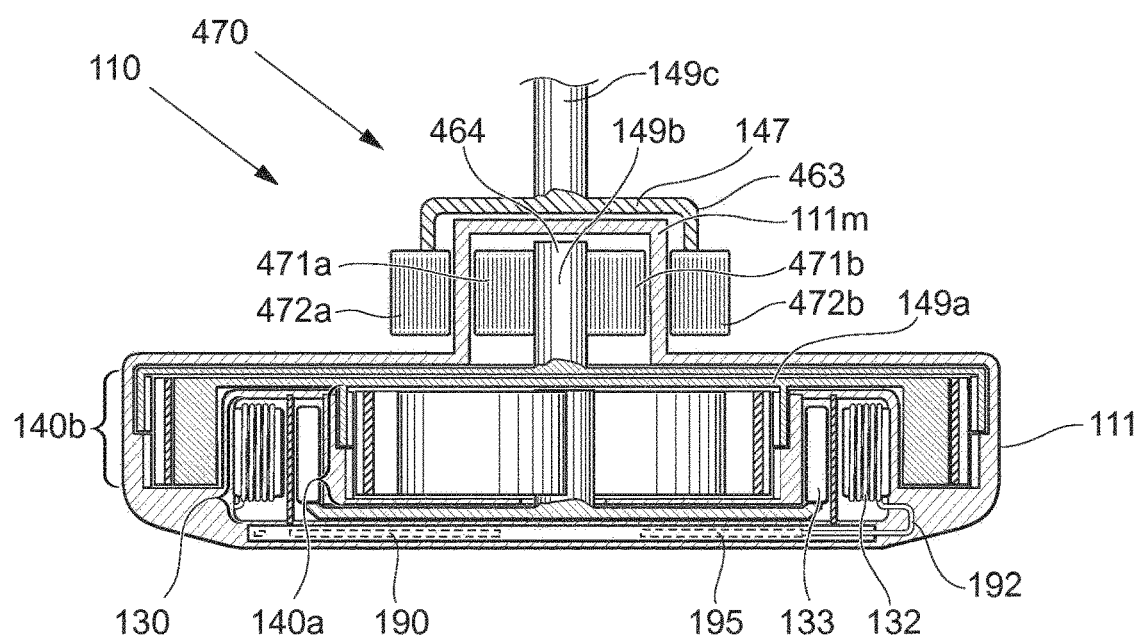
FIG. 22 shows a sectional side view of an embodiment of an implantable operation device, comprising a magnetic coupling.

FIG. 22 shows an embodiment of an implantable operation device 110 comprising a magnetic force coupling 470 connected to the force output 149b of an operation device 110, or more specifically to a force output 149b of a second gear system 140b of the operation device 110. The operation device 110 providing the force to the force output 149b is an operation device 110 comprising an electrical motor 130 and a first and second gear system 140a, 140b, and is further described with reference to FIG. 18a. However, a magnetic force coupling 470 may be added to any of the operation devices disclosed herein, such as the operation devices disclosed with reference to FIGS. 6, 7, 8 9, 10, 11, 12, 16, 17, and 19. The operation of the operation device 110 rotates the force output 149b which in turn propels the rotatable structure 464 comprising the magnets 471a, 471b. The internal magnets 471a, 471b are in magnetic connection with the external magnets 472a, 472b connected to an external rotatable structure 463 connected to the force output 149c. The external rotatable structure 463 is placed radially on the outside of the internal rotatable structure 464.

The force output 149c is in direct or indirect connection with an operable body engaging portion, such that the operation device 110 operates the operable body engaging portion via the magnetic force coupling 470. The internal rotatable structure 464 is enclosed by an enclosure 111m, such that the operation device 110, i.e. the electrical motor 130 and the first and second gear systems 140a, 140b, is hermetically enclosed and thus sealed from bodily fluids when implanted. The enclosure 111m is preferably made from a non-metallic and non magnetic material, such as a polymer material, such as UHMWPE, PEEK or PUR. However, it is also conceivable that the enclosure 111m is made from any of: a carbon material, a boron material, a mixture of material, an alloy of material, a metallic material, titanium, aluminum, a ceramic material, a polymer material, silicone, and Parylene® coated silicone.

In the operation device 110 of FIG. 22, a sealed spaced is further provided in the operation device enclosure 111 comprising a battery 190, adapted to power the electrical motor 130, and a control unit 195 adapted to control the electrical motor 130 and/or additional operable elements of the operable implant.

The battery 190 and/or control unit 195 is in connection with a lead 192 connecting the battery 190 and/or control unit 195 to a wireless energy receiver and/or a wireless communication unit and/or an additional battery 190 for supplying the operation device with additional energy. The electrical motor 130 is a alternating current (AC) electrical motor 130, and the control unit 195 comprises a frequency converter for altering the frequency of an alternating current for controlling the AC electrical motor. In alternative embodiments, where the electrical motor 130 is powered directly from a wireless energy receiver, the battery 190 is only adapted to power the control unit 195.

Figure 23:
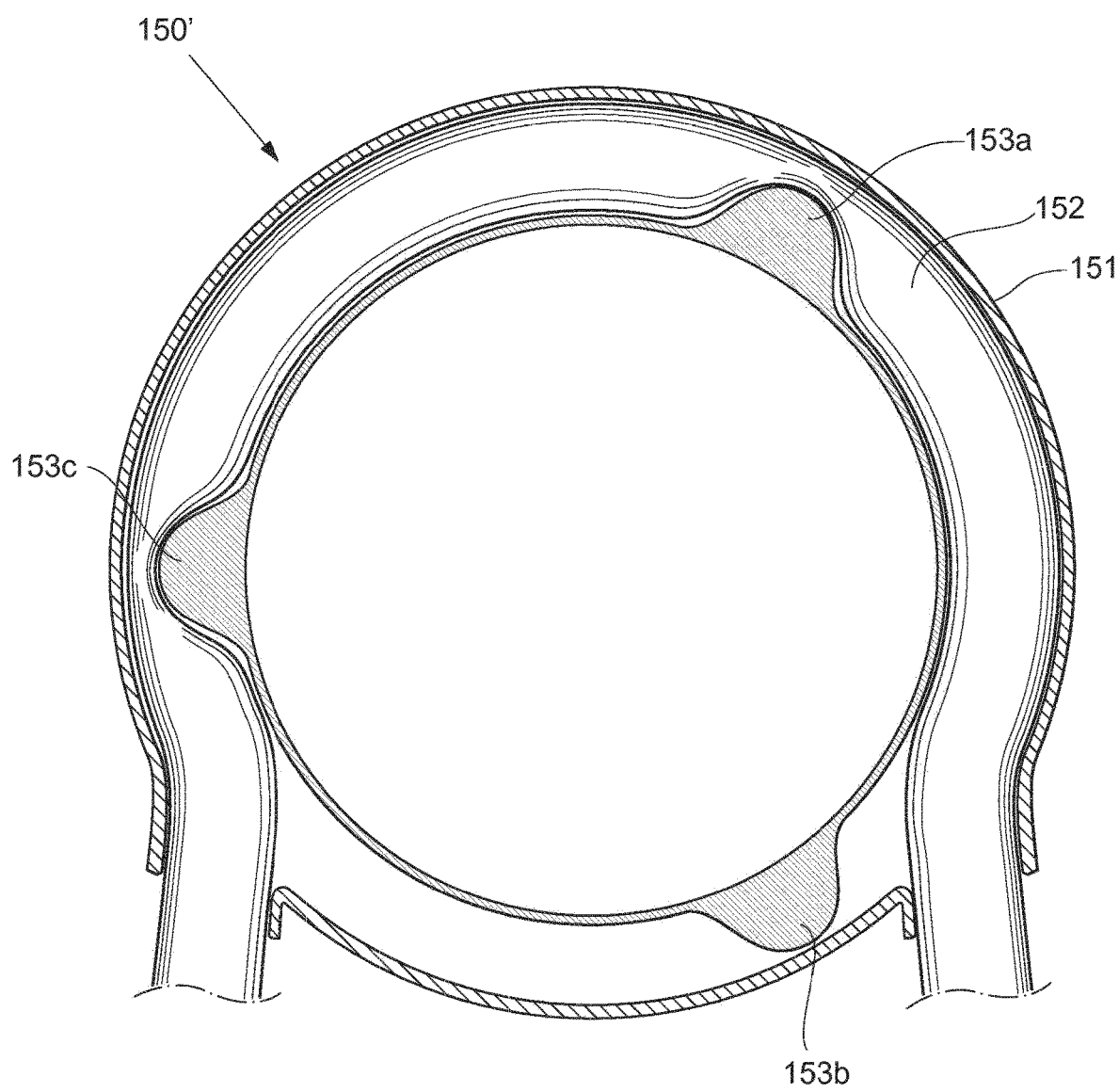
FIG. 23 shows a sectional top view of a peristaltic pump.

FIG. 23 shows an embodiment of an implantable peristaltic pump 150' adapted pump and thus transport a hydraulic fluid to a hydraulically operable body engaging portion of an operable implant. The peristaltic pump 150' could be adapted to be connected to force output of an operation device, such as any of the operation devices (110) disclosed herein. The implantable peristaltic pump 150' comprises a deflectable hollow member 152 for fluid transportation, in form of a tubing made from a resilient material, such as an elastomeric polymer material, such as silicone, Parylene® coated silicone, NBR, Hypalon, Viton, PVC, EPDM, Polyurethane or Natural Rubber. The deflectable hollow member 152 is adapted to be deflected by an operable compression member 153a-153c or wiper, adapted to engage and compress the hollow member 152, and thus transport the hydraulic fluid. The compression members 153a-153c, are propelled by the operation device. The hollow member 152 is placed inside a peristaltic pump housing 151, such that the hollow member 152 is compressed between the operable compression members 153a-153c. The peristaltic pump 150' enables the hydraulic fluid to be completely separated from the bodily fluids, such that the hydraulic fluid can be transported from a fluid reservoir (such as the fluid reservoirs 160 described in other embodiments herein) to a hydraulically operable body engaging portion without the risk of leakage.

Figure 24A:
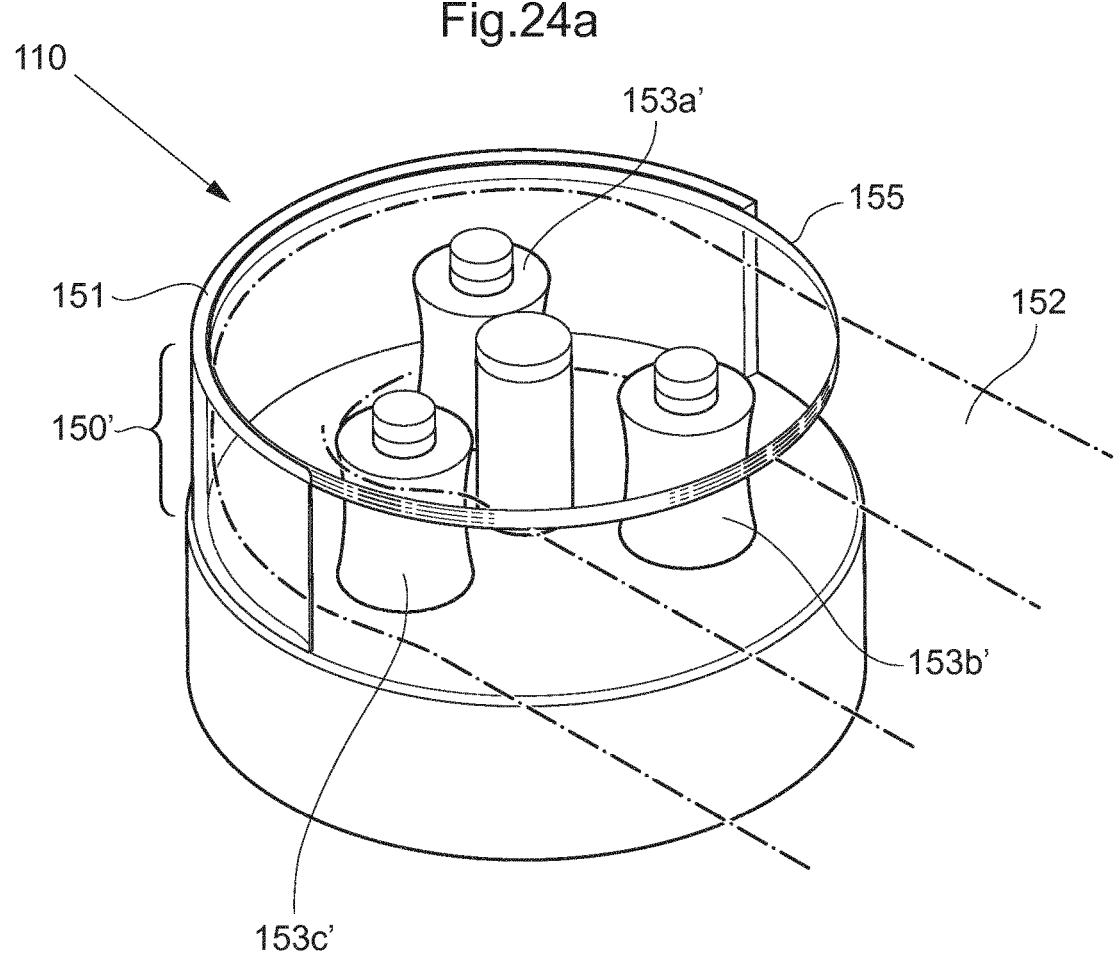
FIG. 24a shows an elevated perspective view of an implantable operation device comprising a peristaltic pump.
Figure 24B:
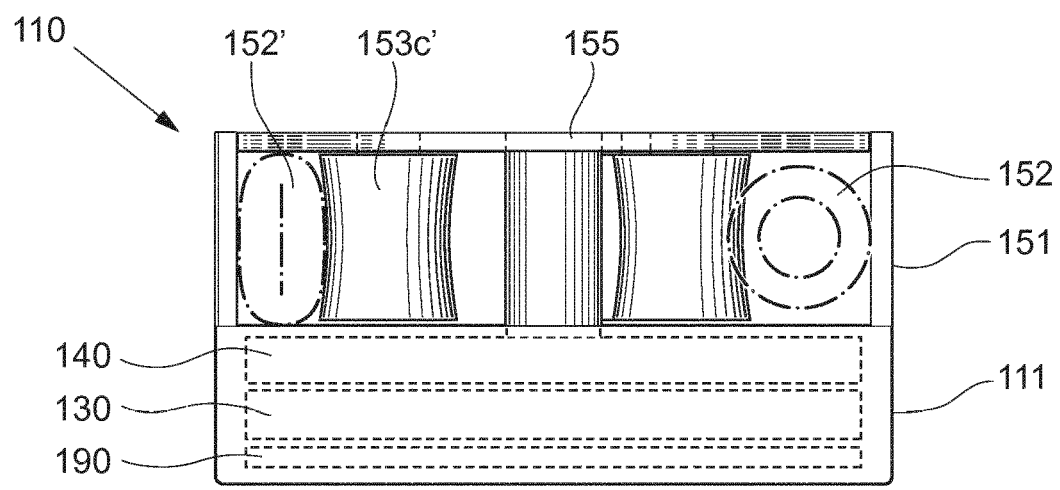
FIG. 24b shows a sectional side view of an implantable operation device comprising a peristaltic pump.

FIGS. 24a and 24b shows an implantable operation device 110 comprising a peristaltic hydraulic pump 150' similar to the peristaltic pump 150' described with reference to FIG. 23. The difference being that the operable compression members comprises rollers 153a'-153c' rotatably connected to a rotatable structure 155 propelled by a force output 149 of the gear system 140. The gear system 140 is in turn connected to an electrical motor 130 adapted to propel the gear system 140. The electrical motor 130 is in the embodiment described in FIG. 24 energized by a battery 190 enclosed in an enclosure 111 enclosing the operation device 110.

The rollers 153a'-153c' sequentially compresses the hollow member 152 and thus transports fluid in the hollow member 152. In FIG. 24b the operation device with the peristaltic pump 150' is shown in section, such that the hollow member 152 is shown in its non-compressed state 152 and its compressed state 152', when the roller 153c' compresses the hollow member 152' against the housing 151 of the peristaltic pump 150'. The electrical motor 130 and the gear system 140 could for example be an electrical motor (130) and gear system (140) described in any of the embodiments herein. As the rollers 153a'-153c' roll against the hollow member 152 they do not wear or rupture the hollow member 152 in the same way as a wiping or sliding operable compression member risks to do, which increases the life span of the hollow member 152.

Figure 25A:
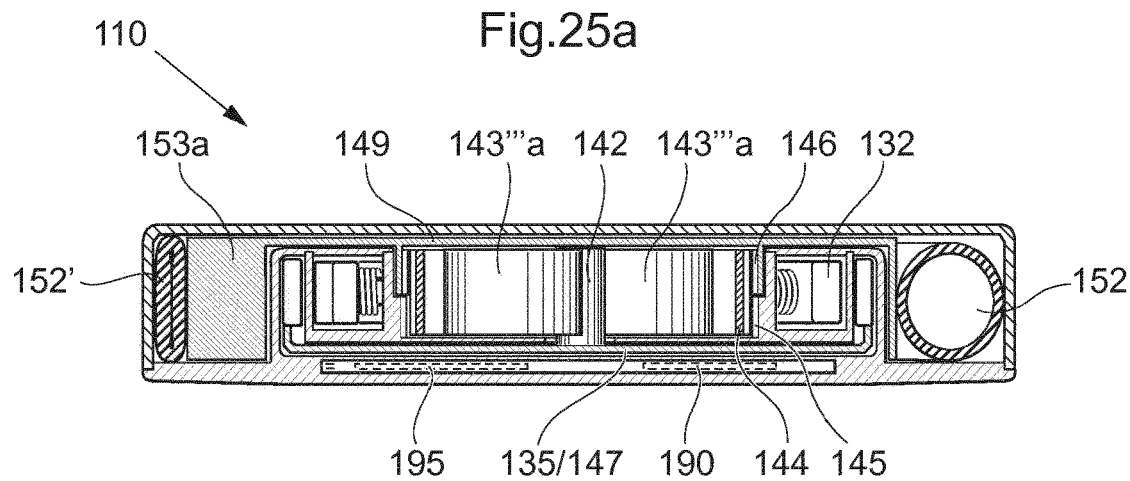
FIG. 25a shows a sectional side view of an implantable operation device comprising a peristaltic pump.
Figure 25B:
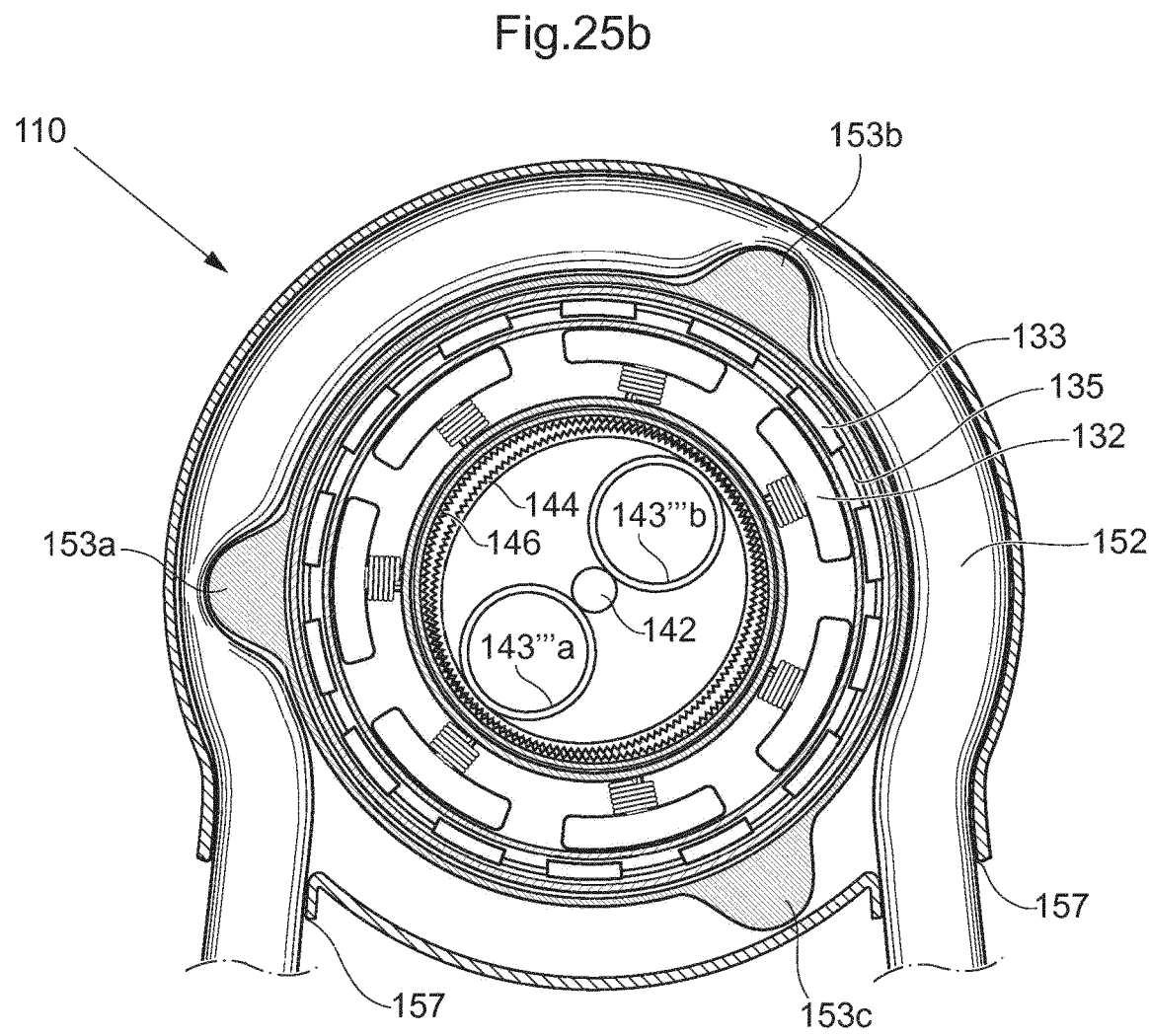
FIG. 25b shows a sectional top view of an implantable operation device comprising a peristaltic pump.

FIGS. 25a and 25b shows an embodiment of an operation device 110 comprising a peristaltic hydraulic pump, such as the peristaltic pump further disclosed with reference to FIG. 23. The peristaltic pump comprising a hollow member 152 for fluid transportation, and operable compression members 153a, 153b 153c adapted to engage and compress the hollow member 152. In the operation device shown in FIGS. 25a and 25*b*, the compression members 153*a*-153*c* are connected to the force output 149 of a gear system in connection with an electrical motor, both placed inside of the peristaltic pump. The electrical motor and gear system are similar to the electrical motor and gear system described with reference to FIG. 7, the difference being that the force output 149 of the gear system of FIGS. 25*a* and 25*b* is connected to, and propels the operable compression member 153*a*, such that the electrical motor operates the peristaltic pump via the gear system.

In further detail, the coils 132 of the electrical motor is connected by means of leads (not shown) to a control unit 195 which in turn is connected to a battery 190. The control unit generates an alternating current (AC) by means of a converter which is used to energize the coils. The alternating current thus sequentially energizes the coils 132 such that a propagating magnetic field is created in the coils 132 propelling the magnets 133 fixated to a rotatable structure 135. The rotatable structure 135 is in turn connected to the force input 142 of the gear system, such that the force input propels the operable elements 143'''*a*, 143'''*b* deflecting the first gear 144 of the gear system and causing relative rotation between the third gear 146 and the second gear 145 which propels the force output 149 of the gear system which is in direct connection with the operable compression members 153*a*, 153*b*, 153*c*.

The hollow member 152 thus forms ¾ of a loop encircling the electrical motor and the gear system and the compressing members 153*a*-153*c* compresses the hollow member 152 towards the outer periphery of the loop and against the housing 151 which is a portion of the operation device enclosure 111.

The hollow member 152 is sealed by means of a sealing member 157, such as a glue, against the enclosure of the operation device 111 such that the entire operation device is hermetically enclosed and sealed against the bodily fluids at the same time as the hydraulic system is hermetically enclosed in the hollow member and thus no hydraulic fluid could leak to the body of the patient and/or to the operation device. Furthermore, the embodiment of FIGS. 25*a* and 25*b*, having the peristaltic pump being placed in the same plane as the electrical motor and the gear system, enables the entire operation device to be made very thin and thus being suitable for subcutaneous implantation.

Figure 26:
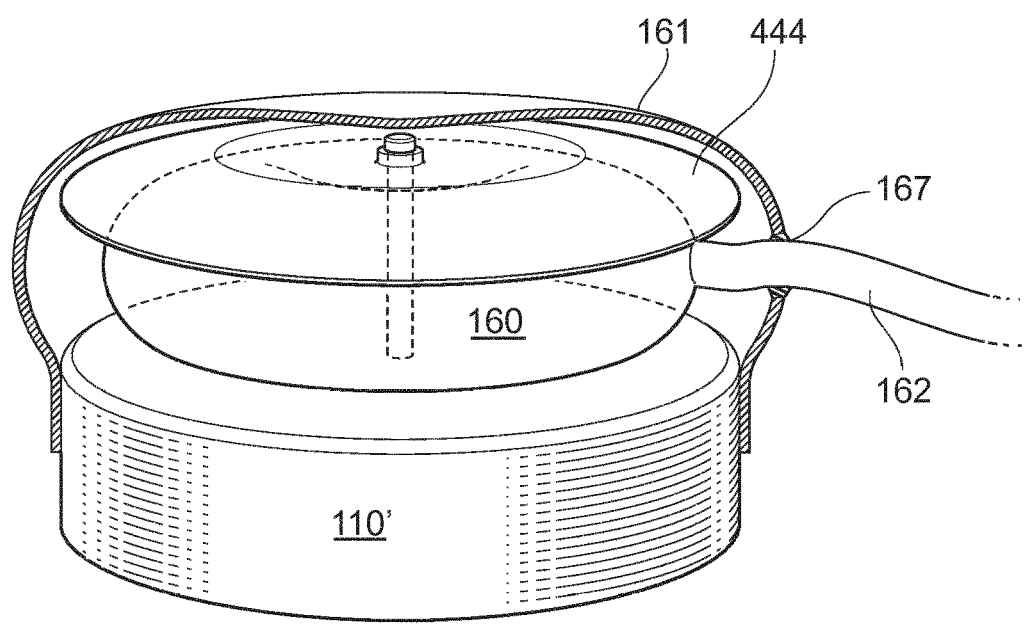
FIG. 26 shows an elevated perspective view of an embodiment of an implantable hydraulic operation device in section.

FIG. 26 shows an embodiment of the operation device in which the operation device comprises a hydraulic pump comprising a torus shaped reservoir 160 adapted to contain a hydraulic fluid. The torus shaped reservoir 160 is adapted to be compressed by a radially extending engaging member 444 operated by the portion of the operation device 110' comprising en electrical motor and gear system, such as any of the combinations of electrical motors gear systems described herein. The embodiment of the operation device shown in FIG. 26 is very similar to the embodiment described for example with reference to FIG. 4. The main difference is that the embodiment shown in FIG. 26 further comprises an additional enclosure 161 enclosing the torus shaped reservoir 160 and the radially extending engaging member 444. The additional enclosure 161 comprises a sealing member 167 adapted to seal between the additional enclosure and the fluid conduit adapted to transport the hydraulic fluid from the torus shaped reservoir 160 to a hydraulically operable body engaging portion, for operating the hydraulically operable body engaging portion. The additional enclosure further seals the operation device 110 from the bodily fluids and reduces the risk that fibrotic tissue in-growth affects the operation of the operation device 110.

Figure 27A:
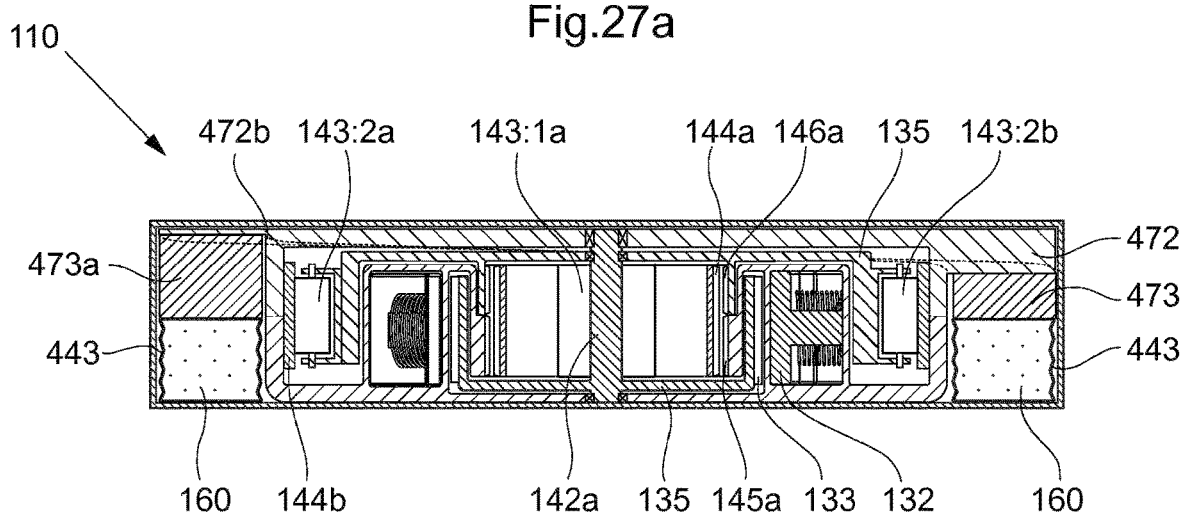
FIG. 27a shows a sectional side view of an implantable hydraulic operation device, in a first state.

FIG. 27*a* shows an operation device 110 according to an embodiment in which the operation device comprises an operable reservoir 160 adapted to contain a hydraulic fluid. The electrical motor and double gear system portion of the operation device is similar to what is operation device described with reference to FIGS. 18*b* and 19. However, the operation device of FIGS. 27*a* and 27*b* additionally comprises a circular reservoir 160 encircling the operation device. The circular reservoir 160 comprises a movable wall portion adapted to compress and expand the circular reservoir 160, thereby altering the volume of the reservoir 160. The third gear 146*b* of the second gear system, rotating along with the interengaging portions between the first and second gears 144*b*, 145*b* (such as further described with reference to FIGS. 27*a* and 27*b*) is connected to an operation spiral 472 adapted to engage a radially fixed corresponding operation spiral 473, such that the operation of the operation spiral 472 in relation to the radially fixed operation spiral 473 moves the radially fixed operation spiral axially, such that the reservoir 160 is compressed.

FIG. 27*a* shows the operation device 110 in a state in which the operation spiral 473 is aligned in relation to the corresponding radially fixated operation spiral, such that the two spirals 472, 473 match and forms a structure being as thin as possible and thus compressing the reservoir 160 minimally i.e. the thinnest portion of the operation spiral 472*b* engages the thickest portion of the radially fixed operation spiral 473*a*.

Figure 27B:
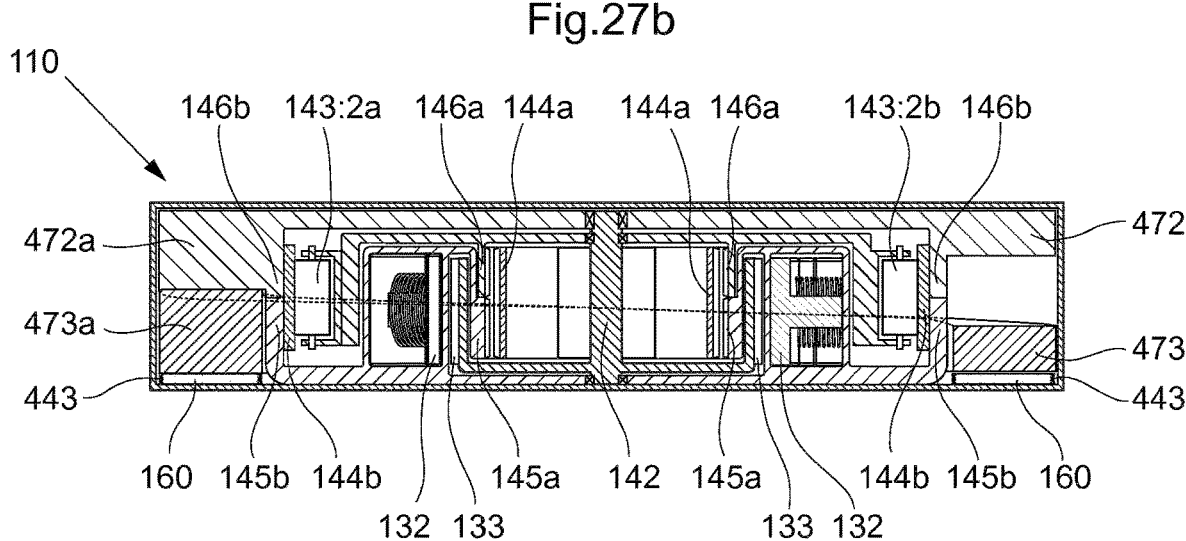
FIG. 27b shows a sectional side view of the implantable hydraulic operation device of FIG. 27a, in a second state.

FIG. 27*b* shows the operation device 110 in a state in which the operation spiral 472 has performed close to a full rotation, such that the thickest portion of the operation spiral 472*a* engages the thickest portion of the radially fixed operation spiral 473*a*, such that the two spirals "mismatch" and forms a structure being as thick as possible and thus compressing the reservoir 160 maximally. One revolution of the operation spiral 472 thus alters the state of the reservoir 160 from being fully expanded to fully compressed, which enables transportation of hydraulic fluid from the reservoir to the hydraulically operable body engaging portion by the operation device 110.

The circular reservoir 160 is compressible by means of a pleated portion 443 enabling the reservoir 160 to be made from a resilient but non-elastic material, such as a non-elastomeric polymer material.

Figure 28A:
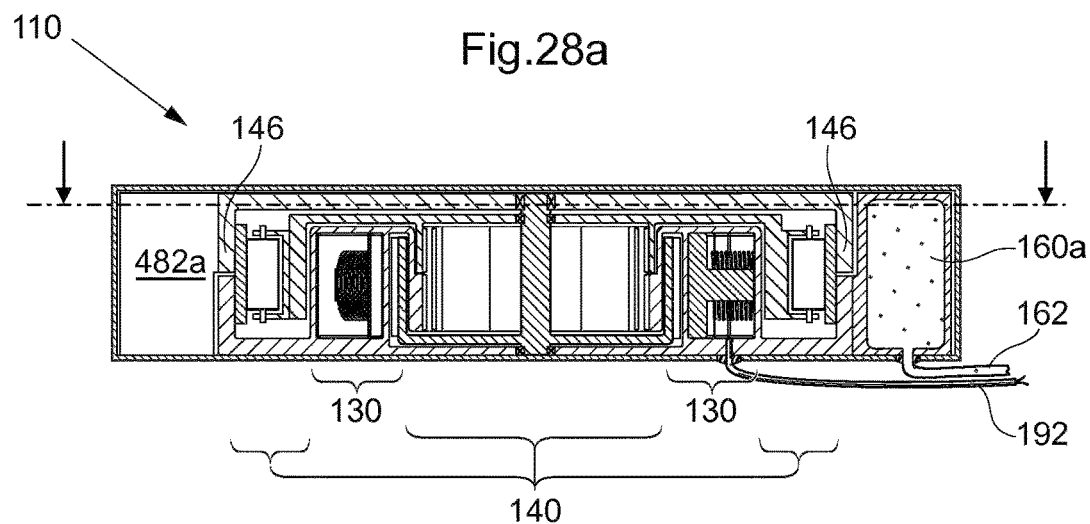
FIG. 28a shows a sectional side view of an implantable hydraulic operation device.
Figure 28C:
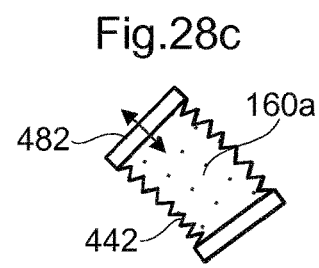
FIG. 28b shows a sectional top view of an implantable hydraulic operation device.
Figure 28B:
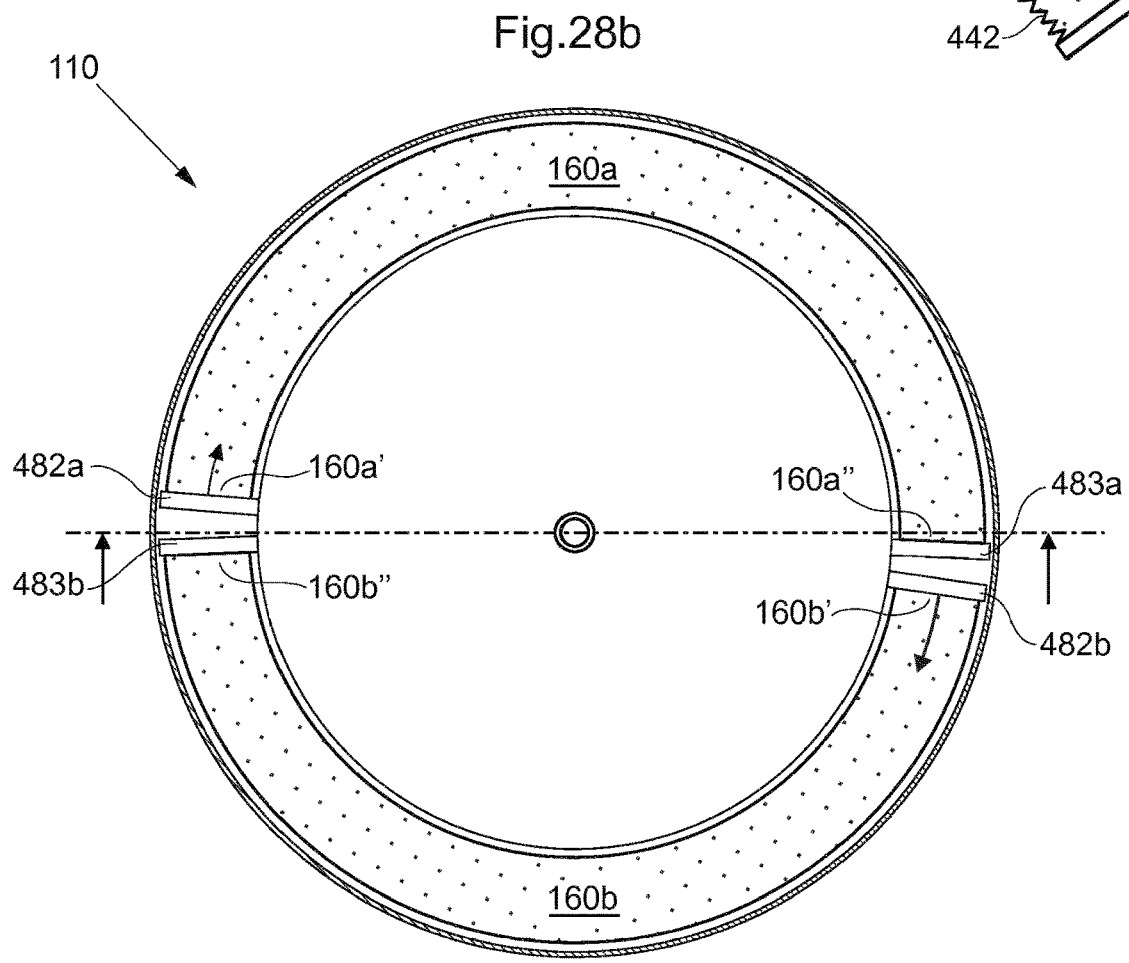

FIGS. 28*a* and 28*b* shows an embodiment of an operation device 110 similar to the embodiment of the operation device 110 shown with reference to FIGS. 27*a* and 27*b*. The electrical motor 130 portion and the gear systems 140 portions are identical. The difference in the operation device is that the third gear 146 of the second (outer) gear system is connected to radially operable operation members 482*a*, 482*b* adapted to engage two reservoirs 160*a*, 160*b*, each radially extending along substantially half the circumference of the operation device 110. The first and second radially extending reservoirs 160*a*, 160*b* comprises walls having pleated portions 442 enabling the compression of the reservoirs 160*a*, 160*b* by the radial movement of the radially operable operation members 482*a*, 482*b*. A first end 160*a*' of the first reservoir 160*a* is connected to a first radially operable operation member 482*a*, and a second end 160*a*" of the first reservoir 160*a* is connected to a first radially fixated member 483*a*. Analogously, a first end 160*b*' of the second reservoir 160*b* is connected to a second radially operable operation member 482*b*, and a second end 160*b*" of the second reservoir 160*b* is connected to a second radially fixated member 483*b*. The first and second reservoirs 160*a*, 160*b* are compressed between the radially operable operation members 482*a*, 482*b* and the radially fixated members 483*a*, 483*b*, respectively, such that the volume in the first and second reservoirs is changed. As the volume in the reservoirs decrease, the fluid contained in the reservoirs is transported from the reservoirs 160*a*, 160*b* to the body engaging portions via fluid conduits 162.

Figure 29:
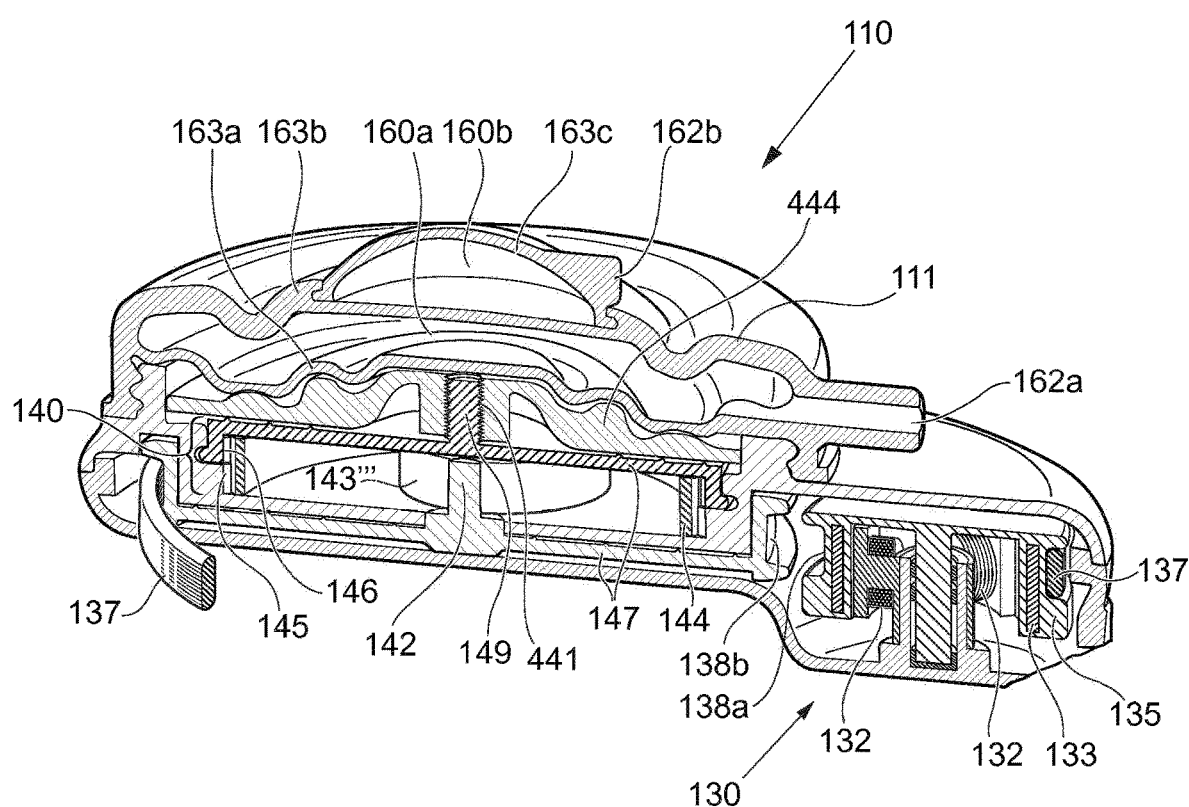
FIG. 29 shows an elevated perspective view of an implantable operation device, in section.

FIG. 29 shows an implantable operation device 110 for operating a body engaging portion of an operable hydraulic implant in section. The operation device comprises a reservoir 160*a* for holding a hydraulic fluid. The reservoir 160*a* comprises a movable wall portion 163*a* adapted to move to alter the volume of the reservoir 160*a* and thereby transport hydraulic fluid from the reservoir 160*a* to the body engaging portion. The operation device further comprising an operation member 444, extending radially and being connected to the movable wall portion 163*a*, such that operation of the operation member 444 alters the volume of the reservoir 160*a*. The operation device 110 further comprises a flexible enclosure 111 adapted to have its volume altered by changing the outer size and shape of the enclosure and enclose the movable wall portion 163*a* and the operation member 444. The movable wall portion 163*a* is adapted to move inside of the enclosure 111, such that the volume of the reservoir 160*a* can be changed by affecting the outer dimensions of the operation device 110 to a lesser extent and in the opposite direction than the change of volume of the reservoir 160*a* by the movement of the movable wall portion 163*a* inside of the enclosure 111. The reservoir 160*a* further comprises a manual portion (reservoir) 160*b* comprising a movable wall portion 163*c* adapted to be compressed by manual force from outside of the body of the patient, such that fluid can be transported from the reservoir 160*b* via a second fluid conduit 162*b* to the body engaging portion by means of manual force, for temporarily increasing the hydraulic pressure at the body engaging portion. The manual portion 160*b* could for example be used in emergencies if an implantable battery runs out of power, or if a patient would like to override an automatic system.

In further detail, the hydraulic operation 110 device shown in FIG. 29 comprises an electrical motor 130, which in the embodiment shown is an alternating current (AC) electrical motor comprising a plurality of coils 132 connected to a static structure, and a plurality of magnets 133 connected to a rotatable structure 135. The plurality of coils 132 and plurality of magnets 133 are magnetically connected such sequential energizing of the coils 132 propels the magnets 133 and thus the rotatable structure 135. The peripheral surface of the rotatable structure 135 comprises or acts like a pulley 138*a* engaging a belt 137, such that operation of the electrical motor 130 propels the belt 137.

The belt 137 is further connected to a second pulley 138*b* connected to a radially extending portion 147 connecting the pulley 138*a* to a force input 142 of a gear system 140, being the gear system described in several embodiments herein, for example with reference to FIGS. 4-7. The force input 142 propels the operable elements 143′′′, which in turn engages and deflects the first gear 144 having teeth interengaging the second gear 145 and third gear 146. The first gear 144 having less teeth than the second gear 145 creating a rotation of the interengaging positions between the first and second gears 144, 145. The third gear 146 has the same amount of teeth as the first gear 144 and thus rotates along with the interengaged positions. The third gear 146 is connected to the force output 149 of the gear system 140 by means of a radially extending portion 147. The force output 149 is a threaded shaft adapted to engage inner threads of a threaded member 441 of a radially extending operation member 444 adapted to engage a movable wall portion 163*a* of the reservoir 160*a*. The interaction between the threaded shaft 149 and the threaded member 441 transforms the radially rotating force generated by the operation of the gear system 140, to a linear, axially reciprocating force. The average thickness of the movable wall portion 163*a* is less than the average thickness of the movable outer wall portion 163*b* of the reservoir 160*a*. The reservoir 160*a* is connected to a fluid conduit 162*a* for transporting fluid from the fluid reservoir 160*a* to the body engaging portion of the hydraulically operable implant 110.

The radially extending operation member 444 presses the movable wall portion 163*a* upwards for compressing the fluid reservoir 160*a*, a vacuum is created beneath the radially extending operation member 444 which forces the outer movable wall 163*b* to move downwards thus compresses the reservoir 160*a* from the outside. The operation thus changes the external size of the operation device 110 by moving a movable wall 163*a* within the operation device 110.

Placed coaxially and on top of the reservoir 160*a* is a second manual reservoir 160*b*. The manual reservoir 160*b* is enclosed by the wall of the first reservoir 160*a* and an external movable wall 163*c* adapted to be compressed by manual operation from the outside of the body of the patient. The second manual reservoir 160*b* comprises a second fluid conduit 162*b* adapted to connect the second manual reservoir 160*b* to the body engaging portion, such that manual compression of the reservoir 160*b* transports fluid from the second manual reservoir 160*b* to the body engaging portion. The manual portion could for example be used in emergencies if an implantable battery runs out of power, or if a patient would like to override an automatic system.

In alternative embodiments, the implantable operation device 110 may additionally comprise an injection port for injecting hydraulic fluid into the reservoir from outside the body of the patient. The injection port may be an integrated portion of the reservoir or may be connected to the reservoir by means of a fluid conduit. The injection port may be adapted to refill or calibrate the fluid amount in the first reservoir and/or in the manual reservoir 160*b*.

The implantable operation device may be implanted subcutaneously and may additionally comprise a fixation member (such as the fixations member described with reference to FIGS. 43*a*-43*e*) adapted to directly or indirectly fixate at least a portion of the implantable operation device to at least one muscular fascia and/or at least one bone fascia and/or at least one cortical bone layer and/or at least one muscular layer and/or fibrotic tissue and/or any part of the abdominal wall and/or any part of the subcutaneous space and its surroundings in the body.

In alternative embodiments, the electrical motor 130 of the operation device may be an electrical motor selected from: an alternating current (AC) electrical motor, a direct current electrical motor, a linear electrical motor, an axial electrical motor, a piezo-electric motor, a two or more phase motor, a three phase motor, a bimetal motor, and a memory metal motor.

Figure 30A:
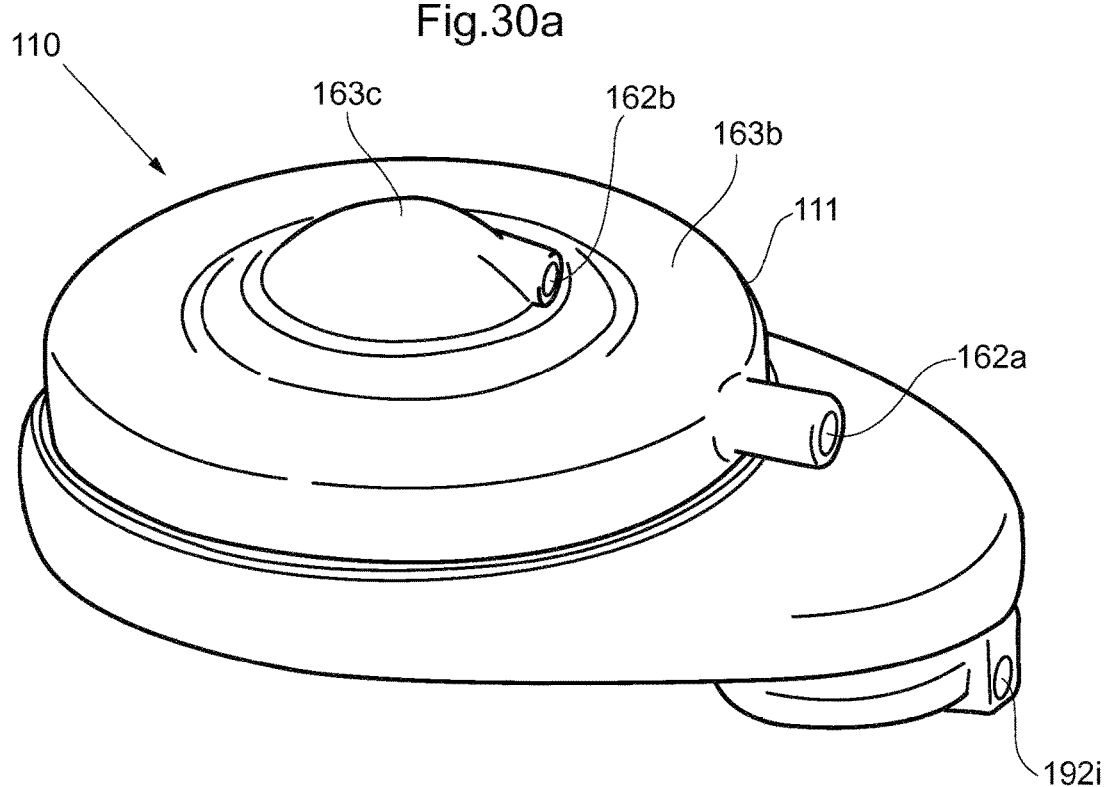
FIG. 30a shows an elevated perspective view of an implantable operation device, in a first state.

FIG. 30*a* shows the hydraulic operation device 110 shown in FIG. 29 in an external view, when the reservoirs (160*a*, 160*b* in FIG. 29) are fully expanded i.e. the movable walls 163*b*, 163*c* are not compressed. The enclosure 111 is made from a resilient polymer material, such as Parylene® coated silicone. In addition to the first and second fluid conduits 162*a*, 162*b* penetrating the enclosure 111, the enclosure 111 further comprises a lead inlet 192*i* for allowing an electrical lead to penetrate the enclosure 111 for powering the electrical motor (130 of FIG. 29). The electrical lead may be connected to a battery located outside of the enclosure 111, or a receiving unit for receiving wireless energy (further disclosed in other embodiments herein) located outside of the enclosure 111.

Figure 30B:
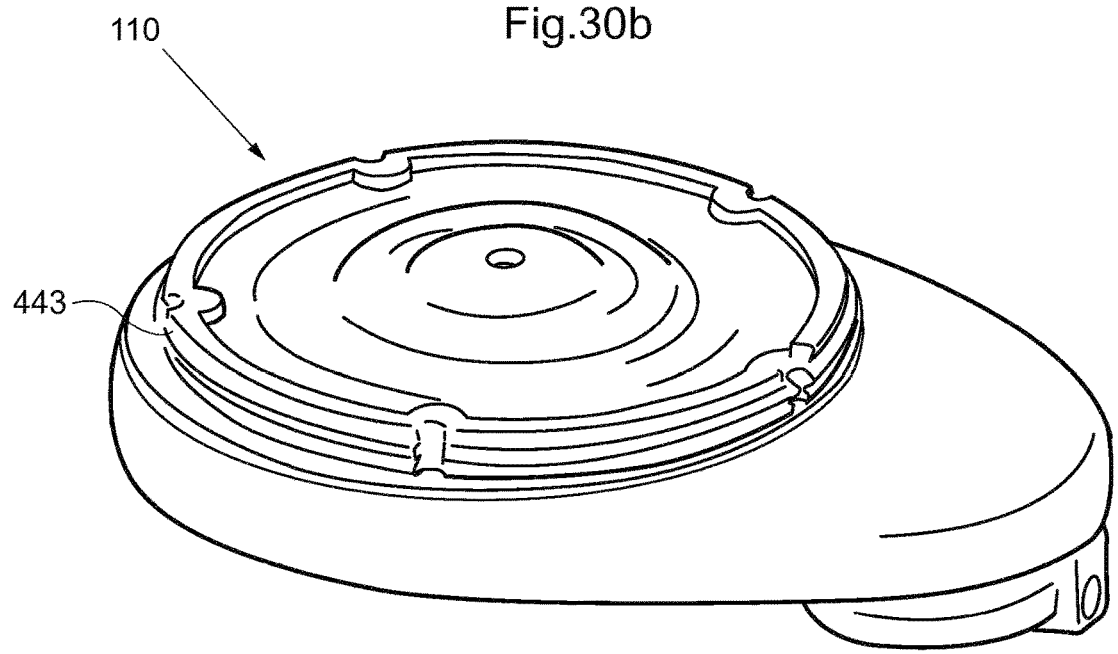
FIG. 30b shows an elevated perspective view of the implantable operation device of FIG. 30a, in a first state.

FIG. 30*b* shows the hydraulic operation device 110 in its fully compressed state, when the volumes of both the first and second reservoirs are compressed to a minimum. In the embodiment shown, the peripheral side wall of the first reservoir (160*a* of FIG. 29) comprises a pleated portion 443 adapted to enable the compression of the first reservoir.

FIG. 31*a*-31*d* shows different embodiments of start resistance delay members positioned between the force output of the electrical motor and the body engaging portion. The start resistance delay members are adapted to enable the electrical motor to operate with at least one of; less force or less friction induced by the direct or indirect connection with the body engaging portion for a time period, such that the electrical motor can start with less resistance.

Figure 31A:
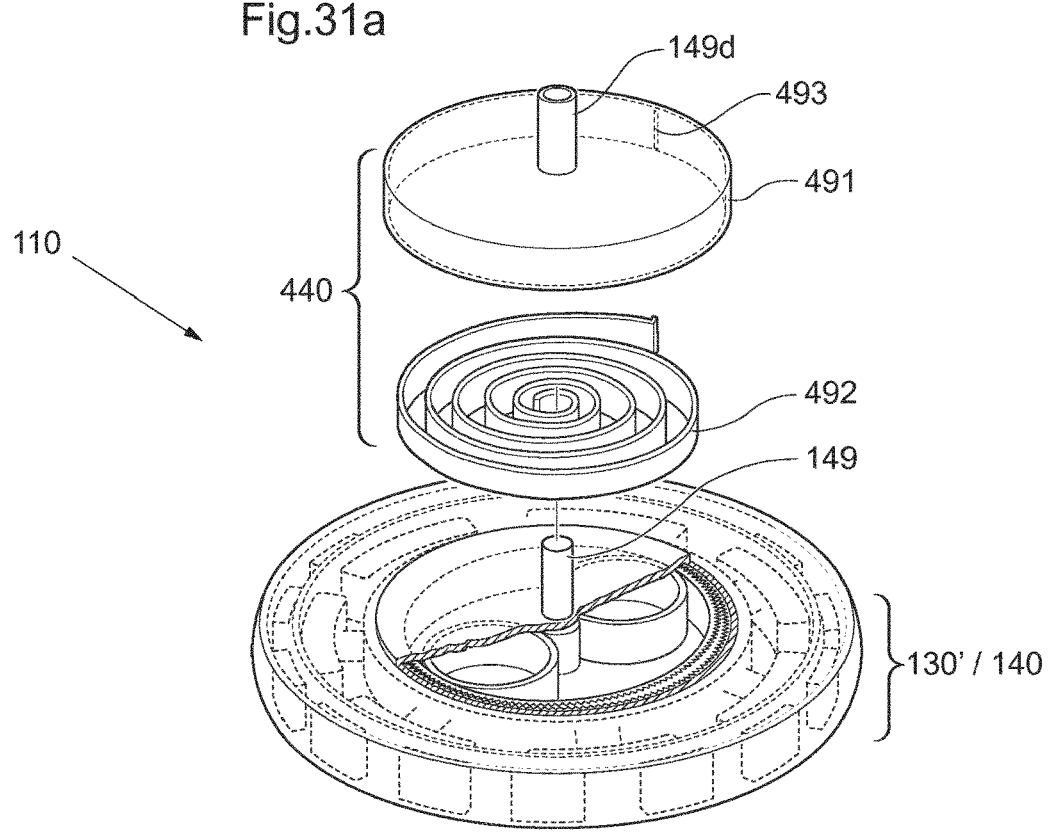
FIG. 31a shows an exploded perspective view of an implantable operation device comprising a start resistance delay.

FIG. 31*a* shows an embodiment of the operation device 110 comprising a start resistance delay 440 positioned between the force output 149 of an electrical motor/gear system 130/140 and a delay force output 149*d*, which in turn is directly or indirectly connected to a body engaging portion of the operable implant. The electrical motor/gear system unit 130/140 shown in FIG. 31*a* is identical to the electrical motor gear system unit described with reference to FIG. 7.

The force output 149 of the electrical motor/gear system 130/140 is connected to the center of a helical spiral spring 492 which in turn is connected to rotatable delay structure 491 such that the rotation of the force output 149 to which the center of the helical spiral spring 492 is connected at a connection point 493 gradually starts rotating the rotatable delay structure 491 to which the spring 492 is connected. When the force output 149 of the gear system 140 has rotated a sufficient number of revolutions, the spring 492 is sufficiently winded such that the rotatable delay structure 491 rotates along with the force output 149 of the gear system 140. During the revolutions required for the spring 492 to start driving the rotatable delay structure 491 the electrical motor has rotated a sufficient amount of revolutions to have a torque large enough to directly or indirectly propel the body engaging portion to which the delay force output is connected. The amount of revolutions that the start resistance delay 440 should delay the electrical motor 130 depends on the time it takes for the electrical motor 130 to reach the velocity needed to create sufficient torque. The spring 492 could for example be a steel spring or a polymer spring made from a resilient polymer material.

Figure 31B:
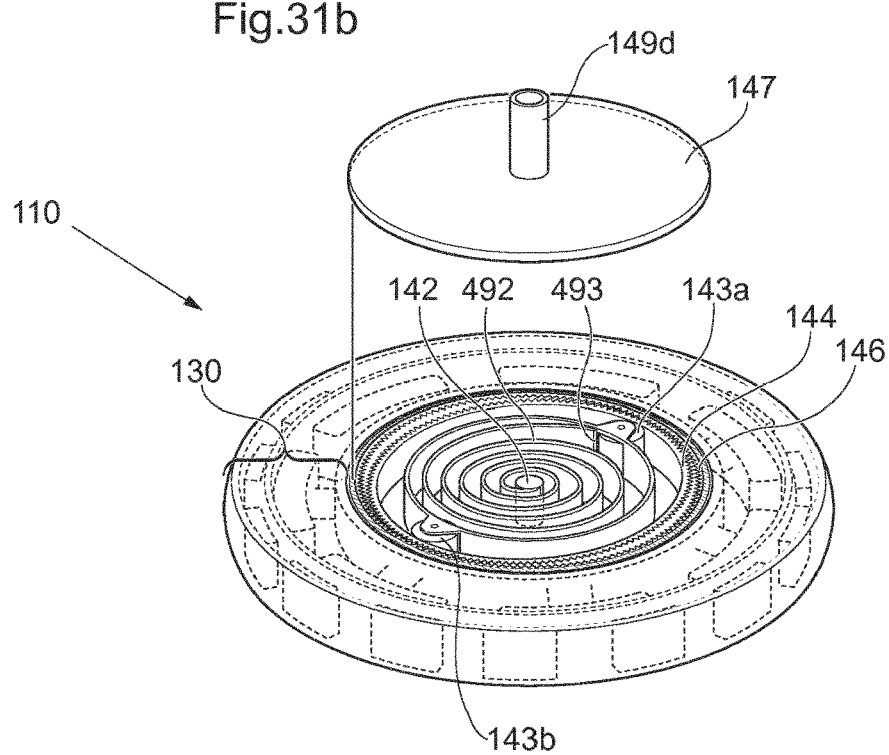
FIG. 31b shows an exploded perspective view of an implantable operation device comprising a start resistance delay.

FIG. 31*b* shows an alternative embodiment of an operation device 110, similar to the embodiment shown in FIG. 31*a*, the difference being that in the embodiment shown in FIG. 31*b*, the spring 492 creating the delay is positioned between the electrical motor 130 and the gear system, centrally inside the gear system. The force input 142 of the gear system is connected to the force output of the electrical motor 130. The center of the helix of the spring 492 is fixated to the force input 142, such that the operation of the electrical motor 130 propels the central part of the spring 492 causing the winding of the spring 492 gradually leading to force being transferred from the force input to the operable elements 143*a*, 143*b* connected to a rotatable structure 491 to which the peripheral part of the spring 492 is fixated at a connection point 493. When the spring 492 is sufficiently winded, the operation of the electrical motor 130, via the gear system, propels operable elements 143*a*, 143*b* engaging and deflecting the first gear 144 such that the third gear 146 rotates along with the interengaging positions between the first 144 and second/third gears (145 not shown) and 146. In the embodiment of FIG. 31*b*, the electrical motor 130 is allowed to reach sufficient velocity for propelling the operable elements 143*a*, 143*b* before the force input of the gear system is transferring force to the operable elements 143*a*, 143*b*.

Figure 31C:
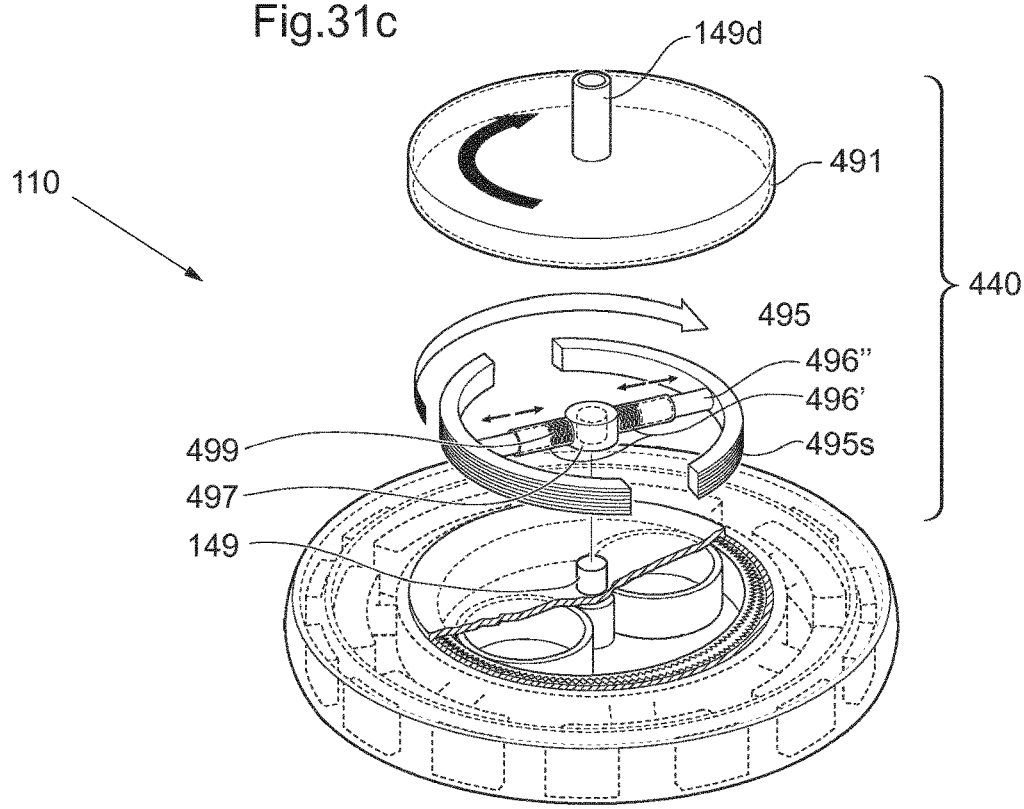
FIG. 31c shows an exploded perspective view of an implantable operation device comprising a start resistance delay.

FIG. 31*c* shows an embodiment of the operation device 110 comprising a start resistance delay 440 being a friction clutch operated by means of centrifugal force. The start resistance delay 440 is positioned between the force output 149 of an electrical motor/gear system 130/140 and a delay force output 149*d*, which in turn is directly or indirectly connected to a body engaging portion of the operable implant. The electrical motor/gear system unit 130/140 shown in FIG. 31*a* is identical to the electrical motor gear system unit described with reference to FIG. 7. The start resistance delay 440 is fixated to the force output 149 of the gear system by means of a connecting portion 497 comprising a recess or hole engaging the force output 149. From the connecting portion 497, two sleeves 496' extends radially in opposite directions. In the sleeves, piston-like shafts 496" are positioned. The portion of the piston-like shaft 496" directed towards the connecting portion 497 is connected to a tension coil spring 499 which in the other end connected to the connecting portion 497. The portion of the piston-like shaft 496" directed towards the periphery of the operation device 110 is connected to arc-shaped rotatable frication elements 495 comprising friction surfaces 495*s* adapted to engage corresponding friction surfaces of the inner surface of a delay structure 491. When the arc-shaped rotatable frication elements 495 stands still, the tension coil springs 499 pulls the arc-shaped rotatable frication elements 495 towards the center of the operation device 110 such that the frication surfaces 495*s* do not engage the friction surfaces of the inner surfaces of the delay structure 491, however as the arc-shaped rotatable frication elements 495 starts to rotate, the arc-shaped rotatable frication elements 495 are pushed radially outwards, by means of centrifugal force, towards the inner surface of the delay structure 491, such that the friction surface 495*s* of the arc-shaped rotatable frication elements 495 engage the friction surfaces of the delay structure 491, such that the delay structure 491 is propelled. The delay structure 491 is connected to the delay force output 149*d* of the operation device, which in turn is directly or indirectly connected to the body engaging portion of the operable implant.

Figure 31D:
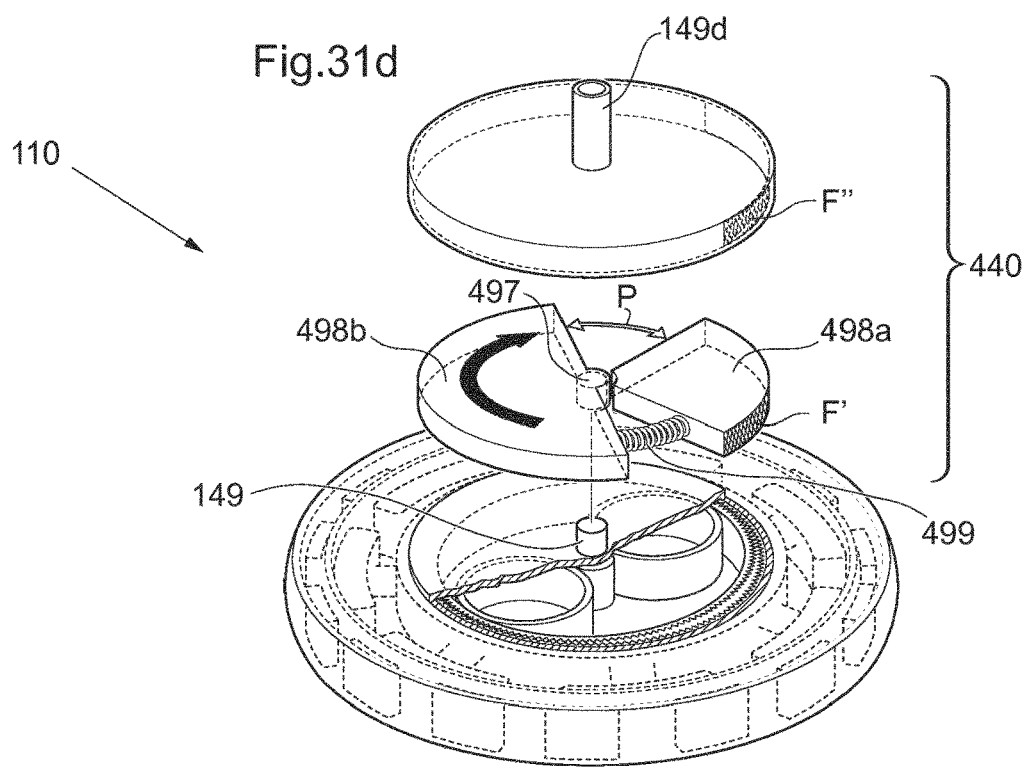
FIG. 31d shows an exploded perspective view of an implantable operation device comprising a start resistance delay.

FIG. 31*d* shows an embodiment of the operation device 110 comprising a start resistance delay 440 operated by means of a mechanical play P. The start resistance delay 440 is positioned between the force output 149 of an electrical motor/gear system 130/140 and a delay force output 149*d*, which in turn is directly or indirectly connected to a body engaging portion of the operable implant 110. The electrical motor/gear system unit 130/140 shown in FIG. 31*a* is identical to the electrical motor gear system unit described with reference to FIG. 7. The start resistance delay 440 is fixated to the force output 149 of the gear system by means of a connecting portion 497 comprising a recess or hole engaging the force output 149. The connecting portion 497 is connected to a semi-cylindrical disc 498*b* connected to a quarter-cylindrical disc 498*a* by means of a spring 499. The position of the quarter-cylindrical disc 498*a* in relation to the semi-cylindrical disc 498*b* creates a radial mechanical play P between the quarter-cylindrical disc 498*a* and the semi-cylindrical disc 498*b* corresponding to a ¼ of a revolution of the semi-cylindrical disc 498*b*. The mechanical play P enables the force output 149 of the gear system to perform ¼ of a revolution, which in turn enables the electrical motor to perform ¼ of a revolution times the transmission of the gear system. The quarter-cylindrical disc 498a is fixated to the delay structure 191 by means of a fixation surface F' of the quarter-cylindrical disc 498a being fixated to a fixation surface F" of the quarter-cylindrical disc 498a. In the embodiment shown in FIG. 31d, the spring 499 returns the semi-cylindrical disc 498a to the starting position when the electrical motor is stopped i.e. resetting the start resistance delay 440, however, it is equally conceivable that the spring is replaced by the electrical motor being programmed to perform a number of reverse revolutions after being stopped for resetting the start resistance delay 440.

Figure 31E:
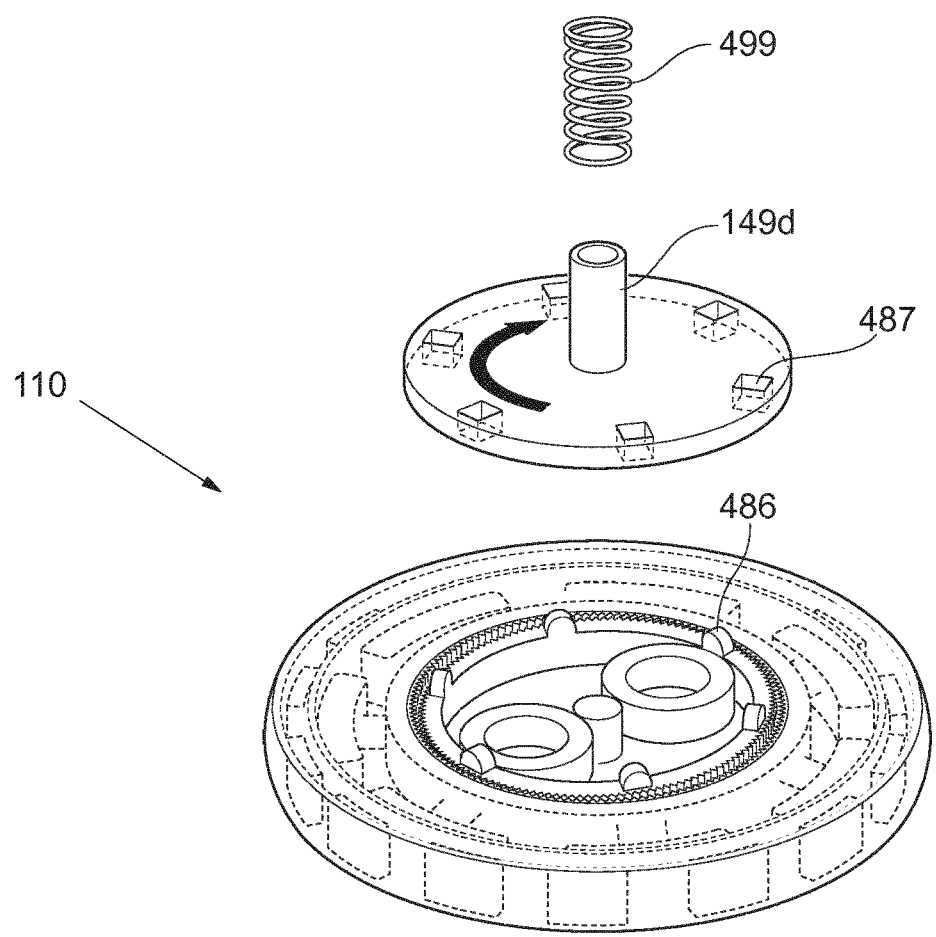
FIG. 31e shows an exploded perspective view of an implantable operation device comprising a coupling.

FIG. 31e shows a coupling which may be used in connection with any of the embodiments of operation devices herein. The coupling could be used to limit the force output of the operation device 110 for safety reasons, such that the risk of damage to any parts of the device operated by the operation device is reduced. The coupling comprises protruding members 486 protruding from the force output of the gear system. The coupling further comprises a disc shaped member comprising recesses 487 which correspond to the protruding members 486 of the gear system. The protruding members 487 are rounded for enabling the protruding members to slip out of the recesses, lifting the disk shaped member against the action of the spring 499 and thus separating the gear system from the force output 149d of the disc shaped member.

FIGS. 32-40 shows alternative methods and devices for transferring force and/or electrical energy from the outside of the body of the patient to the inside of the body of the patient. The different methods and devices may be used with the operable implants of any of the embodiments herein. For example, the use of a reciprocating magnetic field for the transfer of wireless energy reduces the losses in energy transfer, as no energy is consumed with the sheer forces arising from the transfer if a rotating magnetic field.

Figure 32:
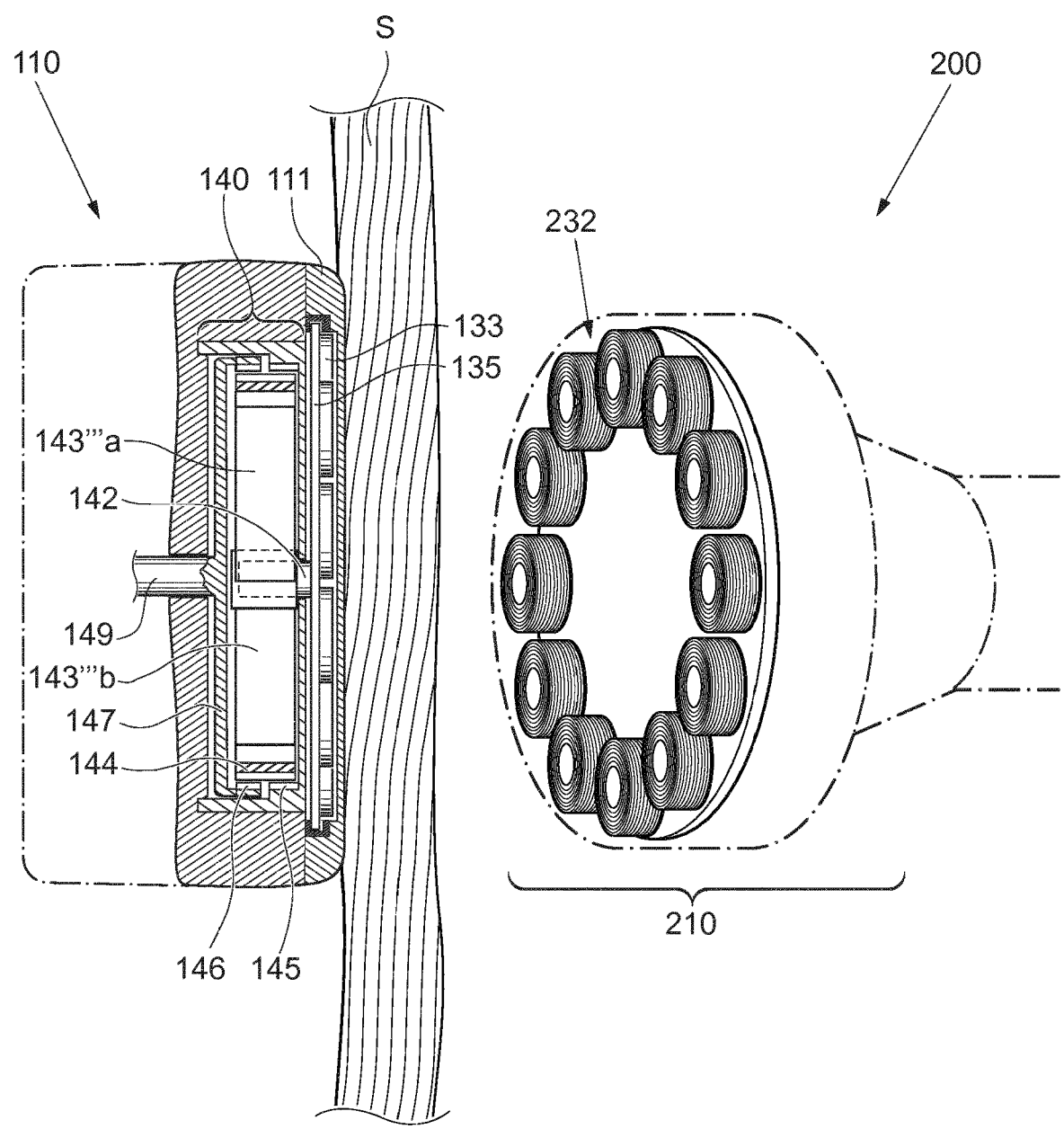
FIG. 32 shows a sectional side view of an implantable operation device placed on the inside of the patient's skin, and an external unit for powering the implantable operation device.

FIG. 32 shows an operation device 110 for an operable implant, when being implanted subcutaneously in the abdominal region of a patient i.e. beneath the skin S. The operation device comprises an enclosure 111 enclosing a rotatable structure 135 comprising a plurality of magnets 133 fixated thereto. The magnets are adapted to be affected by a moving magnetic field created by coils 232 of an external unit 200, such that the magnets 133 and thus the rotatable structure 135 moves along with the moving magnetic field of the external unit 200.

The operation device 110 further comprises a gear system 140 (further disclosed in relation to other embodiments herein, such as with reference to FIGS. 3a, 3b) comprising operable elements 143'''a connected to a force input 142 of the gear system, which in turn is connected to the rotatable structure comprising the magnets 133. By the indirect connection with the rotatable structure 135, the operable elements 143'''a, 143'''b are propelled by the magnets 133 moving along with the moving magnetic field of the external unit 200. The gear system further comprises a first gear 144 having the shape of a hollow cylinder, comprising a first number of teeth, on the peripheral outside thereof, and a second gear 145 having the shape of a hollow cylinder, comprising a greater number of teeth than the first gear 144, on the inside surface thereof. The operable elements 143'''a, 143'''b are adapted to engage the inside of the first gear 144, such that the outside of the first gear 144 is pressed against the inside of the second gear 145 such that the teeth of the first gear 144 are interengaged with the teeth of the second gear 145 in two positions interspaced by positions in which the teeth are not interengaged. The operation of the operable elements 143' 143' advances the positions and thereby causes relative rotation between the first gear 144 and the second gear 145. The gear system further comprises a third gear 146 comprising the same amount of teeth as the first gear 144 and thus rotates along with the interengaged positions between the first 144 and second gear 145. The third gear 146 is connected to a force output of the gear system by means of a radially extending structure 147. The force output 149 may for example be directly or indirectly connected to a body engaging portion of the operable implant or to a threaded member adapted to transform a rotating force to a reciprocating force. The threaded member may in turn be directly or indirectly connected to a movable wall portion of a reservoir for changing the volume of the reservoir (such as further disclosed in relation to other embodiments herein).

The operation device 110 is hermetically enclosed by an enclosure 111. The enclosure could be made from a ceramic material, such as silicon carbide or zirconium carbide, or a polymer material, such as UHWPE or PTFE, or glass. In any instance the enclosure should be made from a material with low permeability, such that migration of bodily fluids through the walls of the enclosure is prevented.

The implantable operation device 110 may additionally comprise a wireless communication unit adapted to at least one of: receive wireless communication signals from an external unit, and transmit wireless communication signals to an external unit.

The external unit 200 for supplying force to the implanted operation device 110 comprises an external drive 210 unit adapted to create a moving magnetic field on the outside of the patient's skin S adapted to affect the magnets 133 of the implanted operation device 110, such that the magnets 133 moves along with the moving magnetic field of the external drive unit 210. The external drive unit comprises a set of coils 232 circularly distributed around a rotational axis of the external unit 200, such that sequential energizing of the coils creates a rotating magnetic field adapted to affect the magnets 133 of the implanted operation device 110, such that the magnets 133 moves along with the moving magnetic field of the external drive unit 210.

The external unit 200 may additionally comprises a wireless communication unit for receiving wireless communication signals from an implantable unit, and/or transmitting wireless communication signals to the implantable unit.

FIG. 33 shows an alternative embodiment of the system for transferring energy from the outside of the body of a patient to an operable implant 100 placed inside the body of the patient. In the alternative embodiment, the device comprises an external unit 200 comprising an external drive unit 210. The external drive unit 210 comprises an external rotatable structure 235 comprising positive and negative permanent magnets 233p, 233n. The rotatable structure 235 is fixated to a shaft connected to an electrical motor 230 in the external unit 200 for rotating the rotatable structure 235. The magnets 233p, 233n of the rotatable structure 235 are adapted to magnetically connect to implanted magnets 133p, 13311 of a reciprocating structure 428. The implanted magnets 133p has positive polarity and are thus alternatingly attracted and repelled by the positive and negative magnets 233p, 233n connected to the rotatable structure 235 of the outside of the body of the patient. As the rotatable structure 235 rotates, an alternating magnetic field is created, causing reciprocation of implanted magnets 133p and thus of the reciprocating structure 428 to which the magnets 133p are connected. The reciprocating structure 428 is in turn connected, directly or indirectly to a body engaging portion of the operable implant, such that the reciprocating movement of the reciprocating structure operates the body engaging portion.

FIG. 34 shows an alternative embodiment of the system for transferring energy from the outside of the body of a patient to an operable implant 100 placed inside the body of the patient, similar to the system shown with reference to FIG. 34. The difference is that the reciprocating structure 428 is connected to a hinged connecting rod 422, which in the other end is connected to a flywheel 423. The flywheel 423 is in turn connected to a gear system 424, in form of a bevel gear for altering the direction of the force supplied to a first shaft 142, being the force input 142 of a hydraulic pump adapted to operate a hydraulically operated body engaging portion 180. The alternating magnetic field generated by the external unit 200, on the outside of the skin S of the patient, thus operates the body engaging portion 180 by means of a hydraulic pump 150 and a fluid conduit 162.

FIG. 35*a* shows a system for transferring rotating force from outside of the patients skin S into the body of the patient. The system is adapted to transfer rotating force with minimal squeezing of the skin S of the patient. The system comprises an external rotating structure 235', having a larger diameter than an internal rotating structure 135'. The external rotating structure 235' comprises magnets 233 arranged on the inside of an external spherical cap 235' such that the radial force rotating the internal rotatable structure 135' is greater than the axial force exerted by the magnets 233. The axial force exerted by the magnets 133, 233 presses the internal rotatable structure 135' against the external rotatable structure 235' and thus squeezes the skin S of the patient between the internal and external rotatable structures 135', 235'. The internal magnets 133 are mounted to a rotatable structure 135' in the form of a rotatable internal spherical cap 135'.

FIG. 35*b* shows an alternative embodiment of the medical system in which the both the internal rotating structure 135' and the external rotating structure 235' comprises repelling magnets 133*c*, 233*c* placed centrally on the internal and external spherical caps 135', 235'. The repelling magnets 133*c*, 233*c* are adapted to decrease the axial forces created by the magnetic connection between the internal and external magnets 133, 233, such that the squeezing effect on the patient's skin S is reduced. In the embodiment shown in FIG. 35*b*, the repelling magnets 133*c*, 233*c* are permanent magnets having a constant magnetic force, however, in alternative embodiments, it is conceivable that the repelling magnets 133', 233' are electromagnets enabling the magnetic force of the repelling magnets 133*c*, 233*c* to be adjusted by altering the current supplied to the electromagnet. In yet another embodiment, the repelling magnet of the external rotating structure 235' could be an axially movable permanent magnet, such that the distance between the skin S of the patient and the permanent magnet can be adjusted, such that the repelling force (and thus the squeezing force), can be adjusted. The magnets 133, 233 and repelling magnets 133*c*, 233*c* could also be used for the purpose of aligning the receiving unit and the external unit (or transmitting unit 220 of the external unit 200) such that the force transfer is optimized.

FIG. 35*c* shows an alternative concept for transferring rotating force from outside the body of the patient to the inside thereof. The concept includes using a plurality of satellite permanent magnets 233 and a plurality of permanent magnets 133 placed on a rotatable disc inside the body of the patient. The plurality of internal and external permanent magnets 133, 233 comprises positive 133*p*, 133*p* and negative 133*n*, 233*n* poles. As the external satellite magnets rotate they propel the rotating disc by the magnetic connection with the satellite magnets 233 as the attracting poles 233*n*, 233*p* of the satellite magnets alternates in alignment with the poles of the permanent magnets 133 of the rotatable disc.

FIG. 36 shows an embodiment of an operable implant 100 comprising an implantable generator 170 for generating electrical current to the operable implant 100. The operable implant 100 comprises a receiving unit 120 comprising a plurality or coils 132 circularly distributed on a disc. The coils 132 are in magnetic connection with an external unit 200 comprising a rotatable structure 235 comprising magnets 233 fixated thereto. The rotation of the magnets 233 generates a moving magnetic field which affects the coils 132, such that electrical current is induced in the coils 132. The receiving unit 120 or generator 170 is connected to an implantable battery 190 by means of a lead 192. A further lead 192' connects the battery 190 to a control unit 195 adapted to control a hydraulic pump 150, which for example could be any of the hydraulic pumps disclosed herein. The hydraulic pump 150 is adapted to transfer a hydraulic fluid from the reservoir 160 to a hydraulically operable body engaging portion 180 by means of a fluid conduit 162.

Now turning the external unit 200, the external unit 200 comprises an external drive unit 210 comprising an electrical motor 230 which by means of a shaft is connected to a rotatable structure 235 to which the external magnets 233 are connected.

FIG. 37 shows an alternative embodiment of the implantable generator 170, in which the implantable generator 170 is an implantable linear generator in which a current is generated in a coil 132 by means of a rod-shaped magnet 133 is moved back and forth in the winding of the coil 132. The external drive unit 210 of the external unit 200 comprises an external rotatable structure 235 comprising positive and negative permanent magnets 233*p*, 233*n*. The rotatable structure 235 is fixated to a shaft connected to an electrical motor 230 in the external unit 200 for rotating the rotatable structure 235. The magnets 233*p*, 233*n* of the rotatable structure 235 are adapted to magnetically connect to implanted magnets 133*p* of a reciprocating structure 428. The implanted magnets 133*p* has positive polarity and are thus alternatingly attracted and repelled by the positive and negative magnets 233*p*, 233*n* connected to the rotatable structure 235 of the outside of the body of the patient. As the rotatable structure 235 rotates, an alternating magnetic field is created, causing reciprocation of implanted magnets 133*p* and thus of the reciprocating structure 428 to which the magnets 133*p* are connected. The reciprocating structure 428 is in turn connected to the rod-shaped magnet 133. The coil 132, in which the current is induced, is connected to an implantable battery 190 by means of leads 192. A further lead 192' connects the battery 190 to a control unit 195 adapted to control a hydraulic pump 150, which for example could be any of the hydraulic pumps disclosed herein. The hydraulic pump 150 is adapted to transfer a hydraulic fluid from the reservoir 160 to a hydraulically operable body engaging portion 180 by means of a fluid conduit 162.

FIG. 38*a*-38*c* schematically shows alternative embodiments for transferring moving force between the outside of the body of the patient, and the inside of the body of the patient, for generating electrical current inside of the body of a patient by means of an electrical generator 170. FIG. 38*a* schematically shows and embodiment in which a permanent magnet 233 is located on the outside of the body of the patient and magnetically connected to a magnet 133 of an implantable generator on the inside of the skin S of the patient. The external magnet 233 is adapted to reciprocate and thus creating a reciprocating magnetic field affecting the magnet 133 on the inside of the skin S of the patient, such that the magnet 133 reciprocates inside of a coil 132 such that an electrical current is generated in the coil 132.

FIG. 38b shows an alternative embodiment similar to the embodiment shown in FIG. 38a. The difference being that the internal magnet 133 is spring loaded by means of a spiral spring 492, such that the reciprocating movement of the internal magnet 133 is created by magnetic force from the magnetic connection with the external unit magnet 233 in one direction, and by the action of the spring 492 in the opposite direction. The external magnet may be adapted to attract the internal magnet 133 or be adapted to repel the internal magnet 133.

FIG. 38c shows an embodiment of the system for transferring force similar to the system shown in FIG. 38c, the difference being that the external magnet 233e is an electromagnet 233e adapted to attract the internal magnet 133. The electromagnet 233e creates the alternating magnetic field by means of altering the electrical current running through the coil of the electromagnet, and thus altering the magnetic force supplied by the electromagnet 233e. Just as in the embodiment described with reference to FIG. 38b, the internal magnet 133 is spring loaded by means of a spiral spring 492.

Figure 39:
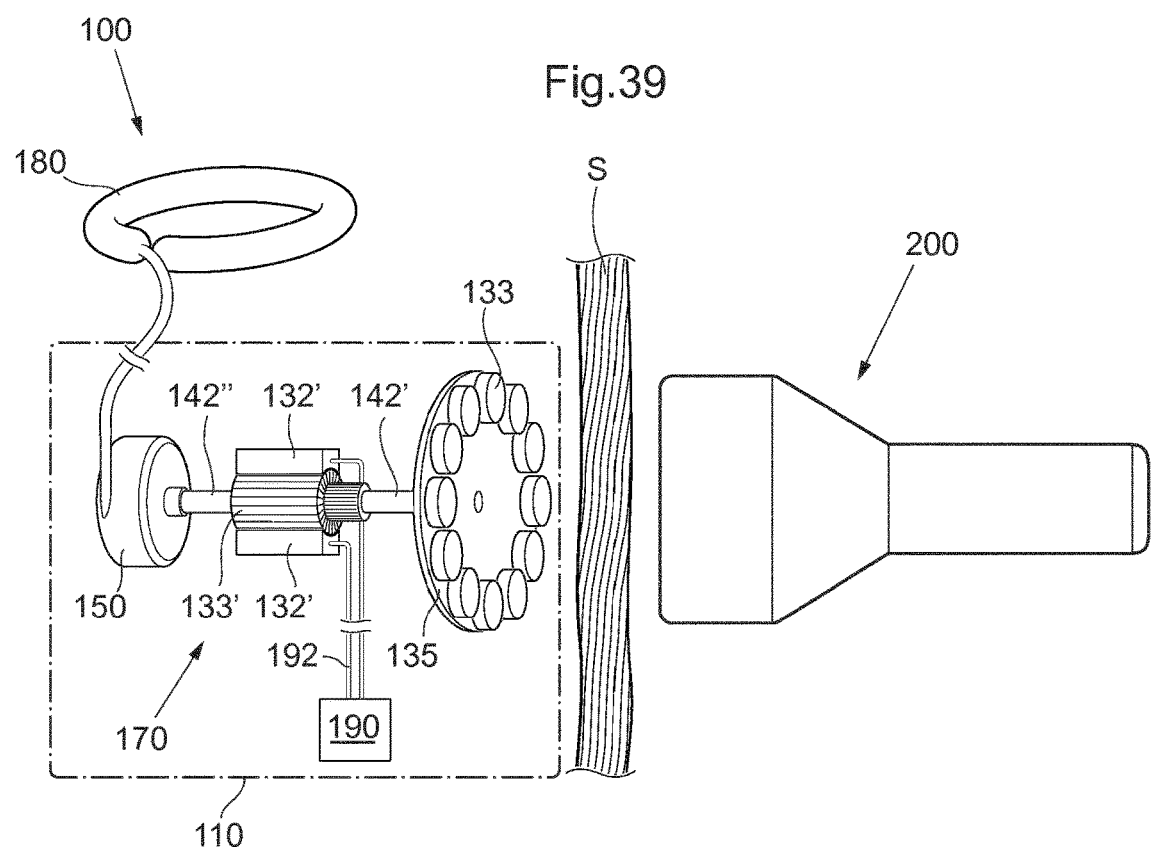
FIG. 39 shows a side view an operable implant and a wireless energy transmitter.

FIG. 39 shows an embodiment of the operable implant 100 adapted to be implanted in the body of a patient. The operable implant 100 comprising an operation device 110, similar to the operation device shown in FIG. 32, and a body engaging portion 180. The operation device 110 comprises a movable part in form of a rotatable structure 135 connected to the body engaging portion 180 via a hydraulic pump 150. The rotatable structure 135 comprises a plurality of magnets 133 connected thereto. The magnets 133 are adapted to magnetically connect to a moving magnetic field generated by the external unit 200 on the outside of the patient's skin S, such that the rotatable structure 135 rotates along with the moving magnetic field. The operation device 110 further comprises an implantable generator 170 connected to the rotatable structure 135 and adapted to transform movement to electrical current, such that the movement of the rotatable structure 135 operates the body engaging portion 180 and generates electrical current.

The implantable generator 170 comprises two coils 132' and several magnets 133 mounded to a shaft being the force input 142', 142" of the implantable generator and the hydraulic pump 150. The movement of the magnets 133' in relation to the coils 132' induces an electrical current in the coils 133'.

The operation device 110 further comprises a battery 190 connected to the implantable generator 170 by means of leads 192.

In an alternative embodiment, the magnets 133 of the rotatable structure 135 may further affect the coils 132' of the generator 170, such that the same magnets may be used for connecting to the external unit 200 and for generating electrical current in the implantable generator 170.

The operable implant 100 may further comprise a control unit for controlling at least one parameter of the operable implant, and the control unit may be connected to the battery 190 such that the battery powers the control unit.

In the embodiment shown in FIG. 39, the body engaging portion 180 is a hydraulically operable body engaging portion 180 connected to the hydraulic pump 150. The hydraulic pump 150 comprises a reservoir adapted to hold hydraulic fluid and being connected to the hydraulic pump, such that the hydraulic pump can transport hydraulic fluid from the reservoir to the body engaging portion 180. The hydraulic pump 150 may comprise a movable wall portion of the reservoir (such as described in relation to other embodiments herein). The fluid is then transported from the reservoir to the body engaging portion 180 by moving the movable wall portion and thereby changing the volume of the reservoir.

In alternative embodiments, the hydraulic pump could be for example a non-valve pump, a pump comprising at least one valve, a peristaltic pump, a membrane pump, a gear pump or a bellows pump.

Figure 40:
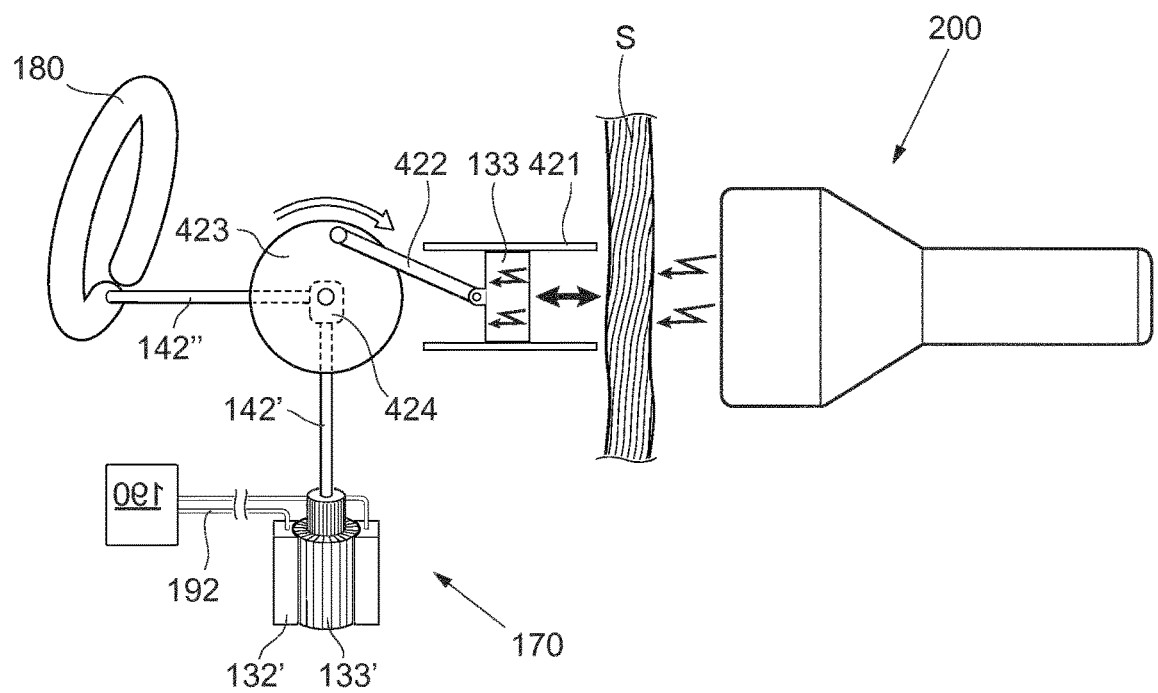
FIG. 40 shows a side view an operable implant and a wireless energy transmitter.

FIG. 40 shows an alternative embodiment of the operable implant, similar to the embodiment described with reference to FIG. 39. The difference is that the implantable operation device of FIG. 40 comprises a magnet 132 adapted to perform a reciprocating movement in a magnet guide 421. The magnet 133 is connected to a hinged connecting rod 422, which in the other end is connected to a flywheel 423. The flywheel 423 is in turn connected to a gear system 424, in form of a bevel gear for altering the direction of the force supplied to a first shaft, being the force input 142' of the implantable generator 170, and a second shaft, being the force input 142" of a mechanically operated body engaging portion 180. The magnet 133 is magnetically connected to a reciprocating magnetic field generated by the external unit 200, on the outside of the skin S of the patient, such that the structure for reciprocating movement (133, 422) moves along with the reciprocating magnetic field. The reciprocating magnetic field is created by the external unit 200 as an alternating magnetic field, i.e. a magnetic field is generated which alternates in magnetic strength.

Figure 41:
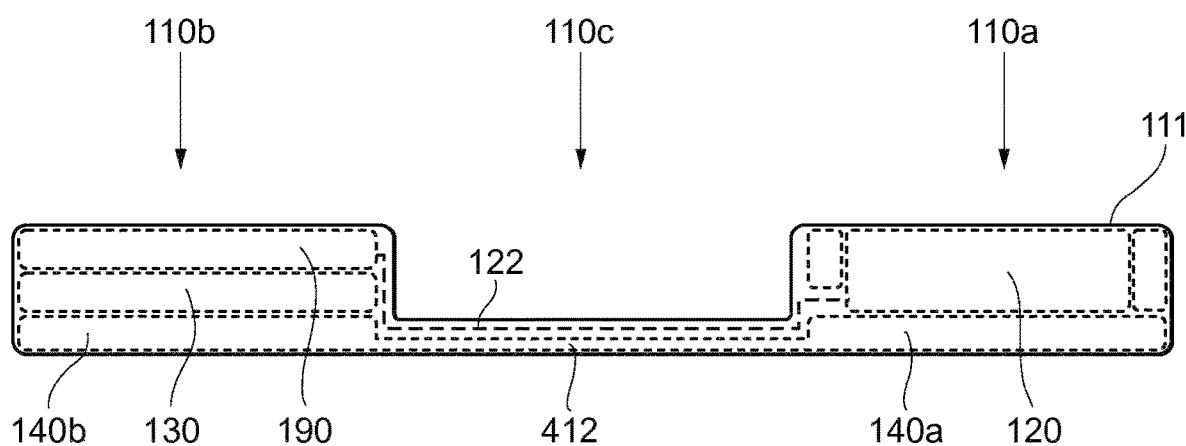
FIG. 41 shows schematic side view an operable implant.

FIG. 41 shows an operation device 110a-100c of an operable implant 100 for implantation in the body of a patient in which the operation device is divided into a first and second unit 110a, 110b. The first unit 110a comprises a receiving unit 120 for receiving wireless energy, and a first gear system 140a adapted to receive mechanical work having a first force and first velocity, and output mechanical work having a different second force and a different second velocity. The receiving unit 120 comprises a coil adapted to transform wireless energy received in form of a magnetic field into electrical energy by means of inductive connection. The second unit 110b of the operation device comprises an electrical motor 130 adapted to transform electrical energy into the mechanical work. The electrical motor 130 is a three phase electrical motor comprising magnetic material, both in form of magnets of the rotor and in the form of iron cores of the coils. The magnetic material creates a magnetic field which disturbs other magnetic fields in proximity, such as the magnetic field used for transferring wireless energy from a transmitting unit of an external unit to the receiving unit 120 of the operation device 110a-110c. For not interfering with the wireless energy transfer, the first unit 110a and the distance element 110c is free from metallic and magnetizable components. For the purpose of reducing the risk that the magnets of the electrical motor 130 placed in the second unit 110a interferes with the magnetic field transferring wireless energy from an external unit to the implanted operation device, the operation device further comprises a distance element 110c adapted to create a distance between the first and second unit 110a, 110b. The distance could for example be a distance of more than 1 cm, more than 2 cm, more than 3 cm, more than 4 cm or more than 5 cm. The distance element 110c comprises a lead 122 for transferring the electrical energy received at the receiving unit 120 of the first unit 110a, to the second unit 110b, and a mechanical transferring member 412 adapted to transfer the mechanical work from the electrical motor 130 in the second unit 110b to the gear system 140a in the first unit 110a. By means of the distance element 110c, the first and second units 110a, 110b are separated such that the receiving unit 120, when receiving wireless energy, is not substantially affected by magnetic material in the second unit 110b.

The second unit 110b additionally comprises a second gear system 140b placed in series between the electrical motor 130 and the first gear system 140a. The second gear system 140b is adapted to receive mechanical work of a first force and velocity from the electrical motor 130 and output mechanical work of a different force and velocity. The force is transferred from the second gear system 140b to the first gear system 140a by means of a mechanical transferring member 412, which for example could be a belt or a rotating shaft. The first and second gear systems 140a, 140b are connected in series such that the first and second gear systems 140a, 140b, together act as a single gear system. The first and/or second gear systems 140a, 140b could for example be gear systems according to any of the embodiments shown herein, such as for example the gear systems described with reference to FIGS. 2a-22. The electrical motor 130 could for example be an alternating current (AC) electrical motor, a direct current (DC) electrical motor, a linear electrical motor, an axial electrical motor, a piezoelectric motor, a three-phase motor, a more than one-phase motor, a bimetal motor or a memory metal motor. In the embodiment shown in FIG. 41, the second unit 110b furthermore comprises a battery 190 adapted to be connected to the receiving unit 120 by means of the lead 122, such that the battery 190 is charged by the wireless energy received by the receiving unit 120.

The first unit may additionally comprise a communication unit adapted to wirelessly communicate with an external unit on the outside of the body of the patient.

The first unit 110a is preferably implanted subcutaneously in the abdominal wall such that the receiving unit 120 can be placed in proximity with a transmitting unit of an external unit transferring wireless energy to the operable implant 100. The operable implant 100 may additionally comprise at least one fixation portion for fixating the operable implant 100 in the body of the patient. The fixation could for example be performed by fixating the second unit 110b to fibrosis, a fascia and/or a muscular layer towards the inside of the subcutaneous space of the patient, while allowing the first unit 110a to rest subcutaneously. Fixating the second unit 110b to the body of the patient indirectly fixates the first unit 110a and reduces the risk that the first unit 110a migrates through the skin of the patient. An alternative way of fixating the operation device 110a-110c is by placing the second unit 110b on the inside of the muscular layers or muscular fascia of the abdominal wall and placing the distance element 110c through the muscular layers or muscular fascia such that the movement of the operation device is limited in both directions by the first and second units 110a, 110b being hindered from passing though the hole made in the muscular layers or muscular fascia.

The first gear system 140a is directly or indirectly connected to a body engaging portion of the operable implant adapted to affect the body of the patient in some way, for example by constricting a luminary organ. The connection between the operation device and the body engaging portion is further described with reference to other embodiments herein.

The operation device is in the embodiment shown in FIG. 41 enclosed by an enclosure adapted to hermetically enclose the operable implant. The enclosure could be an enclosure made from a non-metallic material, such as for example a ceramic material, such as silicon carbide or zirconium carbide, or a polymer material, such as UHWPE or PTFE, or glass. In any instance the enclosure should be made from a material with low permeability, such that migration of bodily fluids through the walls of the enclosure is prevented.

The first or second unit may further comprise a control unit for controlling at least one parameter of at least one of: the operation device, and the body engaging portion. In the embodiment shown in FIG. 41, the electrical motor 130 is an alternating current (AC) motor, and the control unit comprises a frequency converter for altering the frequency of an alternating current for controlling the alternating current motor.

The force output of the first gear system 140a could be indirectly connected to the body engaging portion, for example by the first gear system 140a being connected to a hydraulic pump adapted to transfer mechanical work into hydraulic power for powering a hydraulically operable body engaging portion. The hydraulic pump could for example be a reservoir acting as a hydraulic pump by means of a wall moving (such as further described in several embodiments herein), a non-valve pump, at least one valve pump, at least one peristaltic pump, at least one membrane pump, at least one gear pump, and at least one bellows pump.

The first unit placed subcutaneously may additionally comprise an injection port for refilling a reservoir or in any way calibrating the fluid level in a hydraulic system of the operable implant, such as the fluid level in the hydraulically operable body engaging portion.

Figure 42:
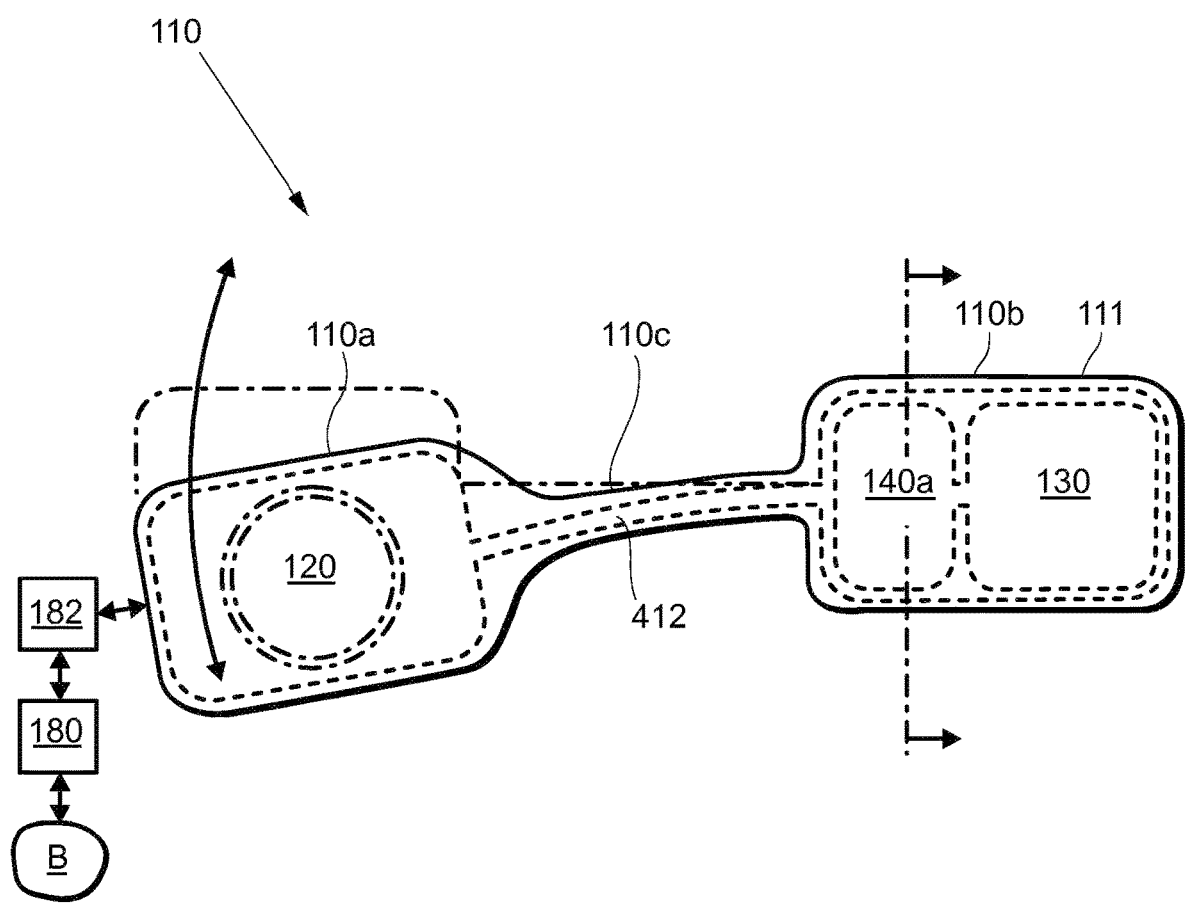
FIG. 42 shows schematic side view an operable implant.

FIG. 42 shows an embodiment of the operation device 110 similar to the embodiment shown with reference to FIG. 42, the main difference being that the operation device of the embodiment shown in FIG. 42 comprises a flexible distance element 110c, such that the first unit 110a can move in relation to the second unit 110b. The flexible distance element comprises a flexible mechanical force transferring member, which for example could be a hydraulic tube for transferring hydraulic force, a flexible rotating shaft for transferring rotational force, a wire, a belt, a rod, and a worm gear, or a gear for changing rotational force in substantially 90 degrees direction. The first unit 110a of the operation device 110 shown in FIG. 42 does not comprise a second gear system, instead, the mechanical force transferring member 412 is in direct connection with a connecting portion 182, such as a mechanical force transferring member or a hydraulic pump, connecting to the body engaging portion 180, which in turn connects to the body of the patient, such that the body of the patient can be affected by the operation device 110. The flexible distance element is for example made from an elastomeric polymer material, such as silicone or polyurethane.

Figure 43A:
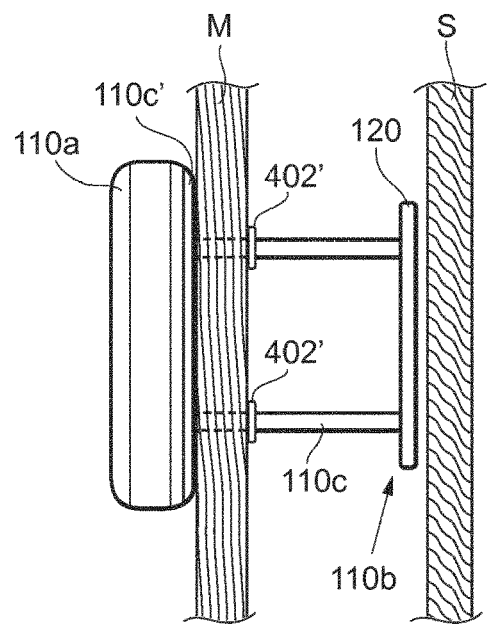
FIG. 43a shows a side view of an operable implant including a fixation and distance creating element.

FIG. 43a shows an embodiment of the operation device 110 similar to the embodiment shown with reference to FIGS. 41 and 42, when fixated to a muscular layer M of the patient. The operation device 110 shown in FIG. 43a comprises a first unit 110a fixated on the inside of a muscular layer M of the abdominal wall, and a second unit 110b placed subcutaneously, i.e. under the skin S of the patient. The first and second units 110a, 110b of the operation device are connected by means of a distance element 110c which pierces the muscular layer M. The first unit 110*a* is placed on the inside of the muscular layer M and on the outside of the muscular layer M limiting elements 402' are positioned, hindering the distance elements 110*c* from moving in the holes in the muscular layer M, and thus fixates both the first and second units 110*a*, 110*b*. The second unit 110*b* comprises the receiving unit 120 for receiving wireless energy and is by means of the distance element separated from the rest of the operation device 110*a*, such that metallic and/or magnetic components of the operation device 110*a* does not interfere with the wireless energy transfer from the outside the patient's body to the inside of the patient's body. Fixating the first unit to the muscular layer M further controls the distance between the skin S and the second unit 110*b*, preventing the second unit 110*b* from being placed so close to the skin S of the patient such that there is a risk that the second unit 110*b* migrates through the skin S of the patient.

Figure 43B:
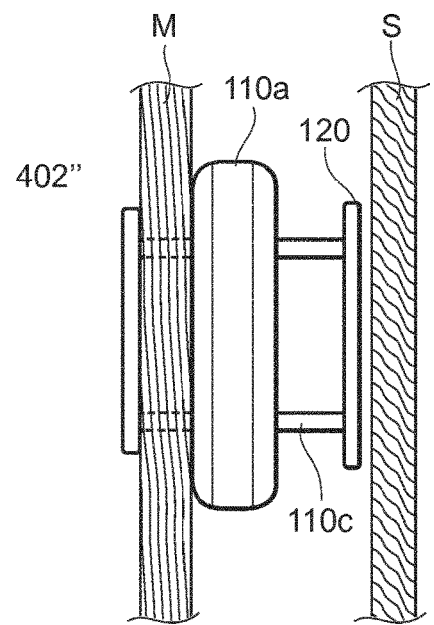
FIG. 43b shows a side view of an operable implant including a fixation and distance creating element.

FIG. 43*b* shows an alternative embodiment of the operation device and distance element 110*c*, in which the first unit 110*a* of the operation device is placed on the outside of the muscular layer M of the abdominal wall. The distance elements 110*c* pierces the muscular layer M of the abdominal wall and connected to a limiting element 402" placed on the inside of the muscular layer M of the abdominal wall. The distance elements 110*c* thus creating a distance between the first unit 110*a* of the operation device, placed on the outside of the muscular layer M and the receiving unit 120 placed subcutaneously.

Figure 43C:
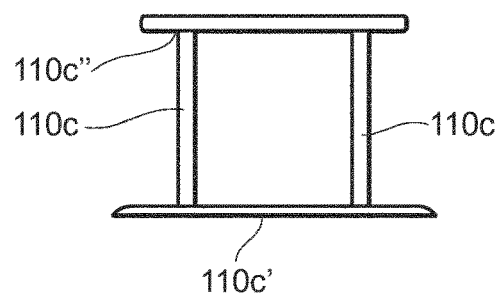
FIGS. 43c and 43d shows two distance elements making up a kit of distance elements.
Figure 43D:
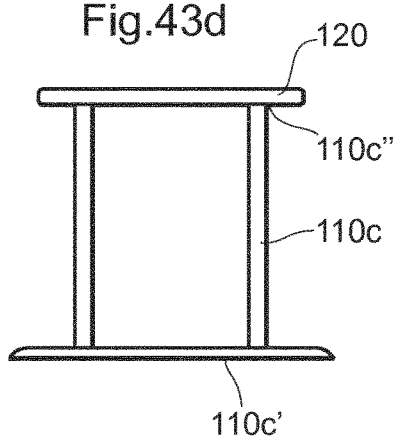

FIGS. 43*c* and 43*d* together represents a surgical kit for an enabling adjustment of a distance between the first and second units 110*a*, 110*b* of the operation device, or between a fixation member of one of the units and the unit comprising the receiving unit 120. FIG. 43*c* shows a first distance element of the surgical kit, made up of two distance elements. The distance element has a first connecting portion 110*c*' adapted to directly or indirectly connect to the at least one part of the operation device of the operable implant, and a second connecting portion 110*c*" adapted to directly connect to the unit 110*b* comprising the receiving unit 120. The first connecting portion 110*c*' acting as a fixation member 110*c*' of the operable implant, such that the operation device remains fixated to the muscular layer M of the patient. FIG. 43*d* shows a second part of the surgical kit comprising a second distance element having a first connecting portion 110*c*' adapted to directly or indirectly connect to at least one part of the operable implant, and a second connecting portion 110*c*" adapted to directly or indirectly connect to the part of the operation device comprising the receiving member 120. The second distance element shown in FIG. 43*d* is adapted to create longer distance between the first and second unit 110*a*, 110*b* than the first distance element. By having a kit of different distance elements to choose from, the surgeon can adjust the distance such that the receiving unit constantly is positioned subcutaneously, without the risk that the receiving unit migrates through the skin of the patient.

Figure 43E:
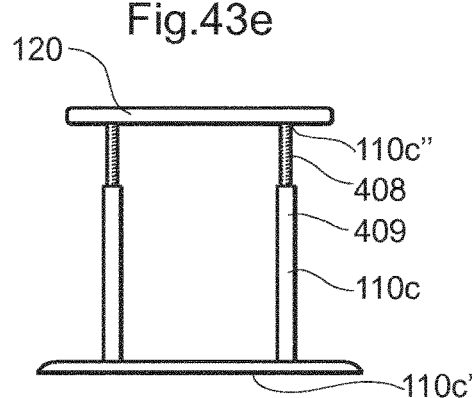
FIG. 43e shows an adjustable distance element.

FIG. 43*e* shows an adjustable distance element 110*c* which in one end 110*c*' is directly or indirectly connected to a part of the operable implant, and in the other end 110*c*" is directly or indirectly connected to the fixation member. The adjustable distance element 110*c* is adapted to adjust the distance between the part of the operable implant and the fixation member, such that the receiving unit can be placed subcutaneously without the risk of the receiving unit migrating through the skin of the patient. The distance element 110*c* is adjustable by means of the distance element comprising a sleeve being threaded on the inside thereof, in which a threaded shaft 408 is positioned, the threaded shaft 408 rotating in the threaded sleeve thus extends of decreases the length of distance element and thus adjusts the distance between the first and second units 110*a*, 110*b* of the operation device.

The fixation member of the operation device may for example be integrated with: a control unit, a receiving unit, for receiving wireless energy, a coil, for receiving wireless energy, a receiving unit, for receiving a magnetic field or an electromagnetic field, a magnetic force transferring coupling, an electrical circuit, a push button for controlling any function of the operable implant, an energy storage device, a pushable construction for adjusting the adjustable distance element, an integrated operation device and receiving unit, for receiving wireless energy or a magnetic field or an electromagnetic field adapted to generate kinetic energy, a casing for enclosing at least one of the different parts of the operable implant, or two or more casings for enclosing at least one of the different parts of the operable implant in each casing.

The adjustable distance element may be operable from outside the body of the patient, such that the distance can be adjusted from outside the body of the patient. The adjustable distance element could be adjustable electrically or manually from outside the body of the patient.

The first and/or second end of the adjustable distance element may be detectable from outside the body of the patient, such that the distance between the first and second ends can be determined by means of for example x-ray or ultrasound.

The distance element 110*c* can be made from an elastic and/or flexible material, such that the first end 110*c*' can flex in relation to the second end 110*b*, which is more comfortable for the patient, especially when the patient moves in a manner affecting the distance element.

The end of the adjustable distance element connected to the receiving unit 120 of the operation device 110 is preferably made from a non-metallic and non-magnetic material, such that the adjustable distance element does not affect the wireless energy transfer between an external unit and the implanted operation device 110.

As the receiving unit 120 receiving wireless energy is positioned in one end of the adjustable distance element 110, the adjustable distance element comprises a lead for transferring electrical current from the receiving unit 120 to the operation device of the operable implant.

Figure 44:
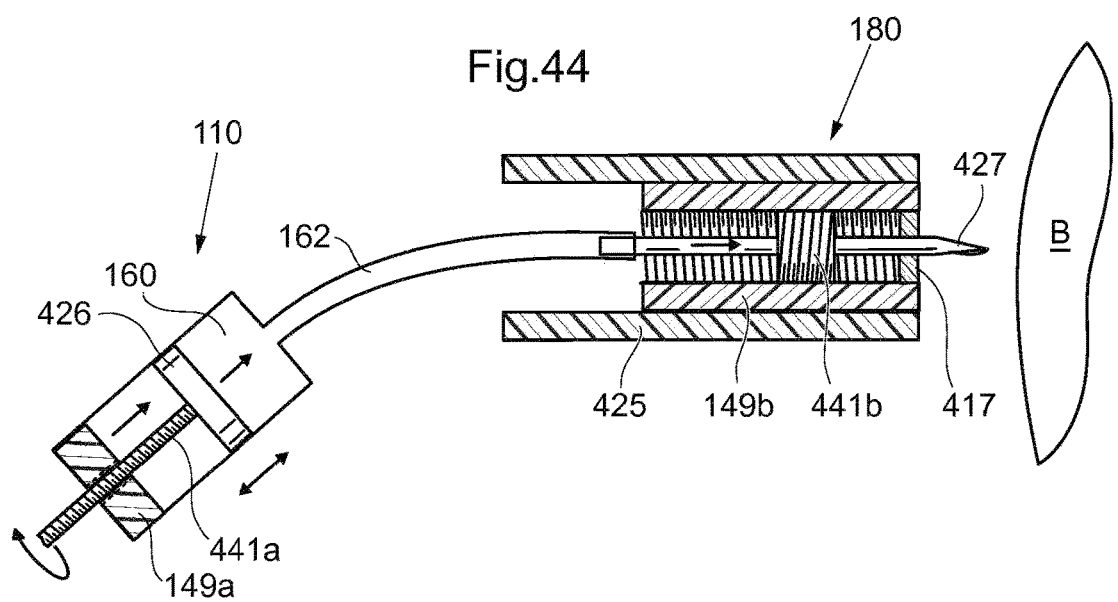
FIG. 44 shows an embodiment of the operable implant in which the body engaging portion is an injection device.

FIG. 44 shows an embodiment of a portion of an operable implant for injecting a fluid into a portion of the body B of the patient. A portion of an implantable operation device 110 is shown. The portion of the operation device comprises a threaded member 441*a* which is adapted to be rotated by a connection with a portion of the operation device adapted to create rotating force. The threaded member is guided in a sleeve 149*a* comprising corresponding internal threads, such that the rotation of the threaded member advances the threaded member axially. The threaded member is in turn connected to a piston 426, being a movable wall portion of a reservoir 160 adapted to contain a hydraulic fluid. The rotation of the treaded member pushes the piston inside the reservoir, decreasing the volume of the reservoir 160 and thereby moving the hydraulic fluid through a fluid conduit 162. The operation device 110 is by means of the fluid conduit 162 connected to a body engaging portion 180 comprising an outer sleeve 425 in which an inner sleeve 149*b* is mounted. The inner sleeve 149*b* is adapted to be rotated to cause axial movement of a threaded portion 441*b* through which a needle 427 is positioned. The needle 427 is adapted to be advanced to inject the fluid into the portion of the body B of the patient. As the needle 427 is advanced, it penetrates a membrane 417 of the body engaging portion. When the needle 427 is retracted it is protected by the membrane 417, such that the in-growth of fibrotic tissue does not damage the function of the body engaging portion 180.

The operable implant shown in FIG. 44 could be used to inject a medicament having a therapeutic affect into e.g. blood vessel or muscle of the patient. Alternatively, the operable implant may be used to deliver a fluid to the body B of the patient for its mechanical properties, such as a volume filling fluid or lubricating fluid.

The threaded member 441*a* of the operation device 110 is may for example be connected to any of the electrical motors described herein, with or without the use of a gear system, such as any of the gear systems disclosed herein. The operable implant may be powered by means of an implantable battery (such as described with reference to other embodiments herein) or by means of wireless energy supplied from outside the body of the patient.

Figure 45A:
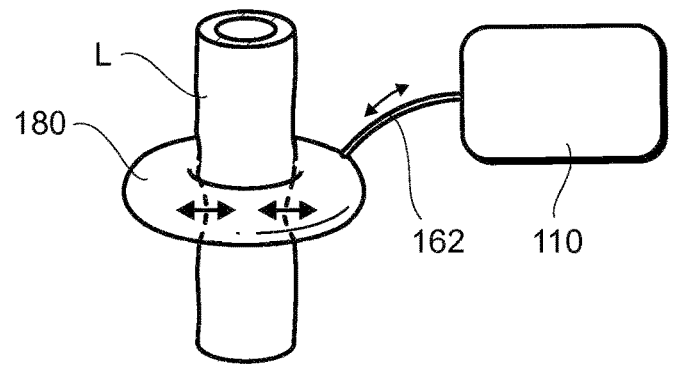
FIG. 45a shows an embodiment of the operable implant in which the body engaging portion is a constriction device.

FIG. 45*a* shows one example of a body engaging portion 180 in which the body engaging portion 180 is adapted to constrict a luminary organ L, such as the urethra, of a patient. The body engaging portion 180 is a torus-shaped hydraulically inflatable body engaging portion connected to an operation device 110, such as any of the operation device shown herein, by means of a fluid conduit 162. The body engaging portion 180 is elastic or collapsible such that the inflation thereof constricts the luminary organ L. In the case in which the luminary organ L is the urethra, the constricting hydraulically operable body engaging portion 180 constricts the urethra and thus stops the flow of urine therein, thus treating incontinence.

Figure 45B:
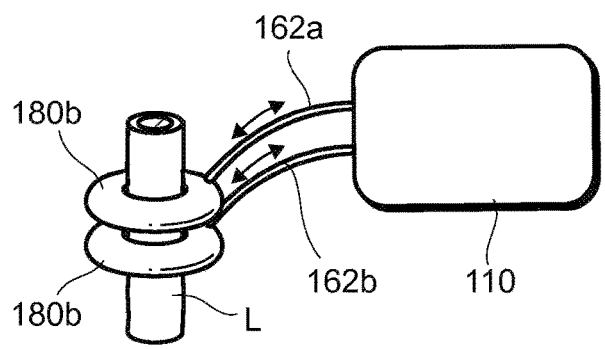
FIG. 45b shows an embodiment of the operable implant in which the body engaging portion is two constriction devices.

FIG. 45*b* shows an embodiment of the operable implant similar to the embodiment described with reference to FIG. 45*a*, the difference being that the embodiment shown in FIG. 45*b* comprises a first and second hydraulically operable body engaging portion 180*a*, 180*b*, both adapted to constrict the luminary organ L to stop the flow of fluid therein. The embodiment shown in FIG. 45*b* thus allows the luminary organ to be constricted in two different places and alternate therebetween, such that the strain on a specific portion of the luminary organ is reduced. The first and second hydraulically operable body engaging portions 180*a*, 180*b* are each connected to a first and second fluid conduit 162*a*, 162*b*, which may be connected to a first and second hydraulic pump, or to a first and second end of a hydraulic pump, such as to a first and second end of a peristaltic hydraulic pump. The operation device 110 may be programmed such that the operable implant alternates automatically between constricting a first and second portion of the luminary organ L for example after a pre-determined time has elapsed.

Figure 45C:
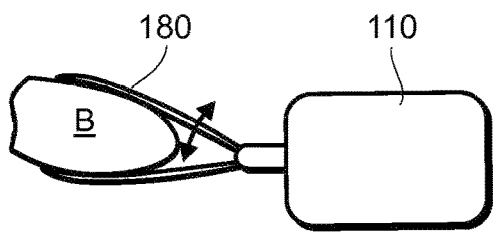
FIG. 45c shows an embodiment of the operable implant in which the body engaging portion is a mechanical body engaging portion.

FIG. 45*c* shows an alternative embodiment of the operable implant, in which the operable implant comprises a body engaging portion adapted to mechanically engage a portion of the body B of the patient. The portion of the body B of the patient could for example be the urethra of the patient, and the mechanical body engaging portion 180 could for example be adapted to lift the urethra to relieve the patient of incontinence. The mechanical body engaging portion 180 could for example be a flexible band, such as a band made from silicone. The operation device 110 connected to the mechanical body engaging portion 180 may be any of the mechanical operation devices shown herein, and could preferably comprise an electrical motor and a gear system. The body engaging portion 180 could be connected to the mechanical operation device 110 such that the force output of the gear system engages the body engaging portion 180.

The different aspects or any part of an aspect or different embodiments or any part of an embodiment may all be combined in any possible way. Any method or any step of method may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description, and please note that any embodiment or part of embodiment as well as any method or part of method could be combined in any way. All examples herein should be seen as part of the general description and therefore possible to combine in any way in general terms.

NUMBERED EMBODIMENTS

In the following, exemplifying numbered embodiments are provided in groups A-AK and numbered within that group. The numbered embodiments are not to be seen as limiting the scope of the invention, which is defined by the appended claims. The reference numerals in the different numbered embodiments are to be seen only as examples of elements in the appended drawings which correspond to elements described in the numbered embodiments.

Numbered Embodiment A 1-36

1. An operable implant adapted to be implanted in the body of a patient, the operable implant comprising an operation device and a body engaging portion, wherein the operation device comprises:
   a first unit comprising:
      a receiving unit for receiving wireless energy, and
      a first gear system adapted to receive mechanical work having a first force and first velocity, and output mechanical work having a different second force and a different second velocity,
      a second unit comprising an electrical motor adapted to transform electrical energy to the mechanical work, and
      a distance element comprising:
         a lead for transferring the electrical energy from the first unit to the second unit, and
         a mechanical transferring member adapted to transfer the mechanical work from the electrical motor in the second unit to the gear system in the first unit, wherein
      the distance element is adapted to separate the first and second units such that the receiving unit, when receiving wireless energy, is not substantially affected by the second unit.
2. The operable implant according to embodiment 1, wherein the receiving unit comprises at least one coil adapted to transform wireless energy received in form of a magnetic field into electrical energy.
3. The operable implant according to embodiment 2, wherein the receiving unit comprises at least a first coil having a first number of windings, and at least a second coil having a second, different number of windings.
4. The operable implant according to any one of the preceding embodiments, wherein the gear system comprises:

an operable element,
a first gear having the shape of a hollow cylinder, comprising a first number of teeth, on the peripheral outside thereof, and
a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

5. The operable implant according to embodiment 4, wherein the operable element comprises at least one of: a planetary gear and a structure or wheel at least partly using friction to interconnect with the first gear.

6. The operable implant according to any one of the preceding embodiments, wherein the second unit comprises a second gear system adapted to receive the mechanical work output from the first gear system with the different second force and the different second velocity as input, and output mechanical work having a third different force and third different velocity, and wherein the gear system of the second unit is connected in series with the gear system of the first unit, via the mechanical transferring member of the distance element.

7. The operable implant according to any one of the preceding embodiments, wherein the first unit comprises a second gear system adapted receive mechanical work of a first force and velocity as input, and output mechanical work having a different force and velocity, and wherein the second gear system is connected in series with the first gear system.

8. The operable implant according to any one of the preceding embodiments, wherein the first unit is adapted to be placed at least in one of the following places: subcutaneously, subcutaneously in the abdominal wall and in the abdomen.

9. The operable implant according to any one of the preceding embodiments, wherein the electrical motor comprises magnetic material and wherein the first unit is substantially unaffected by the magnetic material in the second unit, during wirelessly energy transfer.

10. The operable implant according to any one of embodiments 4-9, wherein the first gear system comprises a third gear, and wherein the inside of the third gear comprises the same amount of teeth as the outside of the first gear, and wherein teeth of the third gear are adapted to interengage with the teeth of the first gear such that the third gear rotates in relation to the second gear, along with the at least one interengaged position.

11. The operable implant according to embodiment 8, wherein the second unit comprises at least one fixation portion for fixating the second unit to at least one of: fibrosis, a fascia and a muscular layer towards the inside of the subcutaneous space of the patient.

12. The operable implant according to any one of the preceding embodiments, wherein the distance element is adapted to be at least one of; placed through the muscular layers of the abdominal wall, and fixated to the muscular fascia facing the subcutaneous space.

13. The operable implant according to any one of the preceding embodiments, wherein the distance element is flexible such that the first and second unit can move in relation to each other.

14. The operable implant according to any one of the preceding embodiments, wherein the mechanical transferring member comprises a mechanical transferring member selected from:
a hydraulic tube for transferring hydraulic force
a rotating shaft for transferring rotational force
a flexible member for transferring rotational force,
a wire,
a belt,
a rod,
a worm gear, and
a gear for changing rotational force in substantially 90 degrees direction.

15. The operable implant according to any one of the preceding embodiments, further comprising an enclosure adapted to hermetically enclose the operable implant.

16. The operable implant according to any one of the preceding embodiments, further comprising a metallic enclosure adapted to enclose at least one of the second unit and the distance element.

17. The operable implant according to embodiment 16, wherein the metallic enclosure comprises at least one of: a titanium enclosure, an aluminum enclosure, and a stainless steel enclosure.

18. The operable implant according to any one of the preceding embodiments, wherein at least one of the first and second units comprises a battery adapted to store electrical energy received at the receiving unit.

19. The operable implant according to any one of the preceding embodiments, wherein the electrical motor comprises an electrical motor selected from:
an alternating current (AC) electrical motor,
a direct current (DC) electrical motor,
a linear electrical motor,
an axial electrical motor,
a piezo-electric motor,
a three-phase motor
a more than one-phase motor
a bimetal motor, and
a memory metal motor.

20. The operable implant according to any one of the preceding embodiments, wherein the implantable system further comprises a control unit for controlling at least one parameter of at least one of:
the operation device, and
the body engaging portion.

21. The operable implant according to embodiment 20, wherein the electrical motor is an alternating current (AC) motor, and the control unit comprises a frequency converter for altering the frequency of an alternating current for controlling the alternating current motor.

22. The operable implant according to any one of the preceding embodiments, wherein the first unit comprises hydraulic pump adapted to transfer mechanical work into hydraulic power for powering a hydraulically operable body engaging portion, wherein the hydraulic pump is connected to the force output of the first or second gear system.

23. The operable implant according to embodiment 22, wherein the hydraulic pump is a hydraulic pump selected from:

at least one reservoir acting as a pump by a wall moving by the mechanical work,
at least one reservoir acting as a pump to move fluid by changing volume,
at least one non-valve pump,
at least one valve pump,
at least one peristaltic pump,
at least one membrane pump,
at least one gear pump, and
at least one bellows pump.
24. The operable implant according to any one of the preceding embodiments, wherein the first unit comprises a reservoir for supplying fluid to a hydraulically operable body engaging portion.
25. The operable implant according to any one of the preceding embodiments, wherein the operable implant comprises a third unit comprising a second reservoir for supplying fluid to a hydraulically operable body engaging portion.
26. The operable implant according to any one of embodiments 24 and 25, wherein the reservoir is operable and comprises at least one movable wall portion.
27. The operable implant according to embodiment 26, wherein the reservoir comprises at least one of; at least one bellows shaped portion, a shape adapted to allow movement although covered with fibrosis and a plate shaped surface, in all cases enabling movement of the at least one movable wall portion.
28. The operable implant according to any one of embodiments 23-27, wherein the reservoir is in fluid connection with a hydraulically operable body engaging portion, and wherein the reservoir is adapted to operate the hydraulically operable body engaging portion by movement of the at least one movable wall portion.
29. The operable implant according to any one of embodiments 23-28, wherein the reservoir is at least one of circular and torus shaped.
30. The operable implant according to any one of embodiments 23-29, further comprising a threaded member arranged to move the wall portion of the reservoir.
31. The operable implant according to any one of embodiments 22-30, further comprising at least one of: a pressure sensor, a flow sensor and position sensor arranged in connection with at least one of the pump and the reservoir for determining at least one of: the pressure or volume in the reservoir, and the pressure or flow from the hydraulic pump.
32. The operable implant according to any one of the preceding embodiments, wherein the first unit comprises an injection port for supplying fluid to at least one of: a/the reservoir, and a/the hydraulically operable body engaging portion.
33. The operable implant according to any one of the preceding embodiments, wherein at least one of the first unit and the distance element is free from at least one of: metallic and magnetizable components.
34. The operable implant according to any one of the preceding embodiments, wherein at least one of the first unit and the distance element is free from magnetic components.
35. The operable implant according to any one of the preceding embodiments, wherein the first unit comprises a communication unit adapted to wirelessly communicate with an external unit on the outside of the body of the patient.
36. The operable implant according to any one of the preceding embodiments, wherein the operable element is adapted to deflect the first gear, and to maintain the first gear deflected such that the teeth of the first gear are interengaged with the teeth of the second gear in at least one of; one position, two positions, three positions, and four or more positions, wherein the two, three or four positions are angularly spaced positions interspaced by positions at which the teeth are not interengaged.

Numbered Embodiment B 1-46

1. An operable implant for implantation in the body of a patient, the operable implant comprising an operation device and a body engaging portion, the operation device comprising:
an electrical motor comprising:
a set of coils circularly distributed around a rotational axis of the electrical motor,
a set of magnets connected to a rotatable structure at least partially axially overlapping said coils, such that sequential energizing of said coils magnetically propels the magnets and causes the rotatable structure to rotate around the rotational axis,
a gear system comprising:
an operable element,
a first gear having the shape of a hollow cylinder, comprising a first number of teeth, on the peripheral outside thereof, and
a second gear having the shape of a hollow cylinder, comprising a greater number of teeth than the first gear, on the inside surface thereof,
wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear,
characterized in that the second gear has a smaller diameter than the rotatable structure and is at least partially placed in the same axial plane, such that the rotatable structure at least partially axially overlaps the second gear, such that the gear system is at least partially placed inside of the electrical motor.
2. The operable implant according to embodiment 1, wherein the operable element is adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.
3. The operable implant according to embodiment 2, wherein the operable element is adapted to deflect the first gear, and to maintain the first gear deflected such that the teeth of the first gear are interengaged with the teeth of the second gear in at least two angularly spaced positions interspaced by positions at which the teeth are not interengaged.
4. The operable implant according to any one of embodiments 1-3, wherein the operable element comprises at least one of; a planet gear and a structure or wheel at least partly using friction to interconnect with the first gear.
5. The operable implant according to any one of embodiments 1-4, wherein the operation device further comprises a second gear system comprising:
an operable element,
a first gear having the shape of a hollow cylinder, comprising a first number of teeth, on the peripheral outside thereof, and
a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein
the first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.
6. The operable implant according to embodiment 5, wherein the first and second gear systems are positioned coaxially, along the rotational axis of the first and second gear systems.
7. The operable implant according to embodiment 6, wherein the second gear of at least one of; the first and second gear system has a smaller diameter than the rotatable structure and is at least partially placed in the same axial plane, such that the rotatable structure at least partially axially overlaps the second gear of at least one of; the first and second gear system, such that at least one of; the first and second gear system is at least partially placed inside of the electrical motor.
8. The operable implant according to embodiment 5, wherein the first and second gears of the second gear system have a larger diameter than the rotatable structure, and are at least partially placed in the same axial plane, such that the first and second gears of the second gear system at least partially axially overlaps the rotatable structure, such that the electrical motor is at least partially placed inside the second gear system.
9. The operable implant according to any one of embodiments 5-8, further comprising a radially extending connecting structure directly or indirectly connecting the first gear of the first gear system to the operable element of the second gear system, to transfer force from the first gear system to the second gear system.
10. The operable implant according to any one of embodiments 5-9, wherein the first gear system comprises a third gear, and wherein the inside of the third gear comprises the same amount of teeth as the outside of the first gear, and wherein teeth of the third gear are adapted to interengage with the teeth of the third gear such that the third gear rotates in relation to the second gear, along with the angularly spaced positions.
11. The operable implant according to any one of embodiments 5-9, wherein the first gear of the first gear system indirectly connects with the operable element of the second gear system via the third gear of embodiment 10.
12. The operable implant according to any one of the preceding embodiments, wherein the rotatable structure is placed radially on the inside of the circularly distributed coils.
13. The operable implant according to any one of the preceding embodiments, wherein the rotatable structure is placed radially on the outside of the circularly distributed coils.
14. The operable implant according to any one of the preceding embodiments, further comprising a coil enclosure adapted to enclose the coils, such that the coils remain enclosed during operation of the operation device.
15. The operable implant according to any one of the embodiments 1-14, wherein the first gear of at least one of; the first and second gear system directly or indirectly connects to a threaded member adapted to transform the radially rotating force to an axially reciprocating force.
16. The operable implant according to embodiment 15, wherein the threaded member is directly or indirectly connected to a movable wall portion of a first reservoir for changing the volume of the first reservoir.
17. The operable implant according to embodiment 16, wherein the threaded member is directly or indirectly connected to a movable wall portion of a second reservoir for changing the volume of the second reservoir.
18. The operable implant according to embodiment 17, wherein the movement of the movable wall portion of the first reservoir by the threaded member in a first direction causes the first reservoir to expand and the volume in the reservoir to increase, and wherein the movement of the movable wall of the second reservoir by the threaded member in a first direction causes the second reservoir to contract and the volume in the second reservoir to decrease.
19. The operable implant according to embodiment 18, wherein the first reservoir is in fluid connection with a first hydraulically operable body engaging portion, and the second reservoir is in fluid connection with a second hydraulically operable body engaging portion, and wherein operation of the electrical motor in a first direction, via the gear system and its direct or indirect connection with the threaded member, causes:
transportation of fluid from the first reservoir to the first hydraulically operable body engaging portion, and
transportation of fluid from the second hydraulically operable body engaging portion to the second reservoir.
20. The operable implant according to any one of embodiments 16-19, wherein the reservoir is at least one of: circular and torus shaped.
21. The operable implant according to any one of the preceding embodiments, wherein the operation device comprises a circular reservoir encircling the operation device, and wherein the circular reservoir comprises a movable wall portion adapted to compress and expand the circular reservoir, thereby altering the volume of the reservoir, and wherein the movable wall portion is connected to the operation device, such that the operation of the operation device changes the volume of the circular reservoir.
22. The operable implant according to any one of embodiments 16-21, wherein a portion of the wall of the reservoir comprises at least one of: a bellows structure, a shape adapted to allow movement although covered with fibrosis, and a plate shaped surface, in all cases enabling movement of the at least one movable wall portion, enabling the compression and/or expansion of the reservoir.
23. The operable implant according to any one of the preceding embodiments, further comprising a peristaltic pump, wherein the peristaltic pump comprises a hollow member for fluid transportation, and an operable compression member adapted to engage and compress the hollow member, and wherein the first gear is in direct or indirect connection with the compression member, such that the operation of the electrical motor operates the compression member such that fluid is transported in the hollow member.
24. The operable implant according to embodiment 23, wherein the operable compression member is connected to the third gear of embodiment 10.
25. The operable implant according to any one of embodiment 23 and 24, wherein hollow member of the peristaltic pump forms a loop or part of a loop adapted to at least partially encircle the operation device in at least partially the same axial plane, and wherein the operation device is adapted to propel the compressing member such that the compression member compresses the hollow member towards the outer periphery of the loop or part of loop.
26. The operable implant according to any one of the preceding embodiments, wherein the operation device comprises an alternating current (AC) motor, and the operation device further comprises a frequency converter for altering the frequency of an alternating current for controlling the alternating current motor.
27. The operable implant according to any one of the preceding embodiments, further comprising a separate unit comprising a receiving unit adapted to receive wireless energy transmitted from outside the body.
28. The operable implant according to embodiment 27, wherein the receiving unit comprises at least one coil adapted to transform wireless energy received in form of a magnetic, electric or electromagnetic field into electrical energy.
29. The operable implant according to embodiment 28, wherein the receiving unit comprises at least a first coil having a first number of windings, and at least a second coil having a second, different number of windings.
30. The operable implant according to any one of embodiments 27-29, wherein the separate unit is adapted to be placed at least one of; subcutaneously and subcutaneously in the abdominal wall.
31. The operable implant according to any one of the preceding embodiments, comprising at least one fixation portion for fixating at least a part of the operable implant to at least one of fibrosis, a fascia and a muscular layer towards the inside of the subcutaneous space of the patient.
32. The operable implant according to any one of embodiments 27-31, further comprising a distance element connecting the operation device and the separate unit, wherein the distance element comprises an electric lead adapted to transfer electrical energy between the separate unit and the operation device.
33. The operable implant according to embodiment 32, wherein the distance element is adapted to be placed through the muscular layers of the abdominal wall and/or fixated to the muscular fascia facing the subcutaneous space.
34. The operable implant according to any one of embodiments 32 and 33, wherein the distance element is flexible such that the first and second unit can move in relation to each other.
35. The operable implant according to any one of embodiments 27-34, wherein the separate unit comprises a reservoir for supplying fluid to a hydraulic implant.
36. The operable implant according to embodiment 35, wherein the distance element comprises a fluid conduit for transportation of fluid from the operation device to separate unit to control the size of the reservoir, or in the opposite direction.
37. The operable implant according to any one of embodiments 32-36, wherein the distance element further comprises a mechanical transferring member adapted to transfer mechanical work from the operation device to the separate unit.
38. The operable implant according to embodiment 37, wherein the mechanical transferring member comprises a mechanical transferring member selected from:
a hydraulic tube for transferring hydraulic force,
a rotating shaft for transferring rotational force,
a flexible member for transferring rotational force,
a wire,
a belt,
a rod,
a worm gear, and
a gear for changing rotational force in substantially 90 degrees direction.
39. The operable implant according to any one of embodiments 27-38, further comprising an enclosure adapted to hermetically enclose the operation device and the separate unit, such that the operation device and the separate unit are sealed from bodily fluids when implanted.
40. The operable implant according to any one of embodiments 27-39, wherein at least one of the operation device and the separate unit comprises a battery adapted to store electrical energy received at the receiving unit.
41. The operable implant according to any one of embodiments 27-40, wherein the separate unit comprises an injection port for supplying fluid to at least one of: a or the reservoir and the body engaging portion being hydraulically operable.
42. The operable implant according to any one of embodiments 27-41, wherein the separate unit, apart from the energy receiving unit, is free from at least one of; metallic, magnetizable and magnetic components.
43. The operable implant according to any one of embodiments 27-42, wherein the separate unit further comprises a control unit for controlling at least one parameter of at least one of:
the operation device, and
the body engaging portion.
44. The operable implant according to any one of embodiments 27-43, wherein the separate unit comprises a communication unit adapted to wirelessly communicate with an external unit on the outside of the body of the patient.

45. The operable implant according to anyone of the preceding embodiments, comprising a hydraulic pump selected from:
   at least one reservoir with a wall moving by the mechanical work acting as a pump,
   at least one reservoir changing volume to move fluid acting as a pump,
   at least one non-valve pump,
   at least one valve pump,
   at least one peristaltic pump,
   at least one membrane pump,
   at least one gear pump, and
   at least one bellows pump.
46. The operable implant according to any one of the preceding embodiments, wherein the electrical motor comprises an electrical motor selected from:
   an alternating current (AC) electrical motor,
   a direct current electrical motor,
   a linear electrical motor,
   an axial electrical motor,
   a piezo-electric motor,
   a three-phase motor
   a more than one-phase motor
   a bimetal motor, and
   a memory metal motor.

Numbered Embodiment C 1-45

1. An operable implant adapted to be implanted in the body of a patient, the operable implant comprising an operation device and a body engaging portion, wherein the operation device comprises:
   an axial electrical motor comprising:
      a set of coils circularly distributed around a rotational axis of the electrical motor,
      a set of magnets connected to a radially extending rotatable structure at least partially radially overlapping said magnets, such that sequential energizing of said coils magnetically axially propels the magnets and causes rotation of the rotatable structure around the rotational axis,
   a gear system comprising:
      an operable element,
      a first gear having the shape of a hollow cylinder, comprising a first number of teeth, on the peripheral outside thereof, and
      a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear,
   wherein the gear system and the axial electrical motor are positioned coaxially, along the rotational axis of electrical motor.
2. The operable implant according to embodiment 1, wherein the operable element comprises at least one of: a planet gear, and a structure or wheel at least partly using friction to interconnect with the first gear.
3. The operable implant according to any one of embodiments 1 and 2, wherein the first set of coils circularly distributed around a rotational axis of the electrical motor are positioned on a magnetizable core structure, and wherein the radially extending rotatable structure comprises a rotatable disc, wherein the magnetizable core structure and the rotatable disc are positioned coaxially and the rotatable disc is connected to a driving shaft connected to the operable element.
4. The operable implant according to embodiment 3, wherein the operation device further comprises a second magnetizable core structure comprising a second sets of coils, wherein the second magnetizable core structure is coaxially positioned to at least partly overlap the magnets of the rotatable disc, such that the first set of coils propels the magnets on the first side thereof; and the second sets of coils propels the magnets on the second side thereof
5. The operable implant according to embodiment 3, wherein the peripheral diameter circular configuration of at least one of the first and second set of coils is smaller than the inner diameter of the first gear, and wherein at least one of the first and second set of coils is positioned in the same axial plane as the first gear, such that the axial electrical motor is at least partially placed inside of the gear system.
6. The operable implant according to embodiment 5, wherein the rotatable disc is directly connected to the operable element.
7. The operable implant according to any one of the preceding embodiments, further comprising a coil enclosure adapted to enclose the coils, such that the coils remain enclosed separated from the magnets during operation of the operation device.
8. The operable implant according to any one of the preceding embodiments, wherein the operable element is adapted to deflect the first gear, and to maintain the first gear deflected such that the teeth of the first gear are interengaged with the teeth of the second gear in one of; one position, two positions, three positions, and four or more positions, wherein the two, three and four positions are angularly spaced positions interspaced by positions at which the teeth are not interengaged.
9. The operable implant according to embodiment 8, wherein the operation device comprises a second gear system comprising:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein
   the first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

10. The operable implant according to embodiment 9, wherein the first and second gear systems are positioned coaxially, along the rotational axis of the first and second gear systems.

11. The operable implant according to embodiment 10, further comprising a radially extending connecting structure directly or indirectly connecting the first gear of the first gear system to the operable element of the second gear system, to transfer force from the first gear system to the second gear system.

12. The operable implant according to any one of embodiments 8-11, wherein the first gear system comprises a third gear, and wherein the inside of third gear comprises the same amount of teeth as the outside of the first gear, and wherein teeth of the third gear are adapted to interengage the teeth of the third gear such that the third gear rotates in relation to the second gear, along with the angularly spaced positions.

13. The operable implant according to any one of embodiments 9-12, wherein the first gear of the first gear system indirectly connects with the operable element of the second gear system via the third gear of embodiment 12.

14. The operable implant according to any one embodiments 8-13, wherein the first gear of the first gear system directly or indirectly connects to a threaded member adapted to transform the radially rotating force to an axially reciprocating force.

15. The operable implant according to embodiment 14, wherein the threaded member is directly or indirectly connected to a movable wall of a reservoir for changing the volume of the reservoir.

16. The operable implant according to embodiment 15, wherein the threaded member is directly or indirectly connected to a movable wall of a second reservoir for changing the volume of the second reservoir.

17. The operable implant according to embodiment 16, wherein the movement of the movable wall of the first reservoir by the threaded member in a first direction causes the first fluid reservoir to expand and the volume in the first fluid reservoir to increase, and wherein the movement of the movable wall of the second reservoir by the threaded member in a first direction causes the second reservoir to contract and the volume in the second reservoir to decrease.

18. The operable implant according to embodiment 17, wherein the first reservoir is in fluid connection with a first hydraulically operable body engaging portion, and the second reservoir is in fluid connection with a second hydraulically operable body engaging portion, and wherein operation of the electrical motor in a first direction, by the via the gear system and its direct or indirect connection with the threaded member, causes: transportation of fluid from the first reservoir to the first hydraulically operable body engaging portion, and transportation of fluid from the second hydraulically operable body engaging portion to the second reservoir.

19. The operable implant according to any one of embodiments 15-18, wherein the reservoir is at least one of circular and torus shaped.

20. The operable implant according to any one of the preceding embodiments, wherein the operation device comprises a circular reservoir encircling the operation device, and wherein the circular reservoir comprises a movable wall portion adapted to compress and expand the circular reservoir, thereby altering the volume of the reservoir, and wherein the movable wall portion is connected to the operation device, such that the operation of the operation device changes the volume of the circular reservoir.

21. The operable implant according to any one of embodiments 16-20, wherein a portion of the wall of the reservoir comprises at least one of; a bellows structure, a shape adapted to allowing movement although covered with fibrosis and a plate shaped surface, in all cases enabling movement of the at least one movable wall portion, enabling the compression and/or expansion of the reservoir.

22. The operable implant according to any one of the preceding embodiments, further comprising a peristaltic pump, wherein the peristaltic pump comprises a hollow member for fluid transportation, and an operable compression member adapted to engage and compress the hollow member, and wherein the first gear is in direct or indirect connection with the compression member, such that the operation of the electrical machine operates the compression member such that fluid is transported in the hollow member.

23. The operable implant according to embodiment 22, wherein the operable compression member is connected to the third gear of embodiment 12.

24. The operable implant according to any one of embodiment 22 and 23, wherein hollow member of the peristaltic pump forms a loop or part of a loop adapted to at least partially encircle the operation device in at least partially the same axial plane, and wherein the operation device is adapted to propel the compressing member such that the compression member compresses the hollow member towards the outer periphery of the loop or part of loop.

25. The operable implant according to any one of the preceding embodiments, wherein the operation device comprises an alternating current (AC) motor, and the operation device further comprises a frequency converter for altering the frequency of an alternating current for controlling the alternating current motor.

26. The operable implant according to any one of the preceding embodiments, further comprising a separate unit comprising a receiving unit adapted to receive wireless energy transmitted from outside the body.

27. The operable implant according to embodiment 26, wherein the receiving unit comprises at least one coil adapted to transform wireless energy received in form of a magnetic, electromagnetic field into electrical energy.

28. The operable implant according to embodiment 27, wherein the receiving unit comprises at least a first coil having a first number of windings, and at least a second coil having a second, different number of windings.

29. The operable implant according to any one of embodiments 26-28, wherein the separate unit is adapted to be placed at least one of; subcutaneously and subcutaneously in the abdominal wall.

30. The operable implant according to any one of the preceding embodiments, comprising at least one fixation portion for fixating at least part of the operable implant to at least one of fibrosis, a fascia and a muscular layer towards the inside of the subcutaneous space of the patient.
31. The operable implant according to any one of embodiments 26-30, further comprising a distance element connecting the operation device and the separate unit, wherein the distance element comprises an electric lead adapted to transfer electrical energy between the separate unit and the operation device.
32. The operable implant according to embodiment 31, wherein the distance element is adapted to be placed through the muscular layers of the abdominal wall and/or fixated to the muscular fascia facing the subcutaneous space.
33. The operable implant according to any one of embodiments 31 and 32, wherein the distance element is flexible such that the first and second unit can move in relation to each other.
34. The operable implant according to any one of embodiments 27-34, wherein the separate unit comprises a reservoir for supplying fluid to a hydraulic implant.
35. The operable implant according to embodiment 35, wherein the distance element comprises a fluid conduit for transportation of fluid from the operation device to control the size of the reservoir, or in the opposite direction.
36. The operable implant according to any one of embodiments 31-35, wherein the distance element further comprises a mechanical transferring member adapted to transfer mechanical work from the operation device to the separate unit.
37. The operable implant according to embodiment 36, wherein the mechanical transferring member comprises a mechanical transferring member selected from:
   a hydraulic tube for transferring hydraulic force,
   a rotating shaft for transferring rotational force,
   a flexible member for transferring rotational force,
   a wire,
   a belt,
   a rod,
   a worm gear, and
   a gear for changing rotational force in substantially 90 degrees direction.
38. The operable implant according to any one of embodiments 26-37, further comprising an enclosure adapted to hermetically enclose the operation device and the separate unit, such that the operation device and the separate unit are sealed from bodily fluids when implanted.
39. The operable implant according to any one of embodiments 26-38, wherein at least one of the operation device and the separate unit comprises a battery adapted to store electrical energy received at the receiving unit.
40. The operable implant according to any one of embodiments 26-39, wherein the separate unit comprises an injection port for supplying fluid to at least one of: a or the reservoir and the body engaging portion being hydraulically operable.
41. The operable implant according to any one of embodiments 26-40, wherein the separate unit, apart from the energy receiving unit, is free from at least one of; metallic, magnetizable and magnetic components.
42. The operable implant according to any one of embodiments 26-41, wherein the separate unit further comprises a control unit for controlling at least one parameter of at least one of:
   the operation device, and
   the body engaging portion.
43. The operable implant according to any one of embodiments 26-42, wherein the separate unit comprises a communication unit adapted to wirelessly communicate with an external unit on the outside of the body of the patient.
44. The operable implant according to any one of the preceding embodiments, wherein the coil enclosure comprises a material selected from:
   a carbon material
   a boron material
   a mixture of material
   a Peek® material
   an alloy of material
   a metallic material,
   titanium,
   aluminum,
   a ceramic material,
   a polymer material,
   polyurethane,
   polyether ether ketone,
   silicone, and
   Parylene® coated silicone.
45. The operable implant according to any one of the preceding embodiments, wherein the operation device comprises an/the electrical motor selected from:
   an alternating current (AC) electrical motor,
   a direct current electrical motor,
   a linear electrical motor,
   an axial electrical motor,
   a piezo-electric motor,
   a three-phase motor
   a more than one-phase motor
   a bimetal motor, and
   a memory metal motor.

Numbered Embodiment D 1-47

1. An operable implant adapted to be implanted in the body of a patient, the operable implant comprising an operation device and a body engaging portion, the operation device comprises an electrical motor comprising a static part comprising a plurality of coils and a movable part comprising a plurality of magnets, such that sequential energizing of said coils magnetically propels the magnets and thus propels the movable part, wherein the operation device further comprises an enclosure adapted to hermetically enclose the coils of the static part, such that a seal is created between the static part and the propelled moving part with the included magnets, such that the coils of the static part are sealed from the bodily fluids, when implanted.
2. The operable implant according to embodiment 1, wherein the operation device further comprises a control unit for controlling at least one of the operation device and the body engaging portion, wherein the enclosure is adapted to enclose the coils and the control unit.
3. The operable implant according to any one of the preceding embodiments, wherein the operation device further comprises at least one electrical circuit adapted to indirectly receive energy drawn from wireless energy supplied from outside the body of the patient, wherein the enclosure is adapted to enclose the coils and the electrical circuit.

4. The operable implant according to any one of embodiments 1-3, comprising a separate wireless energy receiving unit comprising at least one coil adapted to transform wireless energy received in form of a magnetic, electric or electromagnetic field into electrical energy.

5. The operable implant according to embodiment 4, further comprising a distance element adapted to create a distance between the receiving unit and the electrical motor, such that the receiving unit remains substantially unaffected by metallic and/or magnetic parts of the static or movable part of the electrical motor.

6. The operable implant according to any one of the preceding embodiments, wherein the electrical motor is an axial electrical motor, and wherein:
   a. the coils are circularly distributed around a rotational axis of the implantable electrical motor such that the center axis of the helix of the coils are extending in the axial direction of the implantable electrical motor, parallel to the rotational axis, and
   b. the movable part comprises a radially extending rotor on which the magnets are circularly distributed around the rotational axis, the magnets in axial direction facing the coils, such that the magnets at least partially radially overlaps said coils, such that sequential energizing of said coils magnetically axially propels the magnets and causes rotation of the rotor around the rotational axis of the electrical motor.

7. The operable implant according to any one of the preceding embodiments, wherein the electrical motor is a radial electrical motor, and wherein:
   a. the coils are circularly distributed around a rotational axis of the implantable electrical motor such that the center axis of the helix of the coils are extending in the radial direction of the rotational axis of the implantable electrical motors, substantially perpendicular to the rotational axis, and
   b. the movable part comprises an axially extending rotor on which the magnets are circularly distributed around the rotational axis, the magnets in radial direction facing the coils, such that the magnets at least partially axially overlaps said coils, such that sequential energizing of said coils magnetically propels the magnets and causes rotation of the rotor around the rotational axis of the electrical motor.

8. The operable implant according to any one of the preceding embodiments, wherein the electrical motor is a linear electrical motor, and wherein:
   a. the coils are linearly distributed along a direction of movement of the movable part, and
   b. the movable part comprises linearly distributed magnets along a direction of movement of the movable part, such that sequential energizing of the coils magnetically propels the magnets and causes linear movement of the movable part.

9. The operable implant according to any one of embodiments 2-8, wherein the implantable electrical motor is a alternating current (AC) electrical motor, and wherein the control unit comprises a frequency converter for altering the frequency of an alternating current for controlling the alternating current electrical motor.

10. The operable implant according to any one of embodiments 2-9, wherein the implantable electrical motor further comprises a second enclosure adapted to enclose the movable part, such that the movable part is sealed from bodily fluids when implanted.

11. The operable implant according to embodiment 10, wherein the second enclosure is sealingly connected to the first enclosure, such that the enclosure wall between the movable part and the static part is engaged in sealing both the first enclosure and the second enclosure.

12. The operable implant according to any one of the preceding embodiments, wherein at least one of the first and second enclosure comprises a material selected from:
   a. a carbon material
   b. a boron material
   c. a mixture of material
   d. a Peek® material
   e. an alloy of material
   f. a metallic material,
   g. titanium,
   h. aluminum,
   i. a ceramic material,
   j. a polymer material,
   k. polyurethane,
   l. polyether ether ketone,
   m. silicone, and
   n. Parylene® coated silicone.

13. The operable implant according to any one of the preceding embodiments, wherein the second enclosure is sealingly connected to the first enclosure, such that both the movable part and a distance element between the movable part and the static part is sealed by the second enclosure.

14. The operable implant according to any one of the preceding embodiments, further comprising a gear system adapted receive mechanical work having a first force and velocity as input, from the rotating part of the electrical motor, and output mechanical work having a different force and velocity.

15. The operable implant according to embodiment 14, wherein the gear system comprises:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

16. The operable implant according to embodiment 15, wherein the second gear has a smaller diameter and is at least partially placed in the same axial plane as at least one of the movable part and the static part, such that at least one of the movable part and the static part at least partially axially overlaps the second gear, such that the gear system is at least partially placed inside of the electrical motor.

17. The operable implant according to embodiment 15, wherein the operable element is adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.
18. The operable implant according to embodiment 17, wherein the operable element is adapted to deflect the first gear, and to maintain the first gear deflected such that the teeth of the first gear are interengaged with the teeth of the second gear in at least two angularly spaced positions interspaced by positions at which the teeth are not interengaged.
19. The operable implant according to any one of embodiments 15-18, wherein the operation device further comprises a second gear system comprising:
    an operable element,
    a first gear having the shape of a hollow cylinder, comprising a first number of teeth, on the peripheral outside thereof, and
    a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein
    the first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.
20. The operable implant according to embodiment 19, wherein the first and second gear systems are positioned coaxially, along the rotational axis of the first and second gear systems.
21. The operable implant according to embodiment 20, wherein the second gear of at least one of; the first and second gear system has a smaller diameter than the rotatable structure and is at least partially placed in the same axial plane, such that the rotatable structure at least partially axially overlaps the second gear of at least one of; the first and second gear system, such that at least one of; the first and second gear system is at least partially placed inside of the electrical motor.
22. The operable implant according to embodiment 19, wherein the first and second gears of the second gear system have a larger diameter than the rotatable structure, and are at least partially placed in the same axial plane, such that the first and second gears of the second gear system at least partially axially overlaps the rotatable structure, such that the electrical motor is at least partially placed inside the second gear system.
23. The operable implant according to any one of embodiments 16-22, further comprising a radially extending connecting structure directly or indirectly connecting the first gear of the first gear system to the operable element of the second gear system of embodiment 19, to transfer force from the first gear system to the second gear system.
24. The operable implant according to any one of embodiments 19-23, wherein the first gear system comprises a third gear, and wherein the inside of the third gear comprises the same amount of teeth as the outside of the first gear, and wherein teeth of the third gear are adapted to interengage with the teeth of the third gear such that the third gear rotates in relation to the second gear, along with the angularly spaced positions.
25. The operable implant according to any one of embodiments 19-24, wherein the first gear of the first gear system indirectly connects with the operable element of the second gear system via the third gear of embodiment 24.
26. The operable implant according to any one of embodiments 16-25, wherein the rotatable structure is placed radially on the inside of the circularly distributed coils.
27. The operable implant according to any one of embodiments 16-25, wherein the rotatable structure is placed radially on the outside of the circularly distributed coils.
28. The operable implant according to any one of the preceding embodiments, wherein the coils remain enclosed during operation of the operation device.
29. The operable implant according to any one of the embodiments 16-28, wherein the first gear of at least one of; the first and second gear system directly or indirectly connects to a threaded member adapted to transform the radially rotating force to an axially reciprocating force.
30. The operable implant according to embodiment 29, wherein the threaded member is directly or indirectly connected to a movable wall portion of a reservoir.
31. The operable implant according to any one of the preceding embodiments, comprising at least one fixation portion for fixating at least a part of the operable implant to at least one of fibrosis, a fascia and a muscular layer towards the inside of the subcutaneous space of the patient.
32. The operable implant according to any one of the preceding embodiments, further comprising a separate unit comprising a receiving unit adapted to receive wireless energy transmitted from outside the body.
33. The operable implant according to any one of the preceding embodiments, comprising a first reservoir in fluid connection with the body engaging portion being hydraulically operable, and wherein the operation device, is adapted to cause:
    transportation of fluid from the first reservoir to the hydraulically operable body engaging portion.
34. The operable implant according to any one of embodiments 30-33, wherein a portion of the wall of the reservoir comprises at least one of: a bellows structure, a shape adapted to allowing movement although covered with fibrosis and a plate shaped surface, in all cases enabling movement of the at least one movable wall portion, enabling the compression and/or expansion of the reservoir.

35. The operable implant according to embodiment 33, wherein the operation device comprises a hydraulic pump for transporting the fluid from the first reservoir to the hydraulically operable body engaging portion.

36. The operable implant according to embodiment 35, wherein the hydraulic pump is a hydraulic pump selected from:
   at least one reservoir with a wall moving by the mechanical work acting as a pump,
   at least one reservoir changing volume to move fluid acting as a pump,
   at least one non-valve pump,
   at least one valve pump,
   at least one peristaltic pump,
   at least one membrane pump,
   at least one gear pump, and
   at least one bellows pump.

37. The operable implant according to any one of the preceding embodiments, wherein the electrical motor comprises an electrical motor selected from:
   an alternating current (AC) electrical motor,
   a direct current electrical motor,
   a linear electrical motor,
   an axial electrical motor,
   a piezo-electric motor,
   a three-phase motor
   a more than one-phase motor
   a bimetal motor, and
   a memory metal motor.

38. The operable implant according to any one of the preceding embodiments, wherein the operation device comprises:
   a first unit comprising:
     a receiving unit for receiving wireless energy, and
     a first gear system adapted to receive mechanical work having a first force and first velocity, and output mechanical work having a different second force and a different second velocity,
   a second unit comprising an electrical motor adapted to transform electrical energy into the mechanical work, and
   a distance element comprising:
     a lead for transferring the electrical energy from the first unit to the second unit, and
     a mechanical transferring member adapted to transfer the mechanical work from the electrical motor in the second unit to the gear system in the first unit, wherein
   the distance element is adapted to separate the first and second units such that the receiving unit, when receiving wireless energy, is not substantially affected by the second unit.

39. The operable implant according to embodiment 37, wherein the second unit comprises a second gear system adapted to receive the mechanical work output from the first gear system with the different second force and the different second velocity as input, and output mechanical work having a third different force and third different velocity, and wherein the gear system of the second unit is connected in series with the gear system of the first unit, via the mechanical transferring member of the distance element.

40. The operable implant according to any one of embodiments 37-39, wherein the first unit comprises a second gear system adapted receive mechanical work of a first force and velocity as input, and output mechanical work having a different force and velocity, and wherein the second gear system is connected in series with the first gear system.

41. The operable implant according to any one of embodiments 37-40, wherein the first unit is adapted to be placed at least in one of the following places: subcutaneously, subcutaneously in the abdominal wall and in the abdomen.

42. The operable implant according to any one of embodiments 37-41, wherein the motor comprises magnetic material and wherein the first unit is substantially unaffected or not importantly affected by the magnetic material in the second unit, during wirelessly energy transfer.

43. The operable implant according to any one of embodiments 37-42, wherein the first unit comprises a reservoir for supplying fluid to the body engaging portion being hydraulically operable.

44. The operable implant according to any one of embodiments 37-43, wherein the first unit comprises hydraulic pump adapted to transfer mechanical work into hydraulic power for powering a hydraulically operable body engaging portion, wherein the hydraulic pump is connected to the force output of the first or second gear system.

45. The operable implant according to embodiment 6, further comprises a gear system comprising:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear,
   wherein the gear system and the axial electrical motor are positioned coaxially, along the rotational axis of electrical motor.

46. The operable implant according to any one of embodiments 15-45, wherein the operable element comprises at least one of a planet gear, and a structure or wheel at least partly using friction to interconnect with the first gear.

47. The operable implant according to embodiment 45, wherein the first set of coils circularly distributed around a rotational axis of the electrical motor are positioned on a magnetizable core structure, and wherein the radially extending rotatable structure comprises a rotatable disc, wherein a surface part of the magnetizable core structure and the rotatable disc are positioned coaxially and the rotatable disc is connected to a driving shaft connected to the operable element.

Numbered Embodiment E 1-37

1. An operable implant adapted to be implanted in the body of a patient, the operable implant comprising an operation device and a body engaging portion, wherein the operation device comprises:
a. an electrical motor having a force outlet,
b. a gear system connected to the force outlet of the electrical motor, the gear system comprising:
   i. an operable element,
   ii. a first gear having the shape of a hollow cylinder, comprising a first number of teeth, on the peripheral outside thereof, and
   iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and
c. a gear system force outlet connected to the first gear of the gear system and adapted for supplying force directly or indirectly to the body engaging portion, the gear system force outlet comprises a magnetic force coupling for magnetically, directly or indirectly, connecting to the body engaging portion for supplying force, and
d. an enclosure for hermetically enclosing the operation device.

2. The operable implant according to embodiment 1, wherein the magnetic force coupling comprises an inside rotating structure placed inside the enclosure comprising at least one magnet or a portion comprising magnetic or magnetizable material, and wherein the magnet or portion comprising magnetic or magnetizable material is adapted to rotate to transfer force to a corresponding rotating structure on the outside of the hermetic enclosure, for directly or indirectly supplying force to the body engaging portion through the sealed enclosure.

3. The operable implant according to embodiment 2, further comprising the corresponding rotating structure on the outside of the hermetic enclosure, for directly or indirectly supplying force directly or indirectly to the body engaging portion.

4. The operable implant according to any one of the preceding embodiments, further comprising a reservoir for holding a hydraulic fluid, the reservoir comprising a movable wall portion adapted to change the volume of the reservoir, wherein the movable wall portion is directly or indirect connected to the gear system force outlet, such that operation of the electrical motor, via the gear system changes the volume of the reservoir.

5. The operable implant according to embodiment 2, further comprising the corresponding rotating structure on the outside of the hermetic enclosure, wherein the corresponding rotating structure directly or indirectly connects to a threaded member adapted to transform the radially rotating force to an axially reciprocating force.

6. The operable implant according to embodiment 5, wherein the threaded member is directly or indirectly connected to the movable wall of the reservoir of embodiment 4 for changing the volume of the reservoir.

7. The operable implant according to any one of the preceding embodiments, further comprising a peristaltic pump, wherein the peristaltic pump comprises a hollow member for fluid transportation, and an operable compression member adapted to engage and compress the hollow member, and wherein the gear system force outlet via the magnetic coupling connects to the compression member, such that the operation of the electrical motor, via the gear system, operates the compression member, such that fluid is transported in the hollow member.

8. The operable implant according to any one of the preceding embodiments, wherein the operation device further comprises a control unit for controlling at least one of the operation device and the body engaging portion, wherein the enclosure is adapted to enclose the operation device including the control unit.

9. The operable implant according to any one of the preceding embodiments, wherein the operation device further comprises at least one receiving unit adapted to receive wireless energy supplied from outside the body of the patient, wherein the receiving unit is placed separate from the operation device, wherein the enclosure is adapted to include both the operation device, a distance element connecting the operation device and the receiving unit and the receiving unit.

10. The operable implant according to embodiment 9, wherein the distance element is adapted to create a distance between the wireless energy receiver and at least one of the electrical motor and the magnetic coupling, such that the wireless energy receiver remains substantially unaffected or not importantly affected by metallic and/or magnetic components of the electrical motor and the magnetic coupling.

11. The operable implant according to any one of embodiments 9 and 10, wherein the receiving unit comprises at least one coil adapted to transform wireless energy received in form of a magnetic, electric or electromagnetic field into electrical energy.

12. The operable implant according to any one of the preceding embodiments, wherein the electrical motor is an axial electrical motor comprising:
a. a plurality of coils, circularly distributed around a rotational axis of the electrical motor such that the center axis of the helix of the coils are extending in the axial direction of the electrical motor, parallel to the rotational axis of the electrical motor, and
b. magnets, circularly distributed on a radially extending rotatable structure, on which the magnets are circularly distributed around the rotational axis, the magnets in axial direction facing the coils, such that the magnets at least partially radially overlaps the coils, such that sequential energizing of the coils magnetically axially propels the magnets and causes rotation of the rotatable structure around the rotational axis of the electrical motor.

13. The operable implant according to any one of the preceding embodiments, wherein the electrical motor is a radial electrical motor, comprising:
a. a plurality of coils circularly distributed around a rotational axis of the implantable electrical motor, such that the center axis of the helix of the coils are extending in the radial direction of the implantable electrical motor, substantially perpendicular to the rotational axis of the motor, and
b. a plurality of magnets, circularly distributed on an axially extending rotatable structure on which the magnets are circularly distributed around the rotational axis, the magnets in radial direction facing the coils, such that the magnets at least partially axially overlaps the coils, such that sequential energizing of the coils magnetically propels the magnets and causes rotation of the rotatable structure around the rotational axis of the electrical motor.

14. The operable implant according to any one of the preceding embodiments, wherein the electrical motor is a linear electrical motor, and wherein:
   a. the coils are linearly distributed along a direction of movement of a movable part of the linear electrical motor, and
   b. the movable part comprises linearly distributed magnets along a direction of movement of the movable part, such that sequential energizing of the coils magnetically propels the magnets and causes linear movement of the movable part.

15. The operable implant according to any one of embodiments 8-14, wherein the electrical motor is a alternating current (AC) electrical motor, and wherein the control unit comprises a frequency converter for altering the frequency of an alternating current for controlling the alternating current electrical motor.

16. The operable implant according to any one of the preceding embodiments, wherein the enclosure comprises a material selected from:
   a. a carbon material
   b. a boron material
   c. a mixture of material
   d. a Peek® material
   e. an alloy of material
   f. a metallic material,
   g. titanium,
   h. aluminum,
   i. a ceramic material,
   j. a polymer material,
   k. polyurethane,
   l. polyether ether ketone,
   m. silicone, and
   n. Parylene® coated silicone.

17. The operable implant according to any one of the preceding embodiments, wherein the operation device comprising a hydraulic pump for transporting hydraulic fluid from a reservoir according to embodiment 4 to the body engaging portion being hydraulically operable.

18. The operable implant according to any one of the preceding embodiments, wherein the electrical motor comprises an electrical motor selected from:
   an alternating current (AC) electrical motor,
   a direct current electrical motor,
   a linear electrical motor,
   an axial electrical motor,
   a piezo-electric motor,
   a three-phase motor
   a more than one-phase motor
   a bimetal motor, and
   a memory metal motor.

19. The operable implant according to any one of the preceding embodiments, wherein the electrical motor is adapted to drive a comprised hydraulic pump selected from:
   at least one reservoir with a wall moving by the mechanical work acting as a pump,
   at least one reservoir changing volume to move fluid acting as a pump,
   at least one non-valve pump,
   at least one valve pump,
   at least one peristaltic pump,
   at least one membrane pump,
   at least one gear pump, and
   at least one bellows pump.

20. The operable implant according to any one of embodiments 1-18 and 20, wherein the electrical motor comprises:
   a set of coils circularly distributed around a rotational axis of the electrical motor,
   a set of magnets connected to a rotatable structure at least partially axially overlapping said coils, such that sequential energizing of said coils magnetically propels the magnets and causes the rotatable structure to rotate around the rotational axis,
   wherein the second gear has a smaller diameter than the rotatable structure and is at least partially placed in the same axial plane, such that the rotatable structure at least partially axially overlaps the second gear, such that the gear system is at least partially placed inside of the electrical motor.

21. The operable implant according to any one of the preceding embodiments, wherein the operable element is adapted to deflect the first gear, and to maintain the first gear deflected such that the teeth of the first gear are interengaged with the teeth of the second gear in at least one of; one position, two positions, three positions, and four or more positions, wherein the two, three and four positions are angularly spaced positions interspaced by positions at which the teeth are not interengaged.

22. The operable implant according to embodiment 21, wherein the operable element is adapted to deflect the first gear, and to maintain the first gear deflected such that the teeth of the first gear are interengaged with the teeth of the second gear in at least two angularly spaced positions interspaced by positions at which the teeth are not interengaged.

23. The operable implant according to any one of embodiments 1-22, wherein the operation device further comprises a second gear system comprising:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, wherein
   the first gear of the first gear system is directly or indirectly connected to the operable element of the second gear system, such that the first gear system is connected in series with the second gear system, such that the first gear system receives mechanical work having a first force and first velocity and outputs mechanical work having a second, different, force and a second, different, velocity, and the second gear system receives the output mechanical work from the first gear system, as input, and outputs mechanical work with a third different force and third different velocity.

24. The operable implant according to embodiment 23, wherein the first and second gear systems are positioned coaxially, along the rotational axis of the first and second gear systems.

25. The operable implant according to any one of embodiments 20-24, wherein the second gear of at least one of; the first and second gear system has a smaller diameter than the rotatable structure of embodiment 20 and is at least partially placed in the same axial plane, such that the rotatable structure at least partially axially overlaps the second gear of at least one of; the first and second gear system, such that at least one of; the first and second gear system is at least partially placed inside of the electrical motor.

26. The operable implant according to anyone of embodiment 23-25, wherein the first and second gears of the second gear system have a larger diameter than the rotatable structure included from embodiment 20, and are at least partially placed in the same axial plane, such that the first and second gears of the second gear system at least partially axially overlaps the rotatable structure, such that the electrical motor is at least partially placed inside the second gear system.

27. The operable implant according to any one of the preceding embodiments, further comprising a radially extending connecting structure directly or indirectly connecting the first gear of the first gear system to the operable element of the second gear system of embodiment 23, for transferring force from the first gear system to the second gear system.

28. The operable implant according to any one of embodiments 1-22, wherein the first gear system comprises a third gear, and wherein the inside of the third gear comprises the same amount of teeth as the outside of the first gear, and wherein teeth of the third gear are adapted to interengage with the teeth of the first gear such that the third gear rotates in relation to the second gear, along with the angularly spaced positions.

29. The operable implant according to any one of embodiments 1-28, wherein the first gear of the first gear system indirectly connects with the operable element of the second gear system of embodiment 23 via the third gear of embodiment 28.

30. The operable implant according to any one of embodiments 20-25, wherein the rotatable structure of embodiment 20 is placed radially on the inside of the circularly distributed coils.

31. The operable implant according to any one of embodiments 20-25, wherein the rotatable structure of embodiment 20 is placed radially on the outside of the circularly distributed coils.

32. The operable implant according to any one of the preceding embodiments, wherein the coils remain enclosed during operation of the operation device.

33. The operable implant according to any one of the embodiments 20-32, wherein the first gear of at least one of; the first and second gear system directly or indirectly connects to a threaded member adapted to transform the radially rotating force to an axially reciprocating force.

34. The operable implant according to embodiment 33, wherein the threaded member is directly or indirectly connected to a movable wall portion of the reservoir according to embodiment 4.

35. The operable implant according to any one of the preceding embodiments, comprising at least one fixation portion for fixating at least a part of the operable implant to at least one of fibrosis, a fascia and a muscular layer towards the inside of the subcutaneous space of the patient.

36. The operable implant according to any one of the preceding embodiments, wherein the first reservoir of embodiment 4 is in fluid connection with the body engaging portion being hydraulically operable, and wherein the operation device, is adapted to cause: transportation of fluid from the first reservoir to the hydraulically operable body engaging portion.

37. The operable implant according to embodiment 36, wherein a portion of the wall of the reservoir comprises at least one of: a bellows structure, a shape adapted to allowing movement although covered with fibrosis and a plate shaped surface, in all cases enabling movement of the at least one movable wall portion, enabling the compression and/or expansion of the reservoir.

Numbered Embodiment F 1-27

1. An operable implant adapted to be implanted in the body of a patient, the operable implant comprising an operation device and a body engaging portion, wherein the operation device comprises:
   a. an electrical motor having a force output, and
   b. a start resistance delay member positioned between the force output of the electrical motor and the body engaging portion, wherein the start resistance delay member is adapted to enable the electrical motor to operate with at least one of; less force or less friction induced by the direct or indirect connection with the body engaging portion for a time period, such that the electrical motor can start with less resistance.

2. The operable implant according to any one of the preceding embodiments, wherein the force output of the electrical motor is directly or indirectly connected to a force input of a gear system, the gear system comprising:
   a. an operable element,
   b. a first gear having the shape of a hollow cylinder, comprising a first number of teeth, on the peripheral outside thereof, and
   c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the gear system comprises a force output connected to the first gear.

3. The operable implant according to any one of the preceding embodiments, further comprising a second gear system positioned between the first gear system and the start resistance delay, the second gear system comprising:
   a. a force input connected to an operable element, directly or indirectly connected to the force output of the first gear system, b. a first gear having the shape of a hollow cylinder, comprising a first number of teeth, on the peripheral outside thereof, and
c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the second gear system comprises a force output connected to the first gear of the second gear system.
4. The operable implant according to any one of the preceding embodiments, wherein the start resistance delay member is positioned between the force output of the electrical motor and the force input of the gear system.
5. The operable implant according to any one of embodiments 1-3, wherein the start resistance delay member is positioned between the force output of the gear system and the body engaging portion.
6. The operable implant according to embodiment 3, wherein the start resistance delay member is positioned one of:
  a. between the force output of the first gear system and the force input of the second gear systems, and
  b. between the force output of the second gear system and the body engaging portion.
7. The operable implant according to any one of the preceding embodiments, wherein the start resistance delay member comprises a spring.
8. The operable implant according to embodiment 7, wherein the spring is at least one of: a helical spring and a leaf spring.
9. The operable implant according to any one of the preceding embodiments, wherein the start resistance delay member comprise a mechanical play.
10. The operable implant according to embodiment 9, wherein the mechanical play is one of: a radial mechanical play and a linear mechanical play.
11. The operable implant according to embodiment 10, wherein the start resistance delay member comprises a radial mechanical play enabling the force output of the electrical motor to perform at least one of: 1/10 of a revolution, 1/8 of a revolution, 1/6 of a revolution, 1/4 of a revolution, 1/2 of a revolution and 1 revolution, before the force output directly or indirectly engages the driving member.
12. The operable implant according to any one of embodiments 2-11, wherein the start resistance delay member is positioned between one of:
  a. the force output of the first gear system, and the force input of the second gear system, and
  b. the force output of the second gear system, and the body engaging portion,
  wherein the start resistance delay comprises a radial mechanical play enabling the force output of the gear system to perform at least one of: 1/10 of a revolution, 1/8 of a revolution, 1/6 of a revolution, 1/4 of a revolution, 1/2 of a revolution and 1 revolution, before the force output engages the driving member, such that the force output of the electrical motor can perform at least one of 1/10 of a revolution*the transmission of the gear system, 1/8 of a revolution*the transmission of the gear system, 1/6 of a revolution*the transmission of the gear system, 1/4 of a revolution*the transmission of the gear system, 1/2 of a revolution*the transmission of the gear system and 1 revolution*the transmission of the gear system.
13. The operable implant according to any one of the preceding embodiments, wherein the start resistance delay device comprises a friction clutch.
14. The operable implant according to any one of the preceding embodiments, wherein the start resistance delay device comprises at least one element adapted to be operated by centrifugal force, wherein the at least one element is connected to the electrical motor and adapted to engage direct or indirect the body engaging portion when the centrifugal force exerted on the element exceeds a centrifugal delay force.
15. The operable implant according to embodiment 14, wherein the operable element of the first and/or second gear system comprises the element adapted to be operated by centrifugal force, such that the operable element of the gear system engages the first gear when the centrifugal force exerted on the element exceeds the centrifugal delay force.
16. The operable implant according to any one of the preceding embodiments, wherein the electrical motor is an electrical motor selected from:
  an alternating current (AC) electrical motor,
  a direct current electrical motor,
  a linear electrical motor,
  an axial electrical motor,
  a piezo-electric motor,
  a three-phase motor
  a more than one-phase motor
  a bimetal motor, and
  a memory metal motor.
17. The operable implant according to any one of the preceding embodiments, wherein the body engaging portion is a hydraulically operable body engaging portion connected to a hydraulic pump for transporting hydraulic fluid for operating the hydraulically operable body engaging portion.
18. The operable implant according to embodiment 17, wherein the hydraulic pump comprises a reservoir comprising at least one movable wall portion, and wherein the at least one movable wall portion is in direct or indirect connection with the electrical motor, such that the electrical motor is arranged to operate the movable wall portion for changing the volume of the reservoir.
19. The operable implant according to any one of the preceding embodiments, wherein the force output of the electrical motor, directly or indirectly, connects to a threaded member adapted to transform a radially rotating force of the electrical motor to an axially reciprocating force.
20. The operable implant according to embodiment 19, wherein the threaded member is directly or indirectly connected to the movable wall portion of the reservoir of embodiment 17, for changing the volume of the reservoir.
21. The operable implant according to embodiment 20, wherein the threaded member is directly or indirectly connected to a movable wall portion of a second reservoir for changing the volume of the second reservoir.

22. The operable implant according to embodiment 21, wherein the movement of the movable wall portion of the first reservoir by the threaded member in a first direction causes the first fluid reservoir to expand and the volume in the first reservoir to increase, and wherein the movement of the movable wall portion of the second reservoir by the threaded member in a first direction causes the second reservoir to contract and the volume in the second reservoir to decrease.

23. The operable implant according to embodiment 22, wherein the first reservoir is in fluid connection with a first hydraulically operable body engaging portion, and wherein the second reservoir is in fluid connection with a second hydraulically operable body engaging portion, and wherein operation of the electrical motor in a first direction, by the connection with the threaded member, causes:
   a. transportation of fluid from the first reservoir to the first hydraulically operable implant, and
   b. transportation of fluid from the second hydraulic operable body engaging portion to the second fluid reservoir.

24. The operable implant according to any one of embodiments 18-23, wherein the reservoir is at least one of circular and torus shaped.

25. The operable implant according to any one of the preceding embodiments, wherein the operable implant comprises a circular reservoir encircling the operation device, and wherein the circular reservoir comprises a movable wall portion adapted to compress and expand the circular reservoir, thereby altering the volume of the reservoir, and wherein the movable wall portion is connected to the electrical motor, such that the operation of the electrical motor changes the volume of the circular reservoir.

26. The operable implant according to any one of embodiments 18-25, wherein a portion of the wall of the reservoir comprises at least one of; a bellows structure, a shape adapted to allowing movement although covered with fibrosis and a plate shaped surface, in all cases enabling movement of the at least one movable wall portion, enabling the compression and/or expansion of the reservoir.

27. The operable implant according to embodiment 17, wherein the hydraulic pump comprises a peristaltic pump comprising:
   a. a hollow member for fluid transportation, and
   b. an operable compression member adapted to engage and compress the hollow member, and wherein the electrical motor is in direct or indirect connection with the compression member, such that the operation of the electrical machine operates the compression member such that fluid is transported in the hollow member.

Numbered Embodiment G 1-21

1. An operable implant adapted to be implanted in the body of a patient, the operable implant comprising an operation device and a body engaging portion, wherein the operation device comprises:
   a. a first gear system comprising:
      i. an operable element,
      ii. a first gear having the shape of a hollow cylinder, comprising a first number of teeth, on the peripheral outside thereof, and
      iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and
   b. a second gear system comprising:
      i. an operable element,
      ii. a first gear having the shape of a hollow cylinder, comprising a first number of teeth, on the peripheral outside thereof, and
      iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear, wherein
   c. the first gear of the first gear system is directly or indirectly connected to the operable element of the second gear system, such that the first and second gear systems functions as a single gear system.

2. The operable implant according to embodiment 1, wherein the first gear of the first and second gear system comprises a deflectable wall, and wherein the operable element is adapted to deflect the first gear, and to maintain the first gear deflected such that the teeth of the first gear are interengaged with the teeth of the second gear in at least one angularly spaced positions interspaced by positions in which the teeth are not interengaged, and wherein the operation of the pressing element rotatively advances the angularly spaced positions and thereby cause relative rotation between the first gear and the second gear.

3. The operable implant according to embodiment 2, wherein the operable element is adapted to deflect the first gear, and to maintain the first gear deflected such that the teeth of the first gear are interengaged with the teeth of the second gear in at least one of; at least two angularly spaced positions and at least three angularly spaced positions, interspaced by positions at which the teeth are not interengaged.

4. The operable implant according to any one of embodiments 1-3, wherein at least one of the first and second gear systems comprises a third gear having the shape of a hollow cylinder, and wherein the inside of third gear comprises the same amount of teeth as the outside of the first gear, and wherein teeth of the third gear are adapted to interengage the teeth of the first gear such that the third gear rotates in relation to the second gear, along with the at least one interengaged position.

5. The operable implant according to embodiment 4, wherein the first gear system comprises a third gear having the shape of a hollow cylinder, and wherein the inside of third gear comprises the same amount of teeth as the outside of the first gear of the first gear system, and wherein teeth of the third gear are adapted to interengage the teeth of the first gear such that the third gear rotates in relation to the second gear, along with the at least one interengaged position, and wherein the operable element of the second gear system is connected directly or indirectly to the third gear of the first gear system.

6. The operable implant according to any one of the preceding embodiments, wherein the first gear system at least partially is positioned radially inside of the second gear system, such that the second gear system axially at least partially overlaps the first gear system.

7. The operable implant according to any one of the preceding embodiments, wherein the first and second gear systems are positioned coaxially, along the rotational axis of the first and second gear systems.

8. The operable implant according to any one of the preceding embodiments, further comprising a radially extending connecting structure directly or indirectly connecting the first gear of the first gear system with the operable element of the second gear system, to transfer force from the first gear system to the second gear system.

9. The operable implant according to any one of the preceding embodiments, further comprising an enclosure, adapted to hermetically enclose the first and second gear systems, such that the first and second gear systems are sealed from bodily fluids when implanted.

10. The operable implant according to any one of the preceding embodiments, wherein the operable element of at least one of the first and second gear systems comprises at least one of; a planet gear and a structure or wheel comprising a frictional surface connection.

11. The operable implant according to any one of the preceding embodiments, further comprising an electrical motor.

12. The operable implant according to embodiment 11, wherein the electrical motor comprises an electrical motor selected from:
an alternating current (AC) electrical motor,
a direct current electrical motor,
a linear electrical motor,
an axial electrical motor,
a piezo-electric motor,
a three-phase motor,
a more than one-phase motor,
a bimetal motor, and
a memory metal motor.

13. The operable implant according to any one of embodiments 11 and 12, further comprising an enclosure adapted to hermetically enclose the first gear system and the electrical motor.

14. The operable implant according to embodiment 13, further comprising a sealed outlet for rotational force, such that the force can be transferred from the hermetically enclosed first gear system to the second gear system.

15. The operable implant according to any one of embodiments 11 and 12, further comprising a system enclosure adapted to hermetically enclose the first gear system, the second gear system and the electrical motor.

16. The operable implant according to embodiment 15, further comprising a sealed outlet for rotational force, such that the force can be transferred from the hermetically enclosed second gear system to an operable implant.

17. The operable implant according to any one of embodiments 11 and 12, further comprising an enclosure adapted to hermetically enclose the electrical motor.

18. The operable implant according to embodiment 17, further comprising a sealed outlet for rotational force, such that the force can be transferred from the hermetically enclosed motor to the first gear system.

19. The operable implant according to any one of embodiments 11 and 12, further comprising an enclosure adapted to hermetically enclose the static part of the electrical motor, comprising at least one of; at least two coils and at least one core.

20. The operable implant according to embodiment 19, the enclosure of the static part of the motor, comprising a wall, the operable implant adapted to create rotational force from the hermetically enclosed static part wirelessly through the sealed wall, to create rotational force for rotating a rotor part of the motor, comprising at least one of; at least one magnet, magnetizable material and at least one coil, the rotor adapted to directly or indirectly be further connected to the first gear system.

21. The operable implant according to embodiment 20, further comprising an enclosure adapted to hermetically enclose the rotor part of the electrical motor and at least one of; the first gear system and the first and second gear system.

Numbered Embodiment H 1-21

1. An operable implant adapted to be implanted in the body of a patient, the operable implant comprising an operation device and a body engaging portion, wherein the operation device comprises:
    a. at least one of; at least one magnet, at least one magnetic material and at least one magnetizable material adapted to be affected by a moving magnetic field created by an external unit, when implanted, such that the magnet or magnetic or magnetizable material moves along with the moving magnetic field of the external unit, and
    b. a gear system comprising:
        i. an operable element directly or indirectly connected to the at least one magnet, magnetic material, or magnetizable material, such that the operable element is propelled by the magnet or magnetic material moving along with the moving magnetic field of the external unit,
        ii. a first gear having the shape of a hollow cylinder, comprising a first number of teeth, on the peripheral outside thereof, and
        iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions in which the teeth are not interengaged, and wherein the operation of the operable element advances the positions and thereby causes relative rotation between the first gear and the second gear.
2. The operable implant according to embodiment 1, wherein the operation device is adapted to be implanted subcutaneously.
3. The operable implant according to embodiment 2, wherein the operation device is adapted to be implanted subcutaneously in the abdominal region.
4. The operable implant according to any one of the preceding embodiments, wherein the operation device comprises a first unit and a second unit, and wherein the at least one magnet, magnetic material, or magnetizable material is placed in the first unit, and the gear system is placed in the second unit.
5. The operable implant according to embodiment 4, further comprising a distance element adapted to create a distance between the first and second units.
6. The operable implant according to embodiment any one of the embodiments 4 and 5, wherein the distance element is adapted to be at least one of; placed through the muscular layers of the abdominal wall, and fixated to the muscular fascia at the inner side of the subcutaneous space.
7. The operable implant according to any one of embodiments 5 and 6, wherein the distance element is flexible such that the first and second units can move in relation to each other.
8. The operable implant according to any one of embodiments 5-7, wherein the distance element is adapted to be fixated to at least one of; the fascia and muscular layer of the abdominal wall, such that the distance between the first portion of the operation device and the skin of the patient can be controlled.
9. The operable implant according to any one of embodiments 5-8, wherein the distance element comprises a mechanical transferring member adapted to transfer force from the first unit to the second unit, such that force can be transferred from the at least one magnet, magnetic material, or magnetizable material to the operable element of the gear system.
10. The operable implant according to any one of the preceding embodiments, further comprising an enclosure adapted to hermetically enclose at least one of; the operable implant, the operation device, the body engaging portion, the first unit according to embodiment 4, the second unit according to embodiment 4 and the distance element according to embodiment 5, for sealing from the bodily fluids of the patient.
11. The operable implant according to embodiment 10, wherein the enclosure constitutes a reservoir for supplying fluid to a hydraulically operable body engaging portion, such that the at least one magnet, magnetic material, or magnetizable material and gear system is placed inside of the reservoir.
12. The operable implant according to any one of embodiments 1-10, further comprising a reservoir comprising a movable wall portion adapted to change the volume of the reservoir, wherein the movable wall portion is directly or indirectly connected to the first gear of the gear system, such that operation of the gear system changes the volume of the reservoir.
13. The operable implant according to any one of the preceding embodiments, wherein the first gear of the gear system is directly or indirectly connected to a threaded member adapted to transform a rotating force to a reciprocating force.
14. The operable implant according to embodiment 13, wherein the threaded member is directly or indirectly connected to the movable wall portion of the reservoir of embodiment 12 for changing the volume of the reservoir.
15. The operable implant according to any one of the preceding embodiments, further comprising a peristaltic pump, wherein the peristaltic pump comprises a hollow member for fluid transportation, and an operable compression member adapted to engage and compress the hollow member, and wherein first gear of the gear system is in direct or indirect connection with the compression member, such that the operation of the gear system operates the compression member such that fluid is transported in the hollow member.
16. The operable implant according to any one of the preceding embodiments, further comprising a second gear system comprising:
    a. an operable element,
    b. a first gear having the shape of a hollow cylinder, comprising a first number of teeth, on the peripheral outside thereof, and
    c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear, wherein the first gear of the first gear system is connected, directly or indirectly to the operable element of the second gear system, such that the first and second gear systems functions as a single gear system.
17. The operable implant according to any one of the preceding embodiments, wherein the operable element of at least one of the first and second gear systems comprises at least one of; a planet gear and a structure or wheel at least partly using friction to enable rotating force to be transported.
18. The operable implant according to any one of the preceding embodiments, further comprising a wireless communication unit adapted to at least one of:
    a. receive wireless communication signals from an external unit, and
    b. transmit wireless communication signals to an external unit.
19. An external unit for supplying force to an implanted operation device, the external unit comprises:
    a. an external drive unit adapted to create a moving magnetic field on the outside of the patient's skin adapted to affect at least one magnet or magnetic material or magnetizable material of an implanted operation device, such that the magnet or magnetic material moves along with the moving magnetic field of the external drive unit.
20. The external unit for supplying force to an operable implant according to embodiment 19, wherein the external drive unit comprises a set of coils circularly distributed around a rotational axis of the external unit, such that sequential energizing of the coils creates a rotating magnetic field adapted to affect the magnet or magnetic material or magnetizable material of the implanted operation device, such that the magnet or magnetic material moves along with the moving magnetic field of the external drive unit.
21. The external unit for supplying force to an operable implant according to embodiment 19, wherein the external drive unit comprises a rotatable structure comprising at least one magnet or magnetic material, and wherein rotation of the rotatable structure affects the magnet or magnetic material or magnetizable material of the implanted operation device causing rotation thereof, such that the magnet or magnetic material or magnetizable material rotates along with the rotatable structure of the external unit.
22. The external unit for supplying force to an operable implant according to any one of embodiments 19-21, further comprising a wireless communication unit adapted to at least one of:
   a. receive wireless communication signals from an implantable unit, and
   b. transmit wireless communication signals to an implantable unit.
23. A medical system comprising:
   a. an operable implant according to any one of embodiments 1-18, and
   b. an external unit according to any one of embodiments 19-22.
24. The operable implant according to any one of the preceding embodiments, wherein the operation device comprises a rotatable structure adapted to hold at least one of; at least one magnet, at least one magnetic material and at least one magnetizable material, and further adapted to be affected by the moving externally created magnetic field, such that the rotatable structure rotates.
25. The operable implant according to any one of the preceding embodiments, further comprising an enclosure adapted to hermetically enclose at least one of; the rotational structure according to embodiment 24, the reservoir according to embodiment 12, and the treaded member according to embodiment 13, for sealing from the bodily fluids of the patient.
26. The operable implant according to any one of embodiments 11-25, wherein the reservoir comprises a wall portion of at least one of; the enclosure according to embodiment 25 and the enclosure according to embodiment 10.
27. The operable implant according to any one of the preceding embodiments, comprising a reservoir adapted to contain a hydraulic fluid and at least one movable wall portion for changing the volume of the reservoir, wherein the operation device is adapted to operate the movable wall of the reservoir, wherein the operation device comprises a gear system placed within the reservoir, the gear system comprising:
   i. an operable element,
   ii. a first gear having the shape of a hollow cylinder, comprising a first number of teeth, on the peripheral outside thereof, and
   iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

Numbered Embodiment I 1-24

1. An operable implant adapted to be implanted in the body of a patient, the operable implant comprising a hydraulic operation device for supplying hydraulic force and a body engaging portion adapted to receive the hydraulic force, the hydraulic operation device comprising:
   a. a reservoir adapted to contain a hydraulic fluid, the reservoir comprising at least one movable wall portion for changing the volume of the reservoir, and
   b. an operation device adapted to operate the movable wall, wherein the operation device comprises a gear system placed within the reservoir, the gear system comprising:
      i. an operable element,
      ii. a first gear having the shape of a hollow cylinder, comprising a first number of teeth, on the peripheral outside thereof, and
      iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
2. The operable implant according to embodiment 1, wherein the first gear directly or indirectly connects to a threaded member adapted to transform a rotating force to a reciprocating force.
3. The operable implant according to embodiment 2, wherein the threaded member is directly or indirectly connected to the movable wall portion of the reservoir such that operation of the operation device changes the volume of the reservoir.
4. The operable implant according to any one of the preceding embodiments, further comprising a rotatable structure positioned on the inside of the reservoir and connected to the operable element of the gear system, the rotatable structure comprising at least one magnet, at least one magnetic material or at least one magnetizable material adapted to be in magnetic connection with a rotating magnetic field outside of the reservoir, such that the rotating magnetic field on the outside of the reservoir propels the rotatable structure inside of the reservoir.
5. The operable implant according to embodiment 4, wherein the rotatable structure comprises a radially extending disc comprising a plurality of magnets, and wherein the plurality of magnets are adapted to axially be in magnetic connection with the rotating magnetic field.
6. The operable implant according to embodiment 5, further comprising a drive unit comprising a plurality of axially positioned coils circularly distributed around a rotational axis of the rotatable structure positioned on the inside of the reservoir, such that the center axis of the helix of the coils extends in the axial direction, substantially parallel or substantially aligned in the center of the rotational axis of the rotatable structure, and wherein sequential energizing of the coils creates the rotating magnetic field axially propelling the rotatable structure.
7. The operable implant according to embodiment 5, further comprising a magnetic coupling comprising a driving rotatable structure comprising a plurality of magnets circularly distributed around a rotational axis of the rotatable structure, wherein the driving rotatable structure is adapted to be in magnetic connection with the rotatable structure positioned on the inside of the reservoir, and wherein the driving rotatable structure is connected to an electrical motor adapted to propel the driving rotatable structure such that the rotatable structure positioned on the inside of the reservoir rotates along with the driving rotatable structure.
8. The operable implant according to embodiment 4, wherein the rotatable structure comprises an axially extending cylinder comprising a plurality of magnets positioned on the peripheral surface of the cylinder, and wherein the plurality of magnets are adapted to radially be in magnetic connection with the rotating magnetic field.
9. The operable implant according to embodiment 8, further comprising a drive unit comprising a plurality of radially positioned coils circularly distributed around a rotational axis of the rotatable structure positioned on the inside of the reservoir, such that the center axis of the helix of the coils are extending in the radial direction, substantially perpendicular to the rotational axis of the rotatable structure, and wherein sequential energizing of the coils creates the rotating magnetic field propelling the rotatable structure.
10. The operable implant according to embodiment 8, further comprising a drive unit comprising an driving rotatable structure comprising a plurality of magnets circularly distributed around a rotational axis of the rotatable structure, wherein the driving rotatable structure is adapted to radially be in magnetic connection with the rotatable structure positioned on the inside of the reservoir, and wherein the driving rotatable structure is connected to an electrical motor adapted to propel the driving rotatable structure such that the rotatable structure positioned on the inside of the reservoir rotates along with the driving rotatable structure, adapted to rotate radially on the outside thereof.
11. The operable implant according to any one of embodiments 6, 7, 9 and 10, wherein the drive unit is an external drive unit adapted to be positioned on the outside of the skin of the patient and propel the rotatable structure in the hydraulic operation device.
12. The operable implant according to any one of the preceding embodiments, wherein the hydraulic operation device comprises an electrical motor adapted to propel the operable element of the gear system, wherein the electrical motor is an electrical motor selected from:
 a. an alternating current (AC) electrical motor,
 b. a direct current electrical motor,
 c. a linear electrical motor,
 d. an axial electrical motor,
 e. a radial motor
 f. a three phase motor
 g. a more than one phase motor
 h. a piezo-electric motor,
 i. a bimetal motor, and
 j. a memory metal motor.
13. The operable implant according to embodiment 12, wherein the electrical motor is adapted to be positioned on the inside of the reservoir.
14. The operable implant according to any one of the preceding embodiments, further comprising a force transferring member, adapted to at least one of; penetrating a wall of the fluid reservoir, not penetrating a wall of the reservoir, transferring force from outside of the reservoir to inside of the reservoir, and transferring force between the motor and gear system inside the reservoir.
15. The operable implant according to embodiment 14, wherein the force transferring member is connected to an implantable electrical motor and to the operable element of the gear system and adapted to transfer rotational force from the electrical motor to the operable element.
16. The operable implant according to any one of the preceding embodiments, further comprising a second gear system comprising:
 i. an operable element,
 ii. a first gear having the shape of a hollow cylinder, comprising a first number of teeth, on the peripheral outside thereof, and
 iii. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear, wherein
 b. the first gear of the first gear system is connected to the operable element of the second gear system, such that the first and second gear systems functions as a single gear system.
17. The operable implant according to any one of the preceding embodiments, wherein the operable element of at least one of the first and second gear systems comprises at least one of; a planet gear and a wheel or structure adapted to use frictional connection direct or indirect between the operable element and the first gear.
18. The operable implant according to any one of the preceding embodiments, wherein the hydraulic operation device further comprises at least one receiving unit adapted to receive wireless energy supplied from outside the body of the patient.
19. The operable implant according to embodiment 18, wherein the receiving unit comprises at least one coil adapted to transform wireless energy received in form of a magnetic or electromagnetic field into electrical energy.
20. The operable implant according to any one of embodiments 18 and 19, further comprising a distance element adapted to create a distance between the receiving unit and at least one of; the reservoir and the electrical motor, such that the receiving unit remains substantially unaffected by metallic and/or magnetic parts of the reservoir and/or electrical motor.
21. The operable implant according to embodiment 20, wherein the distance element is adapted to at least one of; be placed through the muscular layers of the abdominal wall and be fixated to the fascia of a muscle facing the inside of the subcutaneous space.
22. The operable implant according to any one of embodiments 20 and 21, wherein the distance element is flexible such that the wireless energy receiver can move in relation to the reservoir and/or electrical motor.
23. The operable implant according to any one of embodiments 19-21, wherein the distance element is adapted to be fixated to at least one muscular layer of the abdominal wall, such that at least one of; the distance between the first portion of the implantable unit and the skin of the patient can be controlled and the movement of the distance element including rotation is minimized.
24. The operable implant according to any one of the preceding embodiments, further comprising an injection port for directly or indirectly supplying fluid to the reservoir or the operable implant, being hydraulically operated.

Numbered Embodiment J 1-21

1. An implantable electrical generator for transforming mechanical work to electrical energy, the implantable electrical generator comprising:
    a movable structure comprising at least one magnet or at least one magnetic material or at least one magnetizable material, the movable structure being adapted to be in magnetic connection with an external drive unit creating a moving magnetic field, such that the movable structure moves along with the moving magnetic field, and
    an electrical generator unit connected to the movable structure and being adapted to transform the movements of the movable structure to electrical energy.
2. The implantable electrical generator according to embodiment 1, wherein the electrical generator unit comprises:
    at movable generator portion comprising at least one magnet, wherein the movable generator portion is connected to the movable structure, and
    at least one coil in magnetic connection with the at least one magnet, wherein the electrical current is induced in the coil by the movement of the movable generator portion in relation to the coil.
3. The implantable electrical generator according to embodiment 2, wherein the movable structure comprises a rotatable disc, and wherein the at least one magnet or magnetic material is positioned on the rotatable disc and adapted to be in magnetic connection with an external unit creating a rotating magnetic field, and wherein the electrical generator unit is a rotating electrical generator unit connected to the rotatable disc, such that the rotating electrical generator unit rotates along with, or is part of, the rotatable disc for inducing electrical current.
4. The implantable electrical generator according to embodiment 1, wherein the movable structure is adapted to perform reciprocating movement, and wherein the movable structure is adapted to be in magnetic connection with an external unit creating a reciprocating magnetic field, such that the movable structure performs reciprocating movement along with the reciprocating magnetic field.
5. The implantable electrical generator according to embodiment 4, wherein the movable structure is connected to an elastic element or spring, such that the movable structure can operate in a first direction by the magnetic force supplied by the external unit, and in a second direction by the elastic element or spring.
6. The implantable electrical generator according to embodiment 5, wherein the elastic element comprises at least one of; an elastic material, a flexible material, a construction adapted to create elastic movement, and a spring.
7. The implantable electrical generator according to embodiment 4, wherein the electrical generator unit is a linear electrical generator unit comprising:
    a movable generator portion comprising at least one magnet, wherein the movable generator portion is in connection with the movable structure adapted to perform reciprocating movement, and
    at least one coil in magnetic connection with the at least one magnet, such that reciprocating movement of the movable structure propagates to the movable generator portion and induces current in the at least one coil.
8. The implantable electrical generator according to any one of the preceding embodiments, further comprising a battery connected to the electrical generator unit, wherein the battery is adapted to store electrical energy generated in the generator unit.
9. The implantable electrical generator according to any one of the preceding embodiments, further comprising an enclosure adapted to hermetically enclose the implantable electrical generator, such that the implantable electrical generator is sealed from the bodily fluids of the patient.
10. The implantable electrical generator according to any one of the preceding embodiments, further comprising a wireless communication unit adapted to at least one of:
    receive wireless communication signals from an external unit, and
    transmit wireless communication signals to an external unit.
11. The implantable electrical generator according to any one of the preceding embodiments, wherein the implantable electrical generator is adapted to be implanted subcutaneously.
12. The implantable electrical generator according to embodiment 11, wherein the implantable electrical generator is adapted to be implanted subcutaneously in the abdomen.
13. An external unit for supplying force to an implantable electrical generator, the external unit comprising an external drive unit adapted to create a moving magnetic field on the outside of the patient's skin adapted to affect at least one magnet or at least one magnetic material or at least one magnetizable material of an implantable electrical generator, such that the magnet or magnetic material moves along with the moving magnetic field of the external drive unit.
14. The external unit according to embodiment 13, wherein the external drive unit comprises at least one an electro magnet adapted to be alternatingly energized and not energized, such that an alternating magnetic field is created for affecting at least one magnet or magnetic material of the implantable electrical generator.
15. The external unit according to embodiment 13, wherein the external drive unit comprises at least one permanent magnet, and wherein a positive pole of a permanent magnet is adapted to affect a permanent magnet of the implantable generator, and a negative pole of a permanent magnet is adapted to affect a permanent magnet of the implantable generator, and wherein the at least one permanent magnet is adapted to move such that the positive and negative pole alternatingly affects the permanent magnet of the implantable generator.
16. The external unit according to embodiment 13, wherein the external drive unit comprises a set of circularly distributed coils, such that sequential energizing of the coils creates a rotating magnetic field adapted to affect the magnet, magnetic material, or magnetizable material of the implantable electrical generator, such that the magnet, magnetic material, or magnetizable material rotates along with the rotating magnetic field of the external drive unit.
17. The external unit according to embodiment 13, wherein the external unit comprises a set of linearly distributed coils, such that sequential energizing of the coils creates a linearly moving magnetic field adapted to affect the magnet or magnetic material or magnetizable material of the implantable electrical generator, such that the magnet, magnetic material, or magnetizable material moves along with the linear magnetic field of the external unit.
18. The external unit according to any one of embodiments 13 and 15, wherein the external unit comprises a rotatable structure comprising at least one magnet or magnetic material, and wherein rotation of the rotatable structure affects a magnet or magnetic material of the implantable electrical generator causing rotation thereof, such that the magnet or magnetic material rotates along with the rotatable structure of the external unit.
19. The external unit according to embodiment 13, wherein the external drive unit comprises a reciprocating structure comprising at least one of: magnetic material, a permanent magnet, and an electromagnet, and wherein the reciprocating structure; a) moves the magnetic material, permanent magnet or electromagnet between a first position close to the skin of the patient, and a second position further from the skin of the patient, such that a reciprocating magnetic field adapted to affect the magnet or magnetic material of the implantable electrical generator is created or b) is adapted to intermittently receive electric pulses to the at least one electromagnet to cause movement of the magnetic field, while the reciprocating structure substantially stands still.
20. The external unit according to any one of embodiments 13-19, further comprising a wireless communication unit adapted to at least one of:
receive wireless communication signals from the implantable electrical generator, and
transmit wireless communication signals to the implantable electrical generator.
21. A system for generating electrical current inside of the body of a patient, the system comprises:
an implantable electrical generator according to any one of embodiments 1-12, and
an external unit according to any one of embodiments 13-20.

Numbered Embodiment K 1-24

1. An operable hydraulic implant comprising a hydraulic operation device, the hydraulic operation device comprising an enclosure adapted to hermetically enclose:
   a. a reservoir adapted to contain a hydraulic fluid for operating the operable hydraulic implant, and
   b. a gear system adapted receive mechanical work of a first force and velocity as input, and output mechanical work having a different force and velocity, wherein the reservoir and the gear system is sealed from the bodily fluids when implanted.
2. The operable hydraulic implant according to embodiment 1, wherein the reservoir comprises at least one movable wall portion, for changing the volume of the reservoir.
3. The operable hydraulic implant according to embodiment 2, wherein the gear system is connected to the movable wall for changing the volume of the reservoir.
4. The operable hydraulic implant according to any one of the preceding embodiments, further comprising an electrical motor connected to the gear system and enclosed by the enclosure.
5. The operable hydraulic implant according to any one of the preceding embodiments, wherein the gear system comprises:
   a. an operable element,
   b. a first gear having the shape of a hollow cylinder, comprising a first number of teeth, on the peripheral outside thereof, and
   c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
6. The operable hydraulic implant according to embodiment 5, wherein the operable element of the gear system is adapted to receive mechanical work of a first force and velocity from the electrical motor according to embodiment 4, and wherein the first gear of the gear system is directly or indirectly connected to the at least one movable wall portion for supplying mechanical work having a different second force and velocity to the at least one wall portion, such that operation of the electrical motor moves the movable wall portion and changes the volume of the reservoir.
7. The operable hydraulic implant according to embodiment 6, wherein the first gear of the gear system directly or indirectly connects to a threaded member adapted to transform the radially rotating force to an axially reciprocating force, and wherein the threaded member is directly or indirectly connected to the movable wall portion for changing the volume of the reservoir.
8. The operable hydraulic implant according to embodiment 7, wherein the threaded member is directly or indirectly connected to a movable wall portion of a second fluid reservoir for changing the volume of the second reservoir.

9. The operable hydraulic implant according to embodiment 8, wherein the movement of the movable wall portion of the first reservoir, by the threaded member in a first direction causes the first reservoir to expand and the volume in the first reservoir to increase, and wherein the movement of the movable wall portion of the second reservoir by the threaded member in a first direction causes the second reservoir to contract and the volume in the second reservoir to decrease.

10. The operable hydraulic implant according to embodiment 9, wherein the first reservoir is in fluid connection with a first hydraulically operable body engaging portion, and wherein the second reservoir is in fluid connection with a second hydraulically operable body engaging portion, and wherein operation of the electrical motor unit in a first direction, by the connection with the threaded member, causes:
   a. transportation of fluid from the first reservoir to the first hydraulically operable body engaging portion, and
   b. transportation of fluid from the second hydraulically operable body engaging portion to the second reservoir.

11. The operable hydraulic implant according to any one of the preceding embodiments, wherein a wall of the enclosure constitutes at least a portion of the wall of the reservoir, and wherein at least one movable wall portion is positioned between the reservoir and the gear system, such that the portion of the at least one movable wall portion separates the reservoir from a portion of the enclosure enclosing the gear system, such that the gear system is sealed from the reservoir.

12. The operable hydraulic implant according to any one of the preceding embodiments, further comprising a second gear system enclosed by the enclosure, wherein the second gear system is adapted to receive mechanical work of the different second force and velocity from the output of the first gear system, and output mechanical work having a different third force and velocity.

13. The operable hydraulic implant according to embodiment 12, wherein the second gear system comprises:
   a. an operable element,
   b. a first gear having the shape of a hollow cylinder, comprising a first number of teeth, on the peripheral outside thereof, and
   c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein the first gear of the first gear system is directly or indirectly connected to the operable element of the second gear system, such that the first and second gear systems functions as a single gear system.

14. The operable implant according to any one of the preceding embodiments, wherein the operable element of at least one of the first and second gear systems comprises at least one of; a planet gear and a wheel or structure using a frictional connection.

15. The operable hydraulic implant according to any one of embodiments 4-14, further comprising at least one battery, enclosed by the enclosure, and adapted to energize the electrical motor.

16. The operable hydraulic implant according to any one of the preceding embodiments, further comprising a receiving unit adapted to receive wireless energy transmitted from outside the patient's body.

17. The operable hydraulic implant according to embodiment 16, wherein the receiving unit is enclosed by the enclosure, such that the receiving unit is sealed from the bodily fluids.

18. The operable hydraulic implant according to any one of embodiment 16 and 17, further comprising a distance element adapted to create a distance between the receiving unit and at least one of; the gear system and the electrical motor, such that the receiving unit is removed from metallic and/or magnetic components of the gear system and/or electrical motor.

19. The operable hydraulic implant according to any one of embodiments 16-18, wherein the receiving unit is adapted to charge the battery according to embodiment 15.

20. The operable hydraulic implant according to any one of the preceding embodiments, further comprising a magnetic coupling comprising a first part connected to the operable element of the gear system and enclosed by the enclosure, and a second part being:
   a. positioned on the outside of the enclosure,
   b. connected to an electrical motor positioned such that operation of the electrical motor operates the second part of the magnetic coupling, and
   c. magnetically connected to the first part of the magnetic coupling, such that the first part of the magnetic coupling rotates along with the second part of the magnetic coupling, such that the electrical motor propels the gear system through the wall of the enclosure.

21. The operable hydraulic implant according to embodiment 20, further comprising an implanted electrical motor, and wherein the second part is connected to the implantable electrical motor.

22. The operable hydraulic implant according to embodiment 20, wherein the second part of the magnetic coupling is connected to an external drive unit adapted to propel the first unit from the outside of the patient's body.

23. The implantable hydraulic unit according to any one of embodiments 4-22, wherein the electrical motor is an electrical motor selected from:
   a. an alternating current (AC) electrical motor,
   b. a direct current electrical motor,
   c. a linear electrical motor,
   d. an axial electrical motor,
   e. a radial motor
   f. a three-phase motor
   g. a more than one-phase motor
   h. a piezo-electric motor,
   i. a bimetal motor, and
   j. a memory metal motor.

24. The implantable hydraulic unit according to any one of the preceding embodiments, wherein the enclosure comprises a material selected from:
   a. a carbon material b. a boron material
c. a mixture of material
d. a Peek® material
e. an alloy of material
f. a metallic material,
g. titanium,
h. aluminum,
i. a ceramic material,
j. a polymer material,
k. polyurethane,
l. polyether ether ketone,
m. silicone, and
n. Parylene® coated silicone.

Numbered Embodiment L 1-23

1. An operable implant for implantation in the body of a patient, the operable implant comprising:
   a. at least one fixation member adapted to directly or indirectly fixate the operable implant towards at least one of; at least one muscular fascia, at least one bone fascia, at least one cortical bone layer, at least one muscular layer, fibrotic tissue, any part of the abdominal wall, and any part of the subcutaneous space and it's surroundings in the body, and
   b. at least one adjustable distance element adapted to;
      i. in one end thereof, be directly or indirectly connected to at least a part of the operable implant,
      ii. in the other end thereof, be directly or indirectly connected to the fixation member, and
      iii. adjust the distance between the part of the operable implant connected to the adjustable distance element, and the fixation member.
2. The operable implant according to embodiment 1, comprising at least one part selected from a list consisting of:
   a. an operation device,
   b. a control unit
   c. a receiving unit, for receiving wireless energy,
   d. a coil, for receiving wireless energy,
   e. a receiving unit, for receiving a magnetic field or an electromagnetic field,
   f. a magnetic force transferring coupling,
   g. an electrical circuit,
   h. a push button for controlling any function of the operable implant,
   i. an energy storage device,
   j. a pushable construction for adjusting the adjustable distance element,
   k. an integrated operation device and receiving unit, for receiving wireless energy or a magnetic field or an electromagnetic field adapted to generate kinetic energy,
   l. a casing for enclosing at least one of the different parts of the operable implant
   m. two or more casings for enclosing at least one of the different parts of the operable implant in each casing, and
   n. an integrated unit comprising two or more of the parts according to points a-k above, and wherein the at least one adjustable distance element is adapted to adjust the distance between:
      the fixation member, and
      at least one part of points a-n above.
3. The operable implant according to embodiment 1, wherein the at least one fixation member is integrated with at least one of:
   a. an operation device,
   b. a control unit
   c. a receiving unit, for receiving wireless energy,
   d. a coil, for receiving wireless energy,
   e. a receiving unit, for receiving a magnetic field or an electromagnetic field,
   f. a magnetic force transferring coupling,
   g. an electrical circuit,
   h. a push button for controlling any function of the operable implant,
   i. an energy storage device,
   j. a pushable construction for adjusting the adjustable distance element,
   k. an integrated operation device and receiving unit, for receiving wireless energy or a magnetic field or an electromagnetic field adapted to generate kinetic energy,
   l. a casing for enclosing at least one of the different parts of the operable implant
   m. two or more casings for enclosing at least one of the different parts of the operable implant in each casing, and
   n. an integrated unit comprising two or more of the parts according to point a k above, and wherein the at least one adjustable distance element is adapted to adjust the distance between;
      the fixation member integrated with one or more of the parts of the operable implant, described in points a-n above, and
      one or more parts of the operable implant described in embodiment 2.
4. The operable implant according to any one of embodiments 1-3, wherein the at least one adjustable distance element is adjustable from outside the body of the patient.
5. The operable implant according to embodiment 4, wherein the at least one adjustable distance element is adjustable electrically or manually from outside the body of the patient.
6. The operable implant according to any one of the preceding embodiments, wherein the at least one adjustable distance element, comprises two, three, four or more adjustable distance elements.
7. The operable implant according to any one of the preceding embodiments, wherein the at least one adjustable distance element comprises a threaded member for transferring a rotating movement to a linear movement for adjusting the distance.
8. The operable implant according to any one of the preceding embodiments, wherein the at least one adjustable distance element or operable implant, comprising an x-ray detectable element, such that the distance adjusted by the at least one adjustable distance element can be measured on an x-ray image.
9. The operable implant according to any one of the preceding embodiments, wherein the at least one adjustable distance element or operable implant, comprising an element detectable by means of ultrasound, such that the distance adjusted by the at least one adjustable distance element can be measured by means of ultrasound.
10. The operable implant according to any one of embodiments 2-9, wherein the at least one part of the operable implant is adapted to be placed subcutaneously.
11. The operable implant according to any one of embodiments 2-9, wherein the operation device is adapted to be placed subcutaneously.

12. The operable implant according to any one of the preceding embodiments, wherein the operation device is adapted to be fixated to at least one of, at least one fascia layer and at least one muscular layer of the abdominal wall.
13. The operable implant according to any one of the preceding embodiments, wherein the at least one adjustable distance element is adapted to be placed through at least one of, at least one fascia layer and at least one muscular layer of the abdominal wall.
14. The operable implant according to any one of the preceding embodiments, wherein the at least one adjustable distance element is flexible such that the different parts of the operable implant can flex in relation to each other.
15. The operable implant according to any one of embodiments 2-14, wherein the receiving unit comprises at least one coil adapted to transform wireless energy, received in form of an electric, magnetic or electromagnetic field, into electrical energy.
16. The operable implant according to embodiment 15, wherein the receiving unit comprises at least a first coil having a first number of windings, and at least a second coil having a second, different number of windings.
17. The operable implant according to any one of the preceding embodiments, comprising at least one enclosure adapted to hermetically enclose at least one part according to embodiment 2 and the adjustable distance element.
18. The operable implant according to any one of the preceding embodiments, comprising at least one enclosure adapted to hermetically enclose at least one part according to embodiment 2.
19. The operable implant according to any one of the preceding embodiments, wherein the at least one adjustable distance element comprises a lead for transferring electrical current from the receiving unit to the operation device.
20. The operable implant according to any one of the preceding embodiments, further comprising a control unit for controlling at least one parameter of the operable implant.
21. The operable implant according to embodiment 20, wherein the control unit is adapted to wirelessly communicate with an external unit, such that the control unit can be wirelessly controlled from outside the body.
22. The operable implant according to any one of the preceding embodiments, wherein at least one of; the receiving unit according to embodiment 2 and the at least one adjustable distance element is free from magnetic components.
23. The operable implant according to any one of embodiments 17-18, wherein the at least one enclosure comprises two or more enclosures, wherein the at least one adjustable distance element is adapted to adjust the distance between the enclosures.

Numbered Embodiment M 1-24

1. A surgical kit for an operable implant enabling adjustment of a distance between at least one fixation member of the operable implant and at least one part of the operable implant, the surgical kit comprises:
    a. at least one first distance element having:
        i. a first connecting portion adapted to directly or indirectly connect to the at least one part of the operable implant, and
        ii. a second connecting portion adapted to directly or indirectly connect to the at least one fixation member of the operable implant, for creating a first distance between the at least one part of the operable implant and the at least one fixation member of the operable implant, and
    b. at least one second distance element having:
        i. a first connecting portion adapted to directly or indirectly connect to at least one part of the operable implant, and
        ii. a second connecting portion adapted to directly or indirectly connect to the at least one fixation member of the operable implant for creating a second longer distance between the at least one part of the operable implant and the at least one fixation member of the operable implant.
2. The surgical kit according to embodiment 1, wherein at least one of; the at least one first and second distance elements comprises an x-ray detectable element, such that the distance between the at least one part of the operable implant and the at least one fixation member of the operable implant can be measured on an x-ray image.
3. The surgical kit according to embodiment 1, wherein at least one of; the at least one first and second distance elements comprises an element detectable by means of ultrasound, such that the distance between the at least one part of the operable implant and the at least one fixation member of the operable implant can be measured by means of ultrasound.
4. The surgical kit according to any one of the preceding embodiments, wherein at least one of; the at least one first and second distance elements is adapted to be placed subcutaneously.
5. The surgical kit according to any one of the preceding embodiments, wherein at least one of; the at least one the first and second distance elements is adapted to be fixated to at least one of; at least one muscular fascia, at least one bone fascia, at least one cortical bone layer, at least one muscular layer, fibrotic tissue, any part of the abdominal wall, and any part of the subcutaneous space and it's surroundings in the body.
6. The surgical kit according to embodiment 5, wherein at least one of the first and second distance elements is adapted to create a distance between the muscular layer of the abdominal wall and an operation device of the operable implant.
7. The surgical kit according to any one of the preceding embodiments, wherein at least one of the first and second distance elements are adapted to be placed through at least one of, at least one fascia layer and at least one muscular layer of the abdominal wall.
8. The surgical kit according to any one of the preceding embodiments, wherein at least one of the first and second distance elements is flexible such that the different parts of the operable implant can move in relation to each other.
9. The surgical kit according to any one of the preceding embodiments, wherein at least one of the first and second distance elements is free from magnetic components.
10. The surgical kit according to any one of embodiments 1-9, wherein at least one of the first and second distance element is adapted to guide a lead for transferring electrical current from a wireless energy receiving unit to an operation device of the operable implant.

11. The surgical kit according to any one of the preceding embodiments, wherein at least one of; the first and second distance element is adapted to fixate a wireless energy receiving unit in the body of the patient in an optimal position and hinder the body from rejecting the wireless energy receiving unit.
12. A system for adjusting a distance in an operable implant, the system comprising the surgical kit according to any one of embodiments 1-11 and an operable implant comprising at least one fixation member and at least one part selected from a list consisting of:
   a. an operation device,
   b. a control unit,
   c. a receiving unit, for receiving wireless energy,
   d. a coil, for receiving wireless energy,
   e. a receiving unit, for receiving a magnetic field or an electromagnetic field,
   f. a magnetic force transferring coupling,
   g. an electrical circuit,
   h. a push button for controlling any function of the operable implant,
   i. an energy storage device,
   j. a pushable construction for adjusting the adjustable distance element,
   k. an integrated operation device and receiving unit, for receiving wireless energy or a magnetic field or an electromagnetic field adapted to generate kinetic energy,
   l. a casing for enclosing at least one of the different parts of the operable implant,
   m. two or more casings for enclosing at least one of the different parts of the operable implant in each casing, and
   n. an integrated unit comprising two or more of the parts according to point a-k above, and wherein
   at least one of the first and second distance elements is adapted to create a distance between the fixation member and at least one of the parts a-n above.
13. A system according to embodiment 12, wherein the at least one fixation member is integrated with at least one of:
   a. an operation device,
   b. a control unit
   c. a receiving unit, for receiving wireless energy,
   d. a coil, for receiving wireless energy,
   e. a receiving unit, for receiving a magnetic field or an electromagnetic field,
   f. a magnetic force transferring coupling,
   g. an electric circuit,
   h. a push button for controlling any function of the operable implant,
   i. an energy storage device,
   j. a pushable construction for adjusting the adjustable distance element,
   k. an integrated operation device and receiving unit, for receiving wireless energy or a magnetic field or an electromagnetic field adapted to generate kinetic energy,
   l. a casing for enclosing at least one of the different parts of the operable implant
   m. two or more casings for enclosing at least one of the different parts of the operable implant in each casing, and
   n. an integrated unit comprising two or more of the parts according to a-k above, and wherein
   wherein at least one of; the first and second distance element is adapted to create a distance between;
   the fixation member integrated with one or more of parts a-n above, and
   one or more other parts of the operable implant of embodiment 12.
14. The system according to any one of embodiments 12-13, wherein at least one of the first and second distance elements comprises a lead for transferring electrical current from the wireless energy receiving unit to the operation device.
15. The system according to any one of embodiments 12-14, wherein at least one part of the operable implant is adapted to be placed subcutaneously.
16. The system according to any one of embodiments 12-15, wherein the operation device is adapted to be placed subcutaneously.
17. The system according to embodiment 16, wherein the operation device is adapted to be fixated to at least one of, at least one fascia layer and at least one muscular layer of the abdominal wall.
18. The system according to any one of embodiments 12-17, wherein the receiving unit comprises at least one coil adapted to transform wireless energy, received in form of an electric, magnetic or electromagnetic field, into electrical energy.
19. The system according to embodiment 18, wherein the receiving unit comprises at least a first coil having a first number of windings, and at least a second coil having a second, different number of windings.
20. The system according to any one of embodiments 12-19, comprising at least one enclosure adapted to hermetically enclose at least any one part according to embodiment 12 and the adjustable distance element.
21. The system according to any one of embodiments 12-20, comprising at least one enclosure adapted to hermetically enclose at least one of the parts of embodiment 12.
22. The system according to any one of embodiments 12-21, wherein the control unit is adapted to control at least one parameter of the operable implant.
23. The system according to embodiment 22, wherein the control unit is adapted to wirelessly communicate with an external unit, such that the control unit can be wirelessly controlled from outside the body.
24. The system according to any one of embodiments 20-21, wherein the at least one enclosure comprises two or more enclosures, wherein one of the first and second distance element is adapted to adjust the distance between the two enclosures.

Numbered Embodiment N 1-31

1. An operable implant for implantation in a patient, the operable implant comprises a body engaging portion and an operation device for supplying force to the body engaging portion, the operation device comprises an implantable gear system adapted to, at a force input; receive mechanical work of a first force and velocity, and, at a force output; supply mechanical work having a different second force and second velocity to operate the body engaging portion, the gear system comprising:
   a. an operable element connected to the force input,
   b. a first gear connected to the force output, first gear having the shape of a hollow cylinder, comprising a first number of teeth, on the peripheral outside thereof, and
   c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

2. The operable implant according to embodiment 1, wherein the operable element is adapted to deflect the first gear, and to maintain the first gear deflected such that the teeth of the first gear are interengaged with the teeth of the second gear in one or more angularly spaced positions interspaced by positions at which the teeth are not interengaged.

3. The operable implant according to embodiment 1, wherein the operable element is adapted to deflect the first gear, and to maintain the first gear deflected such that the teeth of the first gear are interengaged with the teeth of the second gear in at least two or more angularly spaced positions interspaced by positions at which the teeth are not interengaged.

4. The operable implant according to any one of embodiments 1-3, wherein the operation device comprises an implantable electrical motor for transforming electrical energy to mechanical work, and wherein the electrical motor is connected to the force input.

5. The operable implant according to embodiment 4, wherein the electrical motor is an electrical motor selected from:
   a. an alternating current (AC) electrical motor,
   b. a direct current electrical motor,
   c. a linear electrical motor,
   d. an axial electrical motor,
   e. a piezo-electric motor,
   f. a three-phase motor
   g. a more than one-phase motor
   h. a bimetal motor, and
   i. a memory metal motor.

6. The operable implant according to any one of embodiments 1-5, further comprising a magnetic coupling connected to the force input, such that mechanical work of the first force and velocity is supplied to the gear system by means of the magnetic coupling.

7. The operable implant according to any one of embodiments 1-5, further comprising a magnetic coupling connected to the force output, such that mechanical work of the second force and velocity is supplied to the body engaging portion by means of the magnetic coupling.

8. The operable implant according to any one of embodiments 6 and 7, wherein the magnetic coupling is adapted to transfer at least one of; rotating force and reciprocating force.

9. The operable implant according to any one of the preceding embodiments, further comprising an enclosure adapted to hermetically enclose the operable implant.

10. The operable implant according to any one of the preceding embodiments, wherein the gear system comprises a third gear having the shape of a hollow cylinder, and wherein the inside of third gear comprises the same amount of teeth as the outside of the first gear, and wherein teeth of the third gear are adapted to interengage the teeth of the first gear such that the third gear rotates in relation to the second gear, along with the at least one interengaged position.

11. The operable implant according to embodiment 10, wherein the third gear is connected to a second gear system, such that the first and second gear systems functions as a single gear system, the second gear system comprising:
   a. a force input adapted to receive mechanical work of the second force and second velocity from the force output of the first gear system, and
   b. a force output adapted to supply mechanical work to the body engaging portion having a different third force and third velocity.

12. The operable implant according to embodiment 11, wherein the second gear system comprises:
   a. an operable element connected to the force input of the second gear system,
   b. a first gear connected to the force output of the second gear system, having the shape of a hollow cylinder, comprising a first number of teeth, on the peripheral outside thereof, and
   c. a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the at least one position and thereby causes relative rotation between the first gear and the second gear 13. The operable implant according to any one of the preceding embodiments, wherein the operable element of at least one of the first and second gear systems comprises at least one of; a planetary gear and a structure or wheel at least partly using friction to enable rotating force to be transported.

14. The operable implant according to any one of the preceding embodiments, wherein the force output of the first or second gear system directly or indirectly connects to a threaded member adapted to transform rotating force to linear force.

15. The operable implant according to embodiment 14, further comprising a reservoir comprising a movable wall portion adapted to change the volume of the reservoir, wherein the threaded member is directly or indirectly connected to the movable wall portion such that operation of the threaded member changes the volume of the reservoir.

16. The operable implant according to embodiment 15, wherein the operable implant comprises a second reservoir comprising a movable wall portion, and wherein the threaded member is directly or indirectly connected to the movable wall portion of the second reservoir for changing the volume of the second reservoir.

17. The operable implant according to embodiment 16, wherein the movement of the movable wall portion of the first reservoir, by the threaded member in a first direction causes the first reservoir to expand and the volume of the first fluid reservoir to increase, and wherein the movement of the movable wall portion of the second reservoir by the threaded member in a first direction causes the second reservoir to contract and the volume of the second reservoir to decrease.
18. The operable implant according to embodiment 17, wherein the first reservoir is in fluid connection with a first body engaging portion, and wherein the second reservoir is in fluid connection with a second body engaging portion, and wherein operation of the operation device in a first direction, by the connection with the threaded member, causes:
   a. transportation of fluid from the first reservoir to the first body engaging portion, and
   b. transportation of fluid from the second body engaging portion to the second reservoir.
19. The operable implant according to any one of embodiments 15-18, wherein the reservoir is at least one of circular and torus shaped.
20. The operable implant according to any one of the preceding embodiments, further comprising a peristaltic pump, wherein the peristaltic pump comprises a hollow member for fluid transportation, and an operable compression member adapted to engage and compress the hollow member, and wherein the force output in direct or indirect connection with the compression member, such that the operation of the operation device operates the compression member such that fluid is transported in the hollow member.
21. The operable implant according to any one of the preceding embodiments, further comprising a friction coupling adapted to limit the torque that can be supplied by the operation device.
22. The operable implant according to any one of the preceding embodiments, further comprising a friction coupling positioned between the operation device and the body engaging portion, such that the torque required to start the operation device is reduced.
23. The operable implant according to embodiments 6, wherein the magnetic coupling comprises a rotating element placed inside a sealed enclosure enclosing at least the gear system of the operable implant, the rotating element comprising at least one magnet or a portion comprising magnetic or magnetizable material, and wherein the magnet or portion comprising magnetic or magnetizable material is adapted to rotate to transfer force to a corresponding rotating element on the outside of the sealed enclosure, for directly or indirectly supplying force to the body engaging portion through the sealed enclosure.
24. The operable implant according to embodiments 7, wherein the magnetic force coupling comprises a rotating element placed inside a sealed enclosure comprising at least one magnet or a portion comprising magnetic or magnetizable material, adapted to be rotated when receiving transfer force from a corresponding external rotating element placed on the outside of the hermetic enclosure and on the outside of the body, for directly supplying force to the rotating element placed inside the sealed enclosure.
25. The operable implant according to any one of the preceding embodiments, further comprising a reservoir for holding a hydraulic fluid, the reservoir comprising a movable wall portion adapted to change the volume of the reservoir, wherein the movable wall portion is directly or indirectly connected to the gear system force outlet, such that operation of the gear system changes the volume of the reservoir.
26. The operable implant according to any one of the preceding embodiments, wherein the electrical motor is a one, two, three or more phase motor, comprising at least one of; an axial electrical motor, a radial electrical motor, and a linear electrical motor.
27. The operable implant according to any one of the preceding embodiments, wherein the operation device comprises an electrical motor comprising a static part comprising a plurality of coils and a movable part comprising a plurality of magnets, such that sequential energizing of said coils magnetically propels the magnets and thus propels the movable part, wherein the operation device further comprises an enclosure adapted to hermetically enclose the coils of the static part, such that a seal is created between the static part and the propelled moving part with the included magnets, such that the coils of the static part are sealed from the bodily fluids, when implanted.
28. The operable implant according to any one of the preceding embodiments, comprising a separate receiving unit adapted to receive wireless energy, the receiving unit comprising at least one coil adapted to transform wireless energy received in form of a magnetic, electric or electromagnetic field into electrical energy.
29. The operable implant according to embodiment 28, further comprising at least one distance element adapted to create a distance between the receiving unit and at least one of the skin of the patient and any metallic, magnetic or magnetizable part of the operable implant, such that the receiving unit remains substantially unaffected by metallic and/or magnetic parts of the operable implant.
30. The operable implant according to embodiment 29, wherein the at least one distance element is adjustable.
31. The operable implant according to any one of the preceding embodiments, comprising at least one fixation member for fixating at least a part of the operable implant to at least one of muscular fascia, bone fascia, cortical bone, muscular layer, fibrotic tissue, and a at least one layer towards the inside of the subcutaneous space of the patient.

Numbered Embodiment O 1-27

1. A medical system for transferring energy from the outside of the body of a patient to an operable implant placed inside the body of the patient, the system comprises:
   an external drive unit, and
   an operable implant, wherein
   the external drive unit comprises an external rotating structure comprising at least one magnet for creating a rotating magnetic field adapted to magnetically connect to at least one of:
      a magnet, magnetizable material or magnetic material of the operable implant for transferring force from the external drive unit to the magnet or magnetic material of the implant in the body of the patient, and
      at least one coil of the operable implant for inducing electrical current in the body of the patient.
2. The medical system according to embodiment 1, wherein the magnet or magnetic material of the operable implant is fixated to an internal rotating structure adapted to rotate along with the rotating magnetic field of the external drive unit for operating the operable implant.
3. The medical system according to embodiment 1, wherein the magnet or magnetic material of the operable implant is fixated to an internal reciprocating structure adapted to reciprocate with the rotating magnetic field of the external drive unit for operating the operable implant.

4. The medical system according to embodiment 3, wherein the internal reciprocating structure is adapted to reciprocate due to the magnetic connection with a magnetic field which shifting polarity, such that the magnets of the internal reciprocating structure is alternatingly attracted and repelled by the rotating magnetic field created by the external drive unit.

5. The medical system according to embodiment 2, wherein the external rotating structure has a larger diameter than the internal rotating structure, and wherein the magnets are arranged such that the radial force, enabling the magnets of the internal rotating structure to rotate along with the magnets of the external rotating structure, is greater than the axial force, exerted by the magnets, pressing the internal structure against the external structure.

6. The medical system according to any one of the preceding embodiments, wherein at least one of the internal rotating structure and the external rotating structure comprises a repelling magnet adapted to decrease the axial forces created by the magnetic connection between the internal and external magnets and/or magnetic material, such that the squeezing effect on the patient's skin is reduced.

7. The medical system according to embodiment 6, wherein the force of the repelling or attracting magnet is adjustable, such that the squeezing effect on the patient's skin can be adjusted.

8. The medical system according to embodiment 7, wherein the attracting magnet is an attracting electromagnet, and wherein the force of the repelling electromagnet is adjusted by altering the current to the electromagnet.

9. The medical system according to embodiment 7, wherein the repelling magnet is a permanent magnet and wherein the force of the repelling permanent magnet is adjusted by altering distance between or position of the permanent magnet in relation to the patient's skin.

10. The medical system according to any one of embodiments 2 and 5-9, wherein the internal rotating structure comprises an internal spherical cap, and wherein the magnets or magnetic material of the internal rotating structure is positioned on the outside of said internal spherical cap, and wherein the external rotating structure comprises an external spherical cap, and wherein the magnets or magnetic material of the external rotating structure is positioned on inside of said external spherical cap, such that rotating force can be transferred radially by means of the magnetic connection between the internal and external spherical caps.

11. The medical system according to embodiment 10, wherein the internal spherical cap comprises a centrally placed magnet, and the external spherical cap comprises a centrally placed magnet, and wherein the magnets of the internal and external spherical caps are adapted to exert repelling forces on each other such that the axial forces created by the magnetic connection between the internal and external magnets and/or magnetic material is reduced, such that the squeezing effect on the patient's skin is reduced.

12. The medical system according to any one of embodiments 2-11, further comprising a gear system connected to the internal rotating structure, the gear system being adapted to receive mechanical work of a first force and velocity and supply mechanical work having a different force and velocity.

13. The medical system according to embodiment 12, wherein the gear system comprises:
    a. an operable element,
    b. a first gear comprising a first number of teeth, on the outside thereof, and
    c. a second gear comprising a greater number of teeth than the first gear, on the inside thereof, wherein the operable element is adapted to press the outside of the first gear towards the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.

14. The medical system according to embodiment 1-13, wherein the operable implant comprises an operation device and a body engaging portion.

15. The operable implant according to any one of the preceding embodiments, wherein the operation device comprises a hydraulic operation device.

16. The operable implant according to embodiment 15, wherein the body engaging portion is a hydraulically operable body engaging portion, and wherein the operable implant further comprises hydraulic pump and a reservoir adapted to hold hydraulic fluid, the reservoir being connected to the hydraulic pump, and wherein the hydraulic pump is adapted to transport hydraulic fluid from the reservoir to the body engaging portion.

17. The operable implant according to any one of embodiments 15, wherein the hydraulic pump comprises a movable wall portion of the reservoir, and wherein the hydraulic pump is adapted to transport hydraulic fluid from the reservoir to the hydraulically operable body engaging portion by moving the movable wall portion and thereby changing the volume of the reservoir.

18. The operable implant according to embodiment 14, wherein operation device comprises an electrical motor comprising a static part comprising a plurality of coils and a movable part comprising a plurality of magnets, such that sequential energizing of said coils magnetically propels the magnets and thus propels the movable part, wherein the operation device further comprises an enclosure adapted to hermetically enclose the coils of the static part, such that a seal is created between the static part and the propelled moving part with the included magnets, such that the coils of the static part are sealed from the bodily fluids, when implanted.

19. The medical system according to any one of the preceding embodiments, further comprising an implantable electrical generator comprising:
    at movable generator portion comprises at least one generator magnet connected to the magnet or magnetic material of the operable implant, such that the movement of the magnet or magnetic material moves the movable generator portion, and
    at least one coil in magnetic connection with the at least one generator magnet, such that electrical current is induced in the coil by the movement of the movable generator portion in relation to the coil.

20. The medical system according to embodiment 19, wherein the movable generator portion is adapted to perform rotating movements.
21. The medical system according to embodiment 20, wherein the implantable electrical generator is an implantable rotational electrical generator, and wherein the movable generator portion is adapted to perform rotating movement, and wherein the at least one coil is in magnetic connection with the at least one magnet, such that rotating movement of the movable generator portion induces current in the at least one coil.
22. The medical system according to embodiment 19, wherein the movable generator portion is adapted to perform reciprocating movements.
23. The medical system according to embodiment 22, wherein the implantable electrical generator is an implantable linear electrical generator, and wherein the movable generator portion is adapted to perform reciprocating movement, and wherein the at least one coil is in magnetic connection with the at least one magnet, such that reciprocating movement of the movable generator portion induces current in the at least one coil.
24. The medical system according to embodiment 1, wherein the operable implant comprises a plurality of coils arranged in a circular configuration, such that the rotating magnetic field by the external drive unit sequentially induces electrical current in the plurality of coils.
25. The medical system according to any one of embodiments 1 and 19-24, further comprising at least one battery or energy storage device connected to the at least one coil, such that the current induced in the at least one coil can be stored as electrical energy in the battery.
26. The medical system according to any one of the preceding embodiments, further comprising an enclosure adapted to hermetically enclose the operable implant, such that the operable implant is sealed from the bodily fluids of the patient.
27. The medical system according to any one of the preceding embodiments, wherein the operable implant is adapted to be implanted subcutaneously.

Numbered Embodiment P 1-25

1. An operable implant adapted to be implanted in the body of a patient, the operable implant comprising an operation device and a body engaging portion, the operation device comprising:
   a movable part directly or indirectly connected to the body engaging portion, the movable part being connected to at least one magnet, magnetizable material or magnetic material, wherein the movable part is adapted to magnetically connect to a moving magnetic field on the outside of the patient's body, such that the movable part moves along with the movable magnetic field,
   an implantable generator connected to the movable part and adapted to transform movement to electrical current, such that the movement of the movable part operates the body engaging portion and generates electrical current.
2. The operable implant according to embodiment 1, wherein the at least one magnet, magnetizable material or magnetic material is connected to a rotating structure and adapted to magnetically connect to a rotating magnetic field on the outside of the skin of the patient, such that the rotating structure rotates along with the rotating magnetic field.
3. The operable implant according to embodiment 1, wherein the at least one magnet, magnetizable material or magnetic material is connected to a structure adapted for reciprocating movement and adapted to magnetically connect to a reciprocating magnetic field on the outside of the skin of the patient, such that the structure for reciprocating movement moves along with the reciprocating magnetic field.
4. The operable implant according to any one of the preceding embodiments, wherein the implantable generator comprises at least one magnet and at least one coil, and wherein the movement of the at least one magnet in relation to the at least one coil induces an electrical current in the at least one coil, and wherein at least one magnet of the movable part adapted to magnetically connect to a moving magnetic field on the outside of the patient's body, also functions as the at least one magnet in the implantable generator.
5. The operable implant according to any one of the preceding embodiments, further comprising a battery or energy storage adapted to be charged by the implantable generator.
6. The operable implant according to embodiment 5, wherein the battery or energy storage is adapted to power the body engaging portion.
7. The operable implant according to any one of the preceding embodiments, further comprising a control unit for controlling at least one parameter of the operable implant.
8. The operable implant according to embodiment 7, wherein the control unit is connected to the battery or energy storage of embodiment 5, and wherein the battery powers the control unit.
9. The operable implant according to any one of the preceding embodiments, wherein the operation device comprises a hydraulic operation device.
10. The operable implant according to embodiment 9, wherein the body engaging portion is a hydraulically operable body engaging portion, and wherein the operable implant further comprises hydraulic pump and a reservoir adapted to hold hydraulic fluid, the reservoir being connected to the hydraulic pump, and wherein the hydraulic pump is adapted to transport hydraulic fluid from the reservoir to the body engaging portion.
11. The operable implant according to any one of embodiments 9, wherein the hydraulic pump comprises a movable wall portion of the reservoir, and wherein the hydraulic pump is adapted to transport hydraulic fluid from the reservoir to the hydraulically operable body engaging portion by moving the movable wall portion and thereby changing the volume of the reservoir.
12. The operable implant according to embodiment 10, wherein the hydraulic pump is a hydraulic pump selected from:
    peristaltic pumps,
    membrane pumps,
    gear pumps, and
    bellows pumps.
13. The operable implant according to any one of the preceding embodiments, wherein the operation device comprises a gear system adapted to receive mechanical work of a first force and velocity as input, and output mechanical work having a different force and velocity.

14. The operable implant according to embodiment 13, wherein the a gear system comprises:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
15. The operable implant according to embodiment 14, wherein the operable element is connected to the movable part, such that the movement of the movable part operates the gear system.
16. The operable implant according to any one of the preceding embodiments, wherein operable implant further comprises an enclosure adapted to enclose the operable implant.
17. The operable implant according to any one of the preceding embodiments, wherein the movable part is adapted to be placed subcutaneously.
18. The operable implant according to any one of the preceding embodiments, wherein the operation device is adapted to at least one fascia, fibrotic tissue, skin, muscular layer or any tissue subcutaneously in the abdominal wall or in the abdomen.
19. The operable implant according to any one of the preceding embodiments, wherein the operation device further comprises a distance element adapted to create a distance between the operation device and the movable part.
20. The operable implant according to embodiment 19, wherein the distance element is adapted to control the position of the movable part hindering the body from rejecting the movable part.
21. The operable implant according to any one of the preceding embodiments, further comprising a wireless communication unit adapted to wirelessly communicate with an external unit.
22. A system including the operable implant according to any one of embodiments 1-21, wherein the system further comprises an external unit comprising an external drive unit for supplying a driving force to the operable implant.
23. The system according to embodiment 22, wherein the external drive unit comprises moving magnets adapted to create the moving magnetic field.
24. The system according to embodiment 22, wherein the external drive unit comprises coils, and wherein sequential energizing of the coils creates the moving magnetic field.
25. The system according to any one of embodiments 22-24, wherein the external drive unit further comprises a wireless communication unit adapted to wirelessly communicate with the operable implant.

Numbered Embodiment Q 1-21

1. An operable hydraulic implant comprising:
   a body engaging portion,
   a powered operation device, in fluid connection with the body engaging portion, the operation device comprises:
   i. a reservoir for holding a hydraulic fluid, wherein the reservoir comprises a movable wall portion adapted to move to alter the volume of the reservoir and thereby transport hydraulic fluid from the reservoir to the body engaging portion, and
   ii. an operation member connected to the movable wall portion, such that operation of the operation member alters the volume of the reservoir, and
   a flexible enclosure adapted to; have its volume altered by changing the outer size and shape of the enclosure and enclose the movable wall portion and the operation member,
   wherein the movable wall portion is adapted to move inside of the enclosure, such that the volume of the reservoir can be changed by affecting the outer dimensions of the operable hydraulic implant by the movement of the movable wall portion inside of the enclosure, and wherein
   the reservoir further comprises a manual portion adapted to be compressed by manual force from outside of the body of the patient, such that fluid can be transported from the reservoir to the body engaging portion of the operable hydraulic implant, by means of manual force, for temporarily increasing the hydraulic pressure at the body engaging portion.
2. The operable hydraulic implant according to embodiment 1, wherein the reservoir is substantially circular or elliptic.
3. The operable hydraulic implant according to any one of embodiments 1 and 2, wherein the average thickness of the movable wall portion is less than the average thickness of the manual portion of the reservoir.
4. The operable hydraulic implant according to any one of the preceding embodiments, wherein the reservoir comprises Parylene® coated silicone.
5. The operable hydraulic implant according to embodiment 1, wherein the operation device is connected to a threaded member adapted to transform a radially rotating force to an axially reciprocating force, and wherein the threaded member is connected to the operation member.
6. The operable hydraulic implant according to embodiment 1, comprising an electrical circuit and a control unit for controlling the operable hydraulic implant.
7. The operable hydraulic implant according to any one of the preceding embodiments, further comprising an injection port for injecting hydraulic fluid into the reservoir from outside the body of the patient.
8. The operable hydraulic implant according to any one of the preceding embodiments, wherein at least a portion of the operable hydraulic implant is adapted to be implanted subcutaneously.
9. The operable hydraulic implant according to any one of the preceding embodiments, further comprising at least one fixation member adapted to directly or indirectly fixate at least a portion of the operable hydraulic implant towards at least one of; at least one muscular fascia, at least one bone fascia, at least one cortical bone layer, at least one muscular layer, fibrotic tissue, any part of the abdominal wall, and any part of the subcutaneous space and its surroundings in the body.
10. The operable hydraulic implant according to any one of the preceding embodiments, further comprising a second body engaging portion and a second reservoir in fluid connection with the second body engaging portion, wherein the second reservoir comprises a movable wall portion adapted to move to alter the volume of the second reservoir and thereby transport hydraulic fluid from the second reservoir to the second body engaging portion.
11. The operable hydraulic implant according to embodiment 10, wherein the movable walls of the first and second reservoirs are connected to the same operation member, adapted to increase or decrease the size of the reservoirs, wherein the volume of the first reservoir is adapted to be changed in the opposite direction as the second reservoir.
12. The operable hydraulic implant according to any one of the preceding embodiments, wherein the operation device comprises an electrical motor connected to the operation member.
13. The operable hydraulic implant according to embodiment 11, wherein the electrical motor is an electrical motor selected from:
   o. an alternating current (AC) electrical motor,
   p. a direct current electrical motor,
   q. a linear electrical motor,
   r. an axial electrical motor,
   s. a piezo-electric motor,
   t. a two or more phase motor
   u. a three phase motor
   v. a bimetal motor, and
   w. a memory metal motor.
14. The operable hydraulic implant according to any one of embodiments 11 and 12, wherein operation of the electrical motor affects both the movable walls of both the first and second reservoirs.
15. The operable hydraulic implant according to any one of the preceding embodiments, wherein the operation device comprises a gear system adapted to receive mechanical work of a first force and velocity and supply mechanical work having a different second force and second velocity.
16. The operable hydraulic implant according to embodiment 15, wherein the gear system comprises a force input connected to an electrical motor, and a force output connected directly or indirectly to the operation member.
17. The operable hydraulic implant according to any one of embodiments 15-16, wherein the gear system comprises:
   an operable element,
   a first gear having the shape of a hollow cylinder, comprising a first number of teeth, on the peripheral outside thereof, and
   a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
18. The operable hydraulic implant according to embodiment 17, wherein the gear system is connected to a threaded member adapted to transform a radially rotating force to an axially reciprocating force, and wherein the threaded member is connected to the operation member.
19. The operable hydraulic implant according to any one of embodiments 1-11, wherein the operation device comprising magnetic coupling adapted to be in magnetic connection with an external portion of a magnetic coupling, adapted to be positioned on the outside of the patients body, such that the internal portion of the magnetic coupling moves along with the external portion of the magnetic coupling, for operating the movable wall portion.
20. The operable hydraulic implant according to any one of the preceding embodiments, further comprising a wireless communication unit for wirelessly communicating with an external unit positioned on the outside of the patient's body.
21. The operable hydraulic implant according to any one of the preceding embodiments, further comprising at least one battery adapted to store electrical energy in the body of the patient.

Numbered Embodiment R 1-22

1. A medical system comprising an operable implant adapted to be placed inside the body of the patient, the operable implant comprising a movable structure adapted for reciprocating movement, the movable structure comprising at least one magnet or magnetic material, wherein the movable structure is adapted to be in magnetic connection with an external unit creating a reciprocating magnetic or electromagnetic field, such that the movable structure reciprocates along with the reciprocating magnetic or electromagnetic field.
2. The medical system according to embodiment 1, wherein the operable implant further comprises an electrical generator connected to the movable structure and being adapted to transform the reciprocating movements of the movable structure to electrical energy.
3. The medical system according to embodiment 2, wherein the electrical generator comprises:
   a movable generator portion comprising at least one magnet, wherein the movable generator portion is connected to the movable structure, and
   at least one coil in magnetic connection with the at least one magnet,
   wherein the electrical current is induced in the coil by the movement of the movable generator portion in relation to the coil.
4. The medical system according to embodiment 3, wherein the at least one magnet of the movable generator portion is the magnet of the movable structure.
5. The medical system according to any one of the preceding embodiments, wherein the operable implant further comprises a force transforming member adapted to transform reciprocating force to rotating force.
6. The medical system according to embodiment 5, wherein the electrical generator is a rotating electrical generator connected to the force transforming member.
7. The medical system according to any one of embodiments 2-4, wherein the electrical generator is a linear electrical generator comprising:
   a reciprocating generator portion comprising at least one magnet, wherein the reciprocating generator portion is in connection with the movable structure adapted to perform reciprocating movement, and at least one coil in magnetic connection with the at least one magnet, such that reciprocating movement of the reciprocating generator portion induces current in the at least one coil.
8. The medical system according to any one of the preceding embodiments, wherein the movable structure is spring loaded in one direction, such that the reciprocating movement is created by magnetic force from the magnetic connection with the external unit in one direction, and by the movable portion being spring loaded in the opposite direction.
9. The medical system according to any one of the preceding embodiments, wherein the operable implant further comprises a battery or energy storing device connected to the electrical generator unit, wherein the battery is adapted to store electrical energy generated in the generator unit.
10. The medical system according to any one of embodiments 1 and 5, wherein the operable implant further comprises body engaging portion in connection with the movable structure, such that movement of the movable structure operates the body engaging portion.
11. The medical system according to any one of the preceding embodiments, further comprising an enclosure adapted to hermetically enclose the operable implant, such that the implantable electrical generator is sealed from the bodily fluids of the patient.
12. The medical system according to any one of the preceding embodiments, wherein the operable implant further comprises a wireless communication unit adapted to at least one of:
  d. receive wireless communication signals from the external unit, and
  e. transmit wireless communication signals to the external unit.
13. The medical system according to any one of the preceding embodiments, wherein the operable implant is adapted to be implanted subcutaneously.
14. The medical system according to embodiment 13, wherein the operable implant is adapted to be implanted subcutaneously in the abdomen.
15. The medical system according to any one of the preceding embodiments, further comprising an external unit comprising an external drive unit adapted to create a reciprocating magnetic field on the outside of the patient's skin adapted to affect at least one magnet or magnetic material of an operable implant such that the magnet or magnetic material reciprocates along with the reciprocating magnetic field of the external unit.
16. The medical system according to embodiment 15, wherein the external drive unit comprises a reciprocating structure comprising at least one magnet, electromagnet or magnetic material, and wherein reciprocation of the reciprocating structure affects a magnet or magnetic material of a movable structure of an implantable electrical generator causing reciprocation thereof.
17. The medical system according to embodiment 15, wherein the external drive unit comprises a rotatable structure comprising at least one magnet, electromagnet or magnetic material, and wherein rotation of the rotatable structure affects a magnet or magnetic material of a movable structure of an implantable electrical generator causing reciprocation thereof.
18. The medical system according to embodiment 15, wherein the rotatable structure of the external drive unit comprises:
  a first magnet or electromagnet creating a positive magnetic field, and
  a second magnet or electromagnet creating a negative magnetic field, such that rotation of the rotatable structure causes the first and second magnet or electromagnet to alternatingly affect the magnet or magnetic material of the operable implant, causing reciprocation thereof
19. The medical system according to embodiment 18, wherein the external drive unit comprises an electromagnet for alternatingly creating a magnetic field with positive and negative polarity, which causes reciprocation of a magnet or magnetic material of an implantable electrical generator.
20. The operable implant according to embodiment 5, further comprising a gear system adapted to receive mechanical work of a first force and velocity as input, and output mechanical work having a different force and velocity, the gear system comprises:
  an operable element,
  a first gear having the shape of a hollow cylinder, comprising a first number of teeth, on the peripheral outside thereof, and
  a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear.
21. The operable implant according to embodiment 5, comprising an operation device and a body engaging portion, the operation device comprises an electrical motor comprising a static part comprising a plurality of coils and a movable part comprising a plurality of magnets, such that sequential energizing of said coils magnetically propels the magnets and thus propels the movable part, wherein the operation device further comprises an enclosure adapted to hermetically enclose the coils of the static part, such that a seal is created between the static part and the propelled moving part with the included magnets, such that the coils of the static part are sealed from the bodily fluids, when implanted.
22. The medical system according to any one of embodiments 15-19, wherein the external unit further comprises a wireless communication unit adapted to at least one of:
  receive wireless communication signals from the operable implant, and
  transmit wireless communication signals to the operable implant.

Numbered Embodiment S 1-22

1. A medical system for creating a magnetic connection between an external unit and an operable implant, the medical system comprises:
  an operable implant comprising at least one of; a magnet, a magnetic material, and a magnetizable material, and an external unit comprising at least one of; an external permanent magnet and an external electro magnet, adapted to magnetically connect to at least one of: the magnet, the magnetic material and the magnetizable material of the operable implant, wherein the magnetic force of the external magnet can be arranged or adjusted such that the squeezing force on the skin of the patient can be arranged or adjusted.
2. The medical system according to embodiment 1, wherein the external magnet comprises at least one permanent magnet, and wherein the external unit further comprises:
a skin contacting portion, and
an adjustment device for adjusting the distance between or position of the permanent magnet in relation to the skin contacting portion.
3. The medical system according to embodiment 1, wherein the operable implant comprises:
at least one of; a first magnet, a first portion of magnetic material and a first portion of magnetizable material, and at least one of: a second magnet, a second portion of magnetic material, and a second portion of magnetizable material, and wherein the external unit comprises:
at least one first magnet or first electro magnet, and
at least a second magnet or second electro magnet, and
wherein at least one of; the first magnet, portion of magnetic material and magnetizable material of the operable implant is adapted to be attracted by the first magnet or first electro magnet of the external unit, and wherein at least one of; the second magnet, portion of magnetic material and magnetizable material of the operable implant is adapted to be repelled by the second magnet or second electro magnet of the external unit for balancing the squeezing force on the skin of the patient.
4. The medical system according to any one of the preceding embodiments, wherein the external unit is adapted to create, in different positions or at different times in the same position, a first and second magnetic field having different polarity, wherein the operable implant is adapted to create, in different positions, a first and second magnetic field having different polarity, wherein the first magnetic field is adapted to decrease the attracting force between the operable implant and the external unit, caused the second magnetic field, such that the squeezing effect on the patient's skin is reduced.
5. The medical system according to any one of the preceding embodiments, wherein the external unit comprises at least one electro magnet, and wherein the external unit comprises a control unit for controlling the magnetic force of the electro magnet.
6. The medical system according to any one of the preceding embodiments, wherein the medical system is adapted to transfer moving force from the external unit to the operable implant by means of magnetic connection, wherein the external unit comprises an external drive unit adapted to create a moving magnetic field adapted to magnetically connect to the operable implant for transferring force from the external drive unit to at least one of; a magnet, a magnetic material and a magnetizable material of the operable implant.
7. The medical system according to embodiment 6, wherein the medical system is adapted to transfer a rotating force through the skin of the patient, and wherein the external drive unit comprises an external rotating structure comprising at least one of; at least one permanent magnet and at least one electro magnet for creating a rotating magnetic field adapted to magnetically connect to an internal rotating structure, such that the internal rotating structure rotates along with the external rotating structure, and wherein the squeezing force on the skin of the patient exerted by the magnets of the internal and external rotating structures is adjusted such that rotating force can be transferred without excessive force to the patient's skin.
8. The medical system according to embodiment 7, wherein the external rotating structure has a larger diameter than the internal rotating structure, and wherein the magnets are arranged such that the radial force, enabling the magnets of the internal rotating structure to rotate along with the magnets of the external rotating structure, is greater than the axial forces pressing the internal structure against the external structure.
9. The medical system according to any one of embodiments 1-8, wherein the external unit is adapted to create a rotating magnetic field comprising both the first and second magnetic field according to embodiment 4, being present in at least one of the following alternatives;
the first magnetic field being created at least when rotating the external rotating structure according to embodiment 7, and comprising at least one of, an angularly intermittent first magnetic field, a central first magnetic field and a peripheral substantially continuous first magnetic field, wherein the first magnetic field is additionally creating at least a part of a magnetic coupling force allowing rotation of the internal rotating structure according to embodiment 7, to join in at least one of; the rotational movement of the external rotating structure and the rotational movement of the magnetic field created by the rotational structure, wherein the force squeezing the skin of the patient is reduced by the first magnetic field,
the first magnetic field being created by one or more negative permanent magnets placed both on the internal and external rotating structure according to embodiment 7, and comprising at least one of; an angularly intermittent first magnetic field, a central first magnetic field, and a peripheral substantially continuous first magnetic field, wherein the first magnetic field is additionally creating at least a part of a magnetic coupling force allowing rotation of the internal rotating structure according to embodiment 7, to join in at least one of; the rotational movement of the external rotating structure and the rotational movement of the magnetic field created by the rotational structure when standing still, wherein the force squeezing the skin of the patient is reduced by the first magnetic field, and
the first magnetic field being created by one or more negative permanent magnets placed both on the internal and external rotating structure according to embodiment 7, creating a repelling magnetic force between the internal and external rotating structure and the permanent magnets is adapted to create at least one of; an angularly intermittent first magnetic field, a central first magnetic field and a peripheral substantially continuous first magnetic field, the first magnetic field being caused by one or more negative permanent magnets placed on at the internal rotating structure according to embodiment 7, the permanent magnets adapted to create at least one of; an angularly intermittent second magnetic fields, a central second magnetic field and a peripheral substantially continuous second magnetic field, the magnetic field caused by the internal rotating structure is adapted to create a magnetic coupling force towards the external unit, the second magnetic field being adapted to be created by the external structure comprising at least one of; two or more coils and two or more positive permanent magnets, adapted to cause at least one of; an angularly intermittent second magnetic fields, a central second magnetic field and a peripheral substantially continuous second magnetic field, and at least one of;

when having two or more permanent magnets, the external rotating structure rotating to cause rotation of the internal rotating structure because of the rotating magnetic field according to embodiment 7 causing a magnetic coupling force, and when having two or more coils, the external rotating structure will stand still while the magnetic field of the external rotating structure rotates by successively energize the coils causing rotation of the internal rotating structure because of the rotating magnetic field according to embodiment 7, and causing at least a part of a magnetic coupling force enabling the rotation of the internal rotating structure, both the second and first magnetic fields being adapted to be created at least partially by the external structure according to embodiment 7, comprising at least one of; one or more coils, one or more positive permanent magnets and one or more negative permanent magnets, adapted to cause at least one of; an angularly intermittent second and first magnetic fields, a central second or first magnetic field and a peripheral substantially continuous second or first magnetic field, and wherein both the second and first magnetic fields are created by one or more negative permanent magnets placed on the internal rotating structure according to embodiment 7, the permanent magnets are adapted to create at least one of; an angularly intermittent second magnetic fields, a central second magnetic field and a peripheral substantially continuous second magnetic field, the magnetic fields created by the internal rotating structure being adapted to create a magnetic coupling force towards the external unit, in at least one of the following alternatives;

when having two or more positive permanent magnets in magnetic coupling with two or more negative permanent magnets of the internal structure according to embodiment 7, the external rotating structure will rotate to cause rotation of the internal rotating structure because of the rotating magnetic field according to embodiment 7 creating at least a part of a magnetic coupling force, when having two or more negative permanent magnets in magnetic coupling with two or more negative permanent magnets of the internal structure according to embodiment 7, the external rotating structure will rotate to cause rotation of the internal rotating structure because of the rotating magnetic field according to embodiment 7 causing at least a part of a magnetic coupling force, and when having two or more coils in magnetic coupling with two or more negative permanent magnets of the internal structure according to embodiment 7, the external rotating structure will stand still and the magnetic field of the external rotating structure will rotate by successively energize the coils to cause rotation of the internal rotating structure because of the rotating magnetic field according to embodiment 7, and creating at least a part of a magnetic coupling force enabling the rotation of the internal rotating structure, and both the second and first magnetic field being adapted to be created at least partially by the internal structure according to embodiment 7, comprising at least one of; one or more coils, one or more positive permanent magnets and one or more negative permanent magnets, adapted to create at least one of; an angularly intermittent second and first magnetic fields, a central second or first magnetic field and a peripheral substantially continuous second or first magnetic field.

10. The medical system according to any one of embodiments 7-9, wherein the internal rotating structure comprises an internal spherical cap, and wherein the magnet or magnetic material of the internal rotating structure is positioned on the outside of said internal spherical cap, and wherein the external rotating structure comprises an external spherical cap, and wherein the magnet of the external rotating structure is positioned on the inside of said external spherical cap, such that rotating force can be transferred radially by means of the magnetic connection between the internal and external spherical caps.

11. The medical system according to any one of the embodiments 7-10, further comprising an implantable electrical generator comprising:
  at least one movable generator portion comprises at least one generator magnet adapted to magnetically connect to at least one of the; magnet, magnetic material and magnetizable material of the operable implant, such that the movement of the at least one of magnet, magnetic material and magnetizable material; moves the movable generator portion or is the generator portion, and
  at least one coil in magnetic connection with the at least one generator magnet, such that electrical current is induced in the coil by the movement of the movable generator portion in relation to the coil.

12. The medical system according to embodiment 11, wherein the movable generator portion is adapted to perform rotating movements.

13. The medical system according to embodiment 11, wherein the implantable electrical generator is an implantable rotational electrical generator, and the movable generator portion is adapted to perform rotating movement placed on the internal rotating structure, and wherein the at least one coil is in magnetic connection with the at least one magnet, such that rotating movement of the movable generator portion induces current in the at least one coil.

14. The medical system according to embodiment 11, wherein the movable generator portion is adapted to perform reciprocating movements.

15. The medical system according to embodiment 14, wherein the implantable electrical generator is an implantable linear electrical generator, and the movable generator portion is adapted to perform reciprocating movement, and wherein the at least one coil is in magnetic connection with the at least one magnet, such that reciprocating movement of the movable generator portion induces current in the at least one coil.

16. The medical system according to any one of embodiments 1-5, wherein the external unit is adapted to create a rotating magnetic field, and wherein the operable implant comprises a plurality of coils arranged in a circular configuration adapted to be in magnetic connection with the rotating magnetic field, such that the rotating magnetic field sequentially induces electrical current in the plurality of coils.

17. The medical system according to any one of embodiments 1-5, wherein the external unit further comprises a wireless energy transmitter, and wherein the operable implant further comprises a wireless energy receiver, such that wireless energy can be transmitted from the external unit to the internal unit.

18. The medical system according to any one of the preceding embodiments, wherein the wireless energy transmitter comprises a wireless energy transmitting coil, and the wireless energy receiver comprises a wireless energy receiving coil.

19. The medical system according to any one of embodiments 11-18, wherein the operable implant further comprises at least one battery adapted to store electrical energy.

20. The medical system according to any one of the preceding embodiments, wherein the external unit comprises a wireless communication unit, and the operable implant comprises a wireless communication unit, such that the external unit and the operable implant can communicate wirelessly.

21. The medical system according to any one of the preceding embodiments, further comprising an enclosure adapted to hermetically enclose the operable implant, such that the operable implant is sealed from the bodily fluids of the patient.

22. The medical system according to any one of the preceding embodiments, wherein the operable implant is adapted to be implanted subcutaneously.

Numbered Embodiment T 1-29

1. An operable implant comprising an operation device for operating the operable implant, the operation device comprising:
    an electrical motor adapted to transfer electrical energy to mechanical work, the electrical motor being adapted to output mechanical work of a first force and velocity, and
    a gear system adapted receive mechanical work of a first force and velocity from the electrical motor as input, and output mechanical work having a second different force and velocity,
    a first force output adapted to output mechanical work from the electrical motor, having a first force and velocity, and
    a second force output adapted to output mechanical work from the gear system, having a second force and velocity.
2. The operable implant according to embodiment 1, further comprising an implantable generator, and wherein the first force output is connected to the implantable generator for generating electrical current inside the body of the patient.
3. The operable implant according to any one of embodiments 1 and 2, further comprising an operable body engaging portion connected to and operated by the second force output of the operation device.
4. The operable implant according to embodiment 3, wherein the operable body engaging portion is a hydraulically operable body engaging portion, and wherein the operation device further comprises a hydraulic pump for transferring hydraulic fluid to the hydraulically operable body engaging portion.
5. The operable implant according to embodiment 4, wherein the hydraulic pump comprises a reservoir adapted to contain a hydraulic fluid, and wherein the reservoir comprises a movable wall portion for changing the volume of the reservoir, and wherein the movable wall portion is connected to the operation device, such that the operation device operates the movable wall portion.
6. The operable implant according to embodiment 4, wherein the hydraulic pump is a hydraulic pump selected from:
    at least one non-valve pump,
    at least one valve pump,
    at least one peristaltic pump,
    at least one membrane pump
    at least one gear pump, and
    at least one bellows pump.
7. The operable implant according to any one of the preceding embodiments, wherein at least one of the first and second force output is connected to a threaded member adapted to transform the radially rotating force to an axially reciprocating force.
8. The operable implant according to embodiment 7, wherein the threaded member is directly or indirectly connected to the movable wall portion of the reservoir of embodiment 5, for changing the volume of the reservoir.
9. The operable implant according to embodiment 7, wherein the threaded member is directly or indirectly mechanically connected to the body engaging portion, such that the body engaging portion is operated via the threaded member.
10. The operable implant according to any one of the preceding embodiments, wherein the gear system comprises:
    an operable element connected to the first force output,
    a first gear having the shape of a hollow cylinder, comprising a first number of teeth, on the peripheral outside thereof, and
    a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein first gear is connected to the second force output for outputting mechanical work having the second force and velocity.

11. The operable implant according to any one of the preceding embodiments, wherein the operation device further comprises a second gear system, and wherein the second gear system is adapted receive mechanical work of a second force and velocity from the first gear system as input, and output mechanical work having a third different force and velocity.

12. The operable implant according to embodiment 11, wherein the operation device further comprises a third force output adapted to output mechanical work from the second gear system, having a third force and velocity.

13. The operable implant according to embodiment 12, wherein the second gear system comprises:
    an operable element connected to the second output,
    a first gear having the shape of a hollow cylinder, comprising a first number of teeth, on the peripheral outside thereof, and
    a second gear having the shape of a hollow cylinder, comprising a greater number of teeth than the first gear, on the inside surface thereof, wherein the operable element is adapted to engage the inside of the first gear, such that the outside of the first gear is pressed against the inside of the second gear such that the teeth of the first gear are interengaged with the teeth of the second gear in at least one position interspaced by positions at which the teeth are not interengaged, and wherein the operation of the operable element advances the positions and thereby causes relative rotation between the first gear and the second gear, and wherein first gear is connected to the third force output for outputting mechanical work having the third force and velocity.

14. The operable implant according to any one of the preceding embodiments, further comprising an enclosure, adapted to enclose the operation device.

15. The operable implant according to embodiment 14, wherein the enclosure comprises a first and second penetration, and wherein the first penetration is adapted for the first force output, and the second penetration is adapted for the second force output.

16. The operable implant according to embodiment 14, wherein the enclosure comprises a first, second and third penetrating force output.

17. The operable implant according to embodiment 16, wherein the enclosure comprises a first, second and third penetration, and wherein the first penetration is adapted for the first force output, the second penetration is adapted for the second force output and the third penetration is adapted for the third force output.

18. The operable implant according to any one of the preceding embodiments, wherein the first force output is connected to a first hydraulic pump for operating a first body engaging portion, and the second force output is connected to a second hydraulic pump for operating a second body engaging portion.

19. The operable implant according to any one of the preceding embodiments, wherein the first force output comprises a first rotatable shaft, and the second force output comprises a second rotatable shaft.

20. The operable implant according to embodiment 19, wherein the enclosure of embodiment 15 comprises at least one of:
    a. a first sealing member adapted to seal between the enclosure and the first rotatable shaft, and
    b. a second sealing member adapted to seal between the enclosure and the second rotatable shaft, wherein the first and second sealing member allow rotation of the rotatable shafts.

21. The operable implant according to embodiment 19, wherein at least one of:
    a. the first rotatable shaft is adapted to be positioned inside of the second rotatable shaft, and
    b. the second rotatable shaft is adapted to be positioned inside of the first rotatable shaft.

22. The operable implant according to any one of embodiments 12-18, wherein the first force output comprises a first rotatable shaft, the second force output comprises a second rotatable shaft, and the third force output comprises a third rotatable shaft.

23. The operable implant according to embodiment 22, wherein the enclosure of embodiment 15 comprises at least one of:
    a. a first sealing member adapted to seal between the enclosure and the first rotatable shaft, and
    b. a second sealing member adapted to seal between the enclosure and the second rotatable shaft,
    c. a third sealing member adapted to seal between the enclosure and the third rotatable shaft, wherein the first and second sealing members allow rotation of the rotatable shafts.

24. The operable implant according to embodiment 22, wherein at least one of:
    a. the first and second rotatable shaft is adapted to be positioned inside of the third rotatable shaft,
    b. the second and third rotatable shaft is adapted to be positioned inside of the first rotatable shaft, and
    c. the first and third rotatable shaft is adapted to be positioned inside of the second rotatable shaft, 25. The operable implant according to any one of the preceding embodiments, further comprising at least one implantable battery, adapted to energize the electrical motor.

26. The operable implant according to any one of the preceding embodiments, further comprising a receiving unit adapted to receive wireless energy transmitted from outside the patient's body.

27. The operable implant according to embodiment 26, wherein the receiving unit is adapted to charge the battery of embodiment 25.

28. The operable implant according to any one of the preceding embodiments, wherein the electrical motor is an electrical motor selected from:
    a. an alternating current (AC) electrical motor,
    b. a direct current electrical motor,
    c. a linear electrical motor,
    d. an axial electrical motor,
    e. a radial motor
    f. a three-phase motor
    g. a more than one-phase motor
    h. a piezo-electric motor,
    i. a bimetal motor, and
    j. a memory metal motor.

29. The operable implant according to any one of embodiments 14-28, wherein the enclosure comprises a material selected from:
    a. a carbon material
    b. a boron material
    c. a mixture of material
    d. a Peek® material
    e. an alloy of material
    f. a metallic material, g. titanium,
h. aluminum,
i. a ceramic material,
j. a polymer material,
k. polyurethane,
l. polyether ether ketone,
m. silicone, and
n. Parylene® coated silicone.

The different aspects or any part of an aspect of the different numbered embodiments or any part of an embodiment may all be combined in any possible way. Any method embodiment or any step of any method embodiment may be seen also as an apparatus description, as well as, any apparatus embodiment, aspect or part of aspect or part of embodiment may be seen as a method description and all may be combined in any possible way down to the smallest detail. Any detailed description should be interpreted in its broadest outline as a general summary description.

The invention claimed is:

1. An operable implant adapted to be implanted in the body of a patient, the operable implant comprising an operation device and a body engaging portion, wherein the operation device comprises:
    a first unit comprising:
        a receiving unit for receiving wireless energy, and
        a first gear system adapted to receive mechanical work having a first force and first velocity, and output mechanical work having a different second force and a different second velocity,
    a second unit comprising an electrical motor adapted to transform electrical energy to the mechanical work, and
    a distance element comprising:
        a lead for transferring the electrical energy from the first unit to the second unit, and
        a mechanical transferring member adapted to transfer the mechanical work from the electrical motor in the second unit to the first gear system in the first unit, wherein
    the distance element is adapted to separate the first and second units such that the receiving unit, when receiving wireless energy, is not substantially affected by the second unit.

2. The operable implant according to claim 1, wherein the receiving unit comprises at least one coil adapted to transform wireless energy received in form of a magnetic field into electrical energy.

3. The operable implant according to claim 2, wherein the receiving unit comprises at least a first coil having a first number of windings, and at least a second coil having a second, different number of windings.

4. The operable implant according to claim 1, wherein the first gear system comprises:
    an operable element,
    a first gear having the shape of a hollow cylinder, comprising a first number of teeth, on the peripheral outside thereof, and
    a second gear having the shape of a hollow cylinder, comprising a greater number of teeth than the first gear, on an inside surface of the second gear, wherein the operable element is adapted to engage an inside surface of the first gear, such that an outside of the first gear is pressed against the inside of the second gear such that the teeth of the first gear are interengaged with the teeth of the second gear in at least one position interspaced by positions at which the teeth are not interengaged, and wherein an operation of the operable element advances positions and thereby causes relative rotation between the first gear and the second gear.

5. The operable implant according to claim 4, wherein the operable element comprises at least one of: a planetary gear and a structure or wheel at least partly using friction to interconnect with the first gear.

6. The operable implant according to claim 4, wherein the first gear system comprises a third gear, and wherein an inside of the third gear comprises the same amount of teeth as the outside of the first gear, and wherein teeth of the third gear are adapted to interengage with the teeth of the first gear such that the third gear rotates in relation to the second gear, along with the at least one interengaged position.

7. The operable implant according to claim 1, wherein the second unit comprises a second gear system adapted to receive the mechanical work output from the first gear system with the different second force and the different second velocity as input, and output mechanical work having a third different force and third different velocity, and wherein the second gear system of the second unit is connected in series with the first gear system of the first unit, via the mechanical transferring member of the distance element.

8. The operable implant according to claim 1, wherein the first unit comprises a second gear system adapted to receive mechanical work of a first force and velocity as input, and output mechanical work having a different force and velocity, and wherein the second gear system is connected in series with the first gear system.

9. The operable implant according to claim 1, wherein the first unit is adapted to be placed at least in one of the following places: subcutaneously, subcutaneously in an abdominal wall and in an abdomen.

10. The operable implant according to claim 9, wherein the second unit comprises at least one fixation portion for fixating the second unit to at least one of: fibrosis, a fascia and a muscular layer towards an inside of a subcutaneous space of the patient.

11. The operable implant according to claim 1, wherein the electrical motor comprises magnetic material and wherein the first unit is substantially unaffected by the magnetic material in the second unit, during wireless energy transfer.

12. The operable implant according to claim 1, wherein the distance element is adapted to be at least one of: placed through muscular layers of an abdominal wall, and fixated to a muscular fascia facing a subcutaneous space.

13. The operable implant according to claim 1, wherein the distance element is flexible such that the first and second unit can move in relation to each other.

14. The operable implant according to claim 1, wherein the mechanical transferring member comprises a mechanical transferring member selected from:
    a hydraulic tube for transferring hydraulic force,
    a rotating shaft for transferring rotational force,
    a flexible member for transferring rotational force,
    a wire,
    a belt,
    a rod,
    a worm gear, and
    a gear for changing rotational force in substantially 90 degrees direction.

15. The operable implant according to claim 1, further comprising an enclosure adapted to hermetically enclose the operable implant.

16. The operable implant according to claim 1, further comprising a metallic enclosure adapted to enclose at least one of the second unit and the distance element.

17. The operable implant according to claim 16, wherein the metallic enclosure comprises at least one of: a titanium enclosure, an aluminum enclosure, and a stainless steel enclosure.

18. The operable implant according to claim 1, wherein at least one of the first and second units comprises a battery adapted to store electrical energy received at the receiving unit.

19. The operable implant according to claim 1, wherein the electrical motor comprises an electrical motor selected from:
- an alternating current (AC) electrical motor,
- a direct current (DC) electrical motor,
- a linear electrical motor,
- an axial electrical motor,
- a piezo-electric motor,
- a three-phase motor,
- a more than one-phase motor,
- a bimetal motor, and
- a memory metal motor.

\* \* \* \* \*